(12) United States Patent
Sagert et al.

(10) Patent No.: US 10,233,244 B2
(45) Date of Patent: Mar. 19, 2019

(54) ANTI-ITGA3 ANTIBODIES, ACTIVATABLE ANTI-ITGA3 ANTIBODIES, AND METHODS OF USE THEREOF

(71) Applicant: CytomX Therapeutics, Inc., South San Francisco, CA (US)

(72) Inventors: Jason Gary Sagert, San Mateo, CA (US); Jonathan Alexander Terrett, Cupertino, CA (US); Luc Roland Desnoyers, San Francisco, CA (US); Shweta Singh, Fremont, CA (US); Annie Yang Weaver, San Mateo, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 46 days.

(21) Appl. No.: 15/146,868

(22) Filed: May 4, 2016

(65) Prior Publication Data

US 2016/0355592 A1 Dec. 8, 2016

Related U.S. Application Data

(60) Provisional application No. 62/156,839, filed on May 4, 2015, provisional application No. 62/258,870, filed on Nov. 23, 2015.

(51) Int. Cl.

| *C07K 16/00* | (2006.01) |
| *C07K 16/46* | (2006.01) |
| *C07K 16/28* | (2006.01) |
| *C07K 7/08* | (2006.01) |
| *A61K 47/68* | (2017.01) |
| *C07K 16/30* | (2006.01) |
| *A61K 39/00* | (2006.01) |

(52) U.S. Cl.
CPC ...... *C07K 16/2839* (2013.01); *A61K 47/6803* (2017.08); *A61K 47/6809* (2017.08); *A61K 47/6849* (2017.08); *A61K 47/6851* (2017.08); *C07K 7/08* (2013.01); *C07K 16/2842* (2013.01); *C07K 16/30* (2013.01); *A61K 2039/505* (2013.01); *C07K 2317/24* (2013.01); *C07K 2317/33* (2013.01); *C07K 2317/732* (2013.01); *C07K 2317/92* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| 3,773,919 A | 11/1973 | Boswell et al. |
| 4,485,045 A | 11/1984 | Regen |
| 4,643,971 A | 2/1987 | Fradet et al. |
| 4,886,745 A | 12/1989 | Morhenn |
| 5,013,556 A | 5/1991 | Woodle et al. |
| 5,030,719 A | 7/1991 | Umemoto et al. |
| 5,151,510 A | 9/1992 | Stec et al. |
| 5,530,101 A * | 6/1996 | Queen ..................... C07K 16/00 424/133.1 |
| 5,618,920 A * | 4/1997 | Robinson ................. C12N 9/88 424/133.1 |
| 7,666,817 B2 | 2/2010 | Daugherty et al. |
| 7,736,647 B2 | 6/2010 | Boumsell et al. |
| 8,513,390 B2 | 8/2013 | Stagliano et al. |
| 8,518,404 B2 | 8/2013 | Daugherty et al. |
| 8,563,269 B2 | 10/2013 | Stagliano et al. |
| 8,809,504 B2 | 8/2014 | Lauermann |
| 2004/0109855 A1 | 6/2004 | Waldmann et al. |
| 2009/0203538 A1 | 8/2009 | Sugioka et al. |
| 2014/0235833 A1 | 8/2014 | Sugioka et al. |

FOREIGN PATENT DOCUMENTS

| EP | 1 324 771 B1 | 6/2011 |
| WO | WO 94/11026 A2 | 5/1994 |
| WO | WO 98/09651 A1 | 3/1998 |
| WO | WO 01/91798 A2 | 12/2001 |
| WO | WO 2007/105027 A1 | 9/2007 |
| WO | WO 2009/025846 A2 | 2/2009 |
| WO | WO 2010/081173 A2 | 7/2010 |
| WO | WO 2010/129609 A2 | 11/2010 |
| WO | WO 2013/192546 A1 | 12/2013 |
| WO | WO 2014/026136 A2 | 2/2014 |

OTHER PUBLICATIONS

Kumagai-Braesch et al., "Identification of Swine and Primate Cellular Adhesion Molecules (CAM) Using Mouse Anti-Human Monoclonal Antibodies," *Xenotransplantation*, vol. 2, May 1, 1995, pp. 88-97.

Fradette, J. et al., "Normal Human Merkel Cells are Present in Epidermal Cell Populations Isolated and Cultured from Glabrous and Hairy Skin Sites," *J. of Investigative Dermatology*, vol. 120(2), Feb. 1, 2003, pp. 313-317.

Irving, "Probodies Empower a New Generation of Antibody Immunotherapies," presented at Keystone Symposia on Molecular and Cellular Biology, Feb. 2015.

Beck, A. et al. (Nov. 1, 2012) "Fourth World Antibody—Drug Conjugate Summit. Feb. 29-Mar. 1, 2012, Frankfurt, Germany" *MABS*, 4(6):637-647.

\* cited by examiner

*Primary Examiner* — Maher M Haddad

(74) *Attorney, Agent, or Firm* — Cooley LLP

(57) ABSTRACT

The invention relates generally to antibodies that bind ITGa3, activatable antibodies that specifically bind to ITGa3 and methods of making and using these anti-ITGa3 antibodies and anti-ITGa3 activatable antibodies in a variety of therapeutic, diagnostic and prophylactic indications.

48 Claims, 20 Drawing Sheets
Specification includes a Sequence Listing.

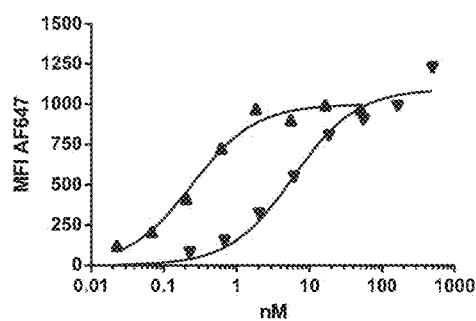
FIGURE 15A – HT29
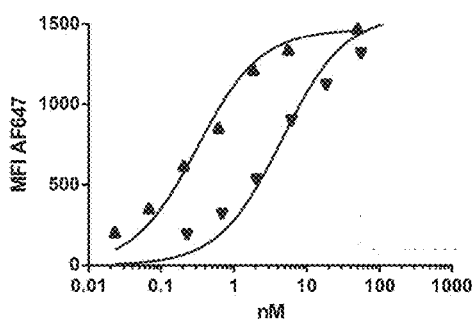
FIGURE 15B – FaDu
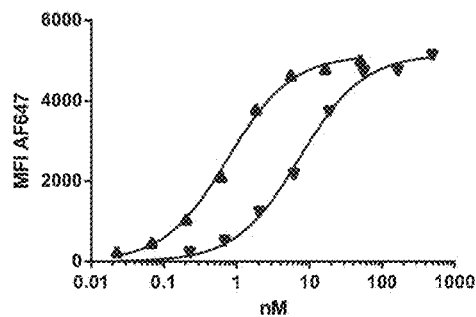
FIGURE 15C – BxPC3
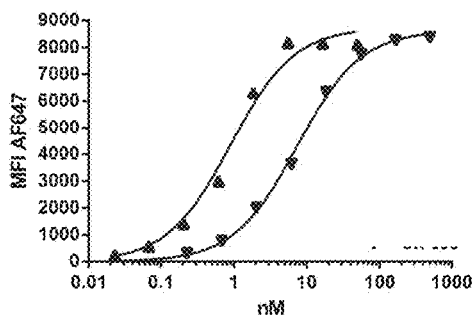
FIGURE 15D – MDA-MB-231
ITGa3 Ab
ITGa3 Act-Ab FIGURE 16A – BxPC3
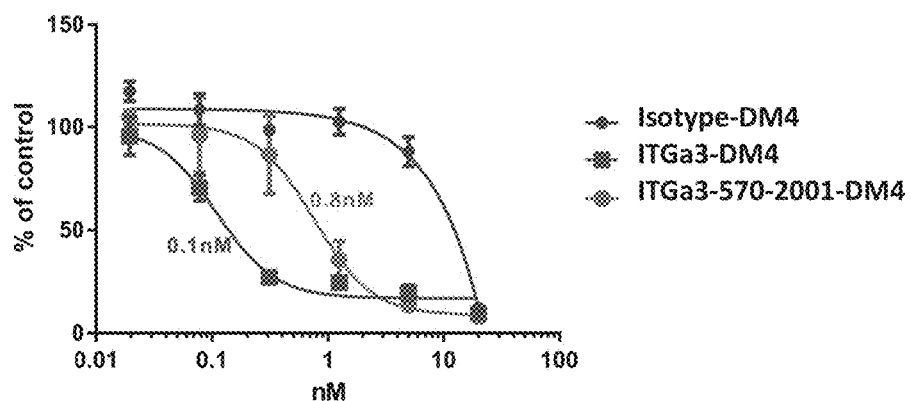
FIGURE 16B – BxPC3
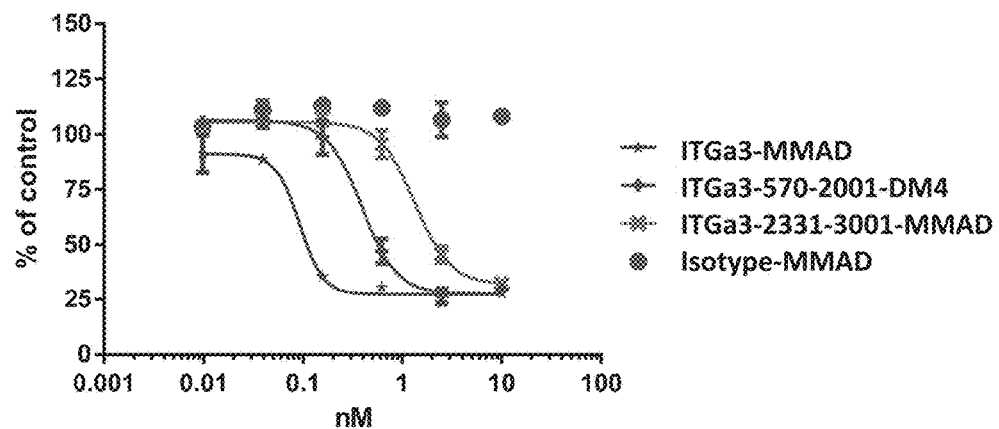

FIGURE 16C – H292
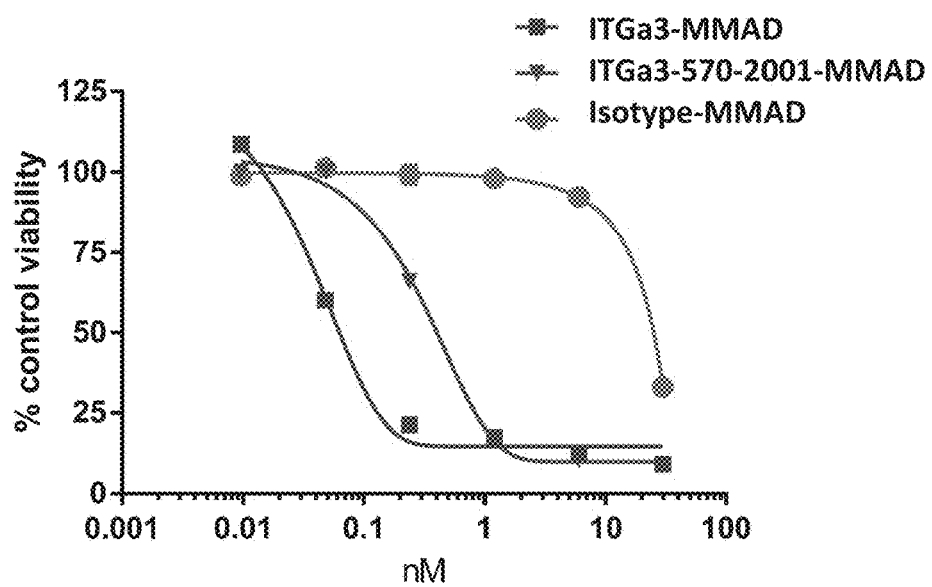
FIGURE 16D – HCC1806
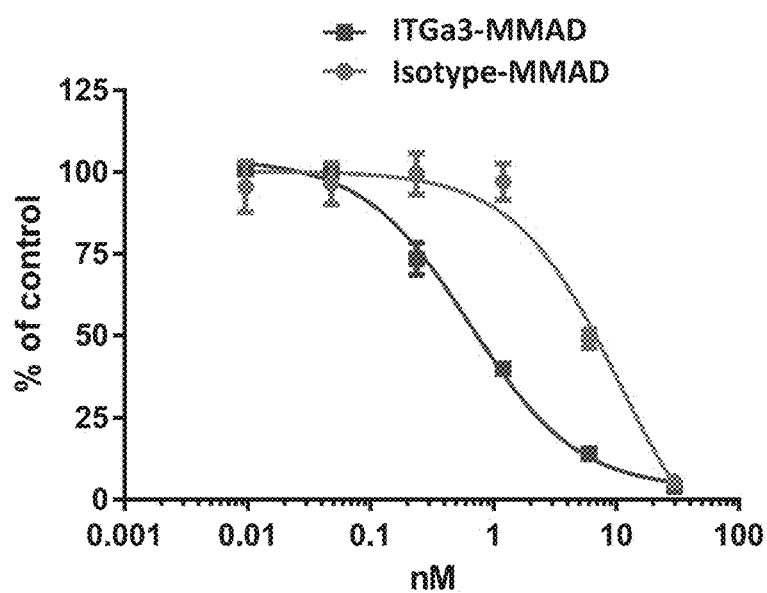

FIGURE 17A – H292
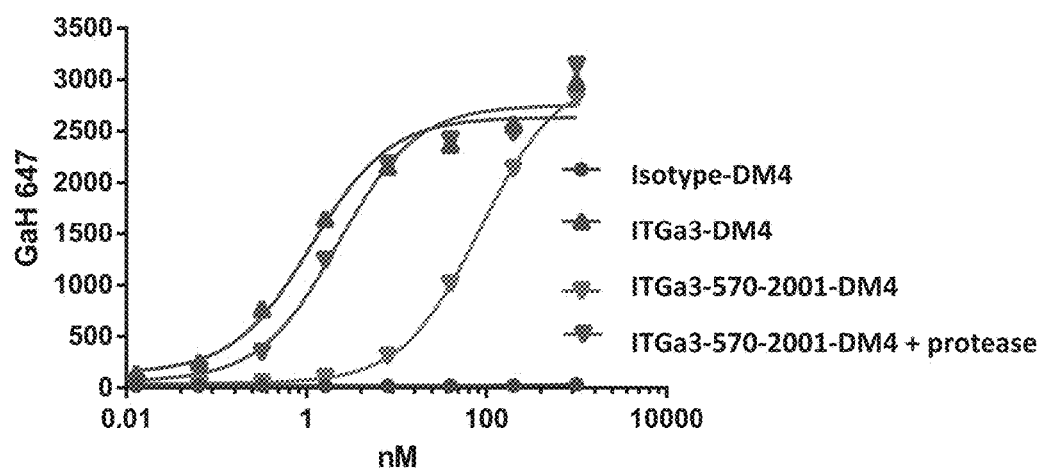
FIGURE 17B – MDA MB 231
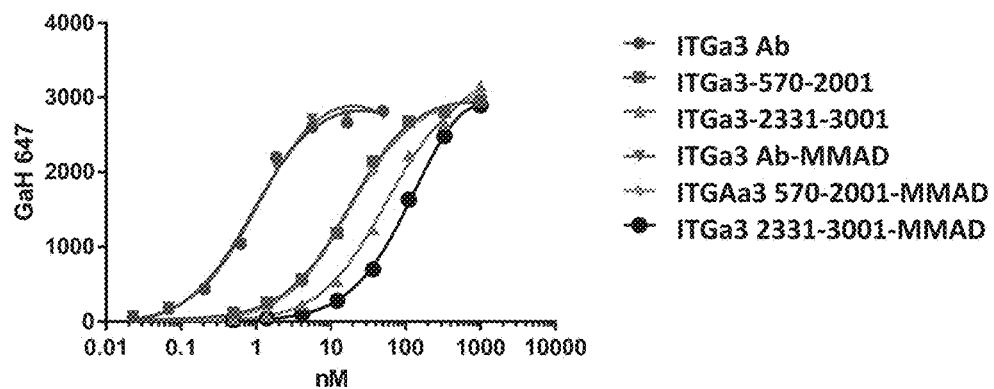

SEQUENCE LISTING

```
<160> NUMBER OF SEQ ID NOS: 471

<210> SEQ ID NO 1
<211> LENGTH: 123
<212> TYPE: PRT
<213> ORGANISM: Artificial Sequence
<220> FEATURE:
<223> OTHER INFORMATION: chemically synthesized

<400> SEQUENCE: 1

Glu Val Gln Leu Gln Glu Ser Gly Ala Glu Leu Val Lys Pro Gly Thr
1               5                   10                  15

Ser Val Arg Leu Ser Cys Lys Ala Ser Gly Tyr Thr Phe Thr Glu Tyr
            20                  25                  30

Ile Ile His Trp Val Lys Gln Arg Ser Gly Gln Gly Leu Glu Trp Ile
        35                  40                  45

Gly Trp Phe Tyr Pro Glu Ser Gly Ser Val Lys Tyr Asn Glu Thr Phe
    50                  55                  60

Lys Gly Arg Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Glu Arg Asp Tyr Gly Tyr Tyr Ala Met Asp Tyr
            100                 105                 110
```

```
Trp Gly Gln Gly Thr Ser Val Thr Val Ser Ser
        115                 120

<210> SEQ ID NO 2
<211> LENGTH: 109
<212> TYPE: PRT
<213> ORGANISM: Artificial Sequence
<220> FEATURE:
<223> OTHER INFORMATION: chemically synthesized

<400> SEQUENCE: 2

Asp Ile Val Met Thr Gln Thr Pro Thr Leu Ala Ala Ser Pro Gly
1               5                   10                  15

Glu Lys Ile Ile Ile Thr Cys Ser Ala Ser Ser Ser Ile Ser Ser Asn
            20                  25                  30

Tyr Leu His Trp Tyr Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65              70                  75                  80

Ala Glu Asp Val Ala Thr Tyr Tyr Cys Gln Gln Gly Ser Ser Ile Pro
                85                  90                  95

Arg Phe Thr Ser Gly Ser Gly Thr Lys Leu Glu Ile Lys
            100                 105

<210> SEQ ID NO 3
<211> LENGTH: 123
<212> TYPE: PRT
<213> ORGANISM: Artificial Sequence
<220> FEATURE:
<223> OTHER INFORMATION: chemically synthesized

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
        35                  40                  45

Gly Trp Phe Tyr Pro Glu Ser Gly Ser Val Lys Tyr Asn Glu Thr Phe
    50                  55                  60

Lys Gly Arg Ala Thr Leu Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
        115                 120

<210> SEQ ID NO 4
<211> LENGTH: 123
<212> TYPE: PRT
<213> ORGANISM: Artificial Sequence
<220> FEATURE:
<223> OTHER INFORMATION: chemically synthesized

<400> SEQUENCE: 4
```

-continued

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
        35                  40                  45

Gly Trp Phe Tyr Pro Glu Ser Gly Ser Val Lys Tyr Ser Glu Thr Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
        115                 120

<210> SEQ ID NO 5
<211> LENGTH: 123
<212> TYPE: PRT
<213> ORGANISM: Artificial Sequence
<220> FEATURE:
<223> OTHER INFORMATION: chemically synthesized

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
        35                  40                  45

Gly Trp Phe Tyr Pro Glu Ser Gly Ser Val Lys Tyr Asn Glu Ala Phe
    50                  55                  60

Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
        115                 120

<210> SEQ ID NO 6
<211> LENGTH: 123
<212> TYPE: PRT
<213> ORGANISM: Artificial Sequence
<220> FEATURE:
<223> OTHER INFORMATION: chemically synthesized

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
        35                  40                  45

Gly Trp Phe Tyr Pro Glu Ser Gly Ser Val Lys Tyr Asn Glu Gly Phe
    50                  55                  60

```
Lys Gly Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
            115                 120
```

<210> SEQ ID NO 7
<211> LENGTH: 123
<212> TYPE: PRT
<213> ORGANISM: Artificial Sequence
<220> FEATURE:
<223> OTHER INFORMATION: chemically synthesized

<400> SEQUENCE: 7

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Glu Tyr
                 20                  25                  30

Ile Ile His Trp Val Arg Gln Ala Pro Gly Gln Gly Leu Glu Trp Ile
             35                  40                  45

Gly Trp Phe Tyr Pro Glu Ser Gly Ser Val Lys Tyr Asn Glu Thr Phe
     50                  55                  60

Lys Gly Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
            115                 120
```

<210> SEQ ID NO 8
<211> LENGTH: 123
<212> TYPE: PRT
<213> ORGANISM: Artificial Sequence
<220> FEATURE:
<223> OTHER INFORMATION: chemically synthesized

<400> SEQUENCE: 8

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Glu Tyr
                 20                  25                  30

Ile Ile His Trp Val Arg Gln Ala Pro Gly Gln Gly Leu Glu Trp Ile
             35                  40                  45

Gly Trp Phe Tyr Pro Glu Ser Gly Ser Val Lys Tyr Ser Glu Thr Phe
     50                  55                  60

Lys Gly Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
```

<210> SEQ ID NO 9
<211> LENGTH: 123
<212> TYPE: PRT
<213> ORGANISM: Artificial Sequence
<220> FEATURE:
<223> OTHER INFORMATION: chemically synthesized

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
        35                  40                  45

Gly Trp Phe Tyr Pro Glu Ser Gly Ser Val Lys Tyr Asn Glu Ala Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
        115                 120
```

<210> SEQ ID NO 10
<211> LENGTH: 123
<212> TYPE: PRT
<213> ORGANISM: Artificial Sequence
<220> FEATURE:
<223> OTHER INFORMATION: chemically synthesized

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
        35                  40                  45

Gly Trp Phe Tyr Pro Glu Ser Gly Ser Val Lys Tyr Asn Glu Gly Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser
        115                 120
```

<210> SEQ ID NO 11
<211> LENGTH: 109
<212> TYPE: PRT
<213> ORGANISM: Artificial Sequence
<220> FEATURE:
<223> OTHER INFORMATION: chemically synthesized

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser Asn
            20                  25                  30

Tyr Leu His Trp Tyr Gln Gln Lys Pro Gly Lys Val Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Val Ala Thr Tyr Tyr Cys Gln Gln Gly Ser Ser Ile Pro
                85                  90                  95

Arg Phe Thr Ser Gly Gly Gly Thr Lys Val Glu Ile Lys
            100                 105

<210> SEQ ID NO 12
<211> LENGTH: 109
<212> TYPE: PRT
<213> ORGANISM: Artificial Sequence
<220> FEATURE:
<223> OTHER INFORMATION: chemically synthesized

<400> SEQUENCE: 12

Asp Ile Gln Met Thr Gln Ser Pro Ser Ser Leu Ser Ala Ser Val Gly
1               5                   10                  15

Asp Arg Val Ile Ile Thr Cys Ser Ala Ser Ser Ser Ile Ser Ser Asn
            20                  25                  30

Tyr Leu His Trp Tyr Gln Gln Lys Pro Gly Lys Val Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Val Ala Thr Tyr Tyr Cys Gln Gln Gly Ser Ser Ile Pro
                85                  90                  95

Arg Phe Thr Ser Gly Gly Gly Thr Lys Val Glu Ile Lys
            100                 105

<210> SEQ ID NO 13
<211> LENGTH: 5
<212> TYPE: PRT
<213> ORGANISM: Artificial Sequence
<220> FEATURE:
<223> OTHER INFORMATION: chemically synthesized

<400> SEQUENCE: 13

Glu Tyr Ile Ile His
1               5

<210> SEQ ID NO 14
<211> LENGTH: 17
<212> TYPE: PRT
<213> ORGANISM: Artificial Sequence
<220> FEATURE:
<223> OTHER INFORMATION: chemically synthesized

<400> SEQUENCE: 14

Trp Phe Tyr Pro Glu Ser Gly Ser Val Lys Tyr Asn Glu Thr Phe Lys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: chemically synthesized

<400> SEQUENCE: 15

Trp Phe Tyr Pro Glu Ser Gly Ser Val Lys Tyr Ser Glu Thr Phe Lys
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: chemically synthesized

<400> SEQUENCE: 16

Trp Phe Tyr Pro Glu Ser Gly Ser Val Lys Tyr Asn Glu Ala Phe Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: chemically synthesized

<400> SEQUENCE: 17

Trp Phe Tyr Pro Glu Ser Gly Ser Val Lys Tyr Asn Glu Gly Phe Lys
1               5                   10                  15

Gly

<210> SEQ ID NO 18
<211> LENGTH: 14
<212> TYPE: PRT
<213> ORGANISM: Artificial Sequence
<220> FEATURE:
<223> OTHER INFORMATION: chemically synthesized

<400> SEQUENCE: 18

His Glu Glu Arg Asp Tyr Tyr Gly Tyr Tyr Ala Met Asp Tyr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: chemically synthesized

<400> SEQUENCE: 19

Ser Ala Ser Ser Ser Ile Ser Ser Asn Tyr Leu His
1               5                   10

<210> SEQ ID NO 20
<211> LENGTH: 6
<212> TYPE: PRT
<213> ORGANISM: Artificial Sequence
<220> FEATURE:

<223> OTHER INFORMATION: chemically synthesized

<400> SEQUENCE: 20

Arg Thr Ser Asn Leu Ala
1               5

<210> SEQ ID NO 21
<211> LENGTH: 10
<212> TYPE: PRT
<213> ORGANISM: Artificial Sequence
<220> FEATURE:
<223> OTHER INFORMATION: chemically synthesized

<400> SEQUENCE: 21

Gln Gln Gly Ser Ser Ile Pro Arg Phe Thr
1               5                   10

<210> SEQ ID NO 22
<211> LENGTH: 15
<212> TYPE: PRT
<213> ORGANISM: Artificial Sequence
<220> FEATURE:
<223> OTHER INFORMATION: chemically synthesized

<400> SEQUENCE: 22

Glu Cys Lys Thr Arg Gln Asp Phe Glu Met His Asp Cys Val Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: chemically synthesized

<400> SEQUENCE: 23

Ile Cys His Asp Pro Tyr Met Asn Ile Asp Tyr Thr Cys Lys Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: chemically synthesized

<400> SEQUENCE: 24

Val Met Cys Tyr Trp Glu Gly Trp Gly Phe Gly Arg Cys Pro Leu
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: chemically synthesized

<400> SEQUENCE: 25

Val Trp Tyr Cys Asp Gly Gly Tyr Asn Glu Cys Ala Thr Arg Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: chemically synthesized

```
<400> SEQUENCE: 26

Gln Cys Met Ser Arg Phe Ala Phe Glu Ile Gly Asp Cys Val Met
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: chemically synthesized

<400> SEQUENCE: 27

Ala Val Trp Cys Asp Ala Tyr Asn Lys Asn Met Cys Trp Ser Thr
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: chemically synthesized

<400> SEQUENCE: 28

Val Trp Tyr Cys Asp Gly Gly Tyr Asn Glu Cys Ala Thr Arg Ser
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: chemically synthesized

<400> SEQUENCE: 29

Glu Cys Lys Thr Arg Gln Asp Phe Glu Met His Asp Cys Val Tyr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: chemically synthesized

<400> SEQUENCE: 30

Lys Cys His Asp Pro Tyr Ile Asn Ile Asp Tyr Thr Cys Asn Asn
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: chemically synthesized

<400> SEQUENCE: 31

Leu Ile Thr Cys Glu Met Leu Met Leu Lys Asn Cys Glu Lys Asn
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: chemically synthesized
```

```
<400> SEQUENCE: 32

Leu Gly Cys Lys Lys Gln His His Thr Asn Asn Thr Cys Asp Arg
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: chemically synthesized

<400> SEQUENCE: 33

Ile Cys His Asp Pro Tyr Met Asn Ile Asp Tyr Thr Cys Lys Leu
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: chemically synthesized

<400> SEQUENCE: 34

Val Met Cys Tyr Trp Glu Gly Trp Gly Phe Gly Arg Cys Pro Leu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: chemically synthesized

<400> SEQUENCE: 35

Thr Cys Pro Thr Arg Trp His Phe Glu Thr Thr Asp Cys Val Met
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: chemically synthesized

<400> SEQUENCE: 36

Ile Cys Gly Ser Arg Leu Asp Phe Glu Leu Asn Asp Cys Val Met
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: chemically synthesized

<400> SEQUENCE: 37

Trp Cys Arg Asp Arg Ser His Phe Glu Thr Gly Asp Cys Val Met
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: chemically synthesized

<400> SEQUENCE: 38
```

```
Ile Cys Thr Ser Arg Trp Glu Phe Glu Asn Arg Asp Cys Val Met
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: chemically synthesized

<400> SEQUENCE: 39

Val Cys Arg Asp Arg Asn Glu Phe Glu Val Gly Asp Cys Val Met
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: chemically synthesized

<400> SEQUENCE: 40

Thr Cys Lys Asn Arg Leu Glu Phe Glu Arg Gly Asp Cys Val Met
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: chemically synthesized

<400> SEQUENCE: 41

Val Cys Ser Ser Arg Leu Glu Phe Glu Gln Lys Asp Cys Val Met
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: chemically synthesized

<400> SEQUENCE: 42

Trp Cys Arg Asp Arg Glu His Phe Glu Lys Gly Asp Cys Val Met
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: chemically synthesized

<400> SEQUENCE: 43

Tyr Cys Ala Asn Arg Tyr Glu Phe Glu Tyr Gly Asp Cys Val Met
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: chemically synthesized

<400> SEQUENCE: 44
```

Thr Cys Leu Ser Arg Tyr Glu Phe Glu Thr Thr Asp Cys Val Met
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: chemically synthesized

<400> SEQUENCE: 45

Val Cys Arg Thr Arg Trp His Phe Glu Thr Thr Asp Cys Val Met
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: chemically synthesized

<400> SEQUENCE: 46

Val Cys Ser Asn Arg Ala Glu Phe Glu Trp Gly Asp Cys Val Met
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: chemically synthesized

<400> SEQUENCE: 47

Val Cys Ala Ser Arg Trp His Phe Glu Asn Thr Asp Cys Val Met
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: chemically synthesized

<400> SEQUENCE: 48

Asn Cys Ala Ser Arg Trp His Phe Glu Asn Glu Asp Cys Val Met
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: chemically synthesized

<400> SEQUENCE: 49

Val Cys Ser Gly Arg Leu Glu Phe Glu Leu Gly Asp Cys Val Met
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: chemically synthesized

<400> SEQUENCE: 50

Val Cys Ser Ser Arg Trp Glu Phe Glu Thr Asn Asp Cys Val Met

<210> SEQ ID NO 51
<211> LENGTH: 15
<212> TYPE: PRT
<213> ORGANISM: Artificial Sequence
<220> FEATURE:
<223> OTHER INFORMATION: chemically synthesized

<400> SEQUENCE: 51

Phe Cys Arg Asp Arg Leu Asp Phe Asp Thr Met Asp Cys Val Met
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: chemically synthesized

<400> SEQUENCE: 52

Cys Cys Met Asp Arg Leu Glu Phe Glu Arg Gly Asp Cys Val Met
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: chemically synthesized

<400> SEQUENCE: 53

Val Cys Gly Ser Arg Asn Glu Phe Glu Thr Gly Asp Cys Val Met
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: chemically synthesized

<400> SEQUENCE: 54

Met Cys Ser Gly Arg Leu Glu Phe Glu Thr Gly Asp Cys Val Met
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature

```
<222> LOCATION: (15)..(15)
<223> OTHER INFORMATION: Xaa can be any naturally occurring amino acid

<400> SEQUENCE: 55

Xaa Cys Xaa Xaa Arg Xaa Xaa Phe Glu Xaa Xaa Asp Cys Val Xaa
1               5                   10                  15

<210> SEQ ID NO 56
<211> LENGTH: 124
<212> TYPE: PRT
<213> ORGANISM: Artificial Sequence
<220> FEATURE:
<223> OTHER INFORMATION: chemically synthesized

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Thr Ala Ala Ser Leu Lys Tyr Tyr Tyr Asp Ser Ser Gly Tyr Tyr
            100                 105                 110

Tyr Trp Gly Gln Gly Thr Leu Val Thr Val Ser Arg
        115                 120

<210> SEQ ID NO 57
<211> LENGTH: 110
<212> TYPE: PRT
<213> ORGANISM: Artificial Sequence
<220> FEATURE:
<223> OTHER INFORMATION: chemically synthesized

<400> SEQUENCE: 57

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Gly Lys Asn Asn Arg Pro Ser Gly Ile Pro Asp Arg Phe Ser Gly Ser
    50                  55                  60

Ser Ser Gly Asp Thr Ala Ser Leu Thr Ile Thr Gly Ala Gln Ala Glu
65                  70                  75                  80

Asp Glu Ala Asn Tyr Tyr Cys Asn Ser Arg Asp Ser Ser Gly Tyr Pro
                85                  90                  95

Ser Trp Val Phe Gly Gly Gly Thr Lys Leu Thr Val Leu Gly
            100                 105                 110

<210> SEQ ID NO 58
<211> LENGTH: 125
<212> TYPE: PRT
<213> ORGANISM: Artificial Sequence
<220> FEATURE:
```

<223> OTHER INFORMATION: chemically synthesized

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Ala Tyr Cys Ser Ser Thr Ser Cys Tyr Arg Asn Ala Phe
            100                 105                 110

Asp Ile Trp Gly Gln Gly Thr Thr Val Thr Val Ser Arg
            115                 120                 125

<210> SEQ ID NO 59
<211> LENGTH: 113
<212> TYPE: PRT
<213> ORGANISM: Artificial Sequence
<220> FEATURE:
<223> OTHER INFORMATION: chemically synthesized

<400> SEQUENCE: 59

Gln Ser Val Leu Thr Gln Pro Pro Ser Val Ser Gly Ala Pro Gly Gln
1               5                   10                  15

Arg Val Asn Ile Ser Cys Ala Gly Ser Ser Ser Asn Ile Gly Ala Gly
            20                  25                  30

Tyr Asp Val His Trp Tyr Gln Gln Ile Pro Gly Thr Ala Pro Lys Leu
        35                  40                  45

Leu Met Tyr Gly Asn Ser Asn Arg Pro Ser Gly Val Pro Asp Arg Phe
    50                  55                  60

Ser Gly Ser Lys Ser Gly Ala Ser Ala Ser Leu Ala Ile Thr Arg Leu
65                  70                  75                  80

Gln Ala Glu Asp Glu Ala Asp Tyr Tyr Cys Gln Ser Tyr Asp Ser Ser
                85                  90                  95

Leu Ser Gly Ser Arg Val Phe Gly Thr Gly Thr Lys Val Thr Val Leu
            100                 105                 110

Gly

<210> SEQ ID NO 60
<211> LENGTH: 122
<212> TYPE: PRT
<213> ORGANISM: Artificial Sequence
<220> FEATURE:
<223> OTHER INFORMATION: chemically synthesized

<400> SEQUENCE: 60

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Thr Val Ile Ser Phe Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Tyr Thr Asn Thr Trp Trp Pro Asp Ala Phe Asp Ile Trp
            100                 105                 110

Gly Gln Gly Thr Thr Val Thr Val Ser Arg
            115                 120

<210> SEQ ID NO 61
<211> LENGTH: 107
<212> TYPE: PRT
<213> ORGANISM: Artificial Sequence
<220> FEATURE:
<223> OTHER INFORMATION: chemically synthesized

<400> SEQUENCE: 61

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Pro
                 85                  90                  95

Thr Phe Gly Pro Gly Thr Lys Val Asp Ile Lys
            100                 105

<210> SEQ ID NO 62
<211> LENGTH: 118
<212> TYPE: PRT
<213> ORGANISM: Artificial Sequence
<220> FEATURE:
<223> OTHER INFORMATION: chemically synthesized

<400> SEQUENCE: 62

Gln Val Gln Leu Gln Glu Ser Gly Pro Gly Leu Val Lys Pro Ser Glu
 1               5                  10                  15

Thr Leu Ser Leu Thr Cys Thr Val Ser Gly Ser Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Leu Tyr Trp Asn Asp Ala Phe Asp Ile Trp Gly Gln Gly Thr
            100                 105                 110

Thr Val Thr Val Ser Arg
```

<210> SEQ ID NO 63
<211> LENGTH: 111
<212> TYPE: PRT
<213> ORGANISM: Artificial Sequence
<220> FEATURE:
<223> OTHER INFORMATION: chemically synthesized

<400> SEQUENCE: 63

Gln Ser Ala Leu Thr Gln Pro Leu Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 64
<211> LENGTH: 118
<212> TYPE: PRT
<213> ORGANISM: Artificial Sequence
<220> FEATURE:
<223> OTHER INFORMATION: chemically synthesized

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Leu Tyr Trp Asn Asp Ala Phe Asp Ile Trp Gly Gln Gly Thr
            100                 105                 110

Thr Val Thr Val Ser Arg
        115

<210> SEQ ID NO 65
<211> LENGTH: 111
<212> TYPE: PRT
<213> ORGANISM: Artificial Sequence
<220> FEATURE:
<223> OTHER INFORMATION: chemically synthesized

<400> SEQUENCE: 65

Gln Ser Val Leu Thr Gln Pro Pro Ser Ala Ser Gly Thr Pro Gly Gln
1               5                   10                  15

-continued

```
Ser Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 66
<211> LENGTH: 126
<212> TYPE: PRT
<213> ORGANISM: Artificial Sequence
<220> FEATURE:
<223> OTHER INFORMATION: chemically synthesized

<400> SEQUENCE: 66

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Ser Trp Leu Trp Gly Ile Gly Gly Asp Ala
            100                 105                 110

Phe Asp Ile Trp Gly Gln Gly Thr Thr Val Thr Val Ser Arg
        115                 120                 125

<210> SEQ ID NO 67
<211> LENGTH: 111
<212> TYPE: PRT
<213> ORGANISM: Artificial Sequence
<220> FEATURE:
<223> OTHER INFORMATION: chemically synthesized

<400> SEQUENCE: 67

Gln Ser Val Leu Thr Gln Pro Pro Ser Val Ser Gly Ala Pro Arg Gln
1               5                   10                  15

Thr Val Thr Ile Ser Cys Ser Gly Ser Ser Asn Ile Gly Gln Asn
            20                  25                  30

Ser Val Thr Trp Tyr Gln Arg Leu Pro Gly Glu Ala Pro Lys Leu Leu
        35                  40                  45

Ile Tyr Tyr Asp Asp Leu Leu His Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ser Trp Asp Asp Ser Leu
```

```
                    85                  90                  95

Lys Gly Pro Val Phe Gly Gly Thr Lys Leu Thr Val Leu Gly
            100                 105                 110
```

<210> SEQ ID NO 68
<211> LENGTH: 112
<212> TYPE: PRT
<213> ORGANISM: Artificial Sequence
<220> FEATURE:
<223> OTHER INFORMATION: chemically synthesized

<400> SEQUENCE: 68

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Phe Asp Tyr Trp Gly Gln Gly Thr Leu Val Thr Val Ser Arg
            100                 105                 110
```

<210> SEQ ID NO 69
<211> LENGTH: 105
<212> TYPE: PRT
<213> ORGANISM: Artificial Sequence
<220> FEATURE:
<223> OTHER INFORMATION: chemically synthesized

<400> SEQUENCE: 69

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Pro Ala Phe
                85                  90                  95

Gly Gly Gly Thr Lys Val Glu Ile Lys
            100                 105
```

<210> SEQ ID NO 70
<211> LENGTH: 124
<212> TYPE: PRT
<213> ORGANISM: Artificial Sequence
<220> FEATURE:
<223> OTHER INFORMATION: chemically synthesized

<400> SEQUENCE: 70

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asn Tyr
            20                  25                  30

Gly Leu Thr Trp Val Arg Gln Ala Pro Gly Gln Gly Leu Glu Trp Met
            35                  40                  45

Gly Trp Ile Ser Thr Tyr Asn Ser Asn Thr Asn Tyr Ala Glu Lys Leu
 50                      55                  60

Gln Gly Arg Val Thr Met Thr Thr Asp Thr Ser Thr Ser Thr Ala Tyr
 65                  70                  75                  80

Met Glu Leu Arg Ser Leu Thr Ser Asp Asp Thr Ala Val Tyr Tyr Cys
                85                  90                  95

Ala Arg Gly Pro Thr Tyr Ser Phe Asp Ser Ser Gly Tyr Phe Phe Asp
                100                 105                 110

Tyr Trp Gly Gln Gly Thr Leu Val Thr Val Ser Arg
            115                 120

<210> SEQ ID NO 71
<211> LENGTH: 109
<212> TYPE: PRT
<213> ORGANISM: Artificial Sequence
<220> FEATURE:
<223> OTHER INFORMATION: chemically synthesized

<400> SEQUENCE: 71

Ser Ser Glu Leu Thr Gln Asp Pro Ala Met Ser Val Ala Leu Gly Gln
1               5                   10                  15

Thr Val Lys Ile Thr Cys Gln Gly Asp Ser Leu Thr Asn Tyr Tyr Pro
            20                  25                  30

Ser Trp Tyr Gln Gln Lys Pro Gly Gln Ala Pro Val Leu Val Met Tyr
            35                  40                  45

Gly Lys Asp Ser Arg Pro Ser Gly Ile Ser Asp Arg Phe Ser Gly Ser
 50                      55                  60

Ser Ser Gly Ile Ser Ala Ser Leu Thr Ile Thr Gly Ala Gln Ala Glu
 65                  70                  75                  80

Asp Glu Ala Asp Tyr Tyr Cys Asn Ser Arg Asp Gly Ser Ala His Arg
                85                  90                  95

Leu Val Phe Gly Gly Gly Thr Lys Leu Thr Val Leu Gly
                100                 105

<210> SEQ ID NO 72
<211> LENGTH: 121
<212> TYPE: PRT
<213> ORGANISM: Artificial Sequence
<220> FEATURE:
<223> OTHER INFORMATION: chemically synthesized

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
 50                      55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
```

```
                85                  90                  95
Ala Arg Asp Arg Tyr Tyr Gly Ser Gly Phe Gly Met Asp Val Trp Gly
                100                 105                 110
Gln Gly Thr Met Val Thr Val Ser Arg
        115                 120

<210> SEQ ID NO 73
<211> LENGTH: 109
<212> TYPE: PRT
<213> ORGANISM: Artificial Sequence
<220> FEATURE:
<223> OTHER INFORMATION: chemically synthesized

<400> SEQUENCE: 73

Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
                20                  25                  30
Ser Trp Tyr Gln Gln Lys Pro Gly Gln Ala Pro Val Leu Val Ile Tyr
            35                  40                  45
Gly Lys Asn Asn Arg Pro Ser Gly Ile Pro Asp Arg Phe Ser Gly Ser
50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Asn His
                85                  90                  95
Trp Val Phe Gly Gly Gly Thr Lys Leu Thr Val Leu Gly
                100                 105

<210> SEQ ID NO 74
<211> LENGTH: 120
<212> TYPE: PRT
<213> ORGANISM: Artificial Sequence
<220> FEATURE:
<223> OTHER INFORMATION: chemically synthesized

<400> SEQUENCE: 74

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Gly Ile Ser Trp Val Arg Gln Ala Pro Gly Gln Gly Leu Glu Trp Met
            35                  40                  45
Gly Trp Ile Ser Ala Tyr Asn Gly Asn Thr Asn Tyr Ala Gln Lys Leu
50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Thr Tyr Ser Ser Gly Trp Tyr Phe Asp Tyr Trp Gly Gln
                100                 105                 110
Gly Thr Leu Val Thr Val Ser Arg
        115                 120

<210> SEQ ID NO 75
<211> LENGTH: 110
<212> TYPE: PRT
<213> ORGANISM: Artificial Sequence
<220> FEATURE:
```

<223> OTHER INFORMATION: chemically synthesized

<400> SEQUENCE: 75

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Tyr Val Phe Gly Thr Gly Thr Lys Val Thr Val Leu Gly
            100                 105                 110

<210> SEQ ID NO 76
<211> LENGTH: 120
<212> TYPE: PRT
<213> ORGANISM: Artificial Sequence
<220> FEATURE:
<223> OTHER INFORMATION: chemically synthesized

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asn Ile Ser Gly Ser Tyr Tyr Phe Asp Tyr Trp Gly Gln
            100                 105                 110

Gly Thr Leu Val Thr Val Ser Arg
        115                 120

<210> SEQ ID NO 77
<211> LENGTH: 110
<212> TYPE: PRT
<213> ORGANISM: Artificial Sequence
<220> FEATURE:
<223> OTHER INFORMATION: chemically synthesized

<400> SEQUENCE: 77

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Val Leu Val Ile Ser
        35                  40                  45

Gly Lys Asn Asn Arg Pro Ser Gly Ile Pro Asp Arg Phe Ser Gly Ser

```
                 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Tyr Pro
                 85                  90                  95

Ser Trp Val Phe Gly Gly Gly Thr Lys Leu Thr Val Leu Gly
                100                 105                 110

<210> SEQ ID NO 78
<211> LENGTH: 119
<212> TYPE: PRT
<213> ORGANISM: Artificial Sequence
<220> FEATURE:
<223> OTHER INFORMATION: chemically synthesized

<400> SEQUENCE: 78

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
             35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg His Trp Gly Asn Tyr Ala Phe Asp Ile Trp Gly Gln Gly
                100                 105                 110

Thr Thr Val Thr Val Ser Arg
            115

<210> SEQ ID NO 79
<211> LENGTH: 111
<212> TYPE: PRT
<213> ORGANISM: Artificial Sequence
<220> FEATURE:
<223> OTHER INFORMATION: chemically synthesized

<400> SEQUENCE: 79

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                85                  90                  95

Ser Gly Gln Val Phe Gly Gly Gly Thr Gln Leu Thr Val Leu Gly
                100                 105                 110

<210> SEQ ID NO 80
<211> LENGTH: 120
```

```
<212> TYPE: PRT
<213> ORGANISM: Artificial Sequence
<220> FEATURE:
<223> OTHER INFORMATION: chemically synthesized

<400> SEQUENCE: 80
```

| | | | | | | | | | | | | | | | |
|---|---|---|---|---|---|---|---|---|---|---|---|---|---|---|---|
| Glu | Val | Gln | Leu | Val | Glu | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | | 35 | | | | | 40 | | | | | 45 | | |
| Gly | Trp | Ile | Ser | Ala | Tyr | Asn | Gly | Asn | Thr | Asn | Tyr | Ala | Gln | Lys | Leu |
| | 50 | | | | | 55 | | | | | 60 | | | | |
| Gln | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Glu | Lys | Tyr | Ser | Ser | Gly | Trp | Tyr | Phe | Asp | Tyr | Trp | Gly | Gln |
| | | | 100 | | | | | 105 | | | | | 110 | | |
| Gly | Thr | Leu | Val | Thr | Val | Ser | Arg | | | | | | | | |
| | | | 115 | | | | 120 | | | | | | | | |

```
<210> SEQ ID NO 81
<211> LENGTH: 110
<212> TYPE: PRT
<213> ORGANISM: Artificial Sequence
<220> FEATURE:
<223> OTHER INFORMATION: chemically synthesized

<400> SEQUENCE: 81
```

| | | | | | | | | | | | | | | | |
|---|---|---|---|---|---|---|---|---|---|---|---|---|---|---|---|
| Ser | Ser | Glu | Leu | Thr | Gln | Asp | Pro | Ala | Val | Ser | Val | Ala | Leu | Gly | Gln |
| 1 | | | | 5 | | | | | 10 | | | | | 15 | |
| Thr | Val | Arg | Ile | Thr | Cys | Gln | Gly | Asp | Ser | Leu | Arg | Ser | Tyr | Tyr | Ala |
| | | | 20 | | | | | 25 | | | | | 30 | | |
| Ser | Trp | Tyr | Gln | Gln | Lys | Pro | Gly | Gln | Ala | Pro | Val | Leu | Val | Ile | Tyr |
| | | | 35 | | | | | 40 | | | | | 45 | | |
| Gly | Lys | Asn | Asn | Arg | Pro | Ser | Gly | Ile | Pro | Asp | Arg | Phe | Ser | Gly | Ser |
| | 50 | | | | | 55 | | | | | 60 | | | | |
| Ser | Ser | Gly | Asn | Thr | Ala | Ser | Leu | Thr | Ile | Thr | Gly | Ala | Gln | Ala | Glu |
| 65 | | | | | 70 | | | | | 75 | | | | | 80 |
| Asp | Glu | Ala | Asp | Tyr | Tyr | Cys | Asn | Ser | Arg | Asp | Ser | Ser | Gly | Asn | His |
| | | | | 85 | | | | | 90 | | | | | 95 | |
| His | Tyr | Val | Phe | Gly | Thr | Gly | Thr | Lys | Val | Thr | Val | Leu | Gly | | |
| | | | 100 | | | | | 105 | | | | | 110 | | |

```
<210> SEQ ID NO 82
<211> LENGTH: 5
<212> TYPE: PRT
<213> ORGANISM: Artificial Sequence
<220> FEATURE:
<223> OTHER INFORMATION: chemically synthesized

<400> SEQUENCE: 82

Ser Tyr Gly Ile Ser
1               5

<210> SEQ ID NO 83
<211> LENGTH: 17
<212> TYPE: PRT
```

```
<213> ORGANISM: Artificial Sequence
<220> FEATURE:
<223> OTHER INFORMATION: chemically synthesized

<400> SEQUENCE: 83

Trp Ile Ser Ala Tyr Asn Gly Asn Thr Asn Tyr Ala Gln Lys Leu Gln
1               5                   10                  15

Gly

<210> SEQ ID NO 84
<211> LENGTH: 15
<212> TYPE: PRT
<213> ORGANISM: Artificial Sequence
<220> FEATURE:
<223> OTHER INFORMATION: chemically synthesized

<400> SEQUENCE: 84

Ala Ala Ser Leu Lys Tyr Tyr Tyr Asp Ser Ser Gly Tyr Tyr Tyr
1               5                   10                  15

<210> SEQ ID NO 85
<211> LENGTH: 11
<212> TYPE: PRT
<213> ORGANISM: Artificial Sequence
<220> FEATURE:
<223> OTHER INFORMATION: chemically synthesized

<400> SEQUENCE: 85

Gln Gly Asp Ser Leu Arg Ser Tyr Tyr Ala Ser
1               5                   10

<210> SEQ ID NO 86
<211> LENGTH: 7
<212> TYPE: PRT
<213> ORGANISM: Artificial Sequence
<220> FEATURE:
<223> OTHER INFORMATION: chemically synthesized

<400> SEQUENCE: 86

Gly Lys Asn Asn Arg Pro Ser
1               5

<210> SEQ ID NO 87
<211> LENGTH: 10
<212> TYPE: PRT
<213> ORGANISM: Artificial Sequence
<220> FEATURE:
<223> OTHER INFORMATION: chemically synthesized

<400> SEQUENCE: 87

Asn Ser Arg Asp Ser Ser Gly Tyr Pro Ser
1               5                   10

<210> SEQ ID NO 88
<211> LENGTH: 5
<212> TYPE: PRT
<213> ORGANISM: Artificial Sequence
<220> FEATURE:
<223> OTHER INFORMATION: chemically synthesized

<400> SEQUENCE: 88

Ser Tyr Tyr Trp Ser
1               5

<210> SEQ ID NO 89
<211> LENGTH: 16
```

<212> TYPE: PRT
<213> ORGANISM: Artificial Sequence
<220> FEATURE:
<223> OTHER INFORMATION: chemically synthesized

<400> SEQUENCE: 89

Arg Ile Tyr Thr Ser Gly Ser Thr Asn Tyr Asn Pro Ser Leu Lys Ser
1               5                   10                  15

<210> SEQ ID NO 90
<211> LENGTH: 17
<212> TYPE: PRT
<213> ORGANISM: Artificial Sequence
<220> FEATURE:
<223> OTHER INFORMATION: chemically synthesized

<400> SEQUENCE: 90

Glu Arg Ala Tyr Cys Ser Ser Thr Ser Cys Tyr Arg Asn Ala Phe Asp
1               5                   10                  15

Ile

<210> SEQ ID NO 91
<211> LENGTH: 14
<212> TYPE: PRT
<213> ORGANISM: Artificial Sequence
<220> FEATURE:
<223> OTHER INFORMATION: chemically synthesized

<400> SEQUENCE: 91

Ala Gly Ser Ser Ser Asn Ile Gly Ala Gly Tyr Asp Val His
1               5                   10

<210> SEQ ID NO 92
<211> LENGTH: 7
<212> TYPE: PRT
<213> ORGANISM: Artificial Sequence
<220> FEATURE:
<223> OTHER INFORMATION: chemically synthesized

<400> SEQUENCE: 92

Gly Asn Ser Asn Arg Pro Ser
1               5

<210> SEQ ID NO 93
<211> LENGTH: 10
<212> TYPE: PRT
<213> ORGANISM: Artificial Sequence
<220> FEATURE:
<223> OTHER INFORMATION: chemically synthesized

<400> SEQUENCE: 93

Gln Ser Tyr Asp Ser Ser Leu Ser Gly Ser
1               5                   10

<210> SEQ ID NO 94
<211> LENGTH: 5
<212> TYPE: PRT
<213> ORGANISM: Artificial Sequence
<220> FEATURE:
<223> OTHER INFORMATION: chemically synthesized

<400> SEQUENCE: 94

Ser Tyr Gly Met His
1               5

<210> SEQ ID NO 95

```
<211> LENGTH: 17
<212> TYPE: PRT
<213> ORGANISM: Artificial Sequence
<220> FEATURE:
<223> OTHER INFORMATION: chemically synthesized

<400> SEQUENCE: 95

Val Ile Ser Phe Asp Gly Ser Asn Lys Tyr Tyr Ala Asp Ser Val Lys
1               5                   10                  15
Gly

<210> SEQ ID NO 96
<211> LENGTH: 13
<212> TYPE: PRT
<213> ORGANISM: Artificial Sequence
<220> FEATURE:
<223> OTHER INFORMATION: chemically synthesized

<400> SEQUENCE: 96

Ala Tyr Thr Asn Thr Trp Trp Pro Asp Ala Phe Asp Ile
1               5                   10

<210> SEQ ID NO 97
<211> LENGTH: 11
<212> TYPE: PRT
<213> ORGANISM: Artificial Sequence
<220> FEATURE:
<223> OTHER INFORMATION: chemically synthesized

<400> SEQUENCE: 97

Gln Ala Ser Gln Asp Ile Ser Asn Tyr Leu Asn
1               5                   10

<210> SEQ ID NO 98
<211> LENGTH: 7
<212> TYPE: PRT
<213> ORGANISM: Artificial Sequence
<220> FEATURE:
<223> OTHER INFORMATION: chemically synthesized

<400> SEQUENCE: 98

Asp Ala Ser Asn Leu Glu Thr
1               5

<210> SEQ ID NO 99
<211> LENGTH: 7
<212> TYPE: PRT
<213> ORGANISM: Artificial Sequence
<220> FEATURE:
<223> OTHER INFORMATION: chemically synthesized

<400> SEQUENCE: 99

Gln Gln Tyr Asp Asn Leu Pro
1               5

<210> SEQ ID NO 100
<211> LENGTH: 16
<212> TYPE: PRT
<213> ORGANISM: Artificial Sequence
<220> FEATURE:
<223> OTHER INFORMATION: chemically synthesized

<400> SEQUENCE: 100

Tyr Ile Tyr Tyr Ser Gly Ser Thr Asn Tyr Asn Pro Ser Leu Lys Ser
1               5                   10                  15
```

```
<210> SEQ ID NO 101
<211> LENGTH: 10
<212> TYPE: PRT
<213> ORGANISM: Artificial Sequence
<220> FEATURE:
<223> OTHER INFORMATION: chemically synthesized

<400> SEQUENCE: 101

Asp Leu Tyr Trp Asn Asp Ala Phe Asp Ile
1               5                   10

<210> SEQ ID NO 102
<211> LENGTH: 13
<212> TYPE: PRT
<213> ORGANISM: Artificial Sequence
<220> FEATURE:
<223> OTHER INFORMATION: chemically synthesized

<400> SEQUENCE: 102

Ser Gly Ser Ser Ser Asn Ile Gly Ser Asn Thr Val Asn
1               5                   10

<210> SEQ ID NO 103
<211> LENGTH: 7
<212> TYPE: PRT
<213> ORGANISM: Artificial Sequence
<220> FEATURE:
<223> OTHER INFORMATION: chemically synthesized

<400> SEQUENCE: 103

Ser Asn Asn Gln Arg Pro Ser
1               5

<210> SEQ ID NO 104
<211> LENGTH: 9
<212> TYPE: PRT
<213> ORGANISM: Artificial Sequence
<220> FEATURE:
<223> OTHER INFORMATION: chemically synthesized

<400> SEQUENCE: 104

Ala Ala Trp Asp Asp Ser Leu Asn Gly
1               5

<210> SEQ ID NO 105
<211> LENGTH: 7
<212> TYPE: PRT
<213> ORGANISM: Artificial Sequence
<220> FEATURE:
<223> OTHER INFORMATION: chemically synthesized

<400> SEQUENCE: 105

Ser Asn Ser Ala Ala Trp Asn
1               5

<210> SEQ ID NO 106
<211> LENGTH: 18
<212> TYPE: PRT
<213> ORGANISM: Artificial Sequence
<220> FEATURE:
<223> OTHER INFORMATION: chemically synthesized

<400> SEQUENCE: 106

Arg Thr Tyr Tyr Arg Ser Lys Trp Tyr Asn Asp Tyr Ala Val Ser Val
1               5                   10                  15
Lys Ser
```

```
<210> SEQ ID NO 107
<211> LENGTH: 14
<212> TYPE: PRT
<213> ORGANISM: Artificial Sequence
<220> FEATURE:
<223> OTHER INFORMATION: chemically synthesized

<400> SEQUENCE: 107

Glu Ser Trp Leu Trp Gly Ile Gly Gly Asp Ala Phe Asp Ile
1               5                   10

<210> SEQ ID NO 108
<211> LENGTH: 13
<212> TYPE: PRT
<213> ORGANISM: Artificial Sequence
<220> FEATURE:
<223> OTHER INFORMATION: chemically synthesized

<400> SEQUENCE: 108

Ser Gly Ser Ser Ser Asn Ile Gly Gln Asn Ser Val Thr
1               5                   10

<210> SEQ ID NO 109
<211> LENGTH: 7
<212> TYPE: PRT
<213> ORGANISM: Artificial Sequence
<220> FEATURE:
<223> OTHER INFORMATION: chemically synthesized

<400> SEQUENCE: 109

Tyr Asp Asp Leu Leu His Ser
1               5

<210> SEQ ID NO 110
<211> LENGTH: 9
<212> TYPE: PRT
<213> ORGANISM: Artificial Sequence
<220> FEATURE:
<223> OTHER INFORMATION: chemically synthesized

<400> SEQUENCE: 110

Ala Ser Trp Asp Asp Ser Leu Lys Gly
1               5

<210> SEQ ID NO 111
<211> LENGTH: 5
<212> TYPE: PRT
<213> ORGANISM: Artificial Sequence
<220> FEATURE:
<223> OTHER INFORMATION: chemically synthesized

<400> SEQUENCE: 111

Ser Asn Tyr Met Ser
1               5

<210> SEQ ID NO 112
<211> LENGTH: 16
<212> TYPE: PRT
<213> ORGANISM: Artificial Sequence
<220> FEATURE:
<223> OTHER INFORMATION: chemically synthesized

<400> SEQUENCE: 112

Val Ile Tyr Ser Gly Gly Ser Thr Tyr Tyr Ala Asp Ser Val Lys Gly
1               5                   10                  15
```

```
<210> SEQ ID NO 113
<211> LENGTH: 4
<212> TYPE: PRT
<213> ORGANISM: Artificial Sequence
<220> FEATURE:
<223> OTHER INFORMATION: chemically synthesized

<400> SEQUENCE: 113

Glu Phe Asp Tyr
1

<210> SEQ ID NO 114
<211> LENGTH: 11
<212> TYPE: PRT
<213> ORGANISM: Artificial Sequence
<220> FEATURE:
<223> OTHER INFORMATION: chemically synthesized

<400> SEQUENCE: 114

Gln Ala Ser Gln Asp Ile Ser Asn Tyr Leu Asn
1               5                   10

<210> SEQ ID NO 115
<211> LENGTH: 7
<212> TYPE: PRT
<213> ORGANISM: Artificial Sequence
<220> FEATURE:
<223> OTHER INFORMATION: chemically synthesized

<400> SEQUENCE: 115

Asp Ala Ser Asn Leu Glu Thr
1               5

<210> SEQ ID NO 116
<211> LENGTH: 5
<212> TYPE: PRT
<213> ORGANISM: Artificial Sequence
<220> FEATURE:
<223> OTHER INFORMATION: chemically synthesized

<400> SEQUENCE: 116

Gln Gln Tyr Asp Asn
1               5

<210> SEQ ID NO 117
<211> LENGTH: 12
<212> TYPE: PRT
<213> ORGANISM: Artificial Sequence
<220> FEATURE:
<223> OTHER INFORMATION: chemically synthesized

<400> SEQUENCE: 117

Asp Arg Tyr Tyr Gly Ser Gly Phe Gly Met Asp Val
1               5                   10

<210> SEQ ID NO 118
<211> LENGTH: 11
<212> TYPE: PRT
<213> ORGANISM: Artificial Sequence
<220> FEATURE:
<223> OTHER INFORMATION: chemically synthesized

<400> SEQUENCE: 118

Gln Gly Asp Ser Leu Thr Asn Tyr Tyr Pro Ser
1               5                   10

<210> SEQ ID NO 119
```

<211> LENGTH: 7
<212> TYPE: PRT
<213> ORGANISM: Artificial Sequence
<220> FEATURE:
<223> OTHER INFORMATION: chemically synthesized

<400> SEQUENCE: 119

Gly Lys Asp Ser Arg Pro Ser
1               5

<210> SEQ ID NO 120
<211> LENGTH: 9
<212> TYPE: PRT
<213> ORGANISM: Artificial Sequence
<220> FEATURE:
<223> OTHER INFORMATION: chemically synthesized

<400> SEQUENCE: 120

Asn Ser Arg Asp Gly Ser Ala His Arg
1               5

<210> SEQ ID NO 121
<211> LENGTH: 5
<212> TYPE: PRT
<213> ORGANISM: Artificial Sequence
<220> FEATURE:
<223> OTHER INFORMATION: chemically synthesized

<400> SEQUENCE: 121

Asn Tyr Gly Leu Thr
1               5

<210> SEQ ID NO 122
<211> LENGTH: 17
<212> TYPE: PRT
<213> ORGANISM: Artificial Sequence
<220> FEATURE:
<223> OTHER INFORMATION: chemically synthesized

<400> SEQUENCE: 122

Trp Ile Ser Thr Tyr Asn Ser Asn Thr Asn Tyr Ala Glu Lys Leu Gln
1               5                   10                  15

Gly

<210> SEQ ID NO 123
<211> LENGTH: 15
<212> TYPE: PRT
<213> ORGANISM: Artificial Sequence
<220> FEATURE:
<223> OTHER INFORMATION: chemically synthesized

<400> SEQUENCE: 123

Gly Pro Thr Tyr Ser Phe Asp Ser Ser Gly Tyr Phe Phe Asp Tyr
1               5                   10                  15

<210> SEQ ID NO 124
<211> LENGTH: 9
<212> TYPE: PRT
<213> ORGANISM: Artificial Sequence
<220> FEATURE:
<223> OTHER INFORMATION: chemically synthesized

<400> SEQUENCE: 124

Asn Ser Arg Asp Ser Ser Gly Asn His
1               5

```
<210> SEQ ID NO 125
<211> LENGTH: 11
<212> TYPE: PRT
<213> ORGANISM: Artificial Sequence
<220> FEATURE:
<223> OTHER INFORMATION: chemically synthesized

<400> SEQUENCE: 125

Asp Thr Tyr Ser Ser Gly Trp Tyr Phe Asp Tyr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: chemically synthesized

<400> SEQUENCE: 126

Gln Gly Asp Ser Leu Arg Asn Tyr Tyr Ala Ser
1               5                   10

<210> SEQ ID NO 127
<211> LENGTH: 10
<212> TYPE: PRT
<213> ORGANISM: Artificial Sequence
<220> FEATURE:
<223> OTHER INFORMATION: chemically synthesized

<400> SEQUENCE: 127

Asn Ser Arg Asp Ser Ser Gly Asn His Leu
1               5                   10

<210> SEQ ID NO 128
<211> LENGTH: 11
<212> TYPE: PRT
<213> ORGANISM: Artificial Sequence
<220> FEATURE:
<223> OTHER INFORMATION: chemically synthesized

<400> SEQUENCE: 128

Leu Asn Ile Ser Gly Ser Tyr Tyr Phe Asp Tyr
1               5                   10

<210> SEQ ID NO 129
<211> LENGTH: 11
<212> TYPE: PRT
<213> ORGANISM: Artificial Sequence
<220> FEATURE:
<223> OTHER INFORMATION: chemically synthesized

<400> SEQUENCE: 129

Gln Gly Asp Ser Leu Arg Ser Tyr Tyr Ala Thr
1               5                   10

<210> SEQ ID NO 130
<211> LENGTH: 7
<212> TYPE: PRT
<213> ORGANISM: Artificial Sequence
<220> FEATURE:
<223> OTHER INFORMATION: chemically synthesized

<400> SEQUENCE: 130

Ser Ser Ser Tyr Tyr Trp Gly
1               5

<210> SEQ ID NO 131
```

```
<211> LENGTH: 16
<212> TYPE: PRT
<213> ORGANISM: Artificial Sequence
<220> FEATURE:
<223> OTHER INFORMATION: chemically synthesized

<400> SEQUENCE: 131

Ser Ile Tyr Tyr Ser Gly Ser Thr Tyr Tyr Asn Pro Ser Leu Lys Ser
1               5                   10                  15

<210> SEQ ID NO 132
<211> LENGTH: 9
<212> TYPE: PRT
<213> ORGANISM: Artificial Sequence
<220> FEATURE:
<223> OTHER INFORMATION: chemically synthesized

<400> SEQUENCE: 132

His Trp Gly Asn Tyr Ala Phe Asp Ile
1               5

<210> SEQ ID NO 133
<211> LENGTH: 13
<212> TYPE: PRT
<213> ORGANISM: Artificial Sequence
<220> FEATURE:
<223> OTHER INFORMATION: chemically synthesized

<400> SEQUENCE: 133

Ser Gly Ser Ser Ser Asn Ile Gly Ser Asn Tyr Val Tyr
1               5                   10

<210> SEQ ID NO 134
<211> LENGTH: 9
<212> TYPE: PRT
<213> ORGANISM: Artificial Sequence
<220> FEATURE:
<223> OTHER INFORMATION: chemically synthesized

<400> SEQUENCE: 134

Ala Ala Trp Asp Asp Ser Leu Ser Gly
1               5

<210> SEQ ID NO 135
<211> LENGTH: 11
<212> TYPE: PRT
<213> ORGANISM: Artificial Sequence
<220> FEATURE:
<223> OTHER INFORMATION: chemically synthesized

<400> SEQUENCE: 135

Glu Lys Tyr Ser Ser Gly Trp Tyr Phe Asp Tyr
1               5                   10

<210> SEQ ID NO 136
<211> LENGTH: 10
<212> TYPE: PRT
<213> ORGANISM: Artificial Sequence
<220> FEATURE:
<223> OTHER INFORMATION: chemically synthesized

<400> SEQUENCE: 136

Asn Ser Arg Asp Ser Ser Gly Asn His His
1               5                   10

<210> SEQ ID NO 137
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 137

Pro Arg Phe Lys Ile Ile Gly Gly
1               5

<210> SEQ ID NO 138
<211> LENGTH: 8
<212> TYPE: PRT
<213> ORGANISM: Artificial Sequence
<220> FEATURE:
<223> OTHER INFORMATION: chemically synthesized

<400> SEQUENCE: 138

Pro Arg Phe Arg Ile Ile Gly Gly
1               5

<210> SEQ ID NO 139
<211> LENGTH: 9
<212> TYPE: PRT
<213> ORGANISM: Artificial Sequence
<220> FEATURE:
<223> OTHER INFORMATION: chemically synthesized

<400> SEQUENCE: 139

Ser Ser Arg His Arg Arg Ala Leu Asp
1               5

<210> SEQ ID NO 140
<211> LENGTH: 14
<212> TYPE: PRT
<213> ORGANISM: Artificial Sequence
<220> FEATURE:
<223> OTHER INFORMATION: chemically synthesized

<400> SEQUENCE: 140

Arg Lys Ser Ser Ile Ile Ile Arg Met Arg Asp Val Val Leu
1               5                   10

<210> SEQ ID NO 141
<211> LENGTH: 15
<212> TYPE: PRT
<213> ORGANISM: Artificial Sequence
<220> FEATURE:
<223> OTHER INFORMATION: chemically synthesized

<400> SEQUENCE: 141

Ser Ser Ser Phe Asp Lys Gly Lys Tyr Lys Lys Gly Asp Asp Ala
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: chemically synthesized

<400> SEQUENCE: 142

Ser Ser Ser Phe Asp Lys Gly Lys Tyr Lys Arg Gly Asp Asp Ala
1               5                   10                  15

<210> SEQ ID NO 143
<211> LENGTH: 4
<212> TYPE: PRT
```

```
<213> ORGANISM: Artificial Sequence
<220> FEATURE:
<223> OTHER INFORMATION: chemically synthesized

<400> SEQUENCE: 143

Ile Glu Gly Arg
1

<210> SEQ ID NO 144
<211> LENGTH: 4
<212> TYPE: PRT
<213> ORGANISM: Artificial Sequence
<220> FEATURE:
<223> OTHER INFORMATION: chemically synthesized

<400> SEQUENCE: 144

Ile Asp Gly Arg
1

<210> SEQ ID NO 145
<211> LENGTH: 7
<212> TYPE: PRT
<213> ORGANISM: Artificial Sequence
<220> FEATURE:
<223> OTHER INFORMATION: chemically synthesized

<400> SEQUENCE: 145

Gly Gly Ser Ile Asp Gly Arg
1               5

<210> SEQ ID NO 146
<211> LENGTH: 6
<212> TYPE: PRT
<213> ORGANISM: Artificial Sequence
<220> FEATURE:
<223> OTHER INFORMATION: chemically synthesized

<400> SEQUENCE: 146

Pro Leu Gly Leu Trp Ala
1               5

<210> SEQ ID NO 147
<211> LENGTH: 8
<212> TYPE: PRT
<213> ORGANISM: Artificial Sequence
<220> FEATURE:
<223> OTHER INFORMATION: chemically synthesized

<400> SEQUENCE: 147

Gly Pro Gln Gly Ile Ala Gly Gln
1               5

<210> SEQ ID NO 148
<211> LENGTH: 8
<212> TYPE: PRT
<213> ORGANISM: Artificial Sequence
<220> FEATURE:
<223> OTHER INFORMATION: chemically synthesized

<400> SEQUENCE: 148

Gly Pro Gln Gly Leu Leu Gly Ala
1               5

<210> SEQ ID NO 149
<211> LENGTH: 5
<212> TYPE: PRT
<213> ORGANISM: Artificial Sequence
```

```
<220> FEATURE:
<223> OTHER INFORMATION: chemically synthesized

<400> SEQUENCE: 149

Gly Ile Ala Gly Gln
1               5

<210> SEQ ID NO 150
<211> LENGTH: 8
<212> TYPE: PRT
<213> ORGANISM: Artificial Sequence
<220> FEATURE:
<223> OTHER INFORMATION: chemically synthesized

<400> SEQUENCE: 150

Gly Pro Leu Gly Ile Ala Gly Ile
1               5

<210> SEQ ID NO 151
<211> LENGTH: 8
<212> TYPE: PRT
<213> ORGANISM: Artificial Sequence
<220> FEATURE:
<223> OTHER INFORMATION: chemically synthesized

<400> SEQUENCE: 151

Gly Pro Glu Gly Leu Arg Val Gly
1               5

<210> SEQ ID NO 152
<211> LENGTH: 8
<212> TYPE: PRT
<213> ORGANISM: Artificial Sequence
<220> FEATURE:
<223> OTHER INFORMATION: chemically synthesized

<400> SEQUENCE: 152

Tyr Gly Ala Gly Leu Gly Val Val
1               5

<210> SEQ ID NO 153
<211> LENGTH: 8
<212> TYPE: PRT
<213> ORGANISM: Artificial Sequence
<220> FEATURE:
<223> OTHER INFORMATION: chemically synthesized

<400> SEQUENCE: 153

Ala Gly Leu Gly Val Val Glu Arg
1               5

<210> SEQ ID NO 154
<211> LENGTH: 8
<212> TYPE: PRT
<213> ORGANISM: Artificial Sequence
<220> FEATURE:
<223> OTHER INFORMATION: chemically synthesized

<400> SEQUENCE: 154

Ala Gly Leu Gly Ile Ser Ser Thr
1               5

<210> SEQ ID NO 155
<211> LENGTH: 8
<212> TYPE: PRT
<213> ORGANISM: Artificial Sequence
<220> FEATURE:
```

```
<223> OTHER INFORMATION: chemically synthesized

<400> SEQUENCE: 155

Glu Pro Gln Ala Leu Ala Met Ser
1               5

<210> SEQ ID NO 156
<211> LENGTH: 8
<212> TYPE: PRT
<213> ORGANISM: Artificial Sequence
<220> FEATURE:
<223> OTHER INFORMATION: chemically synthesized

<400> SEQUENCE: 156

Gln Ala Leu Ala Met Ser Ala Ile
1               5

<210> SEQ ID NO 157
<211> LENGTH: 8
<212> TYPE: PRT
<213> ORGANISM: Artificial Sequence
<220> FEATURE:
<223> OTHER INFORMATION: chemically synthesized

<400> SEQUENCE: 157

Ala Ala Tyr His Leu Val Ser Gln
1               5

<210> SEQ ID NO 158
<211> LENGTH: 8
<212> TYPE: PRT
<213> ORGANISM: Artificial Sequence
<220> FEATURE:
<223> OTHER INFORMATION: chemically synthesized

<400> SEQUENCE: 158

Met Asp Ala Phe Leu Glu Ser Ser
1               5

<210> SEQ ID NO 159
<211> LENGTH: 8
<212> TYPE: PRT
<213> ORGANISM: Artificial Sequence
<220> FEATURE:
<223> OTHER INFORMATION: chemically synthesized

<400> SEQUENCE: 159

Glu Ser Leu Pro Val Val Ala Val
1               5

<210> SEQ ID NO 160
<211> LENGTH: 8
<212> TYPE: PRT
<213> ORGANISM: Artificial Sequence
<220> FEATURE:
<223> OTHER INFORMATION: chemically synthesized

<400> SEQUENCE: 160

Ser Ala Pro Ala Val Glu Ser Glu
1               5

<210> SEQ ID NO 161
<211> LENGTH: 8
<212> TYPE: PRT
<213> ORGANISM: Artificial Sequence
<220> FEATURE:
<223> OTHER INFORMATION: chemically synthesized
```

<400> SEQUENCE: 161

Asp Val Ala Gln Phe Val Leu Thr
1               5

<210> SEQ ID NO 162
<211> LENGTH: 8
<212> TYPE: PRT
<213> ORGANISM: Artificial Sequence
<220> FEATURE:
<223> OTHER INFORMATION: chemically synthesized

<400> SEQUENCE: 162

Val Ala Gln Phe Val Leu Thr Glu
1               5

<210> SEQ ID NO 163
<211> LENGTH: 8
<212> TYPE: PRT
<213> ORGANISM: Artificial Sequence
<220> FEATURE:
<223> OTHER INFORMATION: chemically synthesized

<400> SEQUENCE: 163

Ala Gln Phe Val Leu Thr Glu Gly
1               5

<210> SEQ ID NO 164
<211> LENGTH: 8
<212> TYPE: PRT
<213> ORGANISM: Artificial Sequence
<220> FEATURE:
<223> OTHER INFORMATION: chemically synthesized

<400> SEQUENCE: 164

Pro Val Gln Pro Ile Gly Pro Gln
1               5

<210> SEQ ID NO 165
<211> LENGTH: 5
<212> TYPE: PRT
<213> ORGANISM: Artificial Sequence
<220> FEATURE:
<223> OTHER INFORMATION: chemically synthesized

<400> SEQUENCE: 165

Gly Ser Gly Gly Ser
1               5

<210> SEQ ID NO 166
<211> LENGTH: 4
<212> TYPE: PRT
<213> ORGANISM: Artificial Sequence
<220> FEATURE:
<223> OTHER INFORMATION: chemically synthesized

<400> SEQUENCE: 166

Gly Gly Gly Ser
1

<210> SEQ ID NO 167
<211> LENGTH: 4
<212> TYPE: PRT
<213> ORGANISM: Artificial Sequence
<220> FEATURE:
<223> OTHER INFORMATION: chemically synthesized

```
<400> SEQUENCE: 167

Gly Gly Ser Gly
1

<210> SEQ ID NO 168
<211> LENGTH: 5
<212> TYPE: PRT
<213> ORGANISM: Artificial Sequence
<220> FEATURE:
<223> OTHER INFORMATION: chemically synthesized

<400> SEQUENCE: 168

Gly Gly Ser Gly Gly
1               5

<210> SEQ ID NO 169
<211> LENGTH: 5
<212> TYPE: PRT
<213> ORGANISM: Artificial Sequence
<220> FEATURE:
<223> OTHER INFORMATION: chemically synthesized

<400> SEQUENCE: 169

Gly Ser Gly Ser Gly
1               5

<210> SEQ ID NO 170
<211> LENGTH: 5
<212> TYPE: PRT
<213> ORGANISM: Artificial Sequence
<220> FEATURE:
<223> OTHER INFORMATION: chemically synthesized

<400> SEQUENCE: 170

Gly Ser Gly Gly Gly
1               5

<210> SEQ ID NO 171
<211> LENGTH: 5
<212> TYPE: PRT
<213> ORGANISM: Artificial Sequence
<220> FEATURE:
<223> OTHER INFORMATION: chemically synthesized

<400> SEQUENCE: 171

Gly Gly Gly Ser Gly
1               5

<210> SEQ ID NO 172
<211> LENGTH: 5
<212> TYPE: PRT
<213> ORGANISM: Artificial Sequence
<220> FEATURE:
<223> OTHER INFORMATION: chemically synthesized

<400> SEQUENCE: 172

Gly Ser Ser Ser Gly
1               5

<210> SEQ ID NO 173
<211> LENGTH: 13
<212> TYPE: PRT
<213> ORGANISM: Artificial Sequence
<220> FEATURE:
<223> OTHER INFORMATION: chemically synthesized

<400> SEQUENCE: 173
```

Gly Ser Ser Gly Gly Ser Gly Gly Ser Gly
1               5                   10

<210> SEQ ID NO 174
<211> LENGTH: 11
<212> TYPE: PRT
<213> ORGANISM: Artificial Sequence
<220> FEATURE:
<223> OTHER INFORMATION: chemically synthesized

<400> SEQUENCE: 174

Gly Ser Ser Gly Gly Ser Gly Gly Ser Gly Gly
1               5                   10

<210> SEQ ID NO 175
<211> LENGTH: 12
<212> TYPE: PRT
<213> ORGANISM: Artificial Sequence
<220> FEATURE:
<223> OTHER INFORMATION: chemically synthesized

<400> SEQUENCE: 175

Gly Ser Ser Gly Gly Ser Gly Gly Ser Gly Gly Ser
1               5                   10

<210> SEQ ID NO 176
<211> LENGTH: 16
<212> TYPE: PRT
<213> ORGANISM: Artificial Sequence
<220> FEATURE:
<223> OTHER INFORMATION: chemically synthesized

<400> SEQUENCE: 176

Gly Ser Ser Gly Gly Ser Gly Gly Ser Gly Gly Ser Gly Gly Gly Ser
1               5                   10                  15

<210> SEQ ID NO 177
<211> LENGTH: 10
<212> TYPE: PRT
<213> ORGANISM: Artificial Sequence
<220> FEATURE:
<223> OTHER INFORMATION: chemically synthesized

<400> SEQUENCE: 177

Gly Ser Ser Gly Gly Ser Gly Gly Ser Gly
1               5                   10

<210> SEQ ID NO 178
<211> LENGTH: 11
<212> TYPE: PRT
<213> ORGANISM: Artificial Sequence
<220> FEATURE:
<223> OTHER INFORMATION: chemically synthesized

<400> SEQUENCE: 178

Gly Ser Ser Gly Gly Ser Gly Gly Ser Gly Ser
1               5                   10

<210> SEQ ID NO 179
<211> LENGTH: 4
<212> TYPE: PRT
<213> ORGANISM: Artificial Sequence
<220> FEATURE:
<223> OTHER INFORMATION: chemically synthesized

<400> SEQUENCE: 179

Gly Gly Gly Ser
1

<210> SEQ ID NO 180
<211> LENGTH: 5
<212> TYPE: PRT
<213> ORGANISM: Artificial Sequence
<220> FEATURE:
<223> OTHER INFORMATION: chemically synthesized

<400> SEQUENCE: 180

Gly Ser Ser Gly Thr
1               5

<210> SEQ ID NO 181
<211> LENGTH: 4
<212> TYPE: PRT
<213> ORGANISM: Artificial Sequence
<220> FEATURE:
<223> OTHER INFORMATION: chemically synthesized

<400> SEQUENCE: 181

Gly Ser Ser Gly
1

<210> SEQ ID NO 182
<211> LENGTH: 8
<212> TYPE: PRT
<213> ORGANISM: Artificial Sequence
<220> FEATURE:
<223> OTHER INFORMATION: chemically synthesized

<400> SEQUENCE: 182

Thr Gly Arg Gly Pro Ser Trp Val
1               5

<210> SEQ ID NO 183
<211> LENGTH: 8
<212> TYPE: PRT
<213> ORGANISM: Artificial Sequence
<220> FEATURE:
<223> OTHER INFORMATION: chemically synthesized

<400> SEQUENCE: 183

Ser Ala Arg Gly Pro Ser Arg Trp
1               5

<210> SEQ ID NO 184
<211> LENGTH: 8
<212> TYPE: PRT
<213> ORGANISM: Artificial Sequence
<220> FEATURE:
<223> OTHER INFORMATION: chemically synthesized

<400> SEQUENCE: 184

Thr Ala Arg Gly Pro Ser Phe Lys
1               5

<210> SEQ ID NO 185
<211> LENGTH: 8
<212> TYPE: PRT
<213> ORGANISM: Artificial Sequence
<220> FEATURE:
<223> OTHER INFORMATION: chemically synthesized

<400> SEQUENCE: 185

Leu Ser Gly Arg Ser Asp Asn His

```
<210> SEQ ID NO 186
<211> LENGTH: 8
<212> TYPE: PRT
<213> ORGANISM: Artificial Sequence
<220> FEATURE:
<223> OTHER INFORMATION: chemically synthesized

<400> SEQUENCE: 186

Gly Gly Trp His Thr Gly Arg Asn
1               5

<210> SEQ ID NO 187
<211> LENGTH: 8
<212> TYPE: PRT
<213> ORGANISM: Artificial Sequence
<220> FEATURE:
<223> OTHER INFORMATION: chemically synthesized

<400> SEQUENCE: 187

His Thr Gly Arg Ser Gly Ala Leu
1               5

<210> SEQ ID NO 188
<211> LENGTH: 8
<212> TYPE: PRT
<213> ORGANISM: Artificial Sequence
<220> FEATURE:
<223> OTHER INFORMATION: chemically synthesized

<400> SEQUENCE: 188

Pro Leu Thr Gly Arg Ser Gly Gly
1               5

<210> SEQ ID NO 189
<211> LENGTH: 8
<212> TYPE: PRT
<213> ORGANISM: Artificial Sequence
<220> FEATURE:
<223> OTHER INFORMATION: chemically synthesized

<400> SEQUENCE: 189

Ala Ala Arg Gly Pro Ala Ile His
1               5

<210> SEQ ID NO 190
<211> LENGTH: 8
<212> TYPE: PRT
<213> ORGANISM: Artificial Sequence
<220> FEATURE:
<223> OTHER INFORMATION: chemically synthesized

<400> SEQUENCE: 190

Arg Gly Pro Ala Phe Asn Pro Met
1               5

<210> SEQ ID NO 191
<211> LENGTH: 8
<212> TYPE: PRT
<213> ORGANISM: Artificial Sequence
<220> FEATURE:
<223> OTHER INFORMATION: chemically synthesized

<400> SEQUENCE: 191

Ser Ser Arg Gly Pro Ala Tyr Leu
1               5
```

<210> SEQ ID NO 192
<211> LENGTH: 8
<212> TYPE: PRT
<213> ORGANISM: Artificial Sequence
<220> FEATURE:
<223> OTHER INFORMATION: chemically synthesized

<400> SEQUENCE: 192

Arg Gly Pro Ala Thr Pro Ile Met
1               5

<210> SEQ ID NO 193
<211> LENGTH: 4
<212> TYPE: PRT
<213> ORGANISM: Artificial Sequence
<220> FEATURE:
<223> OTHER INFORMATION: chemically synthesized

<400> SEQUENCE: 193

Arg Gly Pro Ala
1

<210> SEQ ID NO 194
<211> LENGTH: 10
<212> TYPE: PRT
<213> ORGANISM: Artificial Sequence
<220> FEATURE:
<223> OTHER INFORMATION: chemically synthesized

<400> SEQUENCE: 194

Gly Gly Gln Pro Ser Gly Met Trp Gly Trp
1               5                   10

<210> SEQ ID NO 195
<211> LENGTH: 10
<212> TYPE: PRT
<213> ORGANISM: Artificial Sequence
<220> FEATURE:
<223> OTHER INFORMATION: chemically synthesized

<400> SEQUENCE: 195

Phe Pro Arg Pro Leu Gly Ile Thr Gly Leu
1               5                   10

<210> SEQ ID NO 196
<211> LENGTH: 10
<212> TYPE: PRT
<213> ORGANISM: Artificial Sequence
<220> FEATURE:
<223> OTHER INFORMATION: chemically synthesized

<400> SEQUENCE: 196

Val His Met Pro Leu Gly Phe Leu Gly Pro
1               5                   10

<210> SEQ ID NO 197
<211> LENGTH: 8
<212> TYPE: PRT
<213> ORGANISM: Artificial Sequence
<220> FEATURE:
<223> OTHER INFORMATION: chemically synthesized

<400> SEQUENCE: 197

Ser Pro Leu Thr Gly Arg Ser Gly
1               5

<210> SEQ ID NO 198
<211> LENGTH: 8
<212> TYPE: PRT
<213> ORGANISM: Artificial Sequence
<220> FEATURE:
<223> OTHER INFORMATION: chemically synthesized

<400> SEQUENCE: 198

Ser Ala Gly Phe Ser Leu Pro Ala
1               5

<210> SEQ ID NO 199
<211> LENGTH: 9
<212> TYPE: PRT
<213> ORGANISM: Artificial Sequence
<220> FEATURE:
<223> OTHER INFORMATION: chemically synthesized

<400> SEQUENCE: 199

Leu Ala Pro Leu Gly Leu Gln Arg Arg
1               5

<210> SEQ ID NO 200
<211> LENGTH: 8
<212> TYPE: PRT
<213> ORGANISM: Artificial Sequence
<220> FEATURE:
<223> OTHER INFORMATION: chemically synthesized

<400> SEQUENCE: 200

Ser Gly Gly Pro Leu Gly Val Arg
1               5

<210> SEQ ID NO 201
<211> LENGTH: 4
<212> TYPE: PRT
<213> ORGANISM: Artificial Sequence
<220> FEATURE:
<223> OTHER INFORMATION: chemically synthesized

<400> SEQUENCE: 201

Pro Leu Gly Leu
1

<210> SEQ ID NO 202
<211> LENGTH: 7
<212> TYPE: PRT
<213> ORGANISM: Artificial Sequence
<220> FEATURE:
<223> OTHER INFORMATION: chemically synthesized

<400> SEQUENCE: 202

Ile Ser Ser Gly Leu Ser Ser
1               5

<210> SEQ ID NO 203
<211> LENGTH: 8
<212> TYPE: PRT
<213> ORGANISM: Artificial Sequence
<220> FEATURE:
<223> OTHER INFORMATION: chemically synthesized

<400> SEQUENCE: 203

Gln Asn Gln Ala Leu Arg Met Ala
1               5

```
<210> SEQ ID NO 204
<211> LENGTH: 8
<212> TYPE: PRT
<213> ORGANISM: Artificial Sequence
<220> FEATURE:
<223> OTHER INFORMATION: chemically synthesized

<400> SEQUENCE: 204

Ala Gln Asn Leu Leu Gly Met Val
1               5

<210> SEQ ID NO 205
<211> LENGTH: 8
<212> TYPE: PRT
<213> ORGANISM: Artificial Sequence
<220> FEATURE:
<223> OTHER INFORMATION: chemically synthesized

<400> SEQUENCE: 205

Ser Thr Phe Pro Phe Gly Met Phe
1               5

<210> SEQ ID NO 206
<211> LENGTH: 8
<212> TYPE: PRT
<213> ORGANISM: Artificial Sequence
<220> FEATURE:
<223> OTHER INFORMATION: chemically synthesized

<400> SEQUENCE: 206

Pro Val Gly Tyr Thr Ser Ser Leu
1               5

<210> SEQ ID NO 207
<211> LENGTH: 8
<212> TYPE: PRT
<213> ORGANISM: Artificial Sequence
<220> FEATURE:
<223> OTHER INFORMATION: chemically synthesized

<400> SEQUENCE: 207

Asp Trp Leu Tyr Trp Pro Gly Ile
1               5

<210> SEQ ID NO 208
<211> LENGTH: 8
<212> TYPE: PRT
<213> ORGANISM: Artificial Sequence
<220> FEATURE:
<223> OTHER INFORMATION: chemically synthesized

<400> SEQUENCE: 208

Ile Ser Ser Gly Leu Leu Ser Ser
1               5

<210> SEQ ID NO 209
<211> LENGTH: 8
<212> TYPE: PRT
<213> ORGANISM: Artificial Sequence
<220> FEATURE:
<223> OTHER INFORMATION: chemically synthesized

<400> SEQUENCE: 209

Leu Lys Ala Ala Pro Arg Trp Ala
1               5

<210> SEQ ID NO 210
```

```
<211> LENGTH: 8
<212> TYPE: PRT
<213> ORGANISM: Artificial Sequence
<220> FEATURE:
<223> OTHER INFORMATION: chemically synthesized

<400> SEQUENCE: 210

Gly Pro Ser His Leu Val Leu Thr
1               5

<210> SEQ ID NO 211
<211> LENGTH: 8
<212> TYPE: PRT
<213> ORGANISM: Artificial Sequence
<220> FEATURE:
<223> OTHER INFORMATION: chemically synthesized

<400> SEQUENCE: 211

Leu Pro Gly Gly Leu Ser Pro Trp
1               5

<210> SEQ ID NO 212
<211> LENGTH: 8
<212> TYPE: PRT
<213> ORGANISM: Artificial Sequence
<220> FEATURE:
<223> OTHER INFORMATION: chemically synthesized

<400> SEQUENCE: 212

Met Gly Leu Phe Ser Glu Ala Gly
1               5

<210> SEQ ID NO 213
<211> LENGTH: 8
<212> TYPE: PRT
<213> ORGANISM: Artificial Sequence
<220> FEATURE:
<223> OTHER INFORMATION: chemically synthesized

<400> SEQUENCE: 213

Ser Pro Leu Pro Leu Arg Val Pro
1               5

<210> SEQ ID NO 214
<211> LENGTH: 8
<212> TYPE: PRT
<213> ORGANISM: Artificial Sequence
<220> FEATURE:
<223> OTHER INFORMATION: chemically synthesized

<400> SEQUENCE: 214

Arg Met His Leu Arg Ser Leu Gly
1               5

<210> SEQ ID NO 215
<211> LENGTH: 8
<212> TYPE: PRT
<213> ORGANISM: Artificial Sequence
<220> FEATURE:
<223> OTHER INFORMATION: chemically synthesized

<400> SEQUENCE: 215

Leu Ala Ala Pro Leu Gly Leu Leu
1               5

<210> SEQ ID NO 216
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 216

Ala Val Gly Leu Leu Ala Pro Pro
1               5

<210> SEQ ID NO 217
<211> LENGTH: 8
<212> TYPE: PRT
<213> ORGANISM: Artificial Sequence
<220> FEATURE:
<223> OTHER INFORMATION: chemically synthesized

<400> SEQUENCE: 217

Leu Leu Ala Pro Ser His Arg Ala
1               5

<210> SEQ ID NO 218
<211> LENGTH: 8
<212> TYPE: PRT
<213> ORGANISM: Artificial Sequence
<220> FEATURE:
<223> OTHER INFORMATION: chemically synthesized

<400> SEQUENCE: 218

Pro Ala Gly Leu Trp Leu Asp Pro
1               5

<210> SEQ ID NO 219
<211> LENGTH: 7
<212> TYPE: PRT
<213> ORGANISM: Artificial Sequence
<220> FEATURE:
<223> OTHER INFORMATION: chemically synthesized

<400> SEQUENCE: 219

Gly Pro Arg Ser Phe Gly Leu
1               5

<210> SEQ ID NO 220
<211> LENGTH: 6
<212> TYPE: PRT
<213> ORGANISM: Artificial Sequence
<220> FEATURE:
<223> OTHER INFORMATION: chemically synthesized

<400> SEQUENCE: 220

Gly Pro Arg Ser Phe Gly
1               5

<210> SEQ ID NO 221
<211> LENGTH: 12
<212> TYPE: PRT
<213> ORGANISM: Artificial Sequence
<220> FEATURE:
<223> OTHER INFORMATION: chemically synthesized

<400> SEQUENCE: 221

Asn Thr Leu Ser Gly Arg Ser Glu Asn His Ser Gly
1               5                   10

<210> SEQ ID NO 222
<211> LENGTH: 12
<212> TYPE: PRT
```

<213> ORGANISM: Artificial Sequence
<220> FEATURE:
<223> OTHER INFORMATION: chemically synthesized

<400> SEQUENCE: 222

Asn Thr Leu Ser Gly Arg Ser Gly Asn His Gly Ser
1               5                   10

<210> SEQ ID NO 223
<211> LENGTH: 12
<212> TYPE: PRT
<213> ORGANISM: Artificial Sequence
<220> FEATURE:
<223> OTHER INFORMATION: chemically synthesized

<400> SEQUENCE: 223

Thr Ser Thr Ser Gly Arg Ser Ala Asn Pro Arg Gly
1               5                   10

<210> SEQ ID NO 224
<211> LENGTH: 8
<212> TYPE: PRT
<213> ORGANISM: Artificial Sequence
<220> FEATURE:
<223> OTHER INFORMATION: chemically synthesized

<400> SEQUENCE: 224

Thr Ser Gly Arg Ser Ala Asn Pro
1               5

<210> SEQ ID NO 225
<211> LENGTH: 8
<212> TYPE: PRT
<213> ORGANISM: Artificial Sequence
<220> FEATURE:
<223> OTHER INFORMATION: chemically synthesized

<400> SEQUENCE: 225

Val Ala Gly Arg Ser Met Arg Pro
1               5

<210> SEQ ID NO 226
<211> LENGTH: 8
<212> TYPE: PRT
<213> ORGANISM: Artificial Sequence
<220> FEATURE:
<223> OTHER INFORMATION: chemically synthesized

<400> SEQUENCE: 226

Val Val Pro Glu Gly Arg Arg Ser
1               5

<210> SEQ ID NO 227
<211> LENGTH: 8
<212> TYPE: PRT
<213> ORGANISM: Artificial Sequence
<220> FEATURE:
<223> OTHER INFORMATION: chemically synthesized

<400> SEQUENCE: 227

Ile Leu Pro Arg Ser Pro Ala Phe
1               5

<210> SEQ ID NO 228
<211> LENGTH: 8
<212> TYPE: PRT
<213> ORGANISM: Artificial Sequence

```
<220> FEATURE:
<223> OTHER INFORMATION: chemically synthesized

<400> SEQUENCE: 228

Met Val Leu Gly Arg Ser Leu Leu
1               5

<210> SEQ ID NO 229
<211> LENGTH: 8
<212> TYPE: PRT
<213> ORGANISM: Artificial Sequence
<220> FEATURE:
<223> OTHER INFORMATION: chemically synthesized

<400> SEQUENCE: 229

Gln Gly Arg Ala Ile Thr Phe Ile
1               5

<210> SEQ ID NO 230
<211> LENGTH: 8
<212> TYPE: PRT
<213> ORGANISM: Artificial Sequence
<220> FEATURE:
<223> OTHER INFORMATION: chemically synthesized

<400> SEQUENCE: 230

Ser Pro Arg Ser Ile Met Leu Ala
1               5

<210> SEQ ID NO 231
<211> LENGTH: 8
<212> TYPE: PRT
<213> ORGANISM: Artificial Sequence
<220> FEATURE:
<223> OTHER INFORMATION: chemically synthesized

<400> SEQUENCE: 231

Ser Met Leu Arg Ser Met Pro Leu
1               5

<210> SEQ ID NO 232
<211> LENGTH: 13
<212> TYPE: PRT
<213> ORGANISM: Artificial Sequence
<220> FEATURE:
<223> OTHER INFORMATION: chemically synthesized

<400> SEQUENCE: 232

Ile Ser Ser Gly Leu Leu Ser Gly Arg Ser Asp Asn His
1               5                   10

<210> SEQ ID NO 233
<211> LENGTH: 22
<212> TYPE: PRT
<213> ORGANISM: Artificial Sequence
<220> FEATURE:
<223> OTHER INFORMATION: chemically synthesized

<400> SEQUENCE: 233

Ile Ser Ser Gly Leu Leu Ser Ser Gly Gly Ser Gly Gly Ser Leu Ser
1               5                   10                  15

Gly Arg Ser Asp Asn His
            20

<210> SEQ ID NO 234
<211> LENGTH: 22
```

<212> TYPE: PRT
<213> ORGANISM: Artificial Sequence
<220> FEATURE:
<223> OTHER INFORMATION: chemically synthesized

<400> SEQUENCE: 234

Ala Val Gly Leu Leu Ala Pro Pro Gly Thr Ser Thr Ser Gly Arg
1               5                   10                  15

Ser Ala Asn Pro Arg Gly
                20

<210> SEQ ID NO 235
<211> LENGTH: 22
<212> TYPE: PRT
<213> ORGANISM: Artificial Sequence
<220> FEATURE:
<223> OTHER INFORMATION: chemically synthesized

<400> SEQUENCE: 235

Thr Ser Thr Ser Gly Arg Ser Ala Asn Pro Arg Gly Gly Ala Val
1               5                   10                  15

Gly Leu Leu Ala Pro Pro
                20

<210> SEQ ID NO 236
<211> LENGTH: 24
<212> TYPE: PRT
<213> ORGANISM: Artificial Sequence
<220> FEATURE:
<223> OTHER INFORMATION: chemically synthesized

<400> SEQUENCE: 236

Val His Met Pro Leu Gly Phe Leu Gly Pro Gly Gly Thr Ser Thr Ser
1               5                   10                  15

Gly Arg Ser Ala Asn Pro Arg Gly
                20

<210> SEQ ID NO 237
<211> LENGTH: 24
<212> TYPE: PRT
<213> ORGANISM: Artificial Sequence
<220> FEATURE:
<223> OTHER INFORMATION: chemically synthesized

<400> SEQUENCE: 237

Thr Ser Thr Ser Gly Arg Ser Ala Asn Pro Arg Gly Gly Val His
1               5                   10                  15

Met Pro Leu Gly Phe Leu Gly Pro
                20

<210> SEQ ID NO 238
<211> LENGTH: 18
<212> TYPE: PRT
<213> ORGANISM: Artificial Sequence
<220> FEATURE:
<223> OTHER INFORMATION: chemically synthesized

<400> SEQUENCE: 238

Ala Val Gly Leu Leu Ala Pro Pro Gly Gly Leu Ser Gly Arg Ser Asp
1               5                   10                  15

Asn His

<210> SEQ ID NO 239
<211> LENGTH: 18

<212> TYPE: PRT
<213> ORGANISM: Artificial Sequence
<220> FEATURE:
<223> OTHER INFORMATION: chemically synthesized

<400> SEQUENCE: 239

Leu Ser Gly Arg Ser Asp Asn His Gly Gly Ala Val Gly Leu Leu Ala
1               5                   10                  15
Pro Pro

<210> SEQ ID NO 240
<211> LENGTH: 20
<212> TYPE: PRT
<213> ORGANISM: Artificial Sequence
<220> FEATURE:
<223> OTHER INFORMATION: chemically synthesized

<400> SEQUENCE: 240

Val His Met Pro Leu Gly Phe Leu Gly Pro Gly Gly Leu Ser Gly Arg
1               5                   10                  15
Ser Asp Asn His
            20

<210> SEQ ID NO 241
<211> LENGTH: 20
<212> TYPE: PRT
<213> ORGANISM: Artificial Sequence
<220> FEATURE:
<223> OTHER INFORMATION: chemically synthesized

<400> SEQUENCE: 241

Leu Ser Gly Arg Ser Asp Asn His Gly Val His Met Pro Leu Gly
1               5                   10                  15
Phe Leu Gly Pro
            20

<210> SEQ ID NO 242
<211> LENGTH: 22
<212> TYPE: PRT
<213> ORGANISM: Artificial Sequence
<220> FEATURE:
<223> OTHER INFORMATION: chemically synthesized

<400> SEQUENCE: 242

Leu Ser Gly Arg Ser Asp Asn His Gly Gly Ser Gly Gly Ser Ile Ser
1               5                   10                  15
Ser Gly Leu Leu Ser Ser
            20

<210> SEQ ID NO 243
<211> LENGTH: 22
<212> TYPE: PRT
<213> ORGANISM: Artificial Sequence
<220> FEATURE:
<223> OTHER INFORMATION: chemically synthesized

<400> SEQUENCE: 243

Leu Ser Gly Arg Ser Gly Asn His Gly Gly Ser Gly Gly Ser Ile Ser
1               5                   10                  15
Ser Gly Leu Leu Ser Ser
            20

<210> SEQ ID NO 244
<211> LENGTH: 22

```
<212> TYPE: PRT
<213> ORGANISM: Artificial Sequence
<220> FEATURE:
<223> OTHER INFORMATION: chemically synthesized

<400> SEQUENCE: 244

Ile Ser Ser Gly Leu Leu Ser Ser Gly Ser Gly Gly Ser Leu Ser
1               5                   10                  15

Gly Arg Ser Gly Asn His
            20

<210> SEQ ID NO 245
<211> LENGTH: 22
<212> TYPE: PRT
<213> ORGANISM: Artificial Sequence
<220> FEATURE:
<223> OTHER INFORMATION: chemically synthesized

<400> SEQUENCE: 245

Leu Ser Gly Arg Ser Asp Asn His Gly Gly Ser Gly Gly Ser Gln Asn
1               5                   10                  15

Gln Ala Leu Arg Met Ala
            20

<210> SEQ ID NO 246
<211> LENGTH: 22
<212> TYPE: PRT
<213> ORGANISM: Artificial Sequence
<220> FEATURE:
<223> OTHER INFORMATION: chemically synthesized

<400> SEQUENCE: 246

Gln Asn Gln Ala Leu Arg Met Ala Gly Gly Ser Gly Gly Ser Leu Ser
1               5                   10                  15

Gly Arg Ser Asp Asn His
            20

<210> SEQ ID NO 247
<211> LENGTH: 22
<212> TYPE: PRT
<213> ORGANISM: Artificial Sequence
<220> FEATURE:
<223> OTHER INFORMATION: chemically synthesized

<400> SEQUENCE: 247

Leu Ser Gly Arg Ser Gly Asn His Gly Gly Ser Gly Gly Ser Gln Asn
1               5                   10                  15

Gln Ala Leu Arg Met Ala
            20

<210> SEQ ID NO 248
<211> LENGTH: 22
<212> TYPE: PRT
<213> ORGANISM: Artificial Sequence
<220> FEATURE:
<223> OTHER INFORMATION: chemically synthesized

<400> SEQUENCE: 248

Gln Asn Gln Ala Leu Arg Met Ala Gly Gly Ser Gly Gly Ser Leu Ser
1               5                   10                  15

Gly Arg Ser Gly Asn His
            20

<210> SEQ ID NO 249
```

```
<211> LENGTH: 13
<212> TYPE: PRT
<213> ORGANISM: Artificial Sequence
<220> FEATURE:
<223> OTHER INFORMATION: chemically synthesized

<400> SEQUENCE: 249

Ile Ser Ser Gly Leu Leu Ser Gly Arg Ser Gly Asn His
1               5                   10

<210> SEQ ID NO 250
<211> LENGTH: 6
<212> TYPE: PRT
<213> ORGANISM: Artificial Sequence
<220> FEATURE:
<223> OTHER INFORMATION: chemically synthesized

<400> SEQUENCE: 250

Gln Gly Gln Ser Gly Gln
1               5

<210> SEQ ID NO 251
<211> LENGTH: 273
<212> TYPE: PRT
<213> ORGANISM: Artificial Sequence
<220> FEATURE:
<223> OTHER INFORMATION: chemically synthesized

<400> SEQUENCE: 251

Gly Gly Gly Ser Gly Gly Gly Ser Gly Ser Gly Gly Ser Gly
1               5                   10                  15

Gly Gly Gly Ser Gly Gly Gly Glu Ile Val Leu Thr Gln Ser Pro Gly
                20                  25                  30

Thr Leu Ser Leu Ser Pro Gly Glu Arg Ala Thr Leu Ser Cys Arg Ala
            35                  40                  45

Ser Gln Ser Val Ser Ser Ser Tyr Leu Ala Trp Tyr Gln Gln Lys Pro
        50                  55                  60

Gly Gln Ala Pro Arg Leu Leu Ile Tyr Gly Ala Ser Ser Arg Ala Thr
65                  70                  75                  80

Gly Ile Pro Asp Arg Phe Ser Gly Ser Gly Ser Gly Thr Asp Phe Thr
                85                  90                  95

Leu Thr Ile Ser Arg Leu Glu Pro Glu Asp Phe Ala Val Tyr Tyr Cys
            100                 105                 110

Gln Gln Tyr Gly Ser Ser Pro Leu Thr Phe Gly Gly Gly Thr Lys Val
        115                 120                 125

Glu Ile Lys Arg Ser Gly Gly Ser Thr Ile Thr Ser Tyr Asn Val Tyr
130                 135                 140

Tyr Thr Lys Leu Ser Ser Ser Gly Thr Gln Val Gln Leu Val Gln Thr
                145                 150                 155                 160

Gly Gly Gly Val Val Gln Pro Gly Arg Ser Leu Arg Leu Ser Cys Ala
            165                 170                 175

Ala Ser Gly Ser Thr Phe Ser Ser Tyr Ala Met Ser Trp Val Arg Gln
        180                 185                 190

Ala Pro Gly Lys Gly Leu Glu Trp Val Ser Ala Ile Ser Gly Ser Gly
        195                 200                 205

Gly Ser Thr Tyr Tyr Ala Asp Ser Val Lys Gly Arg Phe Thr Ile Ser
    210                 215                 220

Arg Asp Asn Ser Lys Asn Thr Leu Tyr Leu Gln Met Asn Ser Leu Arg
225                 230                 235                 240
```

Ala Glu Asp Thr Ala Val Tyr Tyr Cys Ala Thr Asn Ser Leu Tyr Trp
                245                 250                 255

Tyr Phe Asp Leu Trp Gly Arg Gly Thr Leu Val Thr Val Ser Ser Ala
            260                 265                 270

Ser

<210> SEQ ID NO 252
<211> LENGTH: 264
<212> TYPE: PRT
<213> ORGANISM: Artificial Sequence
<220> FEATURE:
<223> OTHER INFORMATION: chemically synthesized

<400> SEQUENCE: 252

Gly Gly Gly Ser Gly Gly Gly Ser Gly Ser Gly Gly Gly Ser Gly
1               5                   10                  15

Gly Gly Gly Ser Gly Gly Gly Gln Val Gln Leu Gln Gln Ser Gly Ala
                20                  25                  30

Glu Leu Ala Arg Pro Gly Ala Ser Val Lys Met Ser Cys Lys Ala Ser
            35                  40                  45

Gly Tyr Thr Phe Thr Arg Tyr Thr Met His Trp Val Lys Gln Arg Pro
50                  55                  60

Gly Gln Gly Leu Glu Trp Ile Gly Tyr Ile Asn Pro Ser Arg Gly Tyr
65                  70                  75                  80

Thr Asn Tyr Asn Gln Lys Phe Lys Asp Lys Ala Thr Leu Thr Thr Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Cys
        115                 120                 125

Leu Asp Tyr Trp Gly Gln Gly Thr Thr Leu Thr Val Ser Ser Gly Gly
130                 135                 140

Gly Gly Ser Gly Gly Gly Gly Ser Gly Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met Asn Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Ala His Phe Arg Gly Ser Gly Ser Gly
210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg
            260

<210> SEQ ID NO 253
<211> LENGTH: 7
<212> TYPE: PRT
<213> ORGANISM: Artificial Sequence
<220> FEATURE:
<223> OTHER INFORMATION: chemically synthesized

<400> SEQUENCE: 253

Gln Gly Gln Ser Gly Gln Gly
1               5

<210> SEQ ID NO 254
<211> LENGTH: 453
<212> TYPE: PRT
<213> ORGANISM: Artificial Sequence
<220> FEATURE:
<223> OTHER INFORMATION: chemically synthesized

<400> SEQUENCE: 254

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Glu Tyr
            20                  25                  30

Ile Ile His Trp Val Arg Gln Ala Pro Gly Gln Gly Leu Glu Trp Ile
            35                  40                  45

Gly Trp Phe Tyr Pro Glu Ser Gly Ser Val Lys Tyr Asn Glu Thr Phe
        50                  55                  60

Thr Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

```
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
            405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys
    450

<210> SEQ ID NO 255
<211> LENGTH: 256
<212> TYPE: PRT
<213> ORGANISM: Artificial Sequence
<220> FEATURE:
<223> OTHER INFORMATION: chemically synthesized

<400> SEQUENCE: 255

Glu Cys Lys Thr Arg Gln Asp Phe Glu Met His Asp Cys Val Tyr Gly
1               5                   10                  15
Gly Gly Ser Ser Gly Gly Ser Ile Ser Ser Gly Leu Leu Ser Gly Arg
            20                  25                  30
Ser Asp Asn His Gly Gly Gly Ser Asp Ile Gln Met Thr Gln Ser Pro
        35                  40                  45
Ser Ser Leu Ser Ala Ser Val Gly Asp Arg Val Thr Ile Thr Cys Ser
    50                  55                  60
Ala Ser Ser Ser Ile Ser Ser Asn Tyr Leu His Trp Tyr Gln Gln Lys
65                  70                  75                  80
Pro Gly Lys Val Pro Lys Leu Leu Ile Tyr Arg Thr Ser Asn Leu Ala
                85                  90                  95
Ser Gly Val Pro Ser Arg Phe Ser Gly Ser Gly Ser Gly Thr Asp Tyr
            100                 105                 110
Thr Leu Thr Ile Ser Ser Leu Gln Pro Glu Asp Val Ala Thr Tyr Tyr
        115                 120                 125
Cys Gln Gln Gly Ser Ser Ile Pro Arg Phe Thr Ser Gly Gly Gly Thr
    130                 135                 140
Lys Val Glu Ile Lys Arg Thr Val Ala Ala Pro Ser Val Phe Ile Phe
145                 150                 155                 160
Pro Pro Ser Asp Glu Gln Leu Lys Ser Gly Thr Ala Ser Val Val Cys
                165                 170                 175
Leu Leu Asn Asn Phe Tyr Pro Arg Glu Ala Lys Val Gln Trp Lys Val
            180                 185                 190
Asp Asn Ala Leu Gln Ser Gly Asn Ser Gln Glu Ser Val Thr Glu Gln
        195                 200                 205
Asp Ser Lys Asp Ser Thr Tyr Ser Leu Ser Ser Thr Leu Thr Leu Ser
    210                 215                 220
Lys Ala Asp Tyr Glu Lys His Lys Val Tyr Ala Cys Glu Val Thr His
225                 230                 235                 240
Gln Gly Leu Ser Ser Pro Val Thr Lys Ser Phe Asn Arg Gly Glu Cys
                245                 250                 255
```

<210> SEQ ID NO 256
<211> LENGTH: 768
<212> TYPE: DNA
<213> ORGANISM: Artificial Sequence
<220> FEATURE:
<223> OTHER INFORMATION: chemically synthesized

<400> SEQUENCE: 256

```
gagtgcaaga cccggcagga cttcgagatg cacgactgcg tgtacggcgg aggctcctcc      60
ggcggctcca tctcctctgg cctgctgtcc ggcagatccg acaaccatgg cggcggatcc     120
gacatccaga tgacccagtc cccatccagc ctgtccgcct ccgtgggcga cagagtgaca     180
atcacctgtt ccgccagctc ctccatctcc agcaactacc tgcactggta tcagcagaaa     240
cccggcaagg tgcccaagct gctgatctac cggacctcca acctggcctc cggcgtgccc     300
tccagattct ccggctctgg ctccggcacc gactacaccc tgaccatcag ctccctgcag     360
cccgaggacg tggccaccta ctactgccag cagggctcca gcatccccg gttcacctct      420
ggcggaggca ccaaggtgga aatcaagcgg accgtggccg ctcccctccgt gttcatcttc    480
ccacccctccg acgagcagct gaagtccggc accgccagcg tcgtgtgcct gctgaacaac    540
ttctaccccc gcgaggccaa ggtgcagtgg aaggtggaca cgccctgca gtccggcaac     600
tcccaggaat ccgtcaccga gcaggactcc aaggacagca cctactccct gtcctccacc     660
ctgaccctgt ccaaggccga ctacgagaag cacaaggtgt acgcctgcga agtgaccca      720
cagggcctgt ccagccccgt gaccaagtcc ttcaaccgcg gcgagtgc                  768
```

<210> SEQ ID NO 257
<211> LENGTH: 256
<212> TYPE: PRT
<213> ORGANISM: Artificial Sequence
<220> FEATURE:
<223> OTHER INFORMATION: chemically synthesized

<400> SEQUENCE: 257

```
Gln Cys Met Ser Arg Phe Ala Phe Glu Ile Gly Asp Cys Val Met Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175
```

```
Leu Leu Asn Asn Phe Tyr Pro Arg Glu Ala Lys Val Gln Trp Lys Val
                180                 185                 190
Asp Asn Ala Leu Gln Ser Gly Asn Ser Gln Glu Ser Val Thr Glu Gln
            195                 200                 205
Asp Ser Lys Asp Ser Thr Tyr Ser Leu Ser Ser Thr Leu Thr Leu Ser
        210                 215                 220
Lys Ala Asp Tyr Glu Lys His Lys Val Tyr Ala Cys Glu Val Thr His
225                 230                 235                 240
Gln Gly Leu Ser Ser Pro Val Thr Lys Ser Phe Asn Arg Gly Glu Cys
                245                 250                 255
```

<210> SEQ ID NO 258
<211> LENGTH: 768
<212> TYPE: DNA
<213> ORGANISM: Artificial Sequence
<220> FEATURE:
<223> OTHER INFORMATION: chemically synthesized

<400> SEQUENCE: 258

```
cagtgcatgt cacgttttgc ttttgagatt ggtgattgcg ttatgggagg tggctcgagc     60
ggcggctcta tctcttccgg actgctgtcc ggcagatccg acaatcacgg cggaggctct    120
gacatccaga tgacccagtc cccatccagc ctgtccgcct ccgtgggcga cagagtgaca    180
atcacctgtt ccgccagctc ctccatctcc agcaactacc tgcactggta tcagcagaaa    240
cccggcaagg tgcccaagct gctgatctac cggacctcca acctggcctc cggcgtgccc    300
tccagattct ccggctctgg ctccggcacc gactacaccc tgaccatcag ctccctgcag    360
cccgaggacg tggccaccta ctactgccag cagggctcca gcatccccccg gttcacctct    420
ggcggaggca ccaaggtgga aatcaagcgg accgtggccg ctccctccgt gttcatcttc    480
ccaccctccg acgagcagct gaagtccggc accgccagcg tcgtgtgcct gctgaacaac    540
ttctaccccc gcgaggccaa ggtgcagtgg aaggtggaca cgccctgca gtccggcaac    600
tcccaggaat ccgtcaccga gcaggactcc aaggacagca cctactccct gtcctccacc    660
ctgaccctgt ccaaggccga ctacgagaag cacaaggtgt acgcctgcga agtgacccac    720
cagggcctgt ccagccccgt gaccaagtcc ttcaaccgcg cgagtgc                  768
```

<210> SEQ ID NO 259
<211> LENGTH: 256
<212> TYPE: PRT
<213> ORGANISM: Artificial Sequence
<220> FEATURE:
<223> OTHER INFORMATION: chemically synthesized

<400> SEQUENCE: 259

```
Thr Cys Leu Ser Arg Tyr Glu Phe Glu Thr Thr Asp Cys Val Met Gly
1               5                  10                  15
Gly Gly Ser Ser Gly Gly Ser Ile Ser Ser Gly Leu Leu Ser Gly Arg
                20                  25                  30
Ser Asp Asn His Gly Gly Gly Ser Asp Ile Val Met Thr Gln Thr Pro
            35                  40                  45
Thr Thr Leu Ala Ala Ser Pro Gly Glu Lys Ile Ile Ile Thr Cys Ser
        50                  55                  60
Ala Ser Ser Ser Ile Ser Ser Asn Tyr Leu His Trp Tyr Gln Gln Lys
65                  70                  75                  80
Pro Gly Phe Ser Pro Lys Leu Leu Ile Tyr Arg Thr Ser Asn Leu Ala
                85                  90                  95
```

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
    130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 260
<211> LENGTH: 768
<212> TYPE: DNA
<213> ORGANISM: Artificial Sequence
<220> FEATURE:
<223> OTHER INFORMATION: chemically synthesized

<400> SEQUENCE: 260
acgtgcctga gtaggtatga gtttgagacg actgattgcg ttatgggagg tggctcgagc      60
ggcggctcta tctcttccgg actgctgtcc ggcagatccg acaatcacgg cggaggctct     120
gacatccaga tgacccagtc cccatccagc ctgtccgcct ccgtgggcga cagagtgaca     180
atcacctgtt ccgccagctc ctccatctcc agcaactacc tgcactggta tcagcagaaa     240
cccggcaagg tgcccaagct gctgatctac cggacctcca acctggcctc cggcgtgccc     300
tccagattct ccggctctgg ctccggcacc gactacaccc tgaccatcag ctccctgcag     360
cccgaggacg tggccaccta ctactgccag cagggctcca gcatccccg gttcaccctct     420
ggcggaggca ccaaggtgga aatcaagcgg accgtggccg ctccctccgt gttcatcttc     480
ccaccctccg acgagcagct gaagtccggc accgccagcg tcgtgtgcct gctgaacaac     540
ttctacccccc gcgaggccaa ggtgcagtgg aaggtggaca acgccctgca gtccggcaac     600
tcccaggaat ccgtcaccga gcaggactcc aaggacagca cctactccct gtcctccacc     660
ctgaccctgt ccaaggccga ctacgagaag cacaaggtgt acgcctgcga agtgacccac     720
cagggcctgt ccagccccgt gaccaagtcc ttcaaccgcg gcgagtgc              768

<210> SEQ ID NO 261
<211> LENGTH: 256
<212> TYPE: PRT
<213> ORGANISM: Artificial Sequence
<220> FEATURE:
<223> OTHER INFORMATION: chemically synthesized

<400> SEQUENCE: 261

Val Cys Arg Thr Arg Trp His Phe Glu Thr Thr Asp Cys Val Met Gly
1               5                   10                  15

```
Gly Gly Ser Ser Gly Gly Ser Ile Ser Ser Gly Leu Leu Ser Gly Arg
                20                  25                  30

Ser Asp Asn His Gly Gly Ser Asp Ile Val Met Thr Gln Thr Pro
            35                  40                  45

Thr Thr Leu Ala Ala Ser Pro Gly Glu Lys Ile Ile Ile Thr Cys Ser
        50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
                85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
            130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
                225             230                 235             240

Gln Gly Leu Ser Ser Pro Val Thr Lys Ser Phe Asn Arg Gly Glu Cys
                245                 250                 255

<210> SEQ ID NO 262
<211> LENGTH: 768
<212> TYPE: DNA
<213> ORGANISM: Artificial Sequence
<220> FEATURE:
<223> OTHER INFORMATION: chemically synthesized

<400> SEQUENCE: 262
gtgtgccgga ctaggtggca ttttgagact acggattgcg ttatgggagg tggctcgagc      60
ggcggctcta tctcttccgg actgctgtcc ggcagatccg acaatcacgg cggaggctct     120
gacatccaga tgacccagtc cccatccagc ctgtccgcct ccgtgggcga cagagtgaca     180
atcacctgtt ccgccagctc ctccatctcc agcaactacc tgcactggta tcagcagaaa     240
cccggcaagg tgcccaagct gctgatctac cggacctcca acctggcctc cggcgtgccc     300
tccagattct ccggctctgg ctccggcacc gactacaccc tgaccatcag ctccctgcag     360
cccgaggacg tggccaccta ctactgccag cagggctcca gcatccccccg gttcacctct     420
ggcggaggca ccaaggtgga aatcaagcgg accgtggccg ctccctccgt gttcatcttc     480
ccaccctccg acgagcagct gaagtccggc accgccagtc tcgtgtgcct gctgaacaac     540
ttctaccccc gcgaggccaa ggtgcagtgg aaggtggaca acgccctgca gtccggcaac     600
tcccaggaat ccgtcaccga gcaggactcc aaggacagca cctactccct gtcctccacc     660
ctgaccctgt ccaaggccga ctacgagaag cacaaggtgt acgcctgcga agtgacccac     720
```

-continued

```
cagggcctgt ccagccccgt gaccaagtcc ttcaaccgcg gcgagtgc          768
```

<210> SEQ ID NO 263

<400> SEQUENCE: 263

000

<210> SEQ ID NO 264

<400> SEQUENCE: 264

000

<210> SEQ ID NO 265
<211> LENGTH: 21
<212> TYPE: DNA
<213> ORGANISM: Artificial Sequence
<220> FEATURE:
<223> OTHER INFORMATION: chemically synthesized

<400> SEQUENCE: 265

```
cagggccagt ctggacaggg c                                       21
```

<210> SEQ ID NO 266
<211> LENGTH: 21
<212> TYPE: DNA
<213> ORGANISM: Artificial Sequence
<220> FEATURE:
<223> OTHER INFORMATION: chemically synthesized

<400> SEQUENCE: 266

```
caaggccagt ctggccaggg t                                       21
```

<210> SEQ ID NO 267
<211> LENGTH: 6
<212> TYPE: PRT
<213> ORGANISM: Artificial Sequence
<220> FEATURE:
<223> OTHER INFORMATION: chemically synthesized

<400> SEQUENCE: 267

```
Gln Gly Gln Ser Gly Gln
1               5
```

<210> SEQ ID NO 268
<211> LENGTH: 5
<212> TYPE: PRT
<213> ORGANISM: Artificial Sequence
<220> FEATURE:
<223> OTHER INFORMATION: chemically synthesized

<400> SEQUENCE: 268

```
Gln Gly Gln Ser Gly
1               5
```

<210> SEQ ID NO 269
<211> LENGTH: 4
<212> TYPE: PRT
<213> ORGANISM: Artificial Sequence
<220> FEATURE:
<223> OTHER INFORMATION: chemically synthesized

<400> SEQUENCE: 269

```
Gln Gly Gln Ser
1
```

```
<210> SEQ ID NO 270
<211> LENGTH: 3
<212> TYPE: PRT
<213> ORGANISM: Artificial Sequence
<220> FEATURE:
<223> OTHER INFORMATION: chemically synthesized

<400> SEQUENCE: 270

Gln Gly Gln
1

<210> SEQ ID NO 271
<211> LENGTH: 2
<212> TYPE: PRT
<213> ORGANISM: Artificial Sequence
<220> FEATURE:
<223> OTHER INFORMATION: chemically synthesized

<400> SEQUENCE: 271

Gln Gly
1

<210> SEQ ID NO 272
<211> LENGTH: 6
<212> TYPE: PRT
<213> ORGANISM: Artificial Sequence
<220> FEATURE:
<223> OTHER INFORMATION: chemically synthesized

<400> SEQUENCE: 272

Gly Gln Ser Gly Gln Gly
1               5

<210> SEQ ID NO 273
<211> LENGTH: 5
<212> TYPE: PRT
<213> ORGANISM: Artificial Sequence
<220> FEATURE:
<223> OTHER INFORMATION: chemically synthesized

<400> SEQUENCE: 273

Gln Ser Gly Gln Gly
1               5

<210> SEQ ID NO 274
<211> LENGTH: 4
<212> TYPE: PRT
<213> ORGANISM: Artificial Sequence
<220> FEATURE:
<223> OTHER INFORMATION: chemically synthesized

<400> SEQUENCE: 274

Ser Gly Gln Gly
1

<210> SEQ ID NO 275
<211> LENGTH: 3
<212> TYPE: PRT
<213> ORGANISM: Artificial Sequence
<220> FEATURE:
<223> OTHER INFORMATION: chemically synthesized

<400> SEQUENCE: 275

Gly Gln Gly
1
```

```
<210> SEQ ID NO 276
<211> LENGTH: 8
<212> TYPE: PRT
<213> ORGANISM: Artificial Sequence
<220> FEATURE:
<223> OTHER INFORMATION: chemically synthesized

<400> SEQUENCE: 276

Leu Ser Gly Arg Ser Gly Asn His
1               5

<210> SEQ ID NO 277
<211> LENGTH: 9
<212> TYPE: PRT
<213> ORGANISM: Artificial Sequence
<220> FEATURE:
<223> OTHER INFORMATION: chemically synthesized

<400> SEQUENCE: 277

Ser Gly Arg Ser Ala Asn Pro Arg Gly
1               5

<210> SEQ ID NO 278
<211> LENGTH: 8
<212> TYPE: PRT
<213> ORGANISM: Artificial Sequence
<220> FEATURE:
<223> OTHER INFORMATION: chemically synthesized

<400> SEQUENCE: 278

Leu Ser Gly Arg Ser Asp Asp His
1               5

<210> SEQ ID NO 279
<211> LENGTH: 8
<212> TYPE: PRT
<213> ORGANISM: Artificial Sequence
<220> FEATURE:
<223> OTHER INFORMATION: chemically synthesized

<400> SEQUENCE: 279

Leu Ser Gly Arg Ser Asp Ile His
1               5

<210> SEQ ID NO 280
<211> LENGTH: 8
<212> TYPE: PRT
<213> ORGANISM: Artificial Sequence
<220> FEATURE:
<223> OTHER INFORMATION: chemically synthesized

<400> SEQUENCE: 280

Leu Ser Gly Arg Ser Asp Gln His
1               5

<210> SEQ ID NO 281
<211> LENGTH: 8
<212> TYPE: PRT
<213> ORGANISM: Artificial Sequence
<220> FEATURE:
<223> OTHER INFORMATION: chemically synthesized

<400> SEQUENCE: 281

Leu Ser Gly Arg Ser Asp Thr His
1               5

<210> SEQ ID NO 282
```

```
<211> LENGTH: 8
<212> TYPE: PRT
<213> ORGANISM: Artificial Sequence
<220> FEATURE:
<223> OTHER INFORMATION: chemically synthesized

<400> SEQUENCE: 282

Leu Ser Gly Arg Ser Asp Tyr His
1               5

<210> SEQ ID NO 283
<211> LENGTH: 8
<212> TYPE: PRT
<213> ORGANISM: Artificial Sequence
<220> FEATURE:
<223> OTHER INFORMATION: chemically synthesized

<400> SEQUENCE: 283

Leu Ser Gly Arg Ser Asp Asn Pro
1               5

<210> SEQ ID NO 284
<211> LENGTH: 8
<212> TYPE: PRT
<213> ORGANISM: Artificial Sequence
<220> FEATURE:
<223> OTHER INFORMATION: chemically synthesized

<400> SEQUENCE: 284

Leu Ser Gly Arg Ser Ala Asn Pro
1               5

<210> SEQ ID NO 285
<211> LENGTH: 8
<212> TYPE: PRT
<213> ORGANISM: Artificial Sequence
<220> FEATURE:
<223> OTHER INFORMATION: chemically synthesized

<400> SEQUENCE: 285

Leu Ser Gly Arg Ser Ala Asn Ile
1               5

<210> SEQ ID NO 286
<211> LENGTH: 8
<212> TYPE: PRT
<213> ORGANISM: Artificial Sequence
<220> FEATURE:
<223> OTHER INFORMATION: chemically synthesized

<400> SEQUENCE: 286

Leu Ser Gly Arg Ser Asp Asn Ile
1               5

<210> SEQ ID NO 287
<211> LENGTH: 8
<212> TYPE: PRT
<213> ORGANISM: Artificial Sequence
<220> FEATURE:
<223> OTHER INFORMATION: chemically synthesized

<400> SEQUENCE: 287

Met Ile Ala Pro Val Ala Tyr Arg
1               5

<210> SEQ ID NO 288
<211> LENGTH: 8
```

```
<212> TYPE: PRT
<213> ORGANISM: Artificial Sequence
<220> FEATURE:
<223> OTHER INFORMATION: chemically synthesized

<400> SEQUENCE: 288

Arg Pro Ser Pro Met Trp Ala Tyr
1               5

<210> SEQ ID NO 289
<211> LENGTH: 8
<212> TYPE: PRT
<213> ORGANISM: Artificial Sequence
<220> FEATURE:
<223> OTHER INFORMATION: chemically synthesized

<400> SEQUENCE: 289

Trp Ala Thr Pro Arg Pro Met Arg
1               5

<210> SEQ ID NO 290
<211> LENGTH: 8
<212> TYPE: PRT
<213> ORGANISM: Artificial Sequence
<220> FEATURE:
<223> OTHER INFORMATION: chemically synthesized

<400> SEQUENCE: 290

Phe Arg Leu Leu Asp Trp Gln Trp
1               5

<210> SEQ ID NO 291
<211> LENGTH: 5
<212> TYPE: PRT
<213> ORGANISM: Artificial Sequence
<220> FEATURE:
<223> OTHER INFORMATION: chemically synthesized

<400> SEQUENCE: 291

Ile Ser Ser Gly Leu
1               5

<210> SEQ ID NO 292
<211> LENGTH: 7
<212> TYPE: PRT
<213> ORGANISM: Artificial Sequence
<220> FEATURE:
<223> OTHER INFORMATION: chemically synthesized

<400> SEQUENCE: 292

Ile Ser Ser Gly Leu Leu Ser
1               5

<210> SEQ ID NO 293
<211> LENGTH: 6
<212> TYPE: PRT
<213> ORGANISM: Artificial Sequence
<220> FEATURE:
<223> OTHER INFORMATION: chemically synthesized

<400> SEQUENCE: 293

Ile Ser Ser Gly Leu Leu
1               5

<210> SEQ ID NO 294
<211> LENGTH: 19
<212> TYPE: PRT
```

<213> ORGANISM: Artificial Sequence
<220> FEATURE:
<223> OTHER INFORMATION: chemically synthesized

<400> SEQUENCE: 294

Gly Leu Ser Gly Arg Ser Asp Asn His Gly Gly Ala Val Gly Leu Leu
1               5                   10                  15

Ala Pro Pro

<210> SEQ ID NO 295
<211> LENGTH: 21
<212> TYPE: PRT
<213> ORGANISM: Artificial Sequence
<220> FEATURE:
<223> OTHER INFORMATION: chemically synthesized

<400> SEQUENCE: 295

Gly Leu Ser Gly Arg Ser Asp Asn His Gly Gly Val His Met Pro Leu
1               5                   10                  15

Gly Phe Leu Gly Pro
            20

<210> SEQ ID NO 296
<211> LENGTH: 15
<212> TYPE: PRT
<213> ORGANISM: Artificial Sequence
<220> FEATURE:
<223> OTHER INFORMATION: chemically synthesized

<400> SEQUENCE: 296

Ile Ser Ser Gly Leu Leu Ser Gly Arg Ser Ala Asn Pro Arg Gly
1               5                   10                  15

<210> SEQ ID NO 297
<211> LENGTH: 18
<212> TYPE: PRT
<213> ORGANISM: Artificial Sequence
<220> FEATURE:
<223> OTHER INFORMATION: chemically synthesized

<400> SEQUENCE: 297

Ala Val Gly Leu Leu Ala Pro Pro Thr Ser Gly Arg Ser Ala Asn Pro
1               5                   10                  15

Arg Gly

<210> SEQ ID NO 298
<211> LENGTH: 17
<212> TYPE: PRT
<213> ORGANISM: Artificial Sequence
<220> FEATURE:
<223> OTHER INFORMATION: chemically synthesized

<400> SEQUENCE: 298

Ala Val Gly Leu Leu Ala Pro Pro Ser Gly Arg Ser Ala Asn Pro Arg
1               5                   10                  15

Gly

<210> SEQ ID NO 299
<211> LENGTH: 13
<212> TYPE: PRT
<213> ORGANISM: Artificial Sequence
<220> FEATURE:
<223> OTHER INFORMATION: chemically synthesized

<400> SEQUENCE: 299

Ile Ser Ser Gly Leu Leu Ser Gly Arg Ser Asp Asp His
1               5                   10

<210> SEQ ID NO 300
<211> LENGTH: 13
<212> TYPE: PRT
<213> ORGANISM: Artificial Sequence
<220> FEATURE:
<223> OTHER INFORMATION: chemically synthesized

<400> SEQUENCE: 300

Ile Ser Ser Gly Leu Leu Ser Gly Arg Ser Asp Ile His
1               5                   10

<210> SEQ ID NO 301
<211> LENGTH: 13
<212> TYPE: PRT
<213> ORGANISM: Artificial Sequence
<220> FEATURE:
<223> OTHER INFORMATION: chemically synthesized

<400> SEQUENCE: 301

Ile Ser Ser Gly Leu Leu Ser Gly Arg Ser Asp Gln His
1               5                   10

<210> SEQ ID NO 302
<211> LENGTH: 13
<212> TYPE: PRT
<213> ORGANISM: Artificial Sequence
<220> FEATURE:
<223> OTHER INFORMATION: chemically synthesized

<400> SEQUENCE: 302

Ile Ser Ser Gly Leu Leu Ser Gly Arg Ser Asp Thr His
1               5                   10

<210> SEQ ID NO 303
<211> LENGTH: 13
<212> TYPE: PRT
<213> ORGANISM: Artificial Sequence
<220> FEATURE:
<223> OTHER INFORMATION: chemically synthesized

<400> SEQUENCE: 303

Ile Ser Ser Gly Leu Leu Ser Gly Arg Ser Asp Tyr His
1               5                   10

<210> SEQ ID NO 304
<211> LENGTH: 13
<212> TYPE: PRT
<213> ORGANISM: Artificial Sequence
<220> FEATURE:
<223> OTHER INFORMATION: chemically synthesized

<400> SEQUENCE: 304

Ile Ser Ser Gly Leu Leu Ser Gly Arg Ser Asp Asn Pro
1               5                   10

<210> SEQ ID NO 305
<211> LENGTH: 13
<212> TYPE: PRT
<213> ORGANISM: Artificial Sequence
<220> FEATURE:
<223> OTHER INFORMATION: chemically synthesized

<400> SEQUENCE: 305

Ile Ser Ser Gly Leu Leu Ser Gly Arg Ser Ala Asn Pro
1               5                   10

<210> SEQ ID NO 306
<211> LENGTH: 13
<212> TYPE: PRT
<213> ORGANISM: Artificial Sequence
<220> FEATURE:
<223> OTHER INFORMATION: chemically synthesized

<400> SEQUENCE: 306

Ile Ser Ser Gly Leu Leu Ser Gly Arg Ser Ala Asn Ile
1               5                   10

<210> SEQ ID NO 307
<211> LENGTH: 18
<212> TYPE: PRT
<213> ORGANISM: Artificial Sequence
<220> FEATURE:
<223> OTHER INFORMATION: chemically synthesized

<400> SEQUENCE: 307

Ala Val Gly Leu Leu Ala Pro Pro Gly Gly Leu Ser Gly Arg Ser Asp
1               5                   10                  15

Asp His

<210> SEQ ID NO 308
<211> LENGTH: 18
<212> TYPE: PRT
<213> ORGANISM: Artificial Sequence
<220> FEATURE:
<223> OTHER INFORMATION: chemically synthesized

<400> SEQUENCE: 308

Ala Val Gly Leu Leu Ala Pro Pro Gly Gly Leu Ser Gly Arg Ser Asp
1               5                   10                  15

Ile His

<210> SEQ ID NO 309
<211> LENGTH: 18
<212> TYPE: PRT
<213> ORGANISM: Artificial Sequence
<220> FEATURE:
<223> OTHER INFORMATION: chemically synthesized

<400> SEQUENCE: 309

Ala Val Gly Leu Leu Ala Pro Pro Gly Gly Leu Ser Gly Arg Ser Asp
1               5                   10                  15

Gln His

<210> SEQ ID NO 310
<211> LENGTH: 18
<212> TYPE: PRT
<213> ORGANISM: Artificial Sequence
<220> FEATURE:
<223> OTHER INFORMATION: chemically synthesized

<400> SEQUENCE: 310

Ala Val Gly Leu Leu Ala Pro Pro Gly Gly Leu Ser Gly Arg Ser Asp
1               5                   10                  15

Thr His

<210> SEQ ID NO 311
<211> LENGTH: 18

```
<212> TYPE: PRT
<213> ORGANISM: Artificial Sequence
<220> FEATURE:
<223> OTHER INFORMATION: chemically synthesized

<400> SEQUENCE: 311

Ala Val Gly Leu Leu Ala Pro Pro Gly Gly Leu Ser Gly Arg Ser Asp
1               5                   10                  15

Tyr His

<210> SEQ ID NO 312
<211> LENGTH: 18
<212> TYPE: PRT
<213> ORGANISM: Artificial Sequence
<220> FEATURE:
<223> OTHER INFORMATION: chemically synthesized

<400> SEQUENCE: 312

Ala Val Gly Leu Leu Ala Pro Pro Gly Gly Leu Ser Gly Arg Ser Asp
1               5                   10                  15

Asn Pro

<210> SEQ ID NO 313
<211> LENGTH: 18
<212> TYPE: PRT
<213> ORGANISM: Artificial Sequence
<220> FEATURE:
<223> OTHER INFORMATION: chemically synthesized

<400> SEQUENCE: 313

Ala Val Gly Leu Leu Ala Pro Pro Gly Gly Leu Ser Gly Arg Ser Ala
1               5                   10                  15

Asn Pro

<210> SEQ ID NO 314
<211> LENGTH: 18
<212> TYPE: PRT
<213> ORGANISM: Artificial Sequence
<220> FEATURE:
<223> OTHER INFORMATION: chemically synthesized

<400> SEQUENCE: 314

Ala Val Gly Leu Leu Ala Pro Pro Gly Gly Leu Ser Gly Arg Ser Ala
1               5                   10                  15

Asn Ile

<210> SEQ ID NO 315
<211> LENGTH: 13
<212> TYPE: PRT
<213> ORGANISM: Artificial Sequence
<220> FEATURE:
<223> OTHER INFORMATION: chemically synthesized

<400> SEQUENCE: 315

Ile Ser Ser Gly Leu Leu Ser Gly Arg Ser Asp Asn Ile
1               5                   10

<210> SEQ ID NO 316
<211> LENGTH: 18
<212> TYPE: PRT
<213> ORGANISM: Artificial Sequence
<220> FEATURE:
<223> OTHER INFORMATION: chemically synthesized

<400> SEQUENCE: 316
```

```
Ala Val Gly Leu Leu Ala Pro Pro Gly Gly Leu Ser Gly Arg Ser Asp
1               5                   10                  15

Asn Ile

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320
<211> LENGTH: 453
<212> TYPE: PRT
<213> ORGANISM: Artificial Sequence
<220> FEATURE:
<223> OTHER INFORMATION: chemically synthesized

<400> SEQUENCE: 320

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Glu Tyr
                20                  25                  30

Ile Ile His Trp Val Arg Gln Ala Pro Gly Gln Gly Leu Glu Trp Ile
            35                  40                  45

Gly Trp Phe Tyr Pro Glu Ser Gly Ser Val Lys Tyr Asn Glu Gly Phe
        50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Glu Arg Asp Tyr Tyr Gly Tyr Tyr Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 321
<211> LENGTH: 1359
<212> TYPE: DNA
<213> ORGANISM: Artificial Sequence
<220> FEATURE:
<223> OTHER INFORMATION: chemically synthesized

<400> SEQUENCE: 321
caggtgcagc tggtgcagtc tggcgccgaa gtgaagaaac ccggctcctc cgtgaaggtg      60
tcctgcaagg cctccggcta caccttcacc gagtacatca tccactgggt gcgacaggcc     120
ccaggccagg gcctggaatg gatcggctgg ttctaccccg agtccggctc cgtgaagtac     180
aacgagggct tcaagggcag agccaccatc accgccgaca gtccactcc accgcctac      240
atggaactgt cctccctgcg gagcgaggac accgccgtgt actactgcgc cagacacgag     300
gaacgggact actacggcta ctacgccatg gactactggg gccagggcac accgtgacc      360
gtgtcctctg cctccaccaa gggcccctcc gtgttccctc tggcccctc cagcaagtcc     420
acatctggcg gcaccgccgc tctgggctgc ctggtgaaag actacttccc cgagcctgtg     480
acagtgtcct ggaactctgg cgccctgacc tctggcgtgc acaccttccc tgccgtgctg     540
cagtcctccg gcctgtactc cctgtcctcc gtggtgacag tgccctcctc agcctgggc      600
acccagacct acatctgcaa cgtgaaccac aagcccctcca acaccaaggt ggacaagaag     660
gtggaaccca gtcctgcga caagacccac acctgtcccc cctgccctgc ccctgaactg     720

```
ctgggcggac cttccgtgtt tctgttcccc ccaaagccca aggacaccct gatgatctcc    780 cggaccccg aagtgacctg cgtggtggtg gacgtgtccc acgaggaccc tgaagtgaag    840
ttcaattggt acgtggacgg cgtggaagtg cacaacgcca agaccaagcc cagagaggaa    900
cagtacaact ccacctaccg ggtggtgtcc gtgctgaccg tgctgcacca ggactggctg    960
aacggcaaag agtacaagtg caaggtgtcc aacaaggccc tgcctgcccc catcgaaaag   1020
accatctcca aggccaaggg ccagcccgc gagcccagg tgtacacact gcccctagc     1080 cgggaagaga tgaccaagaa ccaggtgtcc ctgacctgtc tggtgaaagg cttctacccc   1140
tccgatatcg ccgtggaatg ggagtccaac ggccagcccg agaacaacta caagaccacc   1200 cccctgtgc tggactccga cggctcattc ttcctgtact ccaagctgac cgtggacaag   1260
tcccggtggc agcagggcaa cgtgttctcc tgcagcgtga tgcacgaggc cctgcacaac   1320
cactacaccc agaagtccct gtccctgagc cccggcaag                          1359
```

<210> SEQ ID NO 322
<211> LENGTH: 216
<212> TYPE: PRT
<213> ORGANISM: Artificial Sequence
<220> FEATURE:
<223> OTHER INFORMATION: chemically synthesized

<400> SEQUENCE: 322

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser Asn
            20                  25                  30

Tyr Leu His Trp Tyr Gln Gln Lys Pro Gly Lys Val Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Val Ala Thr Tyr Tyr Cys Gln Gln Gly Ser Ser Ile Pro
                85                  90                  95

Arg Phe Thr Ser Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 323
<211> LENGTH: 648
<212> TYPE: DNA
<213> ORGANISM: Artificial Sequence
<220> FEATURE:
<223> OTHER INFORMATION: chemically synthesized

<400> SEQUENCE: 323

| | | | | | |
|---|---|---|---|---|---|
| gacatccaga | tgacccagtc | cccatccagc | ctgtccgcct | ccgtgggcga | cagagtgaca | 60 |
| atcacctgtt | ccgccagctc | ctccatctcc | agcaactacc | tgcactggta | tcagcagaaa | 120 |
| cccggcaagg | tgcccaagct | gctgatctac | cggacctcca | acctggcctc | cggcgtgccc | 180 |
| tccagattct | ccggctctgg | ctccggcacc | gactacaccc | tgaccatcag | ctccctgcag | 240 |
| cccgaggacg | tggccaccta | ctactgccag | cagggctcca | gcatccccg | gttcacctct | 300 |
| ggcggaggca | ccaaggtgga | aatcaagcgg | accgtggccg | ctcccctccgt | gttcatcttc | 360 |
| ccacccctccg | acgagcagct | gaagtccggc | accgccagcg | tcgtgtgcct | gctgaacaac | 420 |
| ttctaccccc | gcgaggccaa | ggtgcagtgg | aaggtggaca | acgccctgca | gtccggcaac | 480 |
| tcccaggaat | ccgtcaccga | gcaggactcc | aaggacagca | cctactccct | gtcctccacc | 540 |
| ctgaccctgt | ccaaggccga | ctacgagaag | cacaaggtgt | acgcctgcga | agtgacccac | 600 |
| cagggcctgt | ccagccccgt | gaccaagtcc | ttcaaccgcg | gcgagtgc | | 648 |

<210> SEQ ID NO 324
<211> LENGTH: 263
<212> TYPE: PRT
<213> ORGANISM: Artificial Sequence
<220> FEATURE:
<223> OTHER INFORMATION: chemically synthesized

<400> SEQUENCE: 324

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ile Ser
            20                  25                  30

Ser Gly Leu Leu Ser Gly Arg Ser Asp Asn His Gly Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Ser Ala Ser Ser Ser Ile Ser Ser Asn Tyr
65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
            100                 105                 110

Ser Gly Ser Gly Thr Asp Tyr Thr Leu Thr Ile Ser Ser Leu Gln Pro
        115                 120                 125

Glu Asp Val Ala Thr Tyr Tyr Cys Gln Gln Gly Ser Ser Ile Pro Arg
    130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

```
Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
            245                 250                 255

Ser Phe Asn Arg Gly Glu Cys
            260
```

<210> SEQ ID NO 325
<211> LENGTH: 789
<212> TYPE: DNA
<213> ORGANISM: Artificial Sequence
<220> FEATURE:
<223> OTHER INFORMATION: chemically synthesized

<400> SEQUENCE: 325

```
cagggccagt ctggacaggg cgagtgcaag acccggcagg acttcgagat gcacgactgc      60
gtgtacggcg aggctcctc cggcggctcc atctcctctg cctgctgtc cggcagatcc      120
gacaaccatg gcggcggatc cgacatccag atgacccagt ccccatccag cctgtccgcc      180
tccgtgggcg acagagtgac aatcacctgt tccgccagct cctccatctc agcaactac      240
ctgcactggt atcagcagaa acccggcaag gtgcccaagc tgctgatcta ccggacctcc      300
aacctggcct ccggcgtgcc ctccagattc tccggctctg gctccggcac cgactacacc      360
ctgaccatca gctccctgca gcccgaggac gtggccacct actactgcca gcagggctcc      420
agcatccccc ggttcacctc tggcggaggc accaaggtgg aaatcaagcg gaccgtggcc      480
gctcctccg tgttcatctt cccaccctcc gacgagcagc tgaagtccgg caccgccagc      540
gtcgtgtgcc tgctgaacaa cttctacccc cgcgaggcca aggtgcagtg gaaggtggac      600
aacgccctgc agtccggcaa ctcccaggaa tccgtcaccg agcaggactc caaggacagc      660
acctactccc tgtcctccac cctgaccctg tccaaggccg actacgagaa gcacaaggtg      720
tacgcctgcg aagtgacccca ccagggcctg tccagcccg tgaccaagtc cttcaaccgc      780
ggcgagtgc                                                             789
```

<210> SEQ ID NO 326
<211> LENGTH: 263
<212> TYPE: PRT
<213> ORGANISM: Artificial Sequence
<220> FEATURE:
<223> OTHER INFORMATION: chemically synthesized

<400> SEQUENCE: 326

```
Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ile Ser
            20                  25                  30

Ser Gly Leu Leu Ser Gly Arg Ser Asp Asn His Gly Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Ser Ala Ser Ser Ser Ile Ser Ser Asn Tyr
65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
            100                 105                 110

Ser Gly Ser Gly Thr Asp Tyr Thr Leu Thr Ile Ser Ser Leu Gln Pro
```

```
                    115                 120                 125
Glu Asp Val Ala Thr Tyr Tyr Cys Gln Gln Gly Ser Ser Ile Pro Arg
    130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 327
<211> LENGTH: 789
<212> TYPE: DNA
<213> ORGANISM: Artificial Sequence
<220> FEATURE:
<223> OTHER INFORMATION: chemically synthesized

<400> SEQUENCE: 327
caaggccagt ctggccaggg tcagtgcatg tcacgttttg cttttgagat tggtgattgc      60
gttatgggag gtggctcgag cggcggctct atctcttccg gactgctgtc cggcagatcc     120
gacaatcacg gcggaggctc tgacatccag atgacccagt ccccatccag cctgtccgcc     180
tccgtgggcg acagagtgac aatcacctgt tccgccagct cctccatctc agcaactac      240 ctgcactggt atcagcagaa acccggcaag gtgcccaagc tgctgatcta ccggacctcc     300
aacctggcct ccggcgtgcc ctccagattc tccggctctg gctccggcac cgactacacc     360
ctgaccatca gctccctgca gcccgaggac gtggccacct actactgcca gcagggctcc     420
agcatccccc ggttcacctc tggcggaggc accaaggtgg aaatcaagcg accgtggcc      480 gctccctccg tgttcatctt cccaccctcc gacgagcagc tgaagtccgg caccgccagc     540
gtcgtgtgcc tgctgaacaa cttctacccc cgcgaggcca aggtgcagtg gaaggtggac     600
aacgccctgc agtccggcaa ctcccaggaa tccgtcaccg agcaggactc caaggacagc     660
acctactccc tgtcctccac cctgaccctg tccaaggccg actacgagaa gcacaaggtg     720
tacgcctgcg aagtgaccca ccagggcctg tccagccccg tgaccaagtc cttcaaccgc     780
ggcgagtgc                                                             789

<210> SEQ ID NO 328
<211> LENGTH: 263
<212> TYPE: PRT
<213> ORGANISM: Artificial Sequence
<220> FEATURE:
<223> OTHER INFORMATION: chemically synthesized

<400> SEQUENCE: 328

Gln Gly Gln Ser Gly Gln Gly Thr Cys Leu Ser Arg Tyr Glu Phe Glu
1               5                   10                  15
```

Thr Thr Asp Cys Val Met Gly Gly Ser Ser Gly Gly Ser Ile Ser
            20                  25                  30

Ser Gly Leu Leu Ser Gly Arg Ser Asp Asn His Gly Gly Ser Asp
        35                  40                  45

Ile Val Met Thr Gln Thr Pro Thr Thr Leu Ala Ala Ser Pro Gly Glu
50                  55                  60

Lys Ile Ile Ile Thr Cys Ser Ala Ser Ser Ile Ser Ser Asn Tyr
65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
            100                 105                 110

Ser Gly Ser Gly Thr Ser Tyr Ser Leu Thr Ile Gly Thr Met Glu Ala
        115                 120                 125

Glu Asp Val Ala Thr Tyr Tyr Cys Gln Gln Gly Ser Ser Ile Pro Arg
130                 135                 140

Phe Thr Ser Gly Ser Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 329
<211> LENGTH: 789
<212> TYPE: DNA
<213> ORGANISM: Artificial Sequence
<220> FEATURE:
<223> OTHER INFORMATION: chemically synthesized

<400> SEQUENCE: 329
caaggccagt ctggccaggg tacgtgcctg agtaggtatg agtttgagac gactgattgc      60
gttatgggag gtggctcgag cggcggctct atctcttccg gactgctgtc ggcagatcc      120 gacaatcacg gcggaggctc tgacatccag atgacccagt ccccatccag cctgtccgcc     180
tccgtgggcg acagagtgac aatcacctgt tccgccagct cctccatctc cagcaactac     240
ctgcactggt atcagcagaa acccggcaag gtgcccaagc tgctgatcta ccggacctcc     300
aacctggcct ccggcgtgcc ctccagattc tccggctctg gctccggcac cgactacacc     360
ctgaccatca gctccctgca gcccgaggac gtggccacct actactgcca gcagggctcc     420
agcatccccc ggttcacctc tggcggaggc accaaggtgg aaatcaagcg gaccgtggcc     480 gctcccctccg tgttcatctt cccacccctcc gacgagcagc tgaagtccgg caccgccagc    540
gtcgtgtgcc tgctgaacaa cttctacccc cgcgaggcca aggtgcagtg gaaggtggac     600

-continued

```
aacgccctgc agtccggcaa ctcccaggaa tccgtcaccg agcaggactc caaggacagc    660
acctactccc tgtcctccac cctgaccctg tccaaggccg actacgagaa gcacaaggtg    720
tacgcctgcg aagtgaccca ccagggcctg tccagccccg tgaccaagtc cttcaaccgc    780
ggcgagtgc                                                            789
```

<210> SEQ ID NO 330
<211> LENGTH: 263
<212> TYPE: PRT
<213> ORGANISM: Artificial Sequence
<220> FEATURE:
<223> OTHER INFORMATION: chemically synthesized

<400> SEQUENCE: 330

```
Gln Gly Gln Ser Gly Gln Gly Val Cys Arg Thr Arg Trp His Phe Glu
1               5                   10                  15
Thr Thr Asp Cys Val Met Gly Gly Ser Ser Gly Gly Ser Ile Ser
            20                  25                  30
Ser Gly Leu Leu Ser Gly Arg Ser Asp Asn His Gly Gly Gly Ser Asp
        35                  40                  45
Ile Val Met Thr Gln Thr Pro Thr Thr Leu Ala Ala Ser Pro Gly Glu
    50                  55                  60
Lys Ile Ile Ile Thr Cys Ser Ala Ser Ser Ser Ile Ser Ser Asn Tyr
65                  70                  75                  80
Leu His Trp Tyr Gln Gln Lys Pro Gly Phe Ser Pro Lys Leu Leu Ile
                85                  90                  95
Tyr Arg Thr Ser Asn Leu Ala Ser Gly Val Pro Ala Arg Phe Ser Gly
            100                 105                 110
Ser Gly Ser Gly Thr Ser Tyr Ser Leu Thr Ile Gly Thr Met Glu Ala
        115                 120                 125
Glu Asp Val Ala Thr Tyr Tyr Cys Gln Gln Gly Ser Ser Ile Pro Arg
    130                 135                 140
Phe Thr Ser Gly Ser Gly Thr Lys Leu Glu Ile Lys Arg Thr Val Ala
145                 150                 155                 160
Ala Pro Ser Val Phe Ile Phe Pro Pro Ser Asp Glu Gln Leu Lys Ser
                165                 170                 175
Gly Thr Ala Ser Val Val Cys Leu Leu Asn Asn Phe Tyr Pro Arg Glu
            180                 185                 190
Ala Lys Val Gln Trp Lys Val Asp Asn Ala Leu Gln Ser Gly Asn Ser
        195                 200                 205
Gln Glu Ser Val Thr Glu Gln Asp Ser Lys Asp Ser Thr Tyr Ser Leu
    210                 215                 220
Ser Ser Thr Leu Thr Leu Ser Lys Ala Asp Tyr Glu Lys His Lys Val
225                 230                 235                 240
Tyr Ala Cys Glu Val Thr His Gln Gly Leu Ser Ser Pro Val Thr Lys
                245                 250                 255
Ser Phe Asn Arg Gly Glu Cys
            260
```

<210> SEQ ID NO 331
<211> LENGTH: 789
<212> TYPE: DNA
<213> ORGANISM: Artificial Sequence
<220> FEATURE:
<223> OTHER INFORMATION: chemically synthesized

<400> SEQUENCE: 331

```
caaggccagt ctggccaggg tgtgtgccgg actaggtggc attttgagac tacggattgc      60
gttatgggag gtggctcgag cggcggctct atctcttccg gactgctgtc cggcagatcc     120
gacaatcacg gcggaggctc tgacatccag atgacccagt ccccatccag cctgtccgcc     180
tccgtgggcg acagagtgac aatcacctgt tccgccagct cctccatctc cagcaactac     240
ctgcactggt atcagcagaa accggcaagg tgcccaagc tgctgatcta ccggacctcc      300
aacctggcct ccggcgtgcc ctccagattc tccggctctg gctccggcac cgactacacc     360
ctgaccatca gctccctgca gcccgaggac gtggccacct actactgcca gcagggctcc     420
agcatccccc ggttcaccct ggcggaggc accaaggtgg aaatcaagcg gaccgtggcc      480
gctccctccg tgttcatctt cccaccctcc gacgagcagc tgaagtccgg caccgccagc     540
gtcgtgtgcc tgctgaacaa cttctacccc cgcgaggcca aggtgcagtg gaaggtggac     600
aacgccctgc agtccggcaa ctcccaggaa tccgtcaccg agcaggactc caaggacagc     660
acctactccc tgtcctccac cctgaccctg tccaaggccg actacgagaa gcacaaggtg     720
tacgcctgcg aagtgaccca ccagggcctg tccagccccg tgaccaagtc cttcaaccgc     780
ggcgagtgc                                                             789
```

<210> SEQ ID NO 332
<211> LENGTH: 267
<212> TYPE: PRT
<213> ORGANISM: Artificial Sequence
<220> FEATURE:
<223> OTHER INFORMATION: chemically synthesized
<400> SEQUENCE: 332

```
Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
        115                 120                 125

Ser Leu Gln Pro Glu Asp Val Ala Thr Tyr Tyr Cys Gln Gln Gly Ser
    130                 135                 140

Ser Ile Pro Arg Phe Thr Ser Gly Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220
```

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 333
<211> LENGTH: 267
<212> TYPE: PRT
<213> ORGANISM: Artificial Sequence
<220> FEATURE:
<223> OTHER INFORMATION: chemically synthesized

<400> SEQUENCE: 333

Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ala Val
                20                  25                  30

Gly Leu Leu Ala Pro Pro Gly Gly Leu Ser Gly Arg Ser Asp Asn His
            35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
        115                 120                 125

Ser Leu Gln Pro Glu Asp Val Ala Thr Tyr Tyr Cys Gln Gln Gly Ser
    130                 135                 140

Ser Ile Pro Arg Phe Thr Ser Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 334
<211> LENGTH: 267
<212> TYPE: PRT
<213> ORGANISM: Artificial Sequence
<220> FEATURE:
<223> OTHER INFORMATION: chemically synthesized

<400> SEQUENCE: 334

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Leu Ser Gly Arg Ser Asp Asn His
        35                  40                  45

Gly Gly Ser Asp Ile Val Met Thr Gln Thr Pro Thr Thr Leu Ala Ala
    50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
    130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 335
<211> LENGTH: 267
<212> TYPE: PRT
<213> ORGANISM: Artificial Sequence
<220> FEATURE:
<223> OTHER INFORMATION: chemically synthesized

<400> SEQUENCE: 335

Gln Gly Gln Ser Gly Gln Gly Val Cys Arg Thr Arg Trp His Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Ser Asp Ile Val Met Thr Gln Thr Pro Thr Thr Leu Ala Ala
    50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro

```
                85                  90                  95
Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
    130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
            195                 200                 205

Ser Gly Asn Ser Gln Glu Ser Val Thr Glu Gln Asp Ser Lys Asp Ser
        210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 336
<211> LENGTH: 263
<212> TYPE: PRT
<213> ORGANISM: Artificial Sequence
<220> FEATURE:
<223> OTHER INFORMATION: chemically synthesized

<400> SEQUENCE: 336

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ile Ser
            20                  25                  30

Ser Gly Leu Leu Ser Gly Arg Ser Asp Gln His Gly Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Ser Ala Ser Ser Ile Ser Ser Asn Tyr
65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
            100                 105                 110

Ser Gly Ser Gly Thr Asp Tyr Thr Leu Thr Ile Ser Ser Leu Gln Pro
        115                 120                 125

Glu Asp Val Ala Thr Tyr Tyr Cys Gln Gln Gly Ser Ser Ile Pro Arg
    130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
```

```
                180                 185                 190
Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 337
<211> LENGTH: 263
<212> TYPE: PRT
<213> ORGANISM: Artificial Sequence
<220> FEATURE:
<223> OTHER INFORMATION: chemically synthesized

<400> SEQUENCE: 337

Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ile Ser
            20                  25                  30

Ser Gly Leu Leu Ser Gly Arg Ser Asp Gln His Gly Gly Ser Asp
        35                  40                  45

Ile Gln Met Thr Gln Ser Pro Ser Ser Leu Ser Ala Ser Val Gly Asp
50                  55                  60

Arg Val Thr Ile Thr Cys Ser Ala Ser Ser Ile Ser Ser Asn Tyr
65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
            100                 105                 110

Ser Gly Ser Gly Thr Asp Tyr Thr Leu Thr Ile Ser Ser Leu Gln Pro
        115                 120                 125

Glu Asp Val Ala Thr Tyr Tyr Cys Gln Gln Gly Ser Ser Ile Pro Arg
    130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260
```

<210> SEQ ID NO 338
<211> LENGTH: 263
<212> TYPE: PRT
<213> ORGANISM: Artificial Sequence
<220> FEATURE:
<223> OTHER INFORMATION: chemically synthesized

<400> SEQUENCE: 338

```
Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Ser Ile Ser
            20                  25                  30

Ser Gly Leu Leu Ser Gly Arg Ser Asp Gln His Gly Gly Gly Ser Asp
        35                  40                  45

Ile Val Met Thr Gln Thr Pro Thr Leu Ala Ala Ser Pro Gly Glu
    50                  55                  60

Lys Ile Ile Ile Thr Cys Ser Ala Ser Ser Ile Ser Ser Asn Tyr
65              70                  75                  80

Leu His Trp Tyr Gln Gln Lys Pro Gly Phe Ser Pro Lys Leu Leu Ile
            85                  90                  95

Tyr Arg Thr Ser Asn Leu Ala Ser Gly Val Pro Ala Arg Phe Ser Gly
            100                 105                 110

Ser Gly Ser Gly Thr Ser Tyr Ser Leu Thr Ile Gly Thr Met Glu Ala
        115                 120                 125

Glu Asp Val Ala Thr Tyr Tyr Cys Gln Gln Gly Ser Ser Ile Pro Arg
    130                 135                 140

Phe Thr Ser Gly Ser Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
        260
```

<210> SEQ ID NO 339
<211> LENGTH: 263
<212> TYPE: PRT
<213> ORGANISM: Artificial Sequence
<220> FEATURE:
<223> OTHER INFORMATION: chemically synthesized

<400> SEQUENCE: 339

```
Gln Gly Gln Ser Gly Gln Gly Val Cys Arg Thr Arg Trp His Phe Glu
1               5                   10                  15

Thr Thr Asp Cys Val Met Gly Gly Gly Ser Ser Gly Ser Ile Ser
            20                  25                  30

Ser Gly Leu Leu Ser Gly Arg Ser Asp Gln His Gly Gly Gly Ser Asp
        35                  40                  45
```

```
Ile Val Met Thr Gln Thr Pro Thr Thr Leu Ala Ala Ser Pro Gly Glu
 50                  55                  60

Lys Ile Ile Ile Thr Cys Ser Ala Ser Ser Ile Ser Ser Asn Tyr
 65                  70                  75                  80

Leu His Trp Tyr Gln Gln Lys Pro Gly Phe Ser Pro Lys Leu Leu Ile
                 85                  90                  95

Tyr Arg Thr Ser Asn Leu Ala Ser Gly Val Pro Ala Arg Phe Ser Gly
             100                 105                 110

Ser Gly Ser Gly Thr Ser Tyr Ser Leu Thr Ile Gly Thr Met Glu Ala
             115                 120                 125

Glu Asp Val Ala Thr Tyr Tyr Cys Gln Gln Gly Ser Ser Ile Pro Arg
 130                 135                 140

Phe Thr Ser Gly Ser Gly Thr Lys Leu Glu Ile Lys Arg Thr Val Ala
 145                 150                 155                 160

Ala Pro Ser Val Phe Ile Phe Pro Pro Ser Asp Glu Gln Leu Lys Ser
                 165                 170                 175

Gly Thr Ala Ser Val Val Cys Leu Leu Asn Asn Phe Tyr Pro Arg Glu
             180                 185                 190

Ala Lys Val Gln Trp Lys Val Asp Asn Ala Leu Gln Ser Gly Asn Ser
             195                 200                 205

Gln Glu Ser Val Thr Glu Gln Asp Ser Lys Asp Ser Thr Tyr Ser Leu
 210                 215                 220

Ser Ser Thr Leu Thr Leu Ser Lys Ala Asp Tyr Glu Lys His Lys Val
 225                 230                 235                 240

Tyr Ala Cys Glu Val Thr His Gln Gly Leu Ser Ser Pro Val Thr Lys
                 245                 250                 255

Ser Phe Asn Arg Gly Glu Cys
             260

<210> SEQ ID NO 340
<211> LENGTH: 267
<212> TYPE: PRT
<213> ORGANISM: Artificial Sequence
<220> FEATURE:
<223> OTHER INFORMATION: chemically synthesized

<400> SEQUENCE: 340

Gln Gly Gln Ser Gly Gln Gly Glu Cys Lys Thr Arg Gln Asp Phe Glu
 1               5                  10                  15

Met His Asp Cys Val Tyr Gly Gly Ser Gly Gly Ser Ala Val
                 20                  25                  30

Gly Leu Leu Ala Pro Pro Gly Leu Ser Gly Arg Ser Asp Gln His
             35                  40                  45

Gly Gly Ser Asp Ile Gln Met Thr Gln Ser Pro Ser Ser Leu Ser Ala
 50                  55                  60

Ser Val Gly Asp Arg Val Thr Ile Thr Cys Ser Ala Ser Ser Ile
 65                  70                  75                  80

Ser Ser Asn Tyr Leu His Trp Tyr Gln Gln Lys Pro Gly Lys Val Pro
                 85                  90                  95

Lys Leu Leu Ile Tyr Arg Thr Ser Asn Leu Ala Ser Gly Val Pro Ser
             100                 105                 110

Arg Phe Ser Gly Ser Gly Ser Gly Thr Asp Tyr Thr Leu Thr Ile Ser
             115                 120                 125

Ser Leu Gln Pro Glu Asp Val Ala Thr Tyr Tyr Cys Gln Gln Gly Ser
 130                 135                 140
```

```
Ser Ile Pro Arg Phe Thr Ser Gly Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
                260                 265
```

<210> SEQ ID NO 341
<211> LENGTH: 267
<212> TYPE: PRT
<213> ORGANISM: Artificial Sequence
<220> FEATURE:
<223> OTHER INFORMATION: chemically synthesized

<400> SEQUENCE: 341

```
Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ala Val
                20                  25                  30

Gly Leu Leu Ala Pro Pro Gly Gly Leu Ser Gly Arg Ser Asp Gln His
            35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
        115                 120                 125

Ser Leu Gln Pro Glu Asp Val Ala Thr Tyr Tyr Cys Gln Gln Gly Ser
    130                 135                 140

Ser Ile Pro Arg Phe Thr Ser Gly Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240
```

```
Lys His Lys Val Tyr Ala Cys Glu Val Thr His Gln Gly Leu Ser Ser
            245                 250                 255

Pro Val Thr Lys Ser Phe Asn Arg Gly Glu Cys
            260                 265

<210> SEQ ID NO 342
<211> LENGTH: 267
<212> TYPE: PRT
<213> ORGANISM: Artificial Sequence
<220> FEATURE:
<223> OTHER INFORMATION: chemically synthesized

<400> SEQUENCE: 342

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Gly Leu Ser Gly Arg Ser Asp Gln His
        35                  40                  45

Gly Gly Ser Asp Ile Val Met Thr Gln Thr Pro Thr Thr Leu Ala Ala
    50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
    130                 135                 140

Ser Ile Pro Arg Phe Thr Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 343
<211> LENGTH: 267
<212> TYPE: PRT
<213> ORGANISM: Artificial Sequence
<220> FEATURE:
<223> OTHER INFORMATION: chemically synthesized

<400> SEQUENCE: 343

Gln Gly Gln Ser Gly Gln Gly Val Cys Arg Thr Arg Trp His Phe Glu
1               5                   10                  15
```

```
Thr Thr Asp Cys Val Met Gly Gly Ser Ser Gly Gly Ser Ala Val
             20                  25                  30

Gly Leu Leu Ala Pro Pro Gly Gly Leu Ser Gly Arg Ser Asp Gln His
         35                  40                  45

Gly Gly Ser Asp Ile Val Met Thr Gln Thr Pro Thr Thr Leu Ala Ala
     50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                 85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
    130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 344
<211> LENGTH: 263
<212> TYPE: PRT
<213> ORGANISM: Artificial Sequence
<220> FEATURE:
<223> OTHER INFORMATION: chemically synthesized

<400> SEQUENCE: 344

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ile Ser
             20                  25                  30

Ser Gly Leu Leu Ser Gly Arg Ser Asp Asn Pro Gly Gly Ser Asp
         35                  40                  45

Ile Gln Met Thr Gln Ser Pro Ser Ser Leu Ser Ala Ser Val Gly Asp
     50                  55                  60

Arg Val Thr Ile Thr Cys Ser Ala Ser Ser Ile Ser Ser Asn Tyr
65                  70                  75                  80

Leu His Trp Tyr Gln Gln Lys Pro Gly Lys Val Pro Lys Leu Leu Ile
                 85                  90                  95

Tyr Arg Thr Ser Asn Leu Ala Ser Gly Val Pro Ser Arg Phe Ser Gly
            100                 105                 110
```

```
Ser Gly Ser Gly Thr Asp Tyr Thr Leu Thr Ile Ser Ser Leu Gln Pro
        115                 120                 125

Glu Asp Val Ala Thr Tyr Tyr Cys Gln Gln Gly Ser Ser Ile Pro Arg
130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 345
<211> LENGTH: 263
<212> TYPE: PRT
<213> ORGANISM: Artificial Sequence
<220> FEATURE:
<223> OTHER INFORMATION: chemically synthesized

<400> SEQUENCE: 345

Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ile Ser
                20                  25                  30

Ser Gly Leu Leu Ser Gly Arg Ser Asp Asn Pro Gly Gly Gly Ser Asp
            35                  40                  45

Ile Gln Met Thr Gln Ser Pro Ser Ser Leu Ser Ala Ser Val Gly Asp
50                  55                  60

Arg Val Thr Ile Thr Cys Ser Ala Ser Ser Ile Ser Ser Asn Tyr
65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
            100                 105                 110

Ser Gly Ser Gly Thr Asp Tyr Thr Leu Thr Ile Ser Ser Leu Gln Pro
        115                 120                 125

Glu Asp Val Ala Thr Tyr Tyr Cys Gln Gln Gly Ser Ser Ile Pro Arg
130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205
```

```
Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 346
<211> LENGTH: 263
<212> TYPE: PRT
<213> ORGANISM: Artificial Sequence
<220> FEATURE:
<223> OTHER INFORMATION: chemically synthesized

<400> SEQUENCE: 346

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ile Ser
                20                  25                  30

Ser Gly Leu Leu Ser Gly Arg Ser Asp Asn Pro Gly Gly Ser Asp
            35                  40                  45

Ile Val Met Thr Gln Thr Pro Thr Thr Leu Ala Ala Ser Pro Gly Glu
    50                  55                  60

Lys Ile Ile Ile Thr Cys Ser Ala Ser Ser Ser Ile Ser Ser Asn Tyr
65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
                100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
    130                 135                 140

Phe Thr Ser Gly Ser Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
    195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 347
<211> LENGTH: 263
<212> TYPE: PRT
<213> ORGANISM: Artificial Sequence
```

<220> FEATURE:
<223> OTHER INFORMATION: chemically synthesized

<400> SEQUENCE: 347

```
Gln Gly Gln Ser Gly Gln Gly Val Cys Arg Thr Arg Trp His Phe Glu
1               5                   10                  15

Thr Thr Asp Cys Val Met Gly Gly Ser Ser Gly Gly Ser Ile Ser
            20                  25                  30

Ser Gly Leu Leu Ser Gly Arg Ser Asp Asn Pro Gly Gly Gly Ser Asp
            35                  40                  45

Ile Val Met Thr Gln Thr Pro Thr Thr Leu Ala Ala Ser Pro Gly Glu
        50                  55                  60

Lys Ile Ile Ile Thr Cys Ser Ala Ser Ser Ile Ser Ser Asn Tyr
65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
            100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
130                 135                 140

Phe Thr Ser Gly Ser Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
        210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260
```

<210> SEQ ID NO 348
<211> LENGTH: 267
<212> TYPE: PRT
<213> ORGANISM: Artificial Sequence
<220> FEATURE:
<223> OTHER INFORMATION: chemically synthesized

<400> SEQUENCE: 348

```
Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ala Val
            20                  25                  30

Gly Leu Leu Ala Pro Pro Gly Gly Leu Ser Gly Arg Ser Asp Asn Pro
            35                  40                  45

Gly Gly Ser Asp Ile Gln Met Thr Gln Ser Pro Ser Ser Leu Ser Ala
        50                  55                  60

Ser Val Gly Asp Arg Val Thr Ile Thr Cys Ser Ala Ser Ser Ser Ile
```

```
              65                  70                  75                  80
Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
        130                 135                 140

Ser Ile Pro Arg Phe Thr Ser Gly Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 349
<211> LENGTH: 267
<212> TYPE: PRT
<213> ORGANISM: Artificial Sequence
<220> FEATURE:
<223> OTHER INFORMATION: chemically synthesized

<400> SEQUENCE: 349

Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ala Val
            20                  25                  30

Gly Leu Leu Ala Pro Pro Gly Gly Leu Ser Gly Arg Ser Asp Asn Pro
        35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
        130                 135                 140

Ser Ile Pro Arg Phe Thr Ser Gly Gly Gly Thr Lys Val Glu Ile Lys
145                 150                 155                 160

Arg Thr Val Ala Ala Pro Ser Val Phe Ile Phe Pro Pro Ser Asp Glu
```

165                 170                 175

Gln Leu Lys Ser Gly Thr Ala Ser Val Val Cys Leu Leu Asn Asn Phe
                180                 185                 190

Tyr Pro Arg Glu Ala Lys Val Gln Trp Lys Val Asp Asn Ala Leu Gln
            195                 200                 205

Ser Gly Asn Ser Gln Glu Ser Val Thr Glu Gln Asp Ser Lys Asp Ser
        210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 350
<211> LENGTH: 267
<212> TYPE: PRT
<213> ORGANISM: Artificial Sequence
<220> FEATURE:
<223> OTHER INFORMATION: chemically synthesized

<400> SEQUENCE: 350

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
                20                  25                  30

Gly Leu Leu Ala Pro Pro Gly Gly Leu Ser Gly Arg Ser Asp Asn Pro
            35                  40                  45

Gly Gly Ser Asp Ile Val Met Thr Gln Thr Pro Thr Thr Leu Ala Ala
        50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys

<210> SEQ ID NO 351
<211> LENGTH: 267
<212> TYPE: PRT
<213> ORGANISM: Artificial Sequence
<220> FEATURE:
<223> OTHER INFORMATION: chemically synthesized

<400> SEQUENCE: 351

Gln Gly Gln Ser Gly Gln Gly Val Cys Arg Thr Arg Trp His Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Gly Leu Ser Gly Arg Ser Asp Asn Pro
        35                  40                  45

Gly Gly Ser Asp Ile Val Met Thr Gln Thr Pro Thr Thr Leu Ala Ala
    50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 352
<211> LENGTH: 263
<212> TYPE: PRT
<213> ORGANISM: Artificial Sequence
<220> FEATURE:
<223> OTHER INFORMATION: chemically synthesized

<400> SEQUENCE: 352

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ile Ser
            20                  25                  30

```
Ser Gly Leu Leu Ser Gly Arg Ser Ala Asn Pro Gly Gly Ser Asp
        35                  40                  45

Ile Gln Met Thr Gln Ser Pro Ser Ser Leu Ser Ala Ser Val Gly Asp
 50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
                    85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
                115                 120                 125

Glu Asp Val Ala Thr Tyr Tyr Cys Gln Gln Gly Ser Ser Ile Pro Arg
130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
                180                 185                 190

Ala Lys Val Gln Trp Lys Val Asp Asn Ala Leu Gln Ser Gly Asn Ser
                195                 200                 205

Gln Glu Ser Val Thr Glu Gln Asp Ser Lys Asp Ser Thr Tyr Ser Leu
                210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260

<210> SEQ ID NO 353
<211> LENGTH: 263
<212> TYPE: PRT
<213> ORGANISM: Artificial Sequence
<220> FEATURE:
<223> OTHER INFORMATION: chemically synthesized

<400> SEQUENCE: 353

Gln Gly Gln Ser Gly Gln Gly Gln Cys Met Ser Arg Phe Ala Phe Glu
 1                   5                  10                  15

Ile Gly Asp Cys Val Met Gly Gly Ser Ser Gly Gly Ser Ile Ser
                 20                  25                  30

Ser Gly Leu Leu Ser Gly Arg Ser Ala Asn Pro Gly Gly Ser Asp
        35                  40                  45

Ile Gln Met Thr Gln Ser Pro Ser Ser Leu Ser Ala Ser Val Gly Asp
 50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
                    85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
                115                 120                 125
```

```
Glu Asp Val Ala Thr Tyr Tyr Cys Gln Gln Gly Ser Ser Ile Pro Arg
            130                 135                 140

Phe Thr Ser Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
                180                 185                 190

Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
            260

<210> SEQ ID NO 354
<211> LENGTH: 263
<212> TYPE: PRT
<213> ORGANISM: Artificial Sequence
<220> FEATURE:
<223> OTHER INFORMATION: chemically synthesized

<400> SEQUENCE: 354

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ile Ser
            20                  25                  30

Ser Gly Leu Leu Ser Gly Arg Ser Ala Asn Pro Gly Gly Gly Ser Asp
            35                  40                  45

Ile Val Met Thr Gln Thr Pro Thr Thr Leu Ala Ala Ser Pro Gly Glu
50                  55                  60

Lys Ile Ile Ile Thr Cys Ser Ala Ser Ser Ile Ser Ser Asn Tyr
65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
                100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
            130                 135                 140

Phe Thr Ser Gly Ser Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
                180                 185                 190

Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
    210                 215                 220
```

```
Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260
```

<210> SEQ ID NO 355
<211> LENGTH: 263
<212> TYPE: PRT
<213> ORGANISM: Artificial Sequence
<220> FEATURE:
<223> OTHER INFORMATION: chemically synthesized

<400> SEQUENCE: 355

```
Gln Gly Gln Ser Gly Gln Gly Val Cys Arg Thr Arg Trp His Phe Glu
1               5                   10                  15

Thr Thr Asp Cys Val Met Gly Gly Ser Ser Gly Gly Ser Ile Ser
                20                  25                  30

Ser Gly Leu Leu Ser Gly Arg Ser Ala Asn Pro Gly Gly Gly Ser Asp
            35                  40                  45

Ile Val Met Thr Gln Thr Pro Thr Thr Leu Ala Ala Ser Pro Gly Glu
    50                  55                  60

Lys Ile Ile Ile Thr Cys Ser Ala Ser Ser Ser Ile Ser Ser Asn Tyr
65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
                100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
    130                 135                 140

Phe Thr Ser Gly Ser Gly Thr Lys Leu Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
    195                 200                 205

Gln Glu Ser Val Thr Glu Gln Asp Ser Lys Asp Ser Thr Tyr Ser Leu
210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
                245                 250                 255

Ser Phe Asn Arg Gly Glu Cys
                260
```

<210> SEQ ID NO 356
<211> LENGTH: 267
<212> TYPE: PRT
<213> ORGANISM: Artificial Sequence
<220> FEATURE:
<223> OTHER INFORMATION: chemically synthesized

<400> SEQUENCE: 356

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ala Val
            20                  25                  30

Gly Leu Leu Ala Pro Pro Gly Gly Leu Ser Gly Arg Ser Ala Asn Pro
            35                  40                  45

Gly Gly Ser Asp Ile Gln Met Thr Gln Ser Pro Ser Ser Leu Ser Ala
        50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
                100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
        130                 135                 140

Ser Ile Pro Arg Phe Thr Ser Gly Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
                180                 185                 190

Tyr Pro Arg Glu Ala Lys Val Gln Trp Lys Val Asp Asn Ala Leu Gln
            195                 200                 205

Ser Gly Asn Ser Gln Glu Ser Val Thr Glu Gln Asp Ser Lys Asp Ser
        210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 357
<211> LENGTH: 267
<212> TYPE: PRT
<213> ORGANISM: Artificial Sequence
<220> FEATURE:
<223> OTHER INFORMATION: chemically synthesized

<400> SEQUENCE: 357

Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ala Val
            20                  25                  30

Gly Leu Leu Ala Pro Pro Gly Gly Leu Ser Gly Arg Ser Ala Asn Pro
            35                  40                  45

Gly Gly Ser Asp Ile Gln Met Thr Gln Ser Pro Ser Ser Leu Ser Ala
        50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

```
Lys Leu Leu Ile Tyr Arg Thr Ser Asn Leu Ala Ser Gly Val Pro Ser
                100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
        130                 135                 140

Ser Ile Pro Arg Phe Thr Ser Gly Gly Thr Lys Val Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
                260                 265

<210> SEQ ID NO 358
<211> LENGTH: 267
<212> TYPE: PRT
<213> ORGANISM: Artificial Sequence
<220> FEATURE:
<223> OTHER INFORMATION: chemically synthesized

<400> SEQUENCE: 358

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
                20                  25                  30

Gly Leu Leu Ala Pro Pro Gly Gly Leu Ser Gly Arg Ser Ala Asn Pro
            35                  40                  45

Gly Gly Ser Asp Ile Val Met Thr Gln Thr Pro Thr Thr Leu Ala Ala
        50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
                100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
        130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190
```

Tyr Pro Arg Glu Ala Lys Val Gln Trp Lys Val Asp Asn Ala Leu Gln
            195                 200                 205

Ser Gly Asn Ser Gln Glu Ser Val Thr Glu Gln Asp Ser Lys Asp Ser
        210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 359
<211> LENGTH: 267
<212> TYPE: PRT
<213> ORGANISM: Artificial Sequence
<220> FEATURE:
<223> OTHER INFORMATION: chemically synthesized

<400> SEQUENCE: 359

Gln Gly Gln Ser Gly Gln Gly Val Cys Arg Thr Arg Trp His Phe Glu
1               5                   10                  15

Thr Thr Asp Cys Val Met Gly Gly Ser Ser Gly Gly Ser Ala Val
            20                  25                  30

Gly Leu Leu Ala Pro Gly Gly Leu Ser Gly Arg Ser Ala Asn Pro
                35                  40                  45

Gly Gly Ser Asp Ile Val Met Thr Gln Thr Pro Thr Thr Leu Ala Ala
        50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
130                 135                 140

Ser Ile Pro Arg Phe Thr Ser Gly Ser Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
            195                 200                 205

Ser Gly Asn Ser Gln Glu Ser Val Thr Glu Gln Asp Ser Lys Asp Ser
        210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265

<210> SEQ ID NO 360

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364
<211> LENGTH: 260
<212> TYPE: PRT
<213> ORGANISM: Artificial Sequence
<220> FEATURE:
<223> OTHER INFORMATION: chemically synthesized

<400> SEQUENCE: 364

```
Glu Cys Lys Thr Arg Gln Asp Phe Glu Met His Asp Cys Val Tyr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Gln Met
        35                  40                  45

Thr Gln Ser Pro Ser Ser Leu Ser Ala Ser Val Gly Asp Arg Val Thr
50                  55                  60

Ile Thr Cys Ser Ala Ser Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
```

```
                    225                 230                 235                 240
Glu Val Thr His Gln Gly Leu Ser Ser Pro Val Thr Lys Ser Phe Asn
                245                 250                 255

Arg Gly Glu Cys
            260

<210> SEQ ID NO 365
<211> LENGTH: 260
<212> TYPE: PRT
<213> ORGANISM: Artificial Sequence
<220> FEATURE:
<223> OTHER INFORMATION: chemically synthesized

<400> SEQUENCE: 365

Gln Cys Met Ser Arg Phe Ala Phe Glu Ile Gly Asp Cys Val Met Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Asn His Gly Gly Ser Asp Ile Gln Met
            35                  40                  45

Thr Gln Ser Pro Ser Ser Leu Ser Ala Ser Val Gly Asp Arg Val Thr
        50                  55                  60

Ile Thr Cys Ser Ala Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 366
<211> LENGTH: 260
<212> TYPE: PRT
<213> ORGANISM: Artificial Sequence
<220> FEATURE:
<223> OTHER INFORMATION: chemically synthesized

<400> SEQUENCE: 366
```

```
Thr Cys Leu Ser Arg Tyr Glu Phe Glu Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
            35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
            100                 105                 110

Gly Thr Ser Tyr Ser Leu Thr Ile Gly Thr Met Glu Ala Glu Asp Val
            115                 120                 125

Ala Thr Tyr Tyr Cys Gln Gln Gly Ser Ser Ile Pro Arg Phe Thr Ser
            130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
            195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 367
<211> LENGTH: 260
<212> TYPE: PRT
<213> ORGANISM: Artificial Sequence
<220> FEATURE:
<223> OTHER INFORMATION: chemically synthesized

<400> SEQUENCE: 367

Val Cys Arg Thr Arg Trp His Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
            35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95
```

Ser Asn Leu Ala Ser Gly Val Pro Ala Arg Phe Ser Gly Ser
            100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 368
<211> LENGTH: 256
<212> TYPE: PRT
<213> ORGANISM: Artificial Sequence
<220> FEATURE:
<223> OTHER INFORMATION: chemically synthesized

<400> SEQUENCE: 368

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255

<210> SEQ ID NO 369
<211> LENGTH: 256
<212> TYPE: PRT
<213> ORGANISM: Artificial Sequence
<220> FEATURE:
<223> OTHER INFORMATION: chemically synthesized

<400> SEQUENCE: 369

Gln Cys Met Ser Arg Phe Ala Phe Glu Ile Gly Asp Cys Val Met Gly
1               5                   10                  15

Gly Gly Ser Gly Gly Ser Ile Ser Ser Gly Leu Leu Ser Gly Arg
                20                  25                  30

Ser Asp Gln His Gly Gly Gly Ser Asp Ile Gln Met Thr Gln Ser Pro
            35                  40                  45

Ser Ser Leu Ser Ala Ser Val Gly Asp Arg Val Thr Ile Thr Cys Ser
50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255

<210> SEQ ID NO 370
<211> LENGTH: 256
<212> TYPE: PRT
<213> ORGANISM: Artificial Sequence
<220> FEATURE:
<223> OTHER INFORMATION: chemically synthesized

<400> SEQUENCE: 370

```
Thr Cys Leu Ser Arg Tyr Glu Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Gln His Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
            85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
        130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
            165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255
```

<210> SEQ ID NO 371
<211> LENGTH: 256
<212> TYPE: PRT
<213> ORGANISM: Artificial Sequence
<220> FEATURE:
<223> OTHER INFORMATION: chemically synthesized

<400> SEQUENCE: 371

```
Val Cys Arg Thr Arg Trp His Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Gln His Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
            85                  90                  95

Ser Gly Val Pro Ala Arg Phe Ser Gly Ser Gly Ser Gly Thr Ser Tyr
            100                 105                 110
```

-continued

```
Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
    130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
                180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255
```

<210> SEQ ID NO 372
<211> LENGTH: 260
<212> TYPE: PRT
<213> ORGANISM: Artificial Sequence
<220> FEATURE:
<223> OTHER INFORMATION: chemically synthesized

<400> SEQUENCE: 372

```
Glu Cys Lys Thr Arg Gln Asp Phe Glu Met His Asp Cys Val Tyr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Ser Ala Ser Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
    130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220
```

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
            245                 250                 255

Arg Gly Glu Cys
            260

<210> SEQ ID NO 373
<211> LENGTH: 260
<212> TYPE: PRT
<213> ORGANISM: Artificial Sequence
<220> FEATURE:
<223> OTHER INFORMATION: chemically synthesized

<400> SEQUENCE: 373

Gln Cys Met Ser Arg Phe Ala Phe Glu Ile Gly Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Gln Met
        35                  40                  45

Thr Gln Ser Pro Ser Ser Leu Ser Ala Ser Val Gly Asp Arg Val Thr
50                  55                  60

Ile Thr Cys Ser Ala Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 374
<211> LENGTH: 260
<212> TYPE: PRT
<213> ORGANISM: Artificial Sequence
<220> FEATURE:
<223> OTHER INFORMATION: chemically synthesized

```
<400> SEQUENCE: 374

Thr Cys Leu Ser Arg Tyr Glu Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Val Met
        35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65              70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
            100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 375
<211> LENGTH: 260
<212> TYPE: PRT
<213> ORGANISM: Artificial Sequence
<220> FEATURE:
<223> OTHER INFORMATION: chemically synthesized

<400> SEQUENCE: 375

Val Cys Arg Thr Arg Trp His Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Val Met
        35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65              70                  75                  80

Tyr Gln Gln Lys Pro Gly Phe Ser Pro Lys Leu Leu Ile Tyr Arg Thr
```

```
              85                  90                  95
Ser Asn Leu Ala Ser Gly Val Pro Ala Arg Phe Ser Gly Ser Gly Ser
            100                 105                 110

Gly Thr Ser Tyr Ser Leu Thr Ile Gly Thr Met Glu Ala Glu Asp Val
            115                 120                 125

Ala Thr Tyr Tyr Cys Gln Gln Gly Ser Ser Ile Pro Arg Phe Thr Ser
            130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
                180                 185                 190

Gln Trp Lys Val Asp Asn Ala Leu Gln Ser Gly Asn Ser Gln Glu Ser
                195                 200                 205

Val Thr Glu Gln Asp Ser Lys Asp Ser Thr Tyr Ser Leu Ser Ser Thr
            210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 376
<211> LENGTH: 256
<212> TYPE: PRT
<213> ORGANISM: Artificial Sequence
<220> FEATURE:
<223> OTHER INFORMATION: chemically synthesized

<400> SEQUENCE: 376

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Gln Met Thr Gln Ser Pro
            35                  40                  45

Ser Ser Leu Ser Ala Ser Val Gly Asp Arg Val Thr Ile Thr Cys Ser
        50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
            115                 120                 125

Cys Gln Gln Gly Ser Ser Ile Pro Arg Phe Thr Ser Gly Gly Gly Thr
            130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
```

```
                180             185              190
Asp Asn Ala Leu Gln Ser Gly Asn Ser Gln Glu Ser Val Thr Glu Gln
            195                 200             205

Asp Ser Lys Asp Ser Thr Tyr Ser Leu Ser Thr Leu Thr Leu Ser
    210                 215             220

Lys Ala Asp Tyr Glu Lys His Lys Val Tyr Ala Cys Glu Val Thr His
225             230              235                     240

Gln Gly Leu Ser Ser Pro Val Thr Lys Ser Phe Asn Arg Gly Glu Cys
            245                 250             255
```

<210> SEQ ID NO 377
<211> LENGTH: 256
<212> TYPE: PRT
<213> ORGANISM: Artificial Sequence
<220> FEATURE:
<223> OTHER INFORMATION: chemically synthesized

<400> SEQUENCE: 377

```
Gln Cys Met Ser Arg Phe Ala Phe Glu Ile Gly Asp Cys Val Met Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255
```

<210> SEQ ID NO 378
<211> LENGTH: 256
<212> TYPE: PRT
<213> ORGANISM: Artificial Sequence
<220> FEATURE:
<223> OTHER INFORMATION: chemically synthesized

<400> SEQUENCE: 378

Thr Cys Leu Ser Arg Tyr Glu Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
            85                  90                  95

Ser Gly Val Pro Ala Arg Phe Ser Gly Ser Gly Ser Gly Thr Ser Tyr
        100                 105                 110

Ser Leu Thr Ile Gly Thr Met Glu Ala Glu Asp Val Ala Thr Tyr Tyr
    115                 120                 125

Cys Gln Gln Gly Ser Ser Ile Pro Arg Phe Thr Ser Gly Ser Gly Thr
130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
            165                 170                 175

Leu Leu Asn Asn Phe Tyr Pro Arg Glu Ala Lys Val Gln Trp Lys Val
        180                 185                 190

Asp Asn Ala Leu Gln Ser Gly Asn Ser Gln Glu Ser Val Thr Glu Gln
    195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255

<210> SEQ ID NO 379
<211> LENGTH: 256
<212> TYPE: PRT
<213> ORGANISM: Artificial Sequence
<220> FEATURE:
<223> OTHER INFORMATION: chemically synthesized

<400> SEQUENCE: 379

Val Cys Arg Thr Arg Trp His Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Asn Pro Gly Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
            85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
            115                 120                 125

Cys Gln Gln Gly Ser Ser Ile Pro Arg Phe Thr Ser Gly Ser Gly Thr
130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
            210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 380
<211> LENGTH: 260
<212> TYPE: PRT
<213> ORGANISM: Artificial Sequence
<220> FEATURE:
<223> OTHER INFORMATION: chemically synthesized

<400> SEQUENCE: 380

Glu Cys Lys Thr Arg Gln Asp Phe Glu Met His Asp Cys Val Tyr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn Pro Gly Gly Ser Asp Ile Gln Met
            35                  40                  45

Thr Gln Ser Pro Ser Ser Leu Ser Ala Ser Val Gly Asp Arg Val Thr
50                  55                  60

Ile Thr Cys Ser Ala Ser Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
            115                 120                 125

Ala Thr Tyr Tyr Cys Gln Gln Gly Ser Ser Ile Pro Arg Phe Thr Ser
            130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
            195                 200                 205

-continued

```
Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 381
<211> LENGTH: 260
<212> TYPE: PRT
<213> ORGANISM: Artificial Sequence
<220> FEATURE:
<223> OTHER INFORMATION: chemically synthesized

<400> SEQUENCE: 381

Gln Cys Met Ser Arg Phe Ala Phe Glu Ile Gly Asp Cys Val Met Gly
1               5                   10                  15

Gly Gly Ser Ser Gly Gly Ser Ala Val Gly Leu Ala Pro Pro Gly
                20                  25                  30

Gly Leu Ser Gly Arg Ser Asp Asn Pro Gly Gly Ser Asp Ile Gln Met
            35                  40                  45

Thr Gln Ser Pro Ser Ser Leu Ser Ala Ser Val Gly Asp Arg Val Thr
 50                  55                  60

Ile Thr Cys Ser Ala Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 382
<211> LENGTH: 260
<212> TYPE: PRT
<213> ORGANISM: Artificial Sequence
<220> FEATURE:
```

<223> OTHER INFORMATION: chemically synthesized

<400> SEQUENCE: 382

```
Thr Cys Leu Ser Arg Tyr Glu Phe Glu Thr Thr Asp Cys Val Met Gly
1               5                   10                  15
Gly Gly Ser Ser Gly Gly Ser Ala Val Gly Leu Leu Ala Pro Pro Gly
            20                  25                  30
Gly Leu Ser Gly Arg Ser Asp Asn Pro Gly Gly Ser Asp Ile Val Met
        35                  40                  45
Thr Gln Thr Pro Thr Thr Leu Ala Ala Ser Pro Gly Glu Lys Ile Ile
    50                  55                  60
Ile Thr Cys Ser Ala Ser Ser Ile Ser Ser Asn Tyr Leu His Trp
65                  70                  75                  80
Tyr Gln Gln Lys Pro Gly Phe Ser Pro Lys Leu Leu Ile Tyr Arg Thr
                85                  90                  95
Ser Asn Leu Ala Ser Gly Val Pro Ala Arg Phe Ser Gly Ser Gly Ser
            100                 105                 110
Gly Thr Ser Tyr Ser Leu Thr Ile Gly Thr Met Glu Ala Glu Asp Val
        115                 120                 125
Ala Thr Tyr Tyr Cys Gln Gln Gly Ser Ser Ile Pro Arg Phe Thr Ser
    130                 135                 140
Gly Ser Gly Thr Lys Leu Glu Ile Lys Arg Thr Val Ala Ala Pro Ser
145                 150                 155                 160
Val Phe Ile Phe Pro Pro Ser Asp Glu Gln Leu Lys Ser Gly Thr Ala
                165                 170                 175
Ser Val Val Cys Leu Leu Asn Asn Phe Tyr Pro Arg Glu Ala Lys Val
            180                 185                 190
Gln Trp Lys Val Asp Asn Ala Leu Gln Ser Gly Asn Ser Gln Glu Ser
        195                 200                 205
Val Thr Glu Gln Asp Ser Lys Asp Ser Thr Tyr Ser Leu Ser Ser Thr
    210                 215                 220
Leu Thr Leu Ser Lys Ala Asp Tyr Glu Lys His Lys Val Tyr Ala Cys
225                 230                 235                 240
Glu Val Thr His Gln Gly Leu Ser Ser Pro Val Thr Lys Ser Phe Asn
                245                 250                 255
Arg Gly Glu Cys
            260
```

<210> SEQ ID NO 383
<211> LENGTH: 260
<212> TYPE: PRT
<213> ORGANISM: Artificial Sequence
<220> FEATURE:
<223> OTHER INFORMATION: chemically synthesized

<400> SEQUENCE: 383

```
Val Cys Arg Thr Arg Trp His Phe Glu Thr Thr Asp Cys Val Met Gly
1               5                   10                  15
Gly Gly Ser Ser Gly Gly Ser Ala Val Gly Leu Leu Ala Pro Pro Gly
            20                  25                  30
Gly Leu Ser Gly Arg Ser Asp Asn Pro Gly Gly Ser Asp Ile Val Met
        35                  40                  45
Thr Gln Thr Pro Thr Thr Leu Ala Ala Ser Pro Gly Glu Lys Ile Ile
    50                  55                  60
Ile Thr Cys Ser Ala Ser Ser Ser Ile Ser Ser Asn Tyr Leu His Trp
65                  70                  75                  80
```

```
Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
            100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 384
<211> LENGTH: 256
<212> TYPE: PRT
<213> ORGANISM: Artificial Sequence
<220> FEATURE:
<223> OTHER INFORMATION: chemically synthesized

<400> SEQUENCE: 384

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175
```

```
Leu Leu Asn Asn Phe Tyr Pro Arg Glu Ala Lys Val Gln Trp Lys Val
                180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 385
<211> LENGTH: 256
<212> TYPE: PRT
<213> ORGANISM: Artificial Sequence
<220> FEATURE:
<223> OTHER INFORMATION: chemically synthesized

<400> SEQUENCE: 385

Gln Cys Met Ser Arg Phe Ala Phe Glu Ile Gly Asp Cys Val Met Gly
1               5                   10                  15

Gly Gly Ser Ser Gly Gly Ser Ile Ser Ser Gly Leu Leu Ser Gly Arg
                20                  25                  30

Ser Ala Asn Pro Gly Gly Gly Ser Asp Ile Gln Met Thr Gln Ser Pro
            35                  40                  45

Ser Ser Leu Ser Ala Ser Val Gly Asp Arg Val Thr Ile Thr Cys Ser
        50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
                180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 386
<211> LENGTH: 256
<212> TYPE: PRT
<213> ORGANISM: Artificial Sequence
```

```
<220> FEATURE:
<223> OTHER INFORMATION: chemically synthesized

<400> SEQUENCE: 386

Thr Cys Leu Ser Arg Tyr Glu Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
                85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
            115                 120                 125

Cys Gln Gln Gly Ser Ser Ile Pro Arg Phe Thr Ser Gly Ser Gly Thr
130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 387
<211> LENGTH: 256
<212> TYPE: PRT
<213> ORGANISM: Artificial Sequence
<220> FEATURE:
<223> OTHER INFORMATION: chemically synthesized

<400> SEQUENCE: 387

Val Cys Arg Thr Arg Trp His Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Ala Asn Pro Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
```

```
                    85                  90                  95
Ser Gly Val Pro Ala Arg Phe Ser Gly Ser Gly Ser Gly Thr Ser Tyr
                100                 105                 110

Ser Leu Thr Ile Gly Thr Met Glu Ala Glu Asp Val Ala Thr Tyr Tyr
                115                 120                 125

Cys Gln Gln Gly Ser Ser Ile Pro Arg Phe Thr Ser Gly Ser Gly Thr
                130                 135                 140

Lys Leu Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
                180                 185                 190

Asp Asn Ala Leu Gln Ser Gly Asn Ser Gln Glu Ser Val Thr Glu Gln
                195                 200                 205

Asp Ser Lys Asp Ser Thr Tyr Ser Leu Ser Ser Thr Leu Thr Leu Ser
210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 388
<211> LENGTH: 260
<212> TYPE: PRT
<213> ORGANISM: Artificial Sequence
<220> FEATURE:
<223> OTHER INFORMATION: chemically synthesized

<400> SEQUENCE: 388

Glu Cys Lys Thr Arg Gln Asp Phe Glu Met His Asp Cys Val Tyr Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Ala Asn Pro Gly Gly Ser Asp Ile Gln Met
                35                  40                  45

Thr Gln Ser Pro Ser Ser Leu Ser Ala Ser Val Gly Asp Arg Val Thr
50                  55                  60

Ile Thr Cys Ser Ala Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
                100                 105                 110

Gly Thr Asp Tyr Thr Leu Thr Ile Ser Ser Leu Gln Pro Glu Asp Val
                115                 120                 125

Ala Thr Tyr Tyr Cys Gln Gln Gly Ser Ser Ile Pro Arg Phe Thr Ser
                130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
                180                 185                 190

Gln Trp Lys Val Asp Asn Ala Leu Gln Ser Gly Asn Ser Gln Glu Ser
```

```
                195                 200                 205
Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 389
<211> LENGTH: 260
<212> TYPE: PRT
<213> ORGANISM: Artificial Sequence
<220> FEATURE:
<223> OTHER INFORMATION: chemically synthesized

<400> SEQUENCE: 389

Gln Cys Met Ser Arg Phe Ala Phe Glu Ile Gly Asp Cys Val Met Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Ala Asn Pro Gly Gly Ser Asp Ile Gln Met
            35                  40                  45

Thr Gln Ser Pro Ser Ser Leu Ser Ala Ser Val Gly Asp Arg Val Thr
    50                  55                  60

Ile Thr Cys Ser Ala Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
130                 135                 140

Gly Gly Gly Thr Lys Val Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 390
<211> LENGTH: 260
<212> TYPE: PRT
```

<213> ORGANISM: Artificial Sequence
<220> FEATURE:
<223> OTHER INFORMATION: chemically synthesized

<400> SEQUENCE: 390

```
Thr Cys Leu Ser Arg Tyr Glu Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
        35                  40                  45

Thr Gln Thr Pro Thr Thr Leu Ala Ala Ser Pro Gly Glu Lys Ile Ile
50                  55                  60

Ile Thr Cys Ser Ala Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
            100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260
```

<210> SEQ ID NO 391
<211> LENGTH: 260
<212> TYPE: PRT
<213> ORGANISM: Artificial Sequence
<220> FEATURE:
<223> OTHER INFORMATION: chemically synthesized

<400> SEQUENCE: 391

```
Val Cys Arg Thr Arg Trp His Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Ala Asn Pro Gly Gly Ser Asp Ile Val Met
        35                  40                  45

Thr Gln Thr Pro Thr Thr Leu Ala Ala Ser Pro Gly Glu Lys Ile Ile
50                  55                  60
```

```
Ile Thr Cys Ser Ala Ser Ser Ile Ser Ser Asn Tyr Leu His Trp
 65                  70                  75                  80

Tyr Gln Gln Lys Pro Gly Phe Ser Pro Lys Leu Leu Ile Tyr Arg Thr
                 85                  90                  95

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
            115                 120                 125

Ala Thr Tyr Tyr Cys Gln Gln Gly Ser Ser Ile Pro Arg Phe Thr Ser
        130                 135                 140

Gly Ser Gly Thr Lys Leu Glu Ile Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396
<211> LENGTH: 156
<212> TYPE: PRT
<213> ORGANISM: Artificial Sequence
<220> FEATURE:
<223> OTHER INFORMATION: chemically synthesized

<400> SEQUENCE: 396

Gln Gly Gln Ser Gly Gln Gly Glu Cys Lys Thr Arg Gln Asp Phe Glu
  1               5                  10                  15
```

```
Met His Asp Cys Val Tyr Gly Gly Ser Ser Gly Gly Ser Ile Ser
            20                  25                  30

Ser Gly Leu Leu Ser Gly Arg Ser Asp Asn His Gly Gly Ser Asp
        35                  40                  45

Ile Gln Met Thr Gln Ser Pro Ser Ser Leu Ser Ala Ser Val Gly Asp
 50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
            85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
            115                 120                 125

Glu Asp Val Ala Thr Tyr Tyr Cys Gln Gln Gly Ser Ser Ile Pro Arg
130                 135                 140

Phe Thr Ser Gly Gly Gly Thr Lys Val Glu Ile Lys
145                 150                 155
```

<210> SEQ ID NO 397

<400> SEQUENCE: 397

000

<210> SEQ ID NO 398
<211> LENGTH: 156
<212> TYPE: PRT
<213> ORGANISM: Artificial Sequence
<220> FEATURE:
<223> OTHER INFORMATION: chemically synthesized

<400> SEQUENCE: 398

```
Gln Gly Gln Ser Gly Gln Gly Gln Cys Met Ser Arg Phe Ala Phe Glu
 1               5                  10                  15

Ile Gly Asp Cys Val Met Gly Gly Ser Ser Gly Gly Ser Ile Ser
            20                  25                  30

Ser Gly Leu Leu Ser Gly Arg Ser Asp Asn His Gly Gly Ser Asp
        35                  40                  45

Ile Gln Met Thr Gln Ser Pro Ser Ser Leu Ser Ala Ser Val Gly Asp
 50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
            85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
            115                 120                 125

Glu Asp Val Ala Thr Tyr Tyr Cys Gln Gln Gly Ser Ser Ile Pro Arg
130                 135                 140

Phe Thr Ser Gly Gly Gly Thr Lys Val Glu Ile Lys
145                 150                 155
```

<210> SEQ ID NO 399

<400> SEQUENCE: 399

<210> SEQ ID NO 400
<211> LENGTH: 156
<212> TYPE: PRT
<213> ORGANISM: Artificial Sequence
<220> FEATURE:
<223> OTHER INFORMATION: chemically synthesized

<400> SEQUENCE: 400

```
Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Ser Ile Ser
            20                  25                  30

Ser Gly Leu Leu Ser Gly Arg Ser Asp Asn His Gly Gly Gly Ser Asp
        35                  40                  45

Ile Val Met Thr Gln Thr Pro Thr Leu Ala Ala Ser Pro Gly Glu
    50                  55                  60

Lys Ile Ile Ile Thr Cys Ser Ala Ser Ser Ile Ser Ser Asn Tyr
65              70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
            100                 105                 110

Ser Gly Ser Gly Thr Ser Tyr Ser Leu Thr Ile Gly Thr Met Glu Ala
        115                 120                 125

Glu Asp Val Ala Thr Tyr Tyr Cys Gln Gln Gly Ser Ser Ile Pro Arg
    130                 135                 140

Phe Thr Ser Gly Ser Gly Thr Lys Leu Glu Ile Lys
145                 150                 155
```

<210> SEQ ID NO 401

<400> SEQUENCE: 401

000

<210> SEQ ID NO 402
<211> LENGTH: 149
<212> TYPE: PRT
<213> ORGANISM: Artificial Sequence
<220> FEATURE:
<223> OTHER INFORMATION: chemically synthesized

<400> SEQUENCE: 402

```
Val Cys Arg Thr Arg Trp His Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Asn His Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
    50                  55                  60

Ala Ser Ser Ser Ile Ser Ser Asn Tyr Leu His Trp Tyr Gln Gln Lys
65              70                  75                  80

Pro Gly Phe Ser Pro Lys Leu Leu Ile Tyr Arg Thr Ser Asn Leu Ala
                85                  90                  95

Ser Gly Val Pro Ala Arg Phe Ser Gly Ser Gly Ser Gly Thr Ser Tyr
```

```
                    100                 105                 110
Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Gly Ser Gly Thr
130                 135                 140

Lys Leu Glu Ile Lys
145
```

<210> SEQ ID NO 403

<400> SEQUENCE: 403

000

<210> SEQ ID NO 404
<211> LENGTH: 160
<212> TYPE: PRT
<213> ORGANISM: Artificial Sequence
<220> FEATURE:
<223> OTHER INFORMATION: chemically synthesized

<400> SEQUENCE: 404

```
Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
        115                 120                 125

Ser Leu Gln Pro Glu Asp Val Ala Thr Tyr Tyr Cys Gln Gln Gly Ser
    130                 135                 140

Ser Ile Pro Arg Phe Thr Gly Gly Thr Lys Val Glu Ile Lys
145                 150                 155                 160
```

<210> SEQ ID NO 405
<211> LENGTH: 160
<212> TYPE: PRT
<213> ORGANISM: Artificial Sequence
<220> FEATURE:
<223> OTHER INFORMATION: chemically synthesized

<400> SEQUENCE: 405

```
Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ala Val
            20                  25                  30

Gly Leu Leu Ala Pro Pro Gly Gly Leu Ser Gly Arg Ser Asp Asn His
        35                  40                  45

Gly Gly Ser Asp Ile Gln Met Thr Gln Ser Pro Ser Ser Leu Ser Ala
    50                  55                  60
```

```
Ser Val Gly Asp Arg Val Thr Ile Thr Cys Ser Ala Ser Ser Ser Ile
 65                  70                  75                  80

Ser Ser Asn Tyr Leu His Trp Tyr Gln Gln Lys Pro Gly Lys Val Pro
             85                   90                  95

Lys Leu Leu Ile Tyr Arg Thr Asn Leu Ala Ser Gly Val Pro Ser
            100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
        130                 135                 140

Ser Ile Pro Arg Phe Thr Ser Gly Gly Thr Lys Val Glu Ile Lys
145                 150                 155                 160

<210> SEQ ID NO 406
<211> LENGTH: 160
<212> TYPE: PRT
<213> ORGANISM: Artificial Sequence
<220> FEATURE:
<223> OTHER INFORMATION: chemically synthesized

<400> SEQUENCE: 406

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
             20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Thr Pro Thr Thr Leu Ala Ala
         50                  55                  60

Ser Pro Gly Glu Lys Ile Ile Thr Cys Ser Ala Ser Ser Ser Ile
 65                  70                  75                  80

Ser Ser Asn Tyr Leu His Trp Tyr Gln Gln Lys Pro Gly Phe Ser Pro
             85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
        130                 135                 140

Ser Ile Pro Arg Phe Thr Gly Ser Gly Thr Lys Leu Glu Ile Lys
145                 150                 155                 160

<210> SEQ ID NO 407
<211> LENGTH: 160
<212> TYPE: PRT
<213> ORGANISM: Artificial Sequence
<220> FEATURE:
<223> OTHER INFORMATION: chemically synthesized

<400> SEQUENCE: 407

Gln Gly Gln Ser Gly Gln Gly Val Cys Arg Thr Arg Trp His Phe Glu
1               5                   10                  15

Thr Thr Asp Cys Val Met Gly Gly Gly Ser Ser Gly Gly Ser Ala Val
             20                  25                  30

Gly Leu Leu Ala Pro Pro Gly Gly Leu Ser Gly Arg Ser Asp Asn His
            35                  40                  45

Gly Gly Ser Asp Ile Val Met Thr Gln Thr Pro Thr Thr Leu Ala Ala
```

```
                    50                  55                  60

Ser Pro Gly Glu Lys Ile Ile Thr Cys Ser Ala Ser Ser Ile
 65                  70                  75                  80

Ser Ser Asn Tyr Leu His Trp Tyr Gln Gln Lys Pro Gly Phe Ser Pro
                     85                  90                  95

Lys Leu Leu Ile Tyr Arg Thr Ser Asn Leu Ala Ser Gly Val Pro Ala
                    100                 105                 110

Arg Phe Ser Gly Ser Gly Ser Gly Thr Ser Tyr Ser Leu Thr Ile Gly
                115                 120                 125

Thr Met Glu Ala Glu Asp Val Ala Thr Tyr Tyr Cys Gln Gln Gly Ser
            130                 135                 140

Ser Ile Pro Arg Phe Thr Gly Ser Gly Thr Lys Leu Glu Ile Lys
145                 150                 155                 160

<210> SEQ ID NO 408
<211> LENGTH: 156
<212> TYPE: PRT
<213> ORGANISM: Artificial Sequence
<220> FEATURE:
<223> OTHER INFORMATION: chemically synthesized

<400> SEQUENCE: 408

Gln Gly Gln Ser Gly Gln Gly Glu Cys Lys Thr Arg Gln Asp Phe Glu
 1               5                  10                  15

Met His Asp Cys Val Tyr Gly Gly Ser Ser Gly Gly Ser Ile Ser
                 20                  25                  30

Ser Gly Leu Leu Ser Gly Arg Ser Asp Gln His Gly Gly Gly Ser Asp
            35                  40                  45

Ile Gln Met Thr Gln Ser Pro Ser Ser Leu Ser Ala Ser Val Gly Asp
        50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
                 85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
            115                 120                 125

Glu Asp Val Ala Thr Tyr Tyr Cys Gln Gln Gly Ser Ser Ile Pro Arg
        130                 135                 140

Phe Thr Ser Gly Gly Gly Thr Lys Val Glu Ile Lys
145                 150                 155

<210> SEQ ID NO 409
<211> LENGTH: 156
<212> TYPE: PRT
<213> ORGANISM: Artificial Sequence
<220> FEATURE:
<223> OTHER INFORMATION: chemically synthesized

<400> SEQUENCE: 409

Gln Gly Gln Ser Gly Gln Gly Gln Cys Met Ser Arg Phe Ala Phe Glu
 1               5                  10                  15

Ile Gly Asp Cys Val Met Gly Gly Ser Ser Gly Gly Ser Ile Ser
                 20                  25                  30

Ser Gly Leu Leu Ser Gly Arg Ser Asp Gln His Gly Gly Gly Ser Asp
            35                  40                  45
```

```
Ile Gln Met Thr Gln Ser Pro Ser Ser Leu Ser Ala Ser Val Gly Asp
         50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
                     85                  90                  95

Tyr Arg Thr Ser Asn Leu Ala Ser Gly Val Pro Ser Arg Phe Ser Gly
                 100                 105                 110

Ser Gly Ser Gly Thr Asp Tyr Thr Leu Thr Ile Ser Ser Leu Gln Pro
             115                 120                 125

Glu Asp Val Ala Thr Tyr Tyr Cys Gln Gln Gly Ser Ser Ile Pro Arg
         130                 135                 140

Phe Thr Ser Gly Gly Gly Thr Lys Val Glu Ile Lys
145                 150                 155

<210> SEQ ID NO 410
<211> LENGTH: 156
<212> TYPE: PRT
<213> ORGANISM: Artificial Sequence
<220> FEATURE:
<223> OTHER INFORMATION: chemically synthesized

<400> SEQUENCE: 410

Gln Gly Gln Ser Gly Gln Gly Thr Cys Leu Ser Arg Tyr Glu Phe Glu
 1               5                  10                  15

Thr Thr Asp Cys Val Met Gly Gly Ser Ser Gly Gly Ser Ile Ser
                 20                  25                  30

Ser Gly Leu Leu Ser Gly Arg Ser Asp Gln His Gly Gly Gly Ser Asp
             35                  40                  45

Ile Val Met Thr Gln Thr Pro Thr Thr Leu Ala Ala Ser Pro Gly Glu
         50                  55                  60

Lys Ile Ile Ile Thr Cys Ser Ala Ser Ser Ile Ser Ser Asn Tyr
 65                  70                  75                  80

Leu His Trp Tyr Gln Gln Lys Pro Gly Phe Ser Pro Lys Leu Leu Ile
                     85                  90                  95

Tyr Arg Thr Ser Asn Leu Ala Ser Gly Val Pro Ala Arg Phe Ser Gly
                 100                 105                 110

Ser Gly Ser Gly Thr Ser Tyr Ser Leu Thr Ile Gly Thr Met Glu Ala
             115                 120                 125

Glu Asp Val Ala Thr Tyr Tyr Cys Gln Gln Gly Ser Ser Ile Pro Arg
         130                 135                 140

Phe Thr Ser Gly Ser Gly Thr Lys Leu Glu Ile Lys
145                 150                 155

<210> SEQ ID NO 411
<211> LENGTH: 156
<212> TYPE: PRT
<213> ORGANISM: Artificial Sequence
<220> FEATURE:
<223> OTHER INFORMATION: chemically synthesized

<400> SEQUENCE: 411

Gln Gly Gln Ser Gly Gln Gly Val Cys Arg Thr Arg Trp His Phe Glu
 1               5                  10                  15

Thr Thr Asp Cys Val Met Gly Gly Ser Ser Gly Gly Ser Ile Ser
                 20                  25                  30

Ser Gly Leu Leu Ser Gly Arg Ser Asp Gln His Gly Gly Gly Ser Asp
             35                  40                  45
```

Ile Val Met Thr Gln Thr Pro Thr Thr Leu Ala Ala Ser Pro Gly Glu
                50                  55                  60

Lys Ile Ile Ile Thr Cys Ser Ala Ser Ser Ile Ser Ser Asn Tyr
 65                  70                  75                  80

Leu His Trp Tyr Gln Gln Lys Pro Gly Phe Ser Pro Lys Leu Leu Ile
                    85                  90                  95

Tyr Arg Thr Ser Asn Leu Ala Ser Gly Val Pro Ala Arg Phe Ser Gly
                100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
130                 135                 140

Phe Thr Ser Gly Ser Gly Thr Lys Leu Glu Ile Lys
145                 150                 155

<210> SEQ ID NO 412
<211> LENGTH: 160
<212> TYPE: PRT
<213> ORGANISM: Artificial Sequence
<220> FEATURE:
<223> OTHER INFORMATION: chemically synthesized

<400> SEQUENCE: 412

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ala Val
                20                  25                  30

Gly Leu Leu Ala Pro Pro Gly Gly Leu Ser Gly Arg Ser Asp Gln His
            35                  40                  45

Gly Gly Ser Asp Ile Gln Met Thr Gln Ser Pro Ser Ser Leu Ser Ala
        50                  55                  60

Ser Val Gly Asp Arg Val Thr Ile Thr Cys Ser Ala Ser Ser Ser Ile
 65                 70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
        115                 120                 125

Ser Leu Gln Pro Glu Asp Val Ala Thr Tyr Tyr Cys Gln Gln Gly Ser
130                 135                 140

Ser Ile Pro Arg Phe Thr Ser Gly Gly Thr Lys Val Glu Ile Lys
145                 150                 155                 160

<210> SEQ ID NO 413
<211> LENGTH: 160
<212> TYPE: PRT
<213> ORGANISM: Artificial Sequence
<220> FEATURE:
<223> OTHER INFORMATION: chemically synthesized

<400> SEQUENCE: 413

Gln Gly Gln Ser Gly Gln Gly Gln Cys Met Ser Arg Phe Ala Phe Glu
1               5                   10                  15

Ile Gly Asp Cys Val Met Gly Gly Ser Ser Gly Gly Ser Ala Val
                20                  25                  30

Gly Leu Leu Ala Pro Pro Gly Gly Leu Ser Gly Arg Ser Asp Gln His

```
                35                  40                  45
Gly Gly Ser Asp Ile Gln Met Thr Gln Ser Pro Ser Ser Leu Ser Ala
             50                  55                  60

Ser Val Gly Asp Arg Val Thr Ile Thr Cys Ser Ala Ser Ser Ser Ile
 65                  70                  75                  80

Ser Ser Asn Tyr Leu His Trp Tyr Gln Gln Lys Pro Gly Lys Val Pro
                 85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
            130                 135                 140

Ser Ile Pro Arg Phe Thr Ser Gly Gly Thr Lys Val Glu Ile Lys
145                 150                 155                 160

<210> SEQ ID NO 414
<211> LENGTH: 160
<212> TYPE: PRT
<213> ORGANISM: Artificial Sequence
<220> FEATURE:
<223> OTHER INFORMATION: chemically synthesized

<400> SEQUENCE: 414

Gln Gly Gln Ser Gly Gln Gly Thr Cys Leu Ser Arg Tyr Glu Phe Glu
1               5                  10                  15

Thr Thr Asp Cys Val Met Gly Gly Gly Ser Ser Gly Gly Ser Ala Val
             20                  25                  30

Gly Leu Leu Ala Pro Pro Gly Gly Leu Ser Gly Arg Ser Asp Gln His
                 35                  40                  45

Gly Gly Ser Asp Ile Val Met Thr Gln Thr Pro Thr Thr Leu Ala Ala
             50                  55                  60

Ser Pro Gly Glu Lys Ile Ile Thr Cys Ser Ala Ser Ser Ser Ile
 65                  70                  75                  80

Ser Ser Asn Tyr Leu His Trp Tyr Gln Gln Lys Pro Gly Phe Ser Pro
                 85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
            130                 135                 140

Ser Ile Pro Arg Phe Thr Ser Gly Ser Gly Thr Lys Leu Glu Ile Lys
145                 150                 155                 160

<210> SEQ ID NO 415
<211> LENGTH: 160
<212> TYPE: PRT
<213> ORGANISM: Artificial Sequence
<220> FEATURE:
<223> OTHER INFORMATION: chemically synthesized

<400> SEQUENCE: 415

Gln Gly Gln Ser Gly Gln Gly Val Cys Arg Thr Arg Trp His Phe Glu
1               5                  10                  15

Thr Thr Asp Cys Val Met Gly Gly Gly Ser Ser Gly Gly Ser Ala Val
             20                  25                  30
```

Gly Leu Leu Ala Pro Pro Gly Leu Ser Gly Arg Ser Asp Gln His
                35                  40                  45

Gly Gly Ser Asp Ile Val Met Thr Gln Thr Pro Thr Thr Leu Ala Ala
 50                  55                  60

Ser Pro Gly Glu Lys Ile Ile Ile Thr Cys Ser Ala Ser Ser Ser Ile
 65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
                100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
            130                 135                 140

Ser Ile Pro Arg Phe Thr Gly Ser Gly Thr Lys Leu Glu Ile Lys
145                 150                 155                 160

<210> SEQ ID NO 416
<211> LENGTH: 156
<212> TYPE: PRT
<213> ORGANISM: Artificial Sequence
<220> FEATURE:
<223> OTHER INFORMATION: chemically synthesized

<400> SEQUENCE: 416

Gln Gly Gln Ser Gly Gln Gly Glu Cys Lys Thr Arg Gln Asp Phe Glu
 1               5                   10                  15

Met His Asp Cys Val Tyr Gly Gly Ser Ser Gly Gly Ser Ile Ser
                20                  25                  30

Ser Gly Leu Leu Ser Gly Arg Ser Asp Asn Pro Gly Gly Gly Ser Asp
                35                  40                  45

Ile Gln Met Thr Gln Ser Pro Ser Ser Leu Ser Ala Ser Val Gly Asp
 50                  55                  60

Arg Val Thr Ile Thr Cys Ser Ala Ser Ser Ile Ser Ser Asn Tyr
 65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
            115                 120                 125

Glu Asp Val Ala Thr Tyr Tyr Cys Gln Gln Gly Ser Ser Ile Pro Arg
            130                 135                 140

Phe Thr Ser Gly Gly Gly Thr Lys Val Glu Ile Lys
145                 150                 155

<210> SEQ ID NO 417
<211> LENGTH: 156
<212> TYPE: PRT
<213> ORGANISM: Artificial Sequence
<220> FEATURE:
<223> OTHER INFORMATION: chemically synthesized

<400> SEQUENCE: 417

Gln Gly Gln Ser Gly Gln Gly Gln Cys Met Ser Arg Phe Ala Phe Glu
 1               5                   10                  15

Ile Gly Asp Cys Val Met Gly Gly Gly Ser Ser Gly Gly Ser Ile Ser
                20                  25                  30

```
Ser Gly Leu Leu Ser Gly Arg Ser Asp Asn Pro Gly Gly Gly Ser Asp
        35                  40                  45

Ile Gln Met Thr Gln Ser Pro Ser Ser Leu Ser Ala Ser Val Gly Asp
    50                  55                  60

Arg Val Thr Ile Thr Cys Ser Ala Ser Ser Ile Ser Ser Asn Tyr
65                  70                  75                  80

Leu His Trp Tyr Gln Gln Lys Pro Gly Lys Val Pro Lys Leu Leu Ile
                    85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
            115                 120                 125

Glu Asp Val Ala Thr Tyr Tyr Cys Gln Gln Gly Ser Ser Ile Pro Arg
130                 135                 140

Phe Thr Ser Gly Gly Gly Thr Lys Val Glu Ile Lys
145                 150                 155
```

<210> SEQ ID NO 418
<211> LENGTH: 156
<212> TYPE: PRT
<213> ORGANISM: Artificial Sequence
<220> FEATURE:
<223> OTHER INFORMATION: chemically synthesized

<400> SEQUENCE: 418

```
Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ile Ser
            20                  25                  30

Ser Gly Leu Leu Ser Gly Arg Ser Asp Asn Pro Gly Gly Gly Ser Asp
        35                  40                  45

Ile Val Met Thr Gln Thr Pro Thr Leu Ala Ala Ser Pro Gly Glu
    50                  55                  60

Lys Ile Ile Ile Thr Cys Ser Ala Ser Ser Ile Ser Ser Asn Tyr
65                  70                  75                  80

Leu His Trp Tyr Gln Gln Lys Pro Gly Phe Ser Pro Lys Leu Leu Ile
                    85                  90                  95

Tyr Arg Thr Ser Asn Leu Ala Ser Gly Val Pro Ala Arg Phe Ser Gly
                100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
130                 135                 140

Phe Thr Ser Gly Ser Gly Thr Lys Leu Glu Ile Lys
145                 150                 155
```

<210> SEQ ID NO 419
<211> LENGTH: 156
<212> TYPE: PRT
<213> ORGANISM: Artificial Sequence
<220> FEATURE:
<223> OTHER INFORMATION: chemically synthesized

<400> SEQUENCE: 419

```
Gln Gly Gln Ser Gly Gln Gly Val Cys Arg Thr Arg Trp His Phe Glu
1               5                   10                  15

Thr Thr Asp Cys Val Met Gly Gly Gly Ser Ser Gly Gly Ser Ile Ser
```

```
                    20                  25                  30

Ser Gly Leu Leu Ser Gly Arg Ser Asp Asn Pro Gly Gly Ser Asp
            35                  40                  45

Ile Val Met Thr Gln Thr Pro Thr Leu Ala Ala Ser Pro Gly Glu
 50                  55                  60

Lys Ile Ile Ile Thr Cys Ser Ala Ser Ser Ile Ser Ser Asn Tyr
 65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
                100                 105                 110

Ser Gly Ser Gly Thr Ser Tyr Ser Leu Thr Ile Gly Thr Met Glu Ala
                115                 120                 125

Glu Asp Val Ala Thr Tyr Tyr Cys Gln Gln Gly Ser Ser Ile Pro Arg
            130                 135                 140

Phe Thr Ser Gly Ser Gly Thr Lys Leu Glu Ile Lys
145                 150                 155
```

<210> SEQ ID NO 420
<211> LENGTH: 160
<212> TYPE: PRT
<213> ORGANISM: Artificial Sequence
<220> FEATURE:
<223> OTHER INFORMATION: chemically synthesized

<400> SEQUENCE: 420

```
Gln Gly Gln Ser Gly Gln Gly Glu Cys Lys Thr Arg Gln Asp Phe Glu
 1               5                  10                  15

Met His Asp Cys Val Tyr Gly Gly Ser Ser Gly Gly Ser Ala Val
            20                  25                  30

Gly Leu Leu Ala Pro Pro Gly Gly Leu Ser Gly Arg Ser Asp Asn Pro
            35                  40                  45

Gly Gly Ser Asp Ile Gln Met Thr Gln Ser Pro Ser Ser Leu Ser Ala
            50                  55                  60

Ser Val Gly Asp Arg Val Thr Ile Thr Cys Ser Ala Ser Ser Ser Ile
 65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
                100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
            130                 135                 140

Ser Ile Pro Arg Phe Thr Ser Gly Ser Gly Thr Lys Val Glu Ile Lys
145                 150                 155                 160
```

<210> SEQ ID NO 421
<211> LENGTH: 160
<212> TYPE: PRT
<213> ORGANISM: Artificial Sequence
<220> FEATURE:
<223> OTHER INFORMATION: chemically synthesized

<400> SEQUENCE: 421

```
Gln Gly Gln Ser Gly Gln Gly Gln Cys Met Ser Arg Phe Ala Phe Glu
 1               5                  10                  15
```

Ile Gly Asp Cys Val Met Gly Gly Ser Ser Gly Gly Ser Ala Val
            20                  25                  30

Gly Leu Leu Ala Pro Pro Gly Gly Leu Ser Gly Arg Ser Asp Asn Pro
            35                  40                  45

Gly Gly Ser Asp Ile Gln Met Thr Gln Ser Pro Ser Ser Leu Ser Ala
        50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
                100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
        130                 135                 140

Ser Ile Pro Arg Phe Thr Ser Gly Gly Thr Lys Val Glu Ile Lys
145                 150                 155                 160

<210> SEQ ID NO 422
<211> LENGTH: 160
<212> TYPE: PRT
<213> ORGANISM: Artificial Sequence
<220> FEATURE:
<223> OTHER INFORMATION: chemically synthesized

<400> SEQUENCE: 422

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Gly Leu Ser Gly Arg Ser Asp Asn Pro
            35                  40                  45

Gly Gly Ser Asp Ile Val Met Thr Gln Thr Pro Thr Thr Leu Ala Ala
        50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
                100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
        130                 135                 140

Ser Ile Pro Arg Phe Thr Ser Gly Ser Gly Thr Lys Leu Glu Ile Lys
145                 150                 155                 160

<210> SEQ ID NO 423
<211> LENGTH: 160
<212> TYPE: PRT
<213> ORGANISM: Artificial Sequence
<220> FEATURE:
<223> OTHER INFORMATION: chemically synthesized

<400> SEQUENCE: 423

Gln Gly Gln Ser Gly Gln Gly Val Cys Arg Thr Arg Trp His Phe Glu
1               5                   10                  15

```
Thr Thr Asp Cys Val Met Gly Gly Ser Ser Gly Ser Ala Val
        20                  25                  30

Gly Leu Leu Ala Pro Pro Gly Leu Ser Gly Arg Ser Asp Asn Pro
    35                  40                  45

Gly Gly Ser Asp Ile Val Met Thr Gln Thr Pro Thr Thr Leu Ala Ala
50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
                100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
    130                 135                 140

Ser Ile Pro Arg Phe Thr Gly Ser Gly Thr Lys Leu Glu Ile Lys
145                 150                 155                 160
```

<210> SEQ ID NO 424
<211> LENGTH: 156
<212> TYPE: PRT
<213> ORGANISM: Artificial Sequence
<220> FEATURE:
<223> OTHER INFORMATION: chemically synthesized

<400> SEQUENCE: 424

```
Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Ser Ile Ser
            20                  25                  30

Ser Gly Leu Leu Ser Gly Arg Ser Ala Asn Pro Gly Gly Ser Asp
        35                  40                  45

Ile Gln Met Thr Gln Ser Pro Ser Ser Leu Ser Ala Ser Val Gly Asp
50                  55                  60

Arg Val Thr Ile Thr Cys Ser Ala Ser Ser Ile Ser Ser Asn Tyr
65                  70                  75                  80

Leu His Trp Tyr Gln Gln Lys Pro Gly Lys Val Pro Lys Leu Leu Ile
                85                  90                  95

Tyr Arg Thr Ser Asn Leu Ala Ser Gly Val Pro Ser Arg Phe Ser Gly
                100                 105                 110

Ser Gly Ser Gly Thr Asp Tyr Thr Leu Thr Ile Ser Ser Leu Gln Pro
        115                 120                 125

Glu Asp Val Ala Thr Tyr Tyr Cys Gln Gln Gly Ser Ser Ile Pro Arg
    130                 135                 140

Phe Thr Ser Gly Gly Thr Lys Val Glu Ile Lys
145                 150                 155
```

<210> SEQ ID NO 425
<211> LENGTH: 156
<212> TYPE: PRT
<213> ORGANISM: Artificial Sequence
<220> FEATURE:
<223> OTHER INFORMATION: chemically synthesized

<400> SEQUENCE: 425

```
Gln Gly Gln Ser Gly Gln Gly Gln Cys Met Ser Arg Phe Ala Phe Glu
```

```
                1               5                  10                  15
            Ile Gly Asp Cys Val Met Gly Gly Ser Ser Gly Ser Ile Ser
                           20                  25                  30

Ser Gly Leu Leu Ser Gly Arg Ser Ala Asn Pro Gly Gly Ser Asp
                           35                  40                  45

Ile Gln Met Thr Gln Ser Pro Ser Ser Leu Ser Ala Ser Val Gly Asp
                           50                  55                  60

Arg Val Thr Ile Thr Cys Ser Ala Ser Ser Ile Ser Ser Asn Tyr
             65                70                  75                  80

Leu His Trp Tyr Gln Gln Lys Pro Gly Lys Val Pro Lys Leu Leu Ile
                                85                  90                  95

Tyr Arg Thr Ser Asn Leu Ala Ser Gly Val Pro Ser Arg Phe Ser Gly
                              100                 105                 110

Ser Gly Ser Gly Thr Asp Tyr Thr Leu Thr Ile Ser Ser Leu Gln Pro
                              115                 120                 125

Glu Asp Val Ala Thr Tyr Tyr Cys Gln Gln Gly Ser Ser Ile Pro Arg
                              130                 135                 140

Phe Thr Ser Gly Gly Gly Thr Lys Val Glu Ile Lys
            145                 150                 155

<210> SEQ ID NO 426
<211> LENGTH: 156
<212> TYPE: PRT
<213> ORGANISM: Artificial Sequence
<220> FEATURE:
<223> OTHER INFORMATION: chemically synthesized

<400> SEQUENCE: 426

Gln Gly Gln Ser Gly Gln Gly Thr Cys Leu Ser Arg Tyr Glu Phe Glu
            1               5                  10                  15

Thr Thr Asp Cys Val Met Gly Gly Ser Ser Gly Ser Ile Ser
                           20                  25                  30

Ser Gly Leu Leu Ser Gly Arg Ser Ala Asn Pro Gly Gly Ser Asp
                           35                  40                  45

Ile Val Met Thr Gln Thr Pro Thr Thr Leu Ala Ala Ser Pro Gly Glu
                           50                  55                  60

Lys Ile Ile Ile Thr Cys Ser Ala Ser Ser Ile Ser Ser Asn Tyr
             65                70                  75                  80

Leu His Trp Tyr Gln Gln Lys Pro Gly Phe Ser Pro Lys Leu Leu Ile
                                85                  90                  95

Tyr Arg Thr Ser Asn Leu Ala Ser Gly Val Pro Ala Arg Phe Ser Gly
                              100                 105                 110

Ser Gly Ser Gly Thr Ser Tyr Ser Leu Thr Ile Gly Thr Met Glu Ala
                              115                 120                 125

Glu Asp Val Ala Thr Tyr Tyr Cys Gln Gln Gly Ser Ser Ile Pro Arg
                              130                 135                 140

Phe Thr Ser Gly Ser Gly Thr Lys Leu Glu Ile Lys
            145                 150                 155

<210> SEQ ID NO 427
<211> LENGTH: 156
<212> TYPE: PRT
<213> ORGANISM: Artificial Sequence
<220> FEATURE:
<223> OTHER INFORMATION: chemically synthesized

<400> SEQUENCE: 427
```

Gln Gly Gln Ser Gly Gln Gly Val Cys Arg Thr Arg Trp His Phe Glu
1               5                   10                  15

Thr Thr Asp Cys Val Met Gly Gly Ser Ser Gly Ser Ile Ser
            20              25              30

Ser Gly Leu Leu Ser Gly Arg Ser Ala Asn Pro Gly Gly Ser Asp
        35                  40                  45

Ile Val Met Thr Gln Thr Pro Thr Leu Ala Ala Ser Pro Gly Glu
50              55                  60

Lys Ile Ile Ile Thr Cys Ser Ala Ser Ser Ile Ser Ser Asn Tyr
65              70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
            100                 105                 110

Ser Gly Ser Gly Thr Ser Tyr Ser Leu Thr Ile Gly Thr Met Glu Ala
            115                 120                 125

Glu Asp Val Ala Thr Tyr Tyr Cys Gln Gln Gly Ser Ser Ile Pro Arg
    130                 135                 140

Phe Thr Ser Gly Ser Gly Thr Lys Leu Glu Ile Lys
145                 150                 155

<210> SEQ ID NO 428
<211> LENGTH: 160
<212> TYPE: PRT
<213> ORGANISM: Artificial Sequence
<220> FEATURE:
<223> OTHER INFORMATION: chemically synthesized

<400> SEQUENCE: 428

Gln Gly Gln Ser Gly Gln Gly Glu Cys Lys Thr Arg Gln Asp Phe Glu
1               5                   10                  15

Met His Asp Cys Val Tyr Gly Gly Ser Ser Gly Gly Ser Ala Val
            20              25                  30

Gly Leu Leu Ala Pro Pro Gly Gly Leu Ser Gly Arg Ser Ala Asn Pro
        35                  40                  45

Gly Gly Ser Asp Ile Gln Met Thr Gln Ser Pro Ser Ser Leu Ser Ala
    50                  55                  60

Ser Val Gly Asp Arg Val Thr Ile Thr Cys Ser Ala Ser Ser Ser Ile
65              70                  75                  80

Ser Ser Asn Tyr Leu His Trp Tyr Gln Gln Lys Pro Gly Lys Val Pro
            85                  90                  95

Lys Leu Leu Ile Tyr Arg Thr Ser Asn Leu Ala Ser Gly Val Pro Ser
            100                 105                 110

Arg Phe Ser Gly Ser Gly Ser Gly Thr Asp Tyr Thr Leu Thr Ile Ser
        115                 120                 125

Ser Leu Gln Pro Glu Asp Val Ala Thr Tyr Tyr Cys Gln Gln Gly Ser
    130                 135                 140

Ser Ile Pro Arg Phe Thr Ser Gly Gly Thr Lys Val Glu Ile Lys
145                 150                 155                 160

<210> SEQ ID NO 429
<211> LENGTH: 160
<212> TYPE: PRT
<213> ORGANISM: Artificial Sequence
<220> FEATURE:
<223> OTHER INFORMATION: chemically synthesized

<400> SEQUENCE: 429

Gln Gly Gln Ser Gly Gln Gly Cys Met Ser Arg Phe Ala Phe Glu
1               5                   10                  15

Ile Gly Asp Cys Val Met Gly Gly Ser Ser Gly Gly Ser Ala Val
            20                  25                  30

Gly Leu Leu Ala Pro Pro Gly Gly Leu Ser Gly Arg Ser Ala Asn Pro
            35                  40                  45

Gly Gly Ser Asp Ile Gln Met Thr Gln Ser Pro Ser Ser Leu Ser Ala
        50                  55                  60

Ser Val Gly Asp Arg Val Thr Ile Thr Cys Ser Ala Ser Ser Ser Ile
65                  70                  75                  80

Ser Ser Asn Tyr Leu His Trp Tyr Gln Gln Lys Pro Gly Lys Val Pro
                85                  90                  95

Lys Leu Leu Ile Tyr Arg Thr Ser Asn Leu Ala Ser Gly Val Pro Ser
                100                 105                 110

Arg Phe Ser Gly Ser Gly Ser Gly Thr Asp Tyr Thr Leu Thr Ile Ser
            115                 120                 125

Ser Leu Gln Pro Glu Asp Val Ala Thr Tyr Tyr Cys Gln Gln Gly Ser
    130                 135                 140

Ser Ile Pro Arg Phe Thr Ser Gly Gly Thr Lys Val Glu Ile Lys
145                 150                 155                 160

<210> SEQ ID NO 430
<211> LENGTH: 160
<212> TYPE: PRT
<213> ORGANISM: Artificial Sequence
<220> FEATURE:
<223> OTHER INFORMATION: chemically synthesized

<400> SEQUENCE: 430

Gln Gly Gln Ser Gly Gln Gly Thr Cys Leu Ser Arg Tyr Glu Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Gly Leu Ser Gly Arg Ser Ala Asn Pro
            35                  40                  45

Gly Gly Ser Asp Ile Val Met Thr Gln Thr Pro Thr Thr Leu Ala Ala
        50                  55                  60

Ser Pro Gly Glu Lys Ile Ile Ile Thr Cys Ser Ala Ser Ser Ser Ile
65                  70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
                100                 105                 110

Arg Phe Ser Gly Ser Gly Ser Gly Thr Ser Tyr Ser Leu Thr Ile Gly
            115                 120                 125

Thr Met Glu Ala Glu Asp Val Ala Thr Tyr Tyr Cys Gln Gln Gly Ser
    130                 135                 140

Ser Ile Pro Arg Phe Thr Ser Gly Ser Gly Thr Lys Leu Glu Ile Lys
145                 150                 155                 160

<210> SEQ ID NO 431
<211> LENGTH: 160
<212> TYPE: PRT
<213> ORGANISM: Artificial Sequence
<220> FEATURE:
<223> OTHER INFORMATION: chemically synthesized

<400> SEQUENCE: 431

Gln Gly Gln Ser Gly Gln Gly Val Cys Arg Thr Arg Trp His Phe Glu
1               5                   10                  15

Thr Thr Asp Cys Val Met Gly Gly Ser Ser Gly Gly Ser Ala Val
            20                  25                  30

Gly Leu Leu Ala Pro Pro Gly Leu Ser Gly Arg Ser Ala Asn Pro
        35                  40                  45

Gly Gly Ser Asp Ile Val Met Thr Gln Thr Pro Thr Thr Leu Ala Ala
    50                  55                  60

Ser Pro Gly Glu Lys Ile Ile Ile Thr Cys Ser Ala Ser Ser Ile
65              70                  75                  80

Ser Ser Asn Tyr Leu His Trp Tyr Gln Gln Lys Pro Gly Phe Ser Pro
                85                  90                  95

Lys Leu Leu Ile Tyr Arg Thr Ser Asn Leu Ala Ser Gly Val Pro Ala
            100                 105                 110

Arg Phe Ser Gly Ser Gly Ser Gly Thr Ser Tyr Ser Leu Thr Ile Gly
        115                 120                 125

Thr Met Glu Ala Glu Asp Val Ala Thr Tyr Tyr Cys Gln Gln Gly Ser
    130                 135                 140

Ser Ile Pro Arg Phe Thr Ser Gly Ser Gly Thr Lys Leu Glu Ile Lys
145                 150                 155                 160

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436
<211> LENGTH: 149
<212> TYPE: PRT
<213> ORGANISM: Artificial Sequence
<220> FEATURE:
<223> OTHER INFORMATION: chemically synthesized

<400> SEQUENCE: 436

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Asp Ile Gln Met Thr Gln Ser Pro
        35                  40                  45

-continued

Ser Ser Leu Ser Ala Ser Val Gly Asp Arg Val Thr Ile Thr Cys Ser
            50                  55                  60

Ala Ser Ser Ser Ile Ser Ser Asn Tyr Leu His Trp Tyr Gln Gln Lys
 65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
            115                 120                 125

Cys Gln Gln Gly Ser Ser Ile Pro Arg Phe Thr Ser Gly Gly Gly Thr
            130                 135                 140

Lys Val Glu Ile Lys
145

<210> SEQ ID NO 437

<400> SEQUENCE: 437

000

<210> SEQ ID NO 438
<211> LENGTH: 149
<212> TYPE: PRT
<213> ORGANISM: Artificial Sequence
<220> FEATURE:
<223> OTHER INFORMATION: chemically synthesized

<400> SEQUENCE: 438

Gln Cys Met Ser Arg Phe Ala Phe Glu Ile Gly Asp Cys Val Met Gly
 1               5                  10                  15

Gly Gly Ser Ser Gly Gly Ser Ile Ser Ser Gly Leu Leu Ser Gly Arg
                20                  25                  30

Ser Asp Asn His Gly Gly Gly Ser Asp Ile Gln Met Thr Gln Ser Pro
            35                  40                  45

Ser Ser Leu Ser Ala Ser Val Gly Asp Arg Val Thr Ile Thr Cys Ser
            50                  55                  60

Ala Ser Ser Ser Ile Ser Ser Asn Tyr Leu His Trp Tyr Gln Gln Lys
 65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
            115                 120                 125

Cys Gln Gln Gly Ser Ser Ile Pro Arg Phe Thr Ser Gly Gly Gly Thr
            130                 135                 140

Lys Val Glu Ile Lys
145

<210> SEQ ID NO 439

<400> SEQUENCE: 439

000

<210> SEQ ID NO 440
<211> LENGTH: 149
<212> TYPE: PRT

<213> ORGANISM: Artificial Sequence
<220> FEATURE:
<223> OTHER INFORMATION: chemically synthesized

<400> SEQUENCE: 440

```
Thr Cys Leu Ser Arg Tyr Glu Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Asn His Gly Gly Gly Ser Asp Ile Val Met Thr Gln Thr Pro
        35                  40                  45

Thr Thr Leu Ala Ala Ser Pro Gly Glu Lys Ile Ile Ile Thr Cys Ser
    50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
                85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
    130                 135                 140

Lys Leu Glu Ile Lys
145
```

<210> SEQ ID NO 441

<400> SEQUENCE: 441

000

<210> SEQ ID NO 442
<211> LENGTH: 156
<212> TYPE: PRT
<213> ORGANISM: Artificial Sequence
<220> FEATURE:
<223> OTHER INFORMATION: chemically synthesized

<400> SEQUENCE: 442

```
Gln Gly Gln Ser Gly Gln Gly Val Cys Arg Thr Arg Trp His Phe Glu
1               5                   10                  15

Thr Thr Asp Cys Val Met Gly Gly Gly Ser Ser Gly Gly Ser Ile Ser
            20                  25                  30

Ser Gly Leu Leu Ser Gly Arg Ser Asp Asn His Gly Gly Gly Ser Asp
        35                  40                  45

Ile Val Met Thr Gln Thr Pro Thr Thr Leu Ala Ala Ser Pro Gly Glu
    50                  55                  60

Lys Ile Ile Ile Thr Cys Ser Ala Ser Ser Ser Ile Ser Ser Asn Tyr
65                  70                  75                  80

Leu His Trp Tyr Gln Gln Lys Pro Gly Phe Ser Pro Lys Leu Leu Ile
                85                  90                  95

Tyr Arg Thr Ser Asn Leu Ala Ser Gly Val Pro Ala Arg Phe Ser Gly
            100                 105                 110

Ser Gly Ser Gly Thr Ser Tyr Ser Leu Thr Ile Gly Thr Met Glu Ala
        115                 120                 125

Glu Asp Val Ala Thr Tyr Tyr Cys Gln Gln Gly Ser Ser Ile Pro Arg
    130                 135                 140
```

Phe Thr Ser Gly Ser Gly Thr Lys Leu Glu Ile Lys
145                 150                 155

<210> SEQ ID NO 443

<400> SEQUENCE: 443

000

<210> SEQ ID NO 444
<211> LENGTH: 153
<212> TYPE: PRT
<213> ORGANISM: Artificial Sequence
<220> FEATURE:
<223> OTHER INFORMATION: chemically synthesized

<400> SEQUENCE: 444

Glu Cys Lys Thr Arg Gln Asp Phe Glu Met His Asp Cys Val Tyr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Ser Ala Ser Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
    130                 135                 140

Gly Gly Gly Thr Lys Val Glu Ile Lys
145                 150

<210> SEQ ID NO 445
<211> LENGTH: 153
<212> TYPE: PRT
<213> ORGANISM: Artificial Sequence
<220> FEATURE:
<223> OTHER INFORMATION: chemically synthesized

<400> SEQUENCE: 445

Gln Cys Met Ser Arg Phe Ala Phe Glu Ile Gly Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Ser Ala Ser Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

```
Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
    130                 135                 140

Gly Gly Gly Thr Lys Val Glu Ile Lys
145                 150

<210> SEQ ID NO 446
<211> LENGTH: 153
<212> TYPE: PRT
<213> ORGANISM: Artificial Sequence
<220> FEATURE:
<223> OTHER INFORMATION: chemically synthesized

<400> SEQUENCE: 446

Thr Cys Leu Ser Arg Tyr Glu Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
        35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
            100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
    130                 135                 140

Gly Ser Gly Thr Lys Leu Glu Ile Lys
145                 150

<210> SEQ ID NO 447
<211> LENGTH: 153
<212> TYPE: PRT
<213> ORGANISM: Artificial Sequence
<220> FEATURE:
<223> OTHER INFORMATION: chemically synthesized

<400> SEQUENCE: 447

Val Cys Arg Thr Arg Trp His Phe Glu Thr Thr Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Asn His Gly Gly Ser Asp Ile Val Met
        35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95
```

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
            115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys
145                 150

<210> SEQ ID NO 448
<211> LENGTH: 149
<212> TYPE: PRT
<213> ORGANISM: Artificial Sequence
<220> FEATURE:
<223> OTHER INFORMATION: chemically synthesized

<400> SEQUENCE: 448

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
    130                 135                 140

Lys Val Glu Ile Lys
145

<210> SEQ ID NO 449
<211> LENGTH: 149
<212> TYPE: PRT
<213> ORGANISM: Artificial Sequence
<220> FEATURE:
<223> OTHER INFORMATION: chemically synthesized

<400> SEQUENCE: 449

Gln Cys Met Ser Arg Phe Ala Phe Glu Ile Gly Asp Cys Val Met Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Gln Met Thr Gln Ser Pro
        35                  40                  45

Ser Ser Leu Ser Ala Ser Val Gly Asp Arg Val Thr Ile Thr Cys Ser
    50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala

```
                        85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
            115                 120                 125

Cys Gln Gln Gly Ser Ser Ile Pro Arg Phe Thr Ser Gly Gly Gly Thr
            130                 135                 140

Lys Val Glu Ile Lys
145

<210> SEQ ID NO 450
<211> LENGTH: 149
<212> TYPE: PRT
<213> ORGANISM: Artificial Sequence
<220> FEATURE:
<223> OTHER INFORMATION: chemically synthesized

<400> SEQUENCE: 450

Thr Cys Leu Ser Arg Tyr Glu Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Val Met Thr Gln Thr Pro
            35                  40                  45

Thr Thr Leu Ala Ala Ser Pro Gly Glu Lys Ile Ile Ile Thr Cys Ser
        50                  55                  60

Ala Ser Ser Ser Ile Ser Ser Asn Tyr Leu His Trp Tyr Gln Gln Lys
65                  70                  75                  80

Pro Gly Phe Ser Pro Lys Leu Leu Ile Tyr Arg Thr Ser Asn Leu Ala
                85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
            115                 120                 125

Cys Gln Gln Gly Ser Ser Ile Pro Arg Phe Thr Ser Gly Ser Gly Thr
            130                 135                 140

Lys Leu Glu Ile Lys
145

<210> SEQ ID NO 451
<211> LENGTH: 149
<212> TYPE: PRT
<213> ORGANISM: Artificial Sequence
<220> FEATURE:
<223> OTHER INFORMATION: chemically synthesized

<400> SEQUENCE: 451

Val Cys Arg Thr Arg Trp His Phe Glu Thr Thr Asp Cys Val Met Gly
1               5                   10                  15

Gly Gly Ser Ser Gly Gly Ser Ile Ser Ser Gly Leu Leu Ser Gly Arg
            20                  25                  30

Ser Asp Gln His Gly Gly Gly Ser Asp Ile Val Met Thr Gln Thr Pro
            35                  40                  45

Thr Thr Leu Ala Ala Ser Pro Gly Glu Lys Ile Ile Ile Thr Cys Ser
        50                  55                  60

Ala Ser Ser Ser Ile Ser Ser Asn Tyr Leu His Trp Tyr Gln Gln Lys
65                  70                  75                  80
```

```
Pro Gly Phe Ser Pro Lys Leu Leu Ile Tyr Arg Thr Ser Asn Leu Ala
            85                  90                  95

Ser Gly Val Pro Ala Arg Phe Ser Gly Ser Gly Ser Thr Ser Tyr
            100                 105                 110

Ser Leu Thr Ile Gly Thr Met Glu Ala Glu Asp Val Ala Thr Tyr Tyr
            115                 120                 125

Cys Gln Gln Gly Ser Ser Ile Pro Arg Phe Thr Ser Gly Ser Gly Thr
            130                 135                 140

Lys Leu Glu Ile Lys
145

<210> SEQ ID NO 452
<211> LENGTH: 153
<212> TYPE: PRT
<213> ORGANISM: Artificial Sequence
<220> FEATURE:
<223> OTHER INFORMATION: chemically synthesized

<400> SEQUENCE: 452

Glu Cys Lys Thr Arg Gln Asp Phe Glu Met His Asp Cys Val Tyr Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Gln Met
            35                  40                  45

Thr Gln Ser Pro Ser Ser Leu Ser Ala Ser Val Gly Asp Arg Val Thr
        50                  55                  60

Ile Thr Cys Ser Ala Ser Ser Ile Ser Ser Asn Tyr Leu His Trp
65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
            115                 120                 125

Ala Thr Tyr Tyr Cys Gln Gln Gly Ser Ser Ile Pro Arg Phe Thr Ser
        130                 135                 140

Gly Gly Gly Thr Lys Val Glu Ile Lys
145                 150

<210> SEQ ID NO 453
<211> LENGTH: 153
<212> TYPE: PRT
<213> ORGANISM: Artificial Sequence
<220> FEATURE:
<223> OTHER INFORMATION: chemically synthesized

<400> SEQUENCE: 453

Gln Cys Met Ser Arg Phe Ala Phe Glu Ile Gly Asp Cys Val Met Gly
1               5                   10                  15

Gly Gly Ser Ser Gly Gly Ser Ala Val Gly Leu Leu Ala Pro Pro Gly
            20                  25                  30

Gly Leu Ser Gly Arg Ser Asp Gln His Gly Gly Ser Asp Ile Gln Met
            35                  40                  45

Thr Gln Ser Pro Ser Ser Leu Ser Ala Ser Val Gly Asp Arg Val Thr
        50                  55                  60

Ile Thr Cys Ser Ala Ser Ser Ile Ser Ser Asn Tyr Leu His Trp
65                  70                  75                  80
```

```
Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
                100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
    130                 135                 140

Gly Gly Gly Thr Lys Val Glu Ile Lys
145                 150
```

<210> SEQ ID NO 454
<211> LENGTH: 153
<212> TYPE: PRT
<213> ORGANISM: Artificial Sequence
<220> FEATURE:
<223> OTHER INFORMATION: chemically synthesized

<400> SEQUENCE: 454

```
Thr Cys Leu Ser Arg Tyr Glu Phe Glu Thr Thr Asp Cys Val Met Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Gln His Gly Gly Ser Asp Ile Val Met
            35                  40                  45

Thr Gln Thr Pro Thr Thr Leu Ala Ala Ser Pro Gly Glu Lys Ile Ile
        50                  55                  60

Ile Thr Cys Ser Ala Ser Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
    130                 135                 140

Gly Ser Gly Thr Lys Leu Glu Ile Lys
145                 150
```

<210> SEQ ID NO 455
<211> LENGTH: 153
<212> TYPE: PRT
<213> ORGANISM: Artificial Sequence
<220> FEATURE:
<223> OTHER INFORMATION: chemically synthesized

<400> SEQUENCE: 455

```
Val Cys Arg Thr Arg Trp His Phe Glu Thr Thr Asp Cys Val Met Gly
1               5                   10                  15

Gly Gly Ser Ser Gly Gly Ser Ala Val Gly Leu Leu Ala Pro Pro Gly
                20                  25                  30

Gly Leu Ser Gly Arg Ser Asp Gln His Gly Gly Ser Asp Ile Val Met
            35                  40                  45

Thr Gln Thr Pro Thr Thr Leu Ala Ala Ser Pro Gly Glu Lys Ile Ile
        50                  55                  60

Ile Thr Cys Ser Ala Ser Ser Ser Ile Ser Ser Asn Tyr Leu His Trp
```

```
                65                  70                  75                  80
Tyr Gln Gln Lys Pro Gly Phe Ser Pro Lys Leu Leu Ile Tyr Arg Thr
                    85                  90                  95

Ser Asn Leu Ala Ser Gly Val Pro Ala Arg Phe Ser Gly Ser Gly Ser
                    100                 105                 110

Gly Thr Ser Tyr Ser Leu Thr Ile Gly Thr Met Glu Ala Glu Asp Val
                    115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys
145                 150

<210> SEQ ID NO 456
<211> LENGTH: 149
<212> TYPE: PRT
<213> ORGANISM: Artificial Sequence
<220> FEATURE:
<223> OTHER INFORMATION: chemically synthesized

<400> SEQUENCE: 456

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
                20                  25                  30

Ser Asp Asn Pro Gly Gly Gly Ser Asp Ile Gln Met Thr Gln Ser Pro
                35                  40                  45

Ser Ser Leu Ser Ala Ser Val Gly Asp Arg Val Thr Ile Thr Cys Ser
            50                  55                  60

Ala Ser Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
                100                 105                 110

Thr Leu Thr Ile Ser Ser Leu Gln Pro Glu Asp Val Ala Thr Tyr Tyr
            115                 120                 125

Cys Gln Gln Gly Ser Ser Ile Pro Arg Phe Thr Ser Gly Gly Gly Thr
        130                 135                 140

Lys Val Glu Ile Lys
145

<210> SEQ ID NO 457
<211> LENGTH: 149
<212> TYPE: PRT
<213> ORGANISM: Artificial Sequence
<220> FEATURE:
<223> OTHER INFORMATION: chemically synthesized

<400> SEQUENCE: 457

Gln Cys Met Ser Arg Phe Ala Phe Glu Ile Gly Asp Cys Val Met Gly
1               5                   10                  15

Gly Gly Ser Ser Gly Gly Ser Ile Ser Ser Gly Leu Leu Ser Gly Arg
                20                  25                  30

Ser Asp Asn Pro Gly Gly Gly Ser Asp Ile Gln Met Thr Gln Ser Pro
                35                  40                  45

Ser Ser Leu Ser Ala Ser Val Gly Asp Arg Val Thr Ile Thr Cys Ser
            50                  55                  60
```

```
Ala Ser Ser Ser Ile Ser Ser Asn Tyr Leu His Trp Tyr Gln Gln Lys
 65                  70                  75                  80

Pro Gly Lys Val Pro Lys Leu Leu Ile Tyr Arg Thr Ser Asn Leu Ala
                 85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
        130                 135                 140

Lys Val Glu Ile Lys
145
```

<210> SEQ ID NO 458
<211> LENGTH: 149
<212> TYPE: PRT
<213> ORGANISM: Artificial Sequence
<220> FEATURE:
<223> OTHER INFORMATION: chemically synthesized

<400> SEQUENCE: 458

```
Thr Cys Leu Ser Arg Tyr Glu Phe Glu Thr Thr Asp Cys Val Met Gly
 1               5                  10                  15

Gly Gly Ser Ser Gly Gly Ser Ile Ser Ser Gly Leu Leu Ser Gly Arg
                 20                  25                  30

Ser Asp Asn Pro Gly Gly Gly Ser Asp Ile Val Met Thr Gln Thr Pro
             35                  40                  45

Thr Thr Leu Ala Ala Ser Pro Gly Glu Lys Ile Ile Ile Thr Cys Ser
 50                  55                  60

Ala Ser Ser Ser Ile Ser Ser Asn Tyr Leu His Trp Tyr Gln Gln Lys
 65                  70                  75                  80

Pro Gly Phe Ser Pro Lys Leu Leu Ile Tyr Arg Thr Ser Asn Leu Ala
                 85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
        130                 135                 140

Lys Leu Glu Ile Lys
145
```

<210> SEQ ID NO 459
<211> LENGTH: 149
<212> TYPE: PRT
<213> ORGANISM: Artificial Sequence
<220> FEATURE:
<223> OTHER INFORMATION: chemically synthesized

<400> SEQUENCE: 459

```
Val Cys Arg Thr Arg Trp His Phe Glu Thr Thr Asp Cys Val Met Gly
 1               5                  10                  15

Gly Gly Ser Ser Gly Gly Ser Ile Ser Ser Gly Leu Leu Ser Gly Arg
                 20                  25                  30

Ser Asp Asn Pro Gly Gly Gly Ser Asp Ile Val Met Thr Gln Thr Pro
             35                  40                  45

Thr Thr Leu Ala Ala Ser Pro Gly Glu Lys Ile Ile Ile Thr Cys Ser
 50                  55                  60
```

```
Ala Ser Ser Ser Ile Ser Ser Asn Tyr Leu His Trp Tyr Gln Gln Lys
 65                  70                  75                  80

Pro Gly Phe Ser Pro Lys Leu Leu Ile Tyr Arg Thr Ser Asn Leu Ala
                 85                  90                  95

Ser Gly Val Pro Ala Arg Phe Ser Gly Ser Gly Thr Ser Tyr
            100                 105                 110

Ser Leu Thr Ile Gly Thr Met Glu Ala Glu Asp Val Ala Thr Tyr Tyr
            115                 120                 125

Cys Gln Gln Gly Ser Ser Ile Pro Arg Phe Thr Ser Gly Ser Gly Thr
            130                 135                 140

Lys Leu Glu Ile Lys
145

<210> SEQ ID NO 460
<211> LENGTH: 153
<212> TYPE: PRT
<213> ORGANISM: Artificial Sequence
<220> FEATURE:
<223> OTHER INFORMATION: chemically synthesized

<400> SEQUENCE: 460

Glu Cys Lys Thr Arg Gln Asp Phe Glu Met His Asp Cys Val Tyr Gly
 1               5                  10                  15

Gly Gly Ser Ser Gly Gly Ser Ala Val Gly Leu Leu Ala Pro Pro Gly
                 20                  25                  30

Gly Leu Ser Gly Arg Ser Asp Asn Pro Gly Gly Ser Asp Ile Gln Met
             35                  40                  45

Thr Gln Ser Pro Ser Ser Leu Ser Ala Ser Val Gly Asp Arg Val Thr
 50                  55                  60

Ile Thr Cys Ser Ala Ser Ser Ile Ser Ser Asn Tyr Leu His Trp
 65                  70                  75                  80

Tyr Gln Gln Lys Pro Gly Lys Val Pro Lys Leu Leu Ile Tyr Arg Thr
                 85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
            115                 120                 125

Ala Thr Tyr Tyr Cys Gln Gln Gly Ser Ser Ile Pro Arg Phe Thr Ser
            130                 135                 140

Gly Gly Gly Thr Lys Val Glu Ile Lys
145                 150

<210> SEQ ID NO 461
<211> LENGTH: 153
<212> TYPE: PRT
<213> ORGANISM: Artificial Sequence
<220> FEATURE:
<223> OTHER INFORMATION: chemically synthesized

<400> SEQUENCE: 461

Gln Cys Met Ser Arg Phe Ala Phe Glu Ile Gly Asp Cys Val Met Gly
 1               5                  10                  15

Gly Gly Ser Ser Gly Gly Ser Ala Val Gly Leu Leu Ala Pro Pro Gly
                 20                  25                  30

Gly Leu Ser Gly Arg Ser Asp Asn Pro Gly Gly Ser Asp Ile Gln Met
             35                  40                  45

Thr Gln Ser Pro Ser Ser Leu Ser Ala Ser Val Gly Asp Arg Val Thr
```

50                  55                  60

Ile Thr Cys Ser Ala Ser Ser Ile Ser Ser Asn Tyr Leu His Trp
 65                  70                  75                  80

Tyr Gln Gln Lys Pro Gly Lys Val Pro Lys Leu Leu Ile Tyr Arg Thr
                 85                  90                  95

Ser Asn Leu Ala Ser Gly Val Pro Ser Arg Phe Ser Gly Ser Gly Ser
                100                 105                 110

Gly Thr Asp Tyr Thr Leu Thr Ile Ser Ser Leu Gln Pro Glu Asp Val
            115                 120                 125

Ala Thr Tyr Tyr Cys Gln Gln Gly Ser Ser Ile Pro Arg Phe Thr Ser
        130                 135                 140

Gly Gly Gly Thr Lys Val Glu Ile Lys
145                 150

<210> SEQ ID NO 462
<211> LENGTH: 153
<212> TYPE: PRT
<213> ORGANISM: Artificial Sequence
<220> FEATURE:
<223> OTHER INFORMATION: chemically synthesized

<400> SEQUENCE: 462

Thr Cys Leu Ser Arg Tyr Glu Phe Glu Thr Thr Asp Cys Val Met Gly
 1               5                  10                  15

Gly Gly Ser Ser Gly Gly Ser Ala Val Gly Leu Leu Ala Pro Pro Gly
                20                  25                  30

Gly Leu Ser Gly Arg Ser Asp Asn Pro Gly Gly Ser Asp Ile Val Met
            35                  40                  45

Thr Gln Thr Pro Thr Thr Leu Ala Ala Ser Pro Gly Glu Lys Ile Ile
        50                  55                  60

Ile Thr Cys Ser Ala Ser Ser Ile Ser Ser Asn Tyr Leu His Trp
 65                  70                  75                  80

Tyr Gln Gln Lys Pro Gly Phe Ser Pro Lys Leu Leu Ile Tyr Arg Thr
                 85                  90                  95

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
            115                 120                 125

Ala Thr Tyr Tyr Cys Gln Gln Gly Ser Ser Ile Pro Arg Phe Thr Ser
        130                 135                 140

Gly Ser Gly Thr Lys Leu Glu Ile Lys
145                 150

<210> SEQ ID NO 463
<211> LENGTH: 153
<212> TYPE: PRT
<213> ORGANISM: Artificial Sequence
<220> FEATURE:
<223> OTHER INFORMATION: chemically synthesized

<400> SEQUENCE: 463

Val Cys Arg Thr Arg Trp His Phe Glu Thr Thr Asp Cys Val Met Gly
 1               5                  10                  15

Gly Gly Ser Ser Gly Gly Ser Ala Val Gly Leu Leu Ala Pro Pro Gly
                20                  25                  30

Gly Leu Ser Gly Arg Ser Asp Asn Pro Gly Gly Ser Asp Ile Val Met
            35                  40                  45

Thr Gln Thr Pro Thr Thr Leu Ala Ala Ser Pro Gly Glu Lys Ile Ile
    50                  55                  60

Ile Thr Cys Ser Ala Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
                115                 120                 125

Ala Thr Tyr Tyr Cys Gln Gln Gly Ser Ser Ile Pro Arg Phe Thr Ser
130                 135                 140

Gly Ser Gly Thr Lys Leu Glu Ile Lys
145                 150

<210> SEQ ID NO 464
<211> LENGTH: 149
<212> TYPE: PRT
<213> ORGANISM: Artificial Sequence
<220> FEATURE:
<223> OTHER INFORMATION: chemically synthesized

<400> SEQUENCE: 464

Glu Cys Lys Thr Arg Gln Asp Phe Glu Met His Asp Cys Val Tyr Gly
1               5                   10                  15

Gly Gly Ser Ser Gly Gly Ser Ile Ser Ser Gly Leu Leu Ser Gly Arg
                20                  25                  30

Ser Ala Asn Pro Gly Gly Gly Ser Asp Ile Gln Met Thr Gln Ser Pro
                35                  40                  45

Ser Ser Leu Ser Ala Ser Val Gly Asp Arg Val Thr Ile Thr Cys Ser
            50                  55                  60

Ala Ser Ser Ile Ser Ser Asn Tyr Leu His Trp Tyr Gln Gln Lys
65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
                100                 105                 110

Thr Leu Thr Ile Ser Ser Leu Gln Pro Glu Asp Val Ala Thr Tyr Tyr
                115                 120                 125

Cys Gln Gln Gly Ser Ser Ile Pro Arg Phe Thr Ser Gly Gly Gly Thr
130                 135                 140

Lys Val Glu Ile Lys
145

<210> SEQ ID NO 465
<211> LENGTH: 149
<212> TYPE: PRT
<213> ORGANISM: Artificial Sequence
<220> FEATURE:
<223> OTHER INFORMATION: chemically synthesized

<400> SEQUENCE: 465

Gln Cys Met Ser Arg Phe Ala Phe Glu Ile Gly Asp Cys Val Met Gly
1               5                   10                  15

Gly Gly Ser Ser Gly Gly Ser Ile Ser Ser Gly Leu Leu Ser Gly Arg
                20                  25                  30

Ser Ala Asn Pro Gly Gly Gly Ser Asp Ile Gln Met Thr Gln Ser Pro
                35                  40                  45

-continued

```
Ser Ser Leu Ser Ala Ser Val Gly Asp Arg Val Thr Ile Thr Cys Ser
        50                  55                  60

Ala Ser Ser Ser Ile Ser Ser Asn Tyr Leu His Trp Tyr Gln Gln Lys
 65                  70                  75                  80

Pro Gly Lys Val Pro Lys Leu Leu Ile Tyr Arg Thr Ser Asn Leu Ala
                85                  90                  95

Ser Gly Val Pro Ser Arg Phe Ser Gly Ser Gly Ser Gly Thr Asp Tyr
            100                 105                 110

Thr Leu Thr Ile Ser Ser Leu Gln Pro Glu Asp Val Ala Thr Tyr Tyr
        115                 120                 125

Cys Gln Gln Gly Ser Ser Ile Pro Arg Phe Thr Ser Gly Gly Gly Thr
    130                 135                 140

Lys Val Glu Ile Lys
145

<210> SEQ ID NO 466
<211> LENGTH: 149
<212> TYPE: PRT
<213> ORGANISM: Artificial Sequence
<220> FEATURE:
<223> OTHER INFORMATION: chemically synthesized

<400> SEQUENCE: 466

Thr Cys Leu Ser Arg Tyr Glu Phe Glu Thr Thr Asp Cys Val Met Gly
 1               5                  10                  15

Gly Gly Ser Ser Gly Gly Ser Ile Ser Ser Gly Leu Leu Ser Gly Arg
                20                  25                  30

Ser Ala Asn Pro Gly Gly Gly Ser Asp Ile Val Met Thr Gln Thr Pro
         35                  40                  45

Thr Thr Leu Ala Ala Ser Pro Gly Glu Lys Ile Ile Thr Cys Ser
        50                  55                  60

Ala Ser Ser Ser Ile Ser Ser Asn Tyr Leu His Trp Tyr Gln Gln Lys
 65                  70                  75                  80

Pro Gly Phe Ser Pro Lys Leu Leu Ile Tyr Arg Thr Ser Asn Leu Ala
                85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
    130                 135                 140

Lys Leu Glu Ile Lys
145

<210> SEQ ID NO 467
<211> LENGTH: 149
<212> TYPE: PRT
<213> ORGANISM: Artificial Sequence
<220> FEATURE:
<223> OTHER INFORMATION: chemically synthesized

<400> SEQUENCE: 467

Val Cys Arg Thr Arg Trp His Phe Glu Thr Thr Asp Cys Val Met Gly
 1               5                  10                  15

Gly Gly Ser Ser Gly Gly Ser Ile Ser Ser Gly Leu Leu Ser Gly Arg
                20                  25                  30

Ser Ala Asn Pro Gly Gly Gly Ser Asp Ile Val Met Thr Gln Thr Pro
```

```
                    35                  40                  45
Thr Thr Leu Ala Ala Ser Pro Gly Glu Lys Ile Ile Ile Thr Cys Ser
 50                  55                  60

Ala Ser Ser Ser Ile Ser Ser Asn Tyr Leu His Trp Tyr Gln Gln Lys
 65                  70                  75                  80

Pro Gly Phe Ser Pro Lys Leu Leu Ile Tyr Arg Thr Ser Asn Leu Ala
                 85                  90                  95

Ser Gly Val Pro Ala Arg Phe Ser Gly Ser Gly Ser Gly Thr Ser Tyr
            100                 105                 110

Ser Leu Thr Ile Gly Thr Met Glu Ala Glu Asp Val Ala Thr Tyr Tyr
        115                 120                 125

Cys Gln Gln Gly Ser Ser Ile Pro Arg Phe Thr Ser Gly Ser Gly Thr
130                 135                 140

Lys Leu Glu Ile Lys
145
```

<210> SEQ ID NO 468
<211> LENGTH: 153
<212> TYPE: PRT
<213> ORGANISM: Artificial Sequence
<220> FEATURE:
<223> OTHER INFORMATION: chemically synthesized

<400> SEQUENCE: 468

```
Glu Cys Lys Thr Arg Gln Asp Phe Glu Met His Asp Cys Val Tyr Gly
 1               5                  10                  15

Gly Gly Ser Ser Gly Gly Ser Ala Val Gly Leu Leu Ala Pro Pro Gly
             20                  25                  30

Gly Leu Ser Gly Arg Ser Ala Asn Pro Gly Gly Ser Asp Ile Gln Met
         35                  40                  45

Thr Gln Ser Pro Ser Ser Leu Ser Ala Ser Val Gly Asp Arg Val Thr
 50                  55                  60

Ile Thr Cys Ser Ala Ser Ser Ser Ile Ser Ser Asn Tyr Leu His Trp
 65                  70                  75                  80

Tyr Gln Gln Lys Pro Gly Lys Val Pro Lys Leu Leu Ile Tyr Arg Thr
                 85                  90                  95

Ser Asn Leu Ala Ser Gly Val Pro Ser Arg Phe Ser Gly Ser Gly Ser
            100                 105                 110

Gly Thr Asp Tyr Thr Leu Thr Ile Ser Ser Leu Gln Pro Glu Asp Val
        115                 120                 125

Ala Thr Tyr Tyr Cys Gln Gln Gly Ser Ser Ile Pro Arg Phe Thr Ser
130                 135                 140

Gly Gly Gly Thr Lys Val Glu Ile Lys
145                 150
```

<210> SEQ ID NO 469
<211> LENGTH: 153
<212> TYPE: PRT
<213> ORGANISM: Artificial Sequence
<220> FEATURE:
<223> OTHER INFORMATION: chemically synthesized

<400> SEQUENCE: 469

```
Gln Cys Met Ser Arg Phe Ala Phe Glu Ile Gly Asp Cys Val Met Gly
 1               5                  10                  15

Gly Gly Ser Ser Gly Gly Ser Ala Val Gly Leu Leu Ala Pro Pro Gly
             20                  25                  30
```

Gly Leu Ser Gly Arg Ser Ala Asn Pro Gly Gly Ser Asp Ile Gln Met
            35                  40                  45

Thr Gln Ser Pro Ser Ser Leu Ser Ala Ser Val Gly Asp Arg Val Thr
 50                  55                  60

Ile Thr Cys Ser Ala Ser Ser Ile Ser Ser Asn Tyr Leu His Trp
 65                  70                  75                  80

Tyr Gln Gln Lys Pro Gly Lys Val Pro Lys Leu Leu Ile Tyr Arg Thr
                85                  90                  95

Ser Asn Leu Ala Ser Gly Val Pro Ser Arg Phe Ser Gly Ser Gly Ser
                100                 105                 110

Gly Thr Asp Tyr Thr Leu Thr Ile Ser Ser Leu Gln Pro Glu Asp Val
            115                 120                 125

Ala Thr Tyr Tyr Cys Gln Gln Gly Ser Ser Ile Pro Arg Phe Thr Ser
        130                 135                 140

Gly Gly Gly Thr Lys Val Glu Ile Lys
145                 150

<210> SEQ ID NO 470
<211> LENGTH: 153
<212> TYPE: PRT
<213> ORGANISM: Artificial Sequence
<220> FEATURE:
<223> OTHER INFORMATION: chemically synthesized

<400> SEQUENCE: 470

Thr Cys Leu Ser Arg Tyr Glu Phe Glu Thr Thr Asp Cys Val Met Gly
  1               5                  10                  15

Gly Gly Ser Ser Gly Gly Ser Ala Val Gly Leu Leu Ala Pro Pro Gly
                20                  25                  30

Gly Leu Ser Gly Arg Ser Ala Asn Pro Gly Gly Ser Asp Ile Val Met
            35                  40                  45

Thr Gln Thr Pro Thr Thr Leu Ala Ala Ser Pro Gly Glu Lys Ile Ile
 50                  55                  60

Ile Thr Cys Ser Ala Ser Ser Ile Ser Ser Asn Tyr Leu His Trp
 65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
            115                 120                 125

Ala Thr Tyr Tyr Cys Gln Gln Gly Ser Ser Ile Pro Arg Phe Thr Ser
        130                 135                 140

Gly Ser Gly Thr Lys Leu Glu Ile Lys
145                 150

<210> SEQ ID NO 471
<211> LENGTH: 153
<212> TYPE: PRT
<213> ORGANISM: Artificial Sequence
<220> FEATURE:
<223> OTHER INFORMATION: chemically synthesized

<400> SEQUENCE: 471

Val Cys Arg Thr Arg Trp His Phe Glu Thr Thr Asp Cys Val Met Gly
  1               5                  10                  15

Gly Gly Ser Ser Gly Gly Ser Ala Val Gly Leu Leu Ala Pro Pro Gly
                20                  25                  30

```
Gly Leu Ser Gly Arg Ser Ala Asn Pro Gly Gly Ser Asp Ile Val Met
        35                  40                  45

Thr Gln Thr Pro Thr Thr Leu Ala Ala Ser Pro Gly Glu Lys Ile Ile
    50                  55                  60

Ile Thr Cys Ser Ala Ser Ser Ser Ile Ser Ser Asn Tyr Leu His Trp
65                  70                  75                  80

Tyr Gln Gln Lys Pro Gly Phe Ser Pro Lys Leu Leu Ile Tyr Arg Thr
                85                  90                  95

Ser Asn Leu Ala Ser Gly Val Pro Ala Arg Phe Ser Gly Ser Gly Ser
                100                 105                 110

Gly Thr Ser Tyr Ser Leu Thr Ile Gly Thr Met Glu Ala Glu Asp Val
        115                 120                 125

Ala Thr Tyr Tyr Cys Gln Gln Gly Ser Ser Ile Pro Arg Phe Thr Ser
    130                 135                 140

Gly Ser Gly Thr Lys Leu Glu Ile Lys
145                 150
```

ANTI-ITGA3 ANTIBODIES, ACTIVATABLE ANTI-ITGA3 ANTIBODIES, AND METHODS OF USE THEREOF

RELATED APPLICATIONS

This application claims the benefit of U.S. Provisional Application Nos. 62/156,839, filed May 4, 2015; and 62/258,870, filed Nov. 23, 2015, the contents of each of which are incorporated herein by reference in their entirety.

The contents of the text file named "CYTM_041_001US_SeqList_ST25", which was created on Sep. 13, 2018 and is 362 KB in size, are hereby incorporated by reference in their entirety.

FIELD OF THE INVENTION

The invention relates generally to antibodies that bind ITGa3, activatable antibodies that specifically bind to ITGa3 and methods of making and using these anti-ITGa3 antibodies and anti-ITGa3 activatable antibodies in a variety of therapeutic, diagnostic and prophylactic indications.

BACKGROUND OF THE INVENTION

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

The present disclosure provides antibodies, monoclonal antibodies (mAbs), antigen-binding fragments, and activatable monoclonal antibodies that specifically bind Integrin Alpha 3 (ITGa3), also known as traCD49C; GAP-B3; GAPB3; ILNEB; MSK18; VCA-2; VL3A; VLA3a. The use of the term "ITGa3" herein is intended to cover any variation thereof, such as, by way of non-limiting example, ITGa-3, ITGa3, ITGA-3, ITG a3, ITG-a3, ITG A3, ITGA3, ITG-A3, ITGα3, ITG-α3, ITG α3, and all variations are used herein interchangeably. In some embodiments, the antibodies, the monoclonal antibodies, the antigen-binding fragments, and activatable monoclonal antibodies are internalized by ITGa3-containing cells.

In some embodiments, the antibody includes antibodies or antigen-binding fragments thereof that specifically bind ITGa3. In some embodiments, the antibody or antigen-binding fragment thereof that binds ITGa3 is a monoclonal antibody, domain antibody, single chain, Fab fragment, a F(ab')$_2$ fragment, a scFv, a scAb, a dAb, a single domain heavy chain antibody, or a single domain light chain antibody. In some embodiments, such an antibody or antigen-binding fragment thereof that binds ITGa3 is a mouse, other rodent, chimeric, humanized or fully human monoclonal antibody.

In some embodiments, the antibody or antigen-binding fragment thereof comprises a heavy chain variable region amino acid sequence selected from the group consisting of SEQ ID NO: 1 and 3-10. In some embodiments, the antibody or antigen-binding fragment thereof comprises a heavy chain variable region amino acid sequence selected from the group consisting of SEQ ID NO: 3-10. In some embodiments, the antibody or antigen-binding fragment thereof comprises a heavy chain variable region amino acid sequence selected from the group consisting of SEQ ID NO: 7-10. In some embodiments, the antibody or antigen-binding fragment thereof comprises a heavy chain variable region amino acid sequence SEQ ID NO: 10.

In some embodiments, the antibody or antigen-binding fragment thereof comprises a light chain variable region amino acid sequence selected from the group consisting of SEQ ID NO: 2, 11, and 12. In some embodiments, the antibody or antigen-binding fragment thereof comprises a light chain variable region amino acid sequence selected from the group consisting of SEQ ID NO: 11 and 12. In some embodiments, the antibody or antigen-binding fragment thereof comprises a light chain variable region amino acid sequence SEQ ID NO: 11.

In some embodiments, the antibody or antigen-binding fragment thereof comprises a heavy chain variable region amino acid sequence selected from the group consisting of SEQ ID NO: 1 and 3-10, and a light chain variable region amino acid sequence selected from the group consisting of SEQ ID NO: 2, 11, and 12.

In some embodiments, the antibody or antigen-binding fragment thereof comprises a heavy chain variable region amino acid sequence selected from the group consisting of SEQ ID NO: 3-10, and a light chain variable region amino acid sequence selected from the group consisting of SEQ ID NO: 11 and 12. In some embodiments, the antibody or antigen-binding fragment thereof comprises a heavy chain variable region amino acid sequence selected from the group consisting of SEQ ID NO: 7-10, and a light chain variable region amino acid sequence SEQ ID NO: 11. In some embodiments, the antibody or antigen-binding fragment thereof comprises a heavy chain variable region amino acid sequence SEQ ID NO: 10, and a light chain variable region amino acid sequence SEQ ID NO: 11.

In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 1 and 3-10. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 3-10. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 7-10. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence of SEQ ID NO: 10.

In some embodiments, the antibody or antigen-binding fragment thereof comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 2, 11, and 12. In some embodiments, the antibody or antigen-binding fragment thereof comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 11 and 12. In some embodiments, the antibody or antigen-binding fragment thereof comprises a light chain variable region amino acid sequence that is at least 90%, 91%, 92%, 93%, 94%, 95%, 96%, 97%, 98% or 99% identical to an amino acid sequence SEQ ID NO: 11.

In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 1 and 3-10, and a light chain variable region amino acid sequence that is at least 90%, 91%, 92%, 93%, 94%, 95%, 96%, 97%, 98% or 99% identical to an amino acid sequence selected from the group consisting of SEQ ID NO: 2, 11, and 12.

In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 3-10, and a light chain variable region amino acid sequence that is at least 90%, 91%, 92%, 93%, 94%, 95%, 96%, 97%, 98% or 99% identical to an amino acid sequence selected from the group consisting of SEQ ID NO: 11 and 12. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 7-10, and a light chain variable region amino acid sequence that is at least 90%, 91%, 92%, 93%, 94%, 95%, 96%, 97%, 98% or 99% identical to the amino acid sequence SEQ ID NO: 11. In some embodiments, the antibody or antigen-binding fragment thereof comprises a heavy chain variable region amino acid sequence that is at least 90%, 91%, 92%, 93%, 94%, 95%, 96%, 97%, 98% or 99% identical to the amino acid sequence SEQ ID NO: 10, and a light chain variable region amino acid sequence that is at least 90%, 91%, 92%, 93%, 94%, 95%, 96%, 97%, 98% or 99% identical to the amino acid sequence SEQ ID NO: 11.

In some embodiments, the antibody or antigen-binding fragment thereof comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 comprising the amino acid sequence EYIIH (SEQ ID NO: 13); a VH CDR2 comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

In some embodiments, the antibody or antigen-binding fragment thereof comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence EYIIH (SEQ ID NO: 13); a VH CDR2 sequence that includes a sequence that is at least 90%, 91%, 92%, 93%, 94%, 95%, 96%, 97%, 98%, 99% or more identical to a VH CDR2 sequence comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 sequence that includes a sequence that is at least 90%, 91%, 92%, 93%, 94%, 95%, 96%, 97%, 98%, 99% or more identical to a VH CDR3 sequence comprising the amino acid sequence HEERDYYGYYAMDY (SEQ ID NO: 18); a VL CDR1 sequence that includes a sequence that is at least 90%, 91%, 92%, 93%, 94%, 95%, 96%, 97%, 98%, 99% or more identical to a VL CDR1 sequence comprising the amino acid sequence SASSSISSNYLH (SEQ ID NO: 19); a VL CDR2 sequence that includes a sequence that is at least 90%, 91%, 92%, 93%, 94%, 95%, 96%, 97%, 98%, 99% or more identical to a VL CDR2 sequence comprising the amino acid sequence RTSNLA (SEQ ID NO: 20); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence QQGSSIPRFT (SEQ ID NO: 21).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence EYIIH (SEQ ID NO: 13); a VH CDR2 sequence that includes a sequence that is at least 90%, 91%, 92%, 93%, 94%, 95%, 96%, 97%, 98%, 99% or more identical to a VH CDR2 sequence comprising the amino acid sequence WFYPESGSVKYNEGFKG (SEQ ID NO: 17); a VH CDR3 sequence that includes a sequence that is at least 90%, 91%, 92%, 93%, 94%, 95%, 96%, 97%, 98%, 99% or more identical to a VH CDR3 sequence comprising the amino acid sequence HEERDYYGYYAMDY (SEQ ID NO: 18); a VL CDR1 sequence that includes a sequence that is at least 90%, 91%, 92%, 93%, 94%, 95%, 96%, 97%, 98%, 99% or more identical to a VL CDR1 sequence comprising the amino acid sequence SASSSISSNYLH (SEQ ID NO: 19); a VL CDR2 sequence that includes a sequence that is at least 90%, 91%, 92%, 93%, 94%, 95%, 96%, 97%, 98%, 99% or more identical to a VL CDR2 sequence comprising the amino acid sequence RTSNLA (SEQ ID NO: 20); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence QQGSSIPRFT (SEQ ID NO: 21).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence EYIIH (SEQ ID NO: 13); the VH CDR2 sequence comprises the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); the VH CDR3 sequence comprises the amino acid sequence HEERDYYGYYAMDY (SEQ ID NO: 18); the VL CDR1 sequence comprises the amino acid sequence SASSSISSNYLH (SEQ ID NO: 19); the VL CDR2 sequence comprises the amino acid sequence RTSNLA (SEQ ID NO: 20); and the VL CDR3 sequence comprises the amino acid sequence QQGSSIPRFT (SEQ ID NO: 21).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence EYIIH (SEQ ID NO: 13); the VH CDR2 sequence comprises the amino acid sequence WFYPESGSVKYNEGFKG (SEQ ID NO: 17); the VH CDR3 sequence comprises the amino acid sequence HEERDYYGYYAMDY (SEQ ID NO: 18); the VL CDR1 sequence comprises the amino acid sequence SASSSISSNYLH (SEQ ID NO: 19); the VL CDR2 sequence comprises the amino acid sequence RTSNLA (SEQ ID NO: 20); and the VL CDR3 sequence comprises the amino acid sequence QQGSSIPRFT (SEQ ID NO: 21).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence EYIIH (SEQ ID NO: 13); the VH CDR2 sequence comprises a sequence that is at least 90%, 91%, 92%, 93%, 94%, 95%, 96%, 97%, 98%, 99% or more identical to the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); the VH CDR3 sequence comprises a sequence that is at least 90%, 91%, 92%, 93%, 94%, 95%, 96%, 97%, 98%, 99% or more identical to the amino acid sequence HEERDYYGYYAMDY (SEQ ID NO: 18); the VL CDR1 sequence comprises a sequence that is at least 90%, 91%, 92%, 93%, 94%, 95%, 96%, 97%, 98%, 99% or more identical to the amino acid sequence SASSSISSNYLH (SEQ ID NO: 19); the VL CDR2 sequence comprises a sequence that is at least 90%, 91%, 92%, 93%, 94%, 95%, 96%, 97%, 98%, 99% or more identical to the amino acid sequence RTSNLA (SEQ ID NO: 20); and the VL CDR3 sequence a sequence that is at least 90%, 91%, 92%, 93%, 94%, 95%, 96%, 97%, 98%, 99% or more identical to comprises the amino acid sequence QQGSSIPRFT (SEQ ID NO: 21).

In some embodiments, the antibody or antigen-binding fragment thereof comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence EYIIH (SEQ ID NO: 13); the VH CDR2 sequence comprises a sequence that is at least 90%, 91%, 92%, 93%, 94%, 95%, 96%, 97%, 98%, 99% or more identical to the amino acid sequence WFYPESGSVKYNEGFKG (SEQ ID NO: 17); the VH CDR3 sequence comprises a sequence that is at least 90%, 91%, 92%, 93%, 94%, 95%, 96%, 97%, 98%, 99% or more identical to the amino acid sequence HEERDYYGYYAMDY (SEQ ID NO: 18); the VL CDR1 sequence comprises a sequence that is at least 90%, 91%, 92%, 93%, 94%, 95%, 96%, 97%, 98%, 99% or more identical to the amino acid sequence SASSSISSNYLH (SEQ ID NO: 19); the VL CDR2 sequence comprises a sequence that is at least 90%, 91%, 92%, 93%, 94%, 95%, 96%, 97%, 98%, 99% or more identical to the amino acid sequence RTSNLA (SEQ ID NO: 20); and the VL CDR3 sequence a sequence that is at least 90%, 91%, 92%, 93%, 94%, 95%, 96%, 97%, 98%, 99% or more identical to comprises the amino acid sequence QQGSSIPRFT (SEQ ID NO: 21).

In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 1 and 3-10. In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 3-10. In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 7-10. In some embodiments, the antibody or antigen-binding fragment thereof is encoded by a nucleic acid sequence that comprises a nucleic acid sequence encoding a heavy chain amino acid sequence comprising the amino acid sequence SEQ ID NO: 10.

In some embodiments, the antibody or antigen-binding fragment thereof is encoded by a nucleic acid sequence that comprises a nucleic acid sequence encoding a light chain amino acid sequence comprising an amino acid sequence selected from the group consisting of SEQ ID NO: 2, 11, and 12. In some embodiments, the antibody or antigen-binding fragment thereof is encoded by a nucleic acid sequence that comprises a nucleic acid sequence encoding a light chain amino acid sequence comprising an amino acid sequence selected from the group consisting of SEQ ID NO: 11 and 12. In some embodiments, the antibody or antigen-binding fragment thereof is encoded by a nucleic acid sequence that comprises a nucleic acid sequence encoding a light chain amino acid sequence comprising the amino acid sequence SEQ ID NO: 11 and 12.

In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 1 and 3-10, and a nucleic acid sequence encoding a light chain amino acid sequence comprising an amino acid sequence selected from the group consisting of SEQ ID NO: 2, 11, and 12.

In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 3-10, and a nucleic acid sequence encoding a light chain amino acid sequence comprising an amino acid sequence selected from the group consisting of SEQ ID NO: 11 and 12. In some embodiments, the antibody or antigen-binding fragment thereof is encoded by a nucleic acid sequence that comprises a nucleic acid sequence encoding a heavy chain amino acid sequence comprising an amino acid sequence selected from the group consisting of SEQ ID NO: 7-10, and a nucleic acid sequence encoding a light chain amino acid sequence comprising the amino acid sequence of SEQ ID NO: 11. In some embodiments, the antibody or antigen-binding fragment thereof is encoded by a nucleic acid sequence that comprises a nucleic acid sequence encoding a heavy chain amino acid sequence comprising the amino acid sequence of SEQ ID NO: 7-10, and a nucleic acid sequence encoding a light chain amino acid sequence comprising the amino acid sequence of SEQ ID NO: 11.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 1 and 3-10. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 3-10. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 7-10. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising the amino acid sequence of SEQ ID NO: 10.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 2, 11, and 12. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 11 and 12. In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain amino acid sequence comprising the amino acid sequence of SEQ ID NO: 11.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 1 and 3-10, and a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 2, 11, and 12.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 3-10, and a nucleic acid sequence that is at least 90%, 91%, 92%, 93%, 94%, 95%, 96%, 97%, 98% or 99% identical to a nucleic acid sequence encoding a light chain amino acid sequence comprising an amino acid sequence selected from the group consisting of SEQ ID NO: 11 and 12.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence comprising an amino acid sequence selected from the group consisting of SEQ ID NO: 7-10, and a nucleic acid sequence that is at least 90%, 91%, 92%, 93%, 94%, 95%, 96%, 97%, 98% or 99% identical to a nucleic acid sequence encoding a light chain amino acid sequence comprising the amino acid sequence of SEQ ID NO: 11.

In some embodiments, the antibody or antigen-binding fragment thereof is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain amino acid sequence of SEQ ID NO: 10, and a nucleic acid sequence that is at least 90%, 91%, 92%, 93%, 94%, 95%, 96%, 97%, 98% or 99% identical to a nucleic acid sequence encoding a light chain amino acid sequence comprising the amino acid sequence of SEQ ID NO: 11.

In some embodiments, the antibody or antigen-binding fragment thereof is incorporated in a multispecific antibody or antigen-binding fragment thereof, where at least one arm of the multispecific antibody or antigen-binding fragment thereof specifically binds ITGa3. In some embodiments, the antibody or antigen-binding fragment thereof is incorporated in a bispecific antibody or antigen-binding fragment thereof, where at least one arm of the bispecific antibody or antigen-binding fragment thereof specifically binds ITGa3.

In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 1 and 3-10. In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 3-10. In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 7-10. In some embodiments, at least one arm of the multispecific antibody or antigen-binding fragment thereof, e.g., a bispecific antibody or antigen-binding fragment thereof, comprises a heavy chain variable region amino acid sequence SEQ ID NO: 10.

In some embodiments, at least one arm of the multispecific antibody or antigen-binding fragment thereof, e.g., a bispecific antibody or antigen-binding fragment thereof, comprises a light chain variable region amino acid sequence selected from the group consisting of SEQ ID NO: 2, 11, and 12. In some embodiments, at least one arm of the multispecific antibody or antigen-binding fragment thereof, e.g., a bispecific antibody or antigen-binding fragment thereof, comprises a light chain variable region amino acid sequence selected from the group consisting of SEQ ID NO: 11 and 12. In some embodiments, at least one arm of the multispecific antibody or antigen-binding fragment thereof, e.g., a bispecific antibody or antigen-binding fragment thereof, comprises a light chain variable region amino acid sequence SEQ ID NO: 11.

In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 1 and 3-10, and a light chain variable region amino acid sequence selected from the group consisting of SEQ ID NO: 2, 11, and 12.

In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 3-10, and a light chain variable region amino acid sequence selected from the group consisting of SEQ ID NO: 11 and 12.

In some embodiments, at least one arm of the multispecific antibody or antigen-binding fragment thereof, e.g., a bispecific antibody or antigen-binding fragment thereof, comprises a heavy chain variable region amino acid sequence selected from the group consisting of SEQ ID NO: 7-10, and a light chain variable region amino acid sequence SEQ ID NO: 11. In some embodiments, at least one arm of the multispecific antibody or antigen-binding fragment thereof, e.g., a bispecific antibody or antigen-binding fragment thereof, comprises a heavy chain variable region amino acid sequence SEQ ID NO: 10, and a light chain variable region amino acid sequence SEQ ID NO: 11.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 1 and 3-10. In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 3-10. In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 7-10. In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to the amino acid sequence of SEQ ID NO: 10.

In some embodiments, at least one arm of the multispecific antibody or antigen-binding fragment thereof, e.g., a bispecific antibody or antigen-binding fragment thereof, comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 2, 11, and 12. In some embodiments, at least one arm of the multispecific antibody or antigen-binding fragment thereof, e.g., a bispecific antibody or antigen-binding fragment thereof, comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 11 and 12. In some embodiments, at least one arm of the multispecific antibody or antigen-binding fragment thereof, e.g., a bispecific antibody or antigen-binding fragment thereof, comprises a light chain variable region amino acid sequence that is at least 90%, 91%, 92%, 93%, 94%, 95%, 96%, 97%, 98% or 99% identical to the amino acid sequence of SEQ ID NO: 11.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 1 and 3-10, and a light chain variable region amino acid sequence that is at least 90%, 91%, 92%, 93%, 94%, 95%, 96%, 97%, 98% or 99% identical to an amino acid sequence selected from the group consisting of SEQ ID NO: 2, 11, and 12.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 3-10, and a light chain variable region amino acid sequence that is at least 90%, 91%, 92%, 93%, 94%, 95%, 96%, 97%, 98% or 99% identical to an amino acid sequence selected from the group consisting of SEQ ID NO: 11 and 12.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 7-10, and a light chain variable region amino acid sequence that is at least 90%, 91%, 92%, 93%, 94%, 95%, 96%, 97%, 98% or 99% identical to the amino acid sequence of SEQ ID NO: 11.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to the amino acid sequence of SEQ ID NO: 10, and a light chain variable region amino acid sequence that is at least 90%, 91%, 92%, 93%, 94%, 95%, 96%, 97%, 98% or 99% identical to the amino acid sequence of SEQ ID NO: 11.

In some embodiments, at least one arm of the multispecific antibody or antigen-binding fragment thereof, e.g., a bispecific antibody or antigen-binding fragment thereof, comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 comprising the amino acid sequence EYIIH (SEQ ID NO: 13); a VH CDR2 comprising the amino acid sequence WFYPESGS-VKYNETFKG (SEQ ID NO: 14) or WFYPESGSVKYSET-FKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 comprising the amino acid sequence EYIIH (SEQ ID NO: 13); a VH CDR2 comprising the amino acid sequence WFYPESGS-VKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence EYIIH (SEQ ID NO: 13); a VH CDR2 sequence that includes a sequence that is at least 90%, 91%, 92%, 93%, 94%, 95%, 96%, 97%, 98%, 99% or more identical to a VH CDR2 sequence comprising the amino acid sequence WFYPESGS-VKYNETFKG (SEQ ID NO: 14) or WFYPESGSVKYSET-FKG (SEQ ID NO: 15) or WFYPESGSVKYNEAFKG (SEQ ID NO: 16) or WFYPESGSVKYNEGFKG (SEQ ID NO: 17); a VH CDR3 sequence that includes a sequence that is at least 90%, 91%, 92%, 93%, 94%, 95%, 96%, 97%, 98%, 99% or more identical to a VH CDR3 sequence comprising the amino acid sequence HEERDYY-GYYAMDY (SEQ ID NO: 18); a VL CDR1 sequence that includes a sequence that is at least 90%, 91%, 92%, 93%, 94%, 95%, 96%, 97%, 98%, 99% or more identical to a VL CDR1 sequence comprising the amino acid sequence SASS-SISSNYLH (SEQ ID NO: 19); a VL CDR2 sequence that includes a sequence that is at least 90%, 91%, 92%, 93%, 94%, 95%, 96%, 97%, 98%, 99% or more identical to a VL CDR2 sequence comprising the amino acid sequence RTSNLA (SEQ ID NO: 20); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence EYIIH (SEQ ID NO: 13); a VH CDR2 sequence that includes a sequence that is at least 90%, 91%, 92%, 93%, 94%, 95%, 96%, 97%, 98%, 99% or more identical to a VH CDR2 sequence comprising the amino acid sequence WFYPESGS-VKYNEGFKG (SEQ ID NO: 17); a VH CDR3 sequence that includes a sequence that is at least 90%, 91%, 92%, 93%, 94%, 95%, 96%, 97%, 98%, 99% or more identical to a VH CDR3 sequence comprising the amino acid sequence HEERDYYGYYAMDY (SEQ ID NO: 18); a VL CDR1 sequence that includes a sequence that is at least 90%, 91%, 92%, 93%, 94%, 95%, 96%, 97%, 98%, 99% or more identical to a VL CDR1 sequence comprising the amino acid sequence SASSSISSNYLH (SEQ ID NO: 19); a VL CDR2 sequence that includes a sequence that is at least 90%, 91%, 92%, 93%, 94%, 95%, 96%, 97%, 98%, 99% or more identical to a VL CDR2 sequence comprising the amino acid sequence RTSNLA (SEQ ID NO: 20); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence EYIIH (SEQ ID NO: 13); the VH CDR2 sequence comprises the amino acid sequence WFYPESGSVKYNET-FKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); the VH CDR3 sequence comprises the amino acid sequence HEERDYYGYYAMDY (SEQ ID NO: 18); the VL CDR1 sequence comprises the amino acid sequence SASSSISS-NYLH (SEQ ID NO: 19); the VL CDR2 sequence comprises the amino acid sequence RTSNLA (SEQ ID NO: 20); and the VL CDR3 sequence comprises the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence EYIIH (SEQ ID NO: 13); the VH CDR2 sequence comprises the amino acid sequence WFYPESGSVKYNEG-FKG (SEQ ID NO: 17); the VH CDR3 sequence comprises the amino acid sequence HEERDYYGYYAMDY (SEQ ID NO: 18); the VL CDR1 sequence comprises the amino acid sequence SASSSISSNYLH (SEQ ID NO: 19); the VL CDR2 sequence comprises the amino acid sequence RTSNLA (SEQ ID NO: 20); and the VL CDR3 sequence comprises the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence EYIIH (SEQ ID NO: 13); the VH CDR2 sequence comprises a sequence that is at least 90%, 91%, 92%, 93%, 94%, 95%, 96%, 97%, 98%, 99% or more identical to the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); the VH CDR3 sequence comprises a sequence that is at least 90%, 91%, 92%, 93%, 94%, 95%, 96%, 97%, 98%, 99% or more identical to the amino acid sequence HEERDYY-GYYAMDY (SEQ ID NO: 18); the VL CDR1 sequence comprises a sequence that is at least 90%, 91%, 92%, 93%, 94%, 95%, 96%, 97%, 98%, 99% or more identical to the amino acid sequence SASSSISSNYLH (SEQ ID NO: 19); the VL CDR2 sequence comprises a sequence that is at least 90%, 91%, 92%, 93%, 94%, 95%, 96%, 97%, 98%, 99% or more identical to the amino acid sequence RTSNLA (SEQ ID NO: 20); and the VL CDR3 sequence comprises a sequence that is at least 90%, 91%, 92%, 93%, 94%, 95%, 96%, 97%, 98%, 99% or more identical to the amino acid sequence QQGSSIPRFT (SEQ ID NO: 21).

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence EYIIH (SEQ ID NO: 13); the VH CDR2 sequence comprises a sequence that is at least 90%, 91%, 92%, 93%, 94%, 95%, 96%, 97%, 98%, 99% or more identical to the amino acid sequence WFYPESGSVKYNEGFKG (SEQ ID NO: 17); the VH CDR3 sequence comprises a sequence that is at least 90%, 91%, 92%, 93%, 94%, 95%, 96%, 97%, 98%, 99% or more identical to the amino acid sequence HEERDYYGYYAMDY (SEQ ID NO: 18); the VL CDR1 sequence comprises a sequence that is at least 90%, 91%, 92%, 93%, 94%, 95%, 96%, 97%, 98%, 99% or more identical to the amino acid sequence SASSSISSNYLH (SEQ ID NO: 19); the VL CDR2 sequence comprises a sequence that is at least 90%, 91%, 92%, 93%, 94%, 95%, 96%, 97%, 98%, 99% or more identical to the amino acid sequence RTSNLA (SEQ ID NO: 20); and the VL CDR3 sequence comprises a sequence that is at least 90%, 91%, 92%, 93%, 94%, 95%, 96%, 97%, 98%, 99% or more identical to the amino acid sequence QQGSSIPRFT (SEQ ID NO: 21).

Suitable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a heavy chain variable region amino acid sequence selected from the group consisting of SEQ ID NO: 1 and 3-10, and a light chain variable region amino acid sequence selected from the group consisting of SEQ ID NO: 2, 11, and 12.

In some embodiments, at least one arm of the multispecific antibody or antigen-binding fragment thereof, e.g., a bispecific antibody or antigen-binding fragment thereof, comprises a heavy chain or a heavy chain variable region that comprises or is derived from a heavy chain amino acid sequence or heavy chain variable region amino acid sequence shown in Table 12. In some embodiments, at least one arm of the multispecific antibody or antigen-binding fragment thereof, e.g., a bispecific antibody or antigen-binding fragment thereof, comprises a light chain or a light chain variable region that comprises or is derived from a light chain amino acid sequence or light chain variable region amino acid sequence shown in Table 12. In some embodiments, at least one arm of the multispecific antibody or antigen-binding fragment thereof, e.g., a bispecific antibody or antigen-binding fragment thereof, comprises a heavy chain or a heavy chain variable region amino acid sequence that comprises or is derived from a heavy chain amino acid sequence or heavy chain variable region amino acid sequence shown in Table 12 and a light chain or a light chain variable region amino acid sequence that comprises or is derived from a light chain amino acid sequence or light chain variable region amino acid sequence shown in Table 12.

In some embodiments, at least one arm of the multispecific antibody or antigen-binding fragment thereof, e.g., a bispecific antibody or antigen-binding fragment thereof, comprises a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12. In some embodiments, at least one arm of the multispecific antibody or antigen-binding fragment thereof, e.g., a bispecific antibody or antigen-binding fragment thereof, comprises an amino acid sequence that is at least 90%, 91%, 92%, 93%, 94%, 95%, 96%, 97%, 98% or 99% identical to an amino acid sequence that is selected from the group consisting of the light chain variable region sequences shown in Table 12. In some embodiments, at least one arm of the multispecific antibody or antigen-binding fragment thereof, e.g., a bispecific antibody or antigen-binding fragment thereof, comprises an amino acid sequence that is at least 90%, 91%, 92%, 93%, 94%, 95%, 96%, 97%, 98% or 99% identical to an amino acid sequence selected from the group consisting of the heavy chain variable region sequences shown in Table 12 and a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12.

In some embodiments, at least one arm of the multispecific antibody or antigen-binding fragment thereof, e.g., a bispecific antibody or antigen-binding fragment thereof, comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence shown in Table 13; a VH CDR2 sequence shown in Table 13; a VH CDR3 sequence shown in Table 13; a VL CDR1 sequence shown in Table 13; a VL CDR2 sequence shown in Table 13; and a VL CDR3 sequence shown in Table 13.

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence shown in Table 13; a VH CD2 sequence that includes a sequence that is at least 90%, 91%, 92%, 93%, 94%, 95%, 96%, 97%, 98%, 99% or more identical to a VH CDR2 sequence shown in Table 13; a VH CDR3 sequence that includes a sequence that is at least 90%, 91%, 92%, 93%, 94%, 95%, 96%, 97%, 98%, 99% or more identical to a VH CDR3 sequence shown in Table 13; a VL CDR1 sequence that includes a sequence that is at least 90%, 91%, 92%, 93%, 94%, 95%, 96%, 97%, 98%, 99% or more identical to a VL CDR1 sequence shown in Table 13; a VL CDR2 sequence that includes a sequence that is at least 90%, 91%, 92%, 93%, 94%, 95%, 96%, 97%, 98%, 99% or more identical to a VL CDR2 sequence shown in Table 13; and a VL CDR3 sequence that includes a sequence that is at least 90%, 91%, 92%, 93%, 94%, 95%, 96%, 97%, 98%, 99% or more identical to a VL CDR3 sequence shown in Table 13.

In some embodiments at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, at least one arm of the multispecific antibody or antigen-binding fragment thereof, e.g., a bispecific antibody or antigen-binding fragment thereof, comprises a light chain variable region that comprise a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 13.

In some embodiments, at least one arm of the multispecific antibody or antigen-binding fragment thereof, e.g., a bispecific antibody or antigen-binding fragment thereof, comprises a heavy chain variable region that comprise a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 13.

In some embodiments, at least one arm of the multispecific antibody or antigen-binding fragment thereof, e.g., a bispecific antibody or antigen-binding fragment thereof, comprises a combination of a VH CDR1 sequence, a VH CDR2 sequence, a VH CDR3 sequence, a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of the six CDR sequences (VH CDR1, VH CDR2, VH CDR3, VL CDR1, VL CDR2, and VL CDR3) shown in a single row in Table 13.

In some embodiments, at least one arm of the multispecific antibody or antigen-binding fragment thereof, e.g., a bispecific antibody or antigen-binding fragment thereof, comprises a heavy chain variable region that comprise a combination of a VH CDR1 sequence, a VH CDR2 sequence, and a VH CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three heavy chain CDR sequences (VH CDR1, VH CDR2, VH CDR3) shown in a single row in Table 13.

In some embodiments, at least one arm of the multispecific antibody or antigen-binding fragment thereof, e.g., a bispecific antibody or antigen-binding fragment thereof, comprises a light chain variable region that comprise a combination of a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three light chain CDR sequences (VL CDR1, VL CDR2, VL CDR3) shown in a single row in Table 13.

Suitable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a VH CDR1 comprising the amino acid sequence EYIIH (SEQ ID NO: 13); a VH CDR2 comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a heavy chain variable region amino acid sequence selected from the group consisting of SEQ ID NO: 1 and 3-10, and a light chain variable region amino acid sequence selected from the group consisting of SEQ ID NO: 2, 11, and 12.

Suitable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a heavy chain variable region amino acid sequence SEQ ID NO: 10, and a light chain variable region amino acid sequence SEQ ID NO: 11.

Suitable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a VH CDR1 comprising the amino acid sequence EYIIH (SEQ ID NO: 13); a VH CDR2 comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

The disclosure also provides activatable antibodies that include an antibody or antigen-binding fragment thereof that specifically binds ITGa3 coupled to a masking moiety (MM), such that coupling of the MM reduces the ability of the antibody or antigen-binding fragment thereof to bind ITGa3. In some embodiments, the MM is coupled via a sequence that includes a substrate for a protease, for example, a protease that is active in diseased tissue and/or a protease that is co-localized with ITGa3 at a treatment site in a subject. The activatable anti-ITGa3 antibodies provided herein, also referred to herein interchangeably as anti-ITGa3 activatable antibodies or ITGa3 activatable antibodies, are stable in circulation, activated at intended sites of therapy and/or diagnosis but not in normal, e.g., healthy tissue or other tissue not targeted for treatment and/or diagnosis, and, when activated, exhibit binding to ITGa3 that is at least comparable to the corresponding, unmodified antibody, also referred to herein as the parental antibody.

The invention also provides methods of treating, preventing and/or delaying the onset or progression of, or alleviating a symptom associated with aberrant expression and/or activity of ITGa3 in a subject using activatable antibodies that bind ITGa3, particularly activatable antibodies that bind and neutralize or otherwise inhibit at least one biological activity of ITGa3 and/or ITGa3-mediated signaling.

The invention also provides methods of treating, preventing and/or delaying the onset or progression of, or alleviating a symptom associated with the presence, growth, proliferation, metastasis, and/or activity of cells which are expressing ITGa3 or aberrantly expressing ITGa3 in a subject using activatable antibodies that bind ITGa3, particularly activatable antibodies that bind, target, neutralize, kill, or otherwise inhibit at least one biological activity of cells which are expressing or aberrantly expressing ITGa3.

The invention also provides methods of treating, preventing and/or delaying the onset or progression of, or alleviating a symptom associated with the presence, growth, proliferation, metastasis, and/or activity of cells which are expressing ITGa3 in a subject using activatable antibodies that bind ITGa3, particularly activatable antibodies that bind, target, neutralize, kill, or otherwise inhibit at least one biological activity of cells which are expressing ITGa3.

The invention also provides methods of treating, preventing and/or delaying the onset or progression of, or alleviating a symptom associated with the presence, growth, proliferation, metastasis, and/or activity of cells which are aberrantly expressing ITGa3 in a subject using activatable antibodies that bind ITGa3, particularly activatable antibodies that bind, target, neutralize, kill, or otherwise inhibit at least one biological activity of cells which are aberrantly expressing ITGa3.

The activatable antibodies in an activated state bind ITGa3 and include (i) an antibody or an antigen binding fragment thereof (AB) that specifically binds to ITGa3; (ii) a masking moiety (MM) that, when the activatable antibody is in an uncleaved state, inhibits the binding of the AB to ITGa3; and (c) a cleavable moiety (CM) coupled to the AB, wherein the CM is a polypeptide that functions as a substrate for a protease.

In some embodiments, the activatable antibody in the uncleaved state has the structural arrangement from N-terminus to C-terminus as follows: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 165) and $(GGGS)_n$ (SEQ ID NO: 166), where n is an integer of at least one.

In some embodiments, at least one of LP1 or LP2 comprises an amino acid sequence selected from the group consisting of GGSG (SEQ ID NO: 167), GGSGG (SEQ ID NO: 168), GSGSG (SEQ ID NO: 169), GSGGG (SEQ ID NO: 170), GGGSG (SEQ ID NO: 171), and GSSSG (SEQ ID NO: 172).

In some embodiments, LP1 comprises the amino acid sequence GSSGGSGGSGGSG (SEQ ID NO: 173), GSSGGSGGSGG (SEQ ID NO: 174), GSSGGSGGSGGS (SEQ ID NO: 175), GSSGGSGGSGGSGGGS (SEQ ID NO: 176), GSSGGSGGSG (SEQ ID NO: 177), or GSSGGSGGSGS (SEQ ID NO: 178).

In some embodiments, LP2 comprises the amino acid sequence GSS, GGS, GGGS (SEQ ID NO: 179), GSSGT (SEQ ID NO: 180) or GSSG (SEQ ID NO: 181).

In some embodiments, the AB has a dissociation constant of about 100 nM or less for binding to ITGa3.

In some embodiments, the AB has a dissociation constant of about 100 nM or less for binding to mammalian ITGa3.

In some embodiments, the AB has a dissociation constant of about 10 nM or less for binding to mammalian ITGA3. In some embodiments, the AB has a dissociation constant of about 5 nM or less for binding to ITGA3. In some embodiments, the AB has a dissociation constant of about 1 nM or less for binding to ITGA3. In some embodiments, the AB has a dissociation constant of about 0.5 nM or less for binding to ITGA3. In some embodiments, the AB has a dissociation constant of about 0.1 nM or less for binding to ITGA3. In some embodiments, the AB has a dissociation constant of 0.01 nM to 100 nM, 0.01 nM to 10 nM, 0.01 nM to 5 nM, 0.01 nM to 1 nM, 0.01 to 0.5 nM, 0.01 nm to 0.1 nM, 0.01 nm to 0.05 nM, 0.05 nM to 100 nM, 0.05 nM to 10 nM, 0.05 nM to 5 nM, 0.05 nM to 1 nM, 0.05 to 0.5 nM, 0.05 nm to 0.1 nM, 0.1 nM to 100 nM, 0.1 nM to 10 nM, 0.1 nM to 5 nM, 0.1 nM to 1 nM, 0.1 to 0.5 nM, 0.5 nM to 100 nM, 0.5 nM to 10 nM, 0.5 nM to 5 nM, 0.5 nM to 1 nM, 1 nM to 100 nM, 1 nM to 10 nM, 1 nM to 5 nM, 5 nM to 100 nM, 5 nM to 10 nM, or 10 nM to 100 nM, for binding to mammalian ITGA3.

In some embodiments, the activatable antibody includes an antibody or antigen-binding fragment thereof (AB) that specifically binds ITGa3. In some embodiments, the antibody or antigen-binding fragment thereof that binds ITGa3 is a monoclonal antibody, domain antibody, single chain, Fab fragment, a F(ab')$_2$ fragment, a scFv, a scAb, a dAb, a single domain heavy chain antibody, or a single domain light chain antibody. In some embodiments, such an antibody or antigen-binding fragment thereof that binds ITGa3 is a mouse, other rodent, chimeric, humanized or fully human monoclonal antibody.

In some embodiments, the activatable antibody in an uncleaved state specifically binds to mammalian ITGA3 with a dissociation constant less than or equal to 1 nM, less than or equal to 5 nM, less than or equal to 10 nM, less than or equal to 15 nM, less than or equal to 20 nM, less than or equal to 25 nM, less than or equal to 50 nM, less than or equal to 100 nM, less than or equal to 150 nM, less than or equal to 250 nM, less than or equal to 500 nM, less than or equal to 750 nM, less than or equal to 1000 nM, and/or less than or equal to 2000 nM.

In some embodiments, the activatable antibody in an uncleaved state specifically binds to mammalian ITGA3 with a dissociation constant greater than or equal to 1 nM, greater than or equal to 5 nM, greater than or equal to 10 nM, greater than or equal to 15 nM, greater than or equal to 20 nM, greater than or equal to 25 nM, greater than or equal to 50 nM, greater than or equal to 100 nM, greater than or equal to 150 nM, greater than or equal to 250 nM, greater than or equal to 500 nM, greater than or equal to 750 nM, greater than or equal to 1000 nM, and/or greater than or equal to 2000 nM.

In some embodiments, the mammalian ITGa3 is selected from the group consisting of a human ITGa3 and a cynomolgus monkey ITGa3. In some embodiments, the AB specifically binds to human ITGa3 or cynomolgus monkey ITGa3 with a dissociation constant of less than 1 nM. In some embodiments, the mammalian ITGa3 is a human ITGa3. In some embodiments, the mammalian ITGa3 is a cynomolgus ITGa3.

In some embodiments, the AB has one or more of the following characteristics: (a) the AB specifically binds to human ITGa3; and (b) the AB specifically binds to human ITGa3 and cynomolgus monkey ITGa3.

In some embodiments, the AB has one or more of the following characteristics: (a) the AB specifically binds human ITGa3 and cynomolgus monkey ITGa3; (b) the AB does not inhibit binding of mammalian laminin to mammalian ITGa3; (c) the AB does not inhibit binding of human laminin to human ITGa3; and (d) the AB does not inhibit binding of cynomolgus laminin to cynomolgus ITGa3.

In some embodiments, the AB blocks the ability of a natural ligand or receptor to bind to the mammalian ITGa3 with an EC50 less than or equal to 5 nM, less than or equal to 10 nM, less than or equal to 50 nM, less than or equal to 100 nM, less than or equal to 500 nM, and/or less than or equal to 1000 nM.

In some embodiments, the AB blocks the ability of a natural ligand to bind to the mammalian ITGa3 with an EC50 of 5 nM to 1000 nM, 5 nM to 500 nM, 5 nM to 100 nM 5 nM to 50 nM, 5 nM to 10 nM, 10 nM to 1000 nM, 10 nM to 500 nM, 10 nM to 100 nM 10 nM to 50 nM, 50 nM to 1000 nM, 50 nM to 500 nM, 50 nM to 100 nM, 100 nM to 1000 nM, 100 nM to 500 nM, 500 nM to 1000 nM. In some embodiments, the AB blocks the ability of mammalian CD6 to bind to the mammalian ITGa3 with an EC50 of 5 nM to 1000 nM, 5 nM to 500 nM, 5 nM to 100 nM 5 nM to 50 nM, 5 nM to 10 nM, 10 nM to 1000 nM, 10 nM to 500 nM, 10 nM to 100 nM 10 nM to 50 nM, 50 nM to 1000 nM, 50 nM to 500 nM, 50 nM to 100 nM, 100 nM to 1000 nM, 100 nM to 500 nM, 500 nM to 1000 nM.

In some embodiments, the AB of the present disclosure inhibits or reduces the growth, proliferation, and/or metastasis of cells expressing mammalian ITGa3. Without intending to be bound by any theory, the AB of the present disclosure may inhibit or reduce the growth, proliferation, and/or metastasis of cells expressing mammalian ITGa3 by specifically binding to ITGa3 and inhibiting, blocking, and/or preventing the binding of a natural ligand or receptor to mammalian ITGa3.

In some embodiments, the activatable antibody comprises a heavy chain variable region amino acid sequence selected from the group consisting of SEQ ID NO: 1 and 3-10. In some embodiments, the activatable antibody comprises a heavy chain variable region amino acid sequence selected from the group consisting of SEQ ID NO: 3-10. In some embodiments, the activatable antibody comprises a heavy chain variable region amino acid sequence selected from the group consisting of SEQ ID NO: 7-10. In some embodiments, the activatable antibody comprises a heavy chain variable region amino acid sequence SEQ ID NO: 10.

In some embodiments, the activatable antibody comprises a light chain variable region amino acid sequence selected from the group consisting of SEQ ID NO: 2, 11, and 12. In some embodiments, the activatable antibody comprises a light chain variable region amino acid sequence selected from the group consisting of SEQ ID NO: 11 and 12. In some embodiments, the activatable antibody comprises a light chain variable region amino acid sequence SEQ ID NO: 11.

In some embodiments, the activatable antibody comprises a heavy chain variable region amino acid sequence selected from the group consisting of SEQ ID NO: 1 and 3-10, and a light chain variable region amino acid sequence selected from the group consisting of SEQ ID NO: 2, 11, and 12.

In some embodiments, the activatable antibody comprises a heavy chain variable region amino acid sequence selected from the group consisting of SEQ ID NO: 3-10, and a light chain variable region amino acid sequence selected from the group consisting of SEQ ID NO: 11 and 12. In some embodiments, the activatable antibody comprises a heavy chain variable region amino acid sequence selected from the group consisting of SEQ ID NO: 7-10, and a light chain variable region amino acid sequence SEQ ID NO: 11. In some embodiments, the activatable antibody comprises a heavy chain variable region amino acid sequence SEQ ID NO: 10, and a light chain variable region amino acid sequence SEQ ID NO: 11.

In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 1 and 3-10. In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 3-10. In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 7-10. In some embodiments, the activatable antibody comprises a heavy chain variable region amino acid sequence that is at least 90%, 91%, 92%, 93%, 94%, 95%, 96%, 97%, 98% or 99% identical to the amino acid sequence of SEQ ID NO: 10.

In some embodiments, the activatable antibody comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 2, 11, and 12. In some embodiments, the activatable antibody comprises a light chain variable region amino acid sequence that is at least 90%, 91%, 92%, 93%, 94%, 95%, 96%, 97%, 98% or 99% identical to an amino acid sequence selected from the group consisting of SEQ ID NO: 11 and 12. In some embodiments, the activatable antibody comprises a light chain variable region amino acid sequence that is at least 90%, 91%, 92%, 93%, 94%, 95%, 96%, 97%, 98% or 99% identical to the amino acid sequence of SEQ ID NO: 11.

In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 1 and 3-10, and a light chain variable region amino acid sequence that is at least 90%, 91%, 92%, 93%, 94%, 95%, 96%, 97%, 98% or 99% identical to an amino acid sequence selected from the group consisting of SEQ ID NO: 2, 11, and 12.

In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 3-10, and a light chain variable region amino acid sequence that is at least 90%, 91%, 92%, 93%, 94%, 95%, 96%, 97%, 98% or 99% identical to an amino acid sequence selected from the group consisting of SEQ ID NO: 11 and 12.

In some embodiments, the activatable antibody comprises a heavy chain variable region amino acid sequence that is at least 90%, 91%, 92%, 93%, 94%, 95%, 96%, 97%, 98% or 99% identical to an amino acid sequence selected from the group consisting of SEQ ID NO: 7-10, and a light chain variable region amino acid sequence that is at least 90%, 91%, 92%, 93%, 94%, 95%, 96%, 97%, 98% or 99% identical to the amino acid sequence of SEQ ID NO: 11.

In some embodiments, the activatable antibody comprises a heavy chain variable region amino acid sequence that is at least 90%, 91%, 92%, 93%, 94%, 95%, 96%, 97%, 98% or 99% identical to the amino acid sequence of SEQ ID NO:

10, and a light chain variable region amino acid sequence that is at least 90%, 91%, 92%, 93%, 94%, 95%, 96%, 97%, 98% or 99% identical to the amino acid sequence of SEQ ID NO: 11.

In some embodiments, the activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 comprising the amino acid sequence EYIIH (SEQ ID NO: 13); a VH CDR2 comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

In some embodiments, the activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one complementarity determining region (CDR) sequence is selected from the group consisting of a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence EYIIH (SEQ ID NO: 13); a VH CDR2 sequence that includes a sequence that is at least 90%, 91%, 92%, 93%, 94%, 95%, 96%, 97%, 98%, 99% or more identical to a VH CDR2 sequence comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 sequence that includes a sequence that is at least 90%, 91%, 92%, 93%, 94%, 95%, 96%, 97%, 98%, 99% or more identical to a VH CDR3 sequence comprising the amino acid sequence HEERDYYGYYAMDY (SEQ ID NO: 18); a VL CDR1 sequence that includes a sequence that is at least 90%, 91%, 92%, 93%, 94%, 95%, 96%, 97%, 98%, 99% or more identical to a VL CDR1 sequence comprising the amino acid sequence SASSSISSNYLH (SEQ ID NO: 19); a VL CDR2 sequence that includes a sequence that is at least 90%, 91%, 92%, 93%, 94%, 95%, 96%, 97%, 98%, 99% or more identical to a VL CDR2 sequence comprising the amino acid sequence RTSNLA (SEQ ID NO: 20); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence QQGSSIPRFT (SEQ ID NO: 21).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence comprising the amino acid sequence EYIIH (SEQ ID NO: 13); a VH CDR2 sequence that includes a sequence that is at least 90%, 91%, 92%, 93%, 94%, 95%, 96%, 97%, 98%, 99% or more identical to a VH CDR2 sequence comprising the amino acid sequence WFYPESGSVKYNEGFKG (SEQ ID NO: 17); a VH CDR3 sequence that includes a sequence that is at least 90%, 91%, 92%, 93%, 94%, 95%, 96%, 97%, 98%, 99% or more identical to a VH CDR3 sequence comprising the amino acid sequence HEERDYYGYYAMDY (SEQ ID NO: 18); a VL CDR1 sequence that includes a sequence that is at least 90%, 91%, 92%, 93%, 94%, 95%, 96%, 97%, 98%, 99% or more identical to a VL CDR1 sequence comprising the amino acid sequence SASSSISSNYLH (SEQ ID NO: 19); a VL CDR2 sequence that includes a sequence that is at least 90%, 91%, 92%, 93%, 94%, 95%, 96%, 97%, 98%, 99% or more identical to a VL CDR2 sequence comprising the amino acid sequence RTSNLA (SEQ ID NO: 20); and a VL CDR3 sequence that includes a sequence that is at least 90%, 91%, 92%, 93%, 94%, 95%, 96%, 97%, 98%, 99% or more identical to a VL CDR3 sequence comprising the amino acid sequence QQGSSIPRFT (SEQ ID NO: 21).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence EYIIH (SEQ ID NO: 13); the VH CDR2 sequence comprises the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); the VH CDR3 sequence comprises the amino acid sequence HEERDYYGYYAMDY (SEQ ID NO: 18); the VL CDR1 sequence comprises the amino acid sequence SASSSISSNYLH (SEQ ID NO: 19); the VL CDR2 sequence comprises the amino acid sequence RTSNLA (SEQ ID NO: 20); and the VL CDR3 sequence comprises the amino acid sequence QQGSSIPRFT (SEQ ID NO: 21).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises the amino acid sequence EYIIH (SEQ ID NO: 13); the VH CDR2 sequence comprises the amino acid sequence WFYPESGSVKYNEGFKG (SEQ ID NO: 17); the VH CDR3 sequence comprises the amino acid sequence HEERDYYGYYAMDY (SEQ ID NO: 18); the VL CDR1 sequence comprises the amino acid sequence SASSSISSNYLH (SEQ ID NO: 19); the VL CDR2 sequence comprises the amino acid sequence RTSNLA (SEQ ID NO: 20); and the VL CDR3 sequence comprises the amino acid sequence QQGSSIPRFT (SEQ ID NO: 21).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence EYIIH (SEQ ID NO: 13); the VH CDR2 sequence comprises a sequence that is at least 90%, 91%, 92%, 93%, 94%, 95%, 96%, 97%, 98%, 99% or more identical to the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); the VH CDR3 sequence comprises a sequence that is at least 90%, 91%, 92%, 93%, 94%, 95%, 96%, 97%, 98%, 99% or more identical to the amino acid sequence HEERDYYGYYAMDY (SEQ ID NO: 18); the VL CDR1 sequence comprises a sequence that is at least 90%, 91%, 92%, 93%, 94%, 95%, 96%, 97%, 98%, 99% or more identical to the amino acid sequence SASSSISSNYLH (SEQ ID NO: 19); the VL CDR2 sequence comprises a sequence that is at least 90%, 91%, 92%, 93%, 94%, 95%, 96%, 97%, 98%, 99% or more identical to the amino acid sequence RTSNLA (SEQ ID NO: 20); and the VL CDR3 sequence comprises a sequence that is at least 90%, 91%, 92%, 93%, 94%, 95%, 96%, 97%, 98%, 99% or more identical to the amino acid sequence QQGSSIPRFT (SEQ ID NO: 21).

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence comprises a sequence that is at least 90%, 91%, 92%, 93%, 94%, 95%, 96%, 97%, 98%, 99% or more identical to the amino acid sequence EYIIH (SEQ ID NO: 13); the VH CDR2 sequence comprises a sequence that is at least 90%, 91%, 92%, 93%, 94%, 95%, 96%, 97%, 98%, 99% or more identical to the amino acid sequence WFYPESGSVKYNEGFKG (SEQ ID NO: 17); the VH CDR3 sequence comprises a sequence that is at least 90%, 91%, 92%, 93%, 94%, 95%, 96%, 97%, 98%, 99% or more identical to the amino acid sequence HEERDYYGYYAMDY (SEQ ID NO: 18); the VL CDR1 sequence comprises a sequence that is at least 90%, 91%, 92%, 93%, 94%, 95%, 96%, 97%, 98%, 99% or more identical to the amino acid sequence SASSSISSNYLH (SEQ ID NO: 19); the VL CDR2 sequence comprises a sequence that is at least 90%, 91%, 92%, 93%, 94%, 95%, 96%, 97%, 98%, 99% or more identical to the amino acid sequence RTSNLA (SEQ ID NO: 20); and the VL CDR3 sequence comprises a sequence that is at least 90%, 91%, 92%, 93%, 94%, 95%, 96%, 97%, 98%, 99% or more identical to the amino acid sequence QQGSSIPRFT (SEQ ID NO: 21).

In some embodiments, the AB of the activatable anti-ITGa3 antibody comprises a heavy chain variable region amino acid sequence selected from the group consisting of the heavy chain variable region sequences shown in Table 12. In some embodiments, the AB of the activatable anti-ITGa3 antibody comprises a light chain variable region amino acid sequence selected from the group consisting of the light chain variable region sequences shown in Table 12. In some embodiments, the AB of the activatable anti-ITGa3 antibody comprises a heavy chain variable region amino acid sequence selected from the group consisting of the heavy chain variable region sequences shown in Table 12 and a light chain variable region amino acid sequence selected from the group consisting of the light chain variable region sequences shown in Table 12.

In some embodiments, the AB of the activatable anti-ITGa3 antibody comprises a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12. In some embodiments, the AB of the activatable anti-ITGa3 antibody comprises a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12. In some embodiments, the AB of the activatable anti-ITGa3 antibody comprises a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12 and a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12.

In some embodiments, the activatable antibody comprises a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence shown in Table 13; a VH CDR2 sequence shown in Table 13; a VH CDR3 sequence shown in Table 13; a VL CDR1 sequence shown in Table 13; a VL CDR2 sequence shown in Table 13; and a VL CDR3 sequence shown in Table 13.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence shown in Table 13; a VH CDR2 sequence that includes a sequence that is at least 90%, 91%, 92%, 93%, 94%, 95%, 96%, 97%, 98%, 99% or more identical to a VH CDR2 sequence shown in Table 13; a VH CDR3 sequence that includes a sequence that is at least 90%, 91%, 92%, 93%, 94%, 95%, 96%, 97%, 98%, 99% or more identical to a VH CDR3 sequence shown in Table 13; a VL CDR1 sequence that includes a sequence that is at least 90%, 91%, 92%, 93%, 94%, 95%, 96%, 97%, 98%, 99% or more identical to a VL CDR1 sequence shown in Table 13; a VL CDR2 sequence that includes a sequence that is at least 90%, 91%, 92%, 93%, 94%, 95%, 96%, 97%, 98%, 99% or more identical to a VL CDR2 sequence shown in Table 13; and a VL CDR3 sequence that includes a sequence that is at least 90%, 91%, 92%, 93%, 94%, 95%, 96%, 97%, 98%, 99% or more identical to a VL CDR3 sequence shown in Table 13.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, the activatable antibody comprises a heavy chain that comprises a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 13.

In some embodiments, the activatable antibody comprises a light chain that comprises a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 13.

In some embodiments, the activatable antibody comprises a combination of a VH CDR1 sequence, a VH CDR2 sequence, a VH CDR3 sequence, a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of the six CDR sequences (VH CDR1, VH CDR2, VH CDR3, VL CDR1, VL CDR2, and VL CDR3) shown in a single row in Table 13.

In some embodiments, the activatable antibody comprises a heavy chain variable region that comprises a combination of a VH CDR1 sequence, a VH CDR2 sequence, and a VH CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three heavy chain CDR sequences (VH CDR1, VH CDR2, VH CDR3) shown in a single row in Table 13.

In some embodiments, the activatable antibody comprises a light chain variable region that comprises a combination of a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three light chain CDR sequences (VL CDR1, VL CDR2, VL CDR3) shown in a single row in Table 13.

In some embodiments, the activatable antibody includes may include one or more polypeptides that include the combination of sequences in a given row of Table D or any combination of a mask sequence (MM), a substrate sequence (CM), a light chain variable domain sequence or light chain variable domain CDR sequences, and a heavy chain variable domain sequence or heavy chain variable domain CDR sequences of Table E.

In some embodiments, the antibody drug conjugates (ADCs) and activatable antibody drug conjugates (AADCs) can include one or more polypeptides that include the combination of a light chain sequence or a light chain variable domain sequence, and a heavy chain sequence or a heavy chain variable domain sequences, a linker, and a toxin in a given row of Table F or any combination of a light chain sequence or a light chain variable domain sequence, and a heavy chain sequence or a heavy chain variable domain sequence, a linker, and a toxin of Table F.

In some embodiments, the MM has a dissociation constant for binding to the AB which is greater than the dissociation constant of the AB to ITGa3.

In some embodiments, the MM has a dissociation constant for binding to the AB which is no more than the dissociation constant of the AB to ITGa3.

In some embodiments, the MM has a dissociation constant for binding to the AB which is less than the dissociation constant of the AB to ITGa3.

In some embodiments, the dissociation constant ($K_d$) of the MM towards the AB is no more than 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 times or greater, or between 1-5, 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times or greater than the dissociation constant of the AB towards the target.

In some embodiments, the MM does not interfere or compete with the AB for binding to ITGa3 when the activatable antibody is in a cleaved state.

In some embodiments, the MM is a polypeptide of about 2 to 40 amino acids in length. In some embodiments, the MM is a polypeptide of up to about 40 amino acids in length.

In some embodiments, the MM polypeptide sequence is different from that of ITGa3. In some embodiments, the MM polypeptide sequence is no more than 50% identical to any natural binding partner of the AB. In some embodiments, the MM polypeptide sequence is different from that of ITGa3 and is no more than 40%, 30%, 25%, 20%, 15%, or 10% identical to any natural binding partner of the AB.

In some embodiments, the coupling of the MM to the AB reduces the ability of the AB to bind ITGa3 such that the dissociation constant ($K_d$) of the AB when coupled to the MM towards ITGa3 is at least two times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least five times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least 10 times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least 20 times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least 40 times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least 100 times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least 1000 times greater than the $K_d$ of the AB when not coupled to the MM towards ITGa3.

In some embodiments, the coupling of the MM to the AB reduces the ability of the AB to bind ITGa3 such that the dissociation constant ($K_d$) of the AB when coupled to the MM towards ITGa3 is at least 10,000 times greater than the $K_d$ of the AB when not coupled to the MM towards ITGa3.

In some embodiments, in the presence of ITGa3, the MM reduces the ability of the AB to bind ITGa3 by at least 90% when the CM is uncleaved, as compared to when the CM is cleaved when assayed in vitro using a target displacement assay such as, for example, the assay described in PCT Publication No. WO 2010/081173, the contents of which are hereby incorporated by reference in their entirety.

In some embodiments, MM comprises an amino acid sequence selected from the group consisting of SEQ ID NO: 22-54.

In some embodiments, the protease that cleaves the CM is active, e.g., up-regulated or otherwise unregulated, in diseased tissue, and the protease cleaves the CM in the activatable antibody when the activatable antibody is exposed to the protease.

In some embodiments, the protease is co-localized with ITGa3 in a tissue, and the protease cleaves the CM in the activatable antibody when the activatable antibody is exposed to the protease.

In some embodiments, the CM is positioned in the activatable antibody such that when the activatable antibody is in the uncleaved state, binding of the activatable antibody to ITGa3 is reduced to occur with a dissociation constant that is at least twofold greater than the dissociation constant of an unmodified AB binding to ITGa3, whereas in the cleaved state (i.e., when the activatable antibody is in the cleaved state), the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least fivefold greater than the dissociation constant of an unmodified AB binding to ITGa3, whereas in the cleaved state (i.e., when the activatable antibody is in the cleaved state), the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least 10-fold greater than the dissociation constant of an unmodified AB binding to ITGa3, whereas in the cleaved state (i.e., when the activatable antibody is in the cleaved state), the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least 20-fold greater than the dissociation constant of an unmodified AB binding to ITGa3, whereas in the cleaved state (i.e., when the activatable antibody is in the cleaved state), the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least 40-fold greater than the dissociation constant of an unmodified AB binding to ITGa3, whereas in the cleaved state (i.e., when the activatable antibody is in the cleaved state), the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least 50-fold greater than the dissociation constant of an unmodified AB binding to ITGa3, whereas in the cleaved state, the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least 100-fold greater than the dissociation constant of an unmodified AB binding to ITGa3, whereas in the cleaved state, the AB binds ITGa3.

In some embodiments, the CM is positioned in the activatable antibody such that when the activatable antibody is in the uncleaved state, binding of the activatable antibody to ITGa3 is reduced to occur with a dissociation constant that is at least 200-fold greater than the dissociation constant of an unmodified AB binding to ITGa3, whereas in the cleaved state, the AB binds ITGa3.

In some embodiments, the CM is a polypeptide of up to 15 amino acids in length.

In some embodiments, the CM is a polypeptide that includes a first cleavable moiety (CM1) that is a substrate for at least one matrix metalloprotease (MMP) and a second cleavable moiety (CM2) that is a substrate for at least one serine protease (SP). In some embodiments, each of the CM1 substrate sequence and the CM2 substrate sequence of the CM1-CM2 substrate is independently a polypeptide of up to 15 amino acids in length.

In some embodiments, the CM is a substrate for at least one protease that is or is believed to be up-regulated or otherwise unregulated in cancer. In some embodiments, the CM is a substrate for at least one protease that is or is believed to be up-regulated in inflammation. In some embodiments, the CM is a substrate for at least one protease that is or is believed to be up-regulated or otherwise unregulated in autoimmunity.

In some embodiments, the CM is a substrate for at least one protease selected from the group consisting of a matrix metalloprotease (MMP), thrombin, a neutrophil elastase, a cysteine protease, legumain, and a serine protease, such as matriptase (MT-SP1), and urokinase (uPA). Without being bound by theory, it is believed that these proteases are up-regulated or otherwise unregulated in at least one of cancer, inflammation, or autoimmunity.

Exemplary substrates include but are not limited to substrates cleavable by one or more of the following enzymes or proteases listed in Table 4.

In some embodiments, the CM is selected for use with a specific protease, for example a protease that is known to be co-localized with the target of the activatable antibody.

In some embodiments, the CM is a substrate for at least one MMP. Examples of MMPs include the MMPs listed in the Table 4. In some embodiments, the CM is a substrate for a protease selected from the group consisting of MMP 9, MMP14, MMP1, MMP3, MMP13, MMP17, MMP11, and MMP19. In some embodiments the CM is a substrate for MMP9. In some embodiments, the CM is a substrate for MMP14.

In some embodiments, the CM is a substrate that includes the sequence TGRGPSWV (SEQ ID NO: 182); SARGPSRW (SEQ ID NO: 183); TARGPSFK (SEQ ID NO: 184); LSGRSDNH (SEQ ID NO: 185); GGWHTGRN (SEQ ID NO: 186); HTGRSGAL (SEQ ID NO: 187); PLTGRSGG (SEQ ID NO: 188); AARGPAIH (SEQ ID NO: 189); RGPAFNPM (SEQ ID NO: 190); SSRGPAYL (SEQ ID NO: 191); RGPATPIM (SEQ ID NO: 192); RGPA (SEQ ID NO: 193); GGQPSGMWGW (SEQ ID NO: 194); FPRPLGITGL (SEQ ID NO: 195); VHMPLGFLGP (SEQ ID NO: 196); SPLTGRSG (SEQ ID NO: 197); SAGFSLPA (SEQ ID NO: 198); LAPLGLQRR (SEQ ID NO: 199); SGGPLGVR (SEQ ID NO: 200); PLGL (SEQ ID NO: 201); LSGRSGNH (SEQ ID NO: 276); SGRSANPRG (SEQ ID NO: 277); LSGRSDDH (SEQ ID NO: 278); LSGRSDIH (SEQ ID NO: 279); LSGRSDQH (SEQ ID NO: 280); LSGRSDTH (SEQ ID NO: 281); LSGRSDYH (SEQ ID NO: 282); LSGRSDNP (SEQ ID NO: 283); LSGRSANP (SEQ ID NO: 284); LSGRSANI (SEQ ID NO: 285); LSGRSDNI (SEQ ID NO: 286); MIAPVAYR (SEQ ID NO: 287); RPSPMWAY (SEQ ID NO: 288); WATPRPMR (SEQ ID NO: 289); FRLLDWQW (SEQ ID NO: 290); ISSGL (SEQ ID NO: 291); ISSGLLS (SEQ ID NO: 292); and/or ISSGLL (SEQ ID NO: 293).

In some embodiments, the CM comprises the amino acid sequence LSGRSDNH (SEQ ID NO: 185). In some embodiments, the CM comprises the amino acid sequence TGRGPSWV (SEQ ID NO: 182). In some embodiments, the CM comprises the amino acid sequence PLTGRSGG (SEQ ID NO: 188). In some embodiments, the CM comprises the amino acid sequence GGQPSGMWGW (SEQ ID NO: 194). In some embodiments, the CM comprises the amino acid sequence FPRPLGITGL (SEQ ID NO: 195). In some embodiments, the CM comprises the amino acid sequence VHMPLGFLGP (SEQ ID NO: 196). In some embodiments, the CM comprises the amino acid sequence PLGL (SEQ ID NO: 201). In some embodiments, the CM comprises the amino acid sequence SARGPSRW (SEQ ID NO: 183). In some embodiments, the CM comprises the amino acid sequence TARGPSFK (SEQ ID NO: 184). In some embodiments, the CM comprises the amino acid sequence GGWHTGRN (SEQ ID NO: 186). In some embodiments, the CM comprises the amino acid sequence HTGRSGAL (SEQ ID NO: 187). In some embodiments, the CM comprises the amino acid sequence AARGPAIH (SEQ ID NO: 189). In some embodiments, the CM comprises the amino acid sequence RGPAFNPM (SEQ ID NO: 190). In some embodiments, the CM comprises the amino acid sequence SSRGPAYL (SEQ ID NO: 191). In some embodiments, the CM comprises the amino acid sequence RGPATPIM (SEQ ID NO: 192). In some embodiments, the CM comprises the amino acid sequence RGPA (SEQ ID NO: 193).

In some embodiments, the CM is a substrate for an MMP and includes the sequence ISSGLSS (SEQ ID NO: 202); QNQALRMA (SEQ ID NO: 203); AQNLLGMV (SEQ ID NO: 204); STFPFGMF (SEQ ID NO: 205); PVGYTSSL (SEQ ID NO: 206); DWLYWPGI (SEQ ID NO: 207), ISSGLLSS (SEQ ID NO: 208), LKAAPRWA (SEQ ID NO: 209); GPSHLVLT (SEQ ID NO: 210); LPGGLSPW (SEQ ID NO: 211); MGLFSEAG (SEQ ID NO: 212); SPLPLRVP (SEQ ID NO: 213); RMHLRSLG (SEQ ID NO: 214); LAAPLGLL (SEQ ID NO: 215); AVGLLAPP (SEQ ID NO: 216); LLAPSHRA (SEQ ID NO: 217); and/or PAGLWLDP (SEQ ID NO: 218).

In some embodiments, the CM comprises the amino acid sequence ISSGLSS (SEQ ID NO: 202). In some embodiments, the CM comprises the amino acid sequence QNQALRMA (SEQ ID NO: 203). In some embodiments, the CM comprises the amino acid sequence AQNLLGMV (SEQ ID NO: 204). In some embodiments, the CM comprises the amino acid sequence STFPFGMF (SEQ ID NO: 205). In some embodiments, the CM comprises the amino acid sequence PVGYTSSL (SEQ ID NO: 206). In some embodiments, the CM comprises the amino acid sequence DWLYWPGI (SEQ ID NO: 207). In some embodiments, the CM comprises the amino acid sequence ISSGLLSS (SEQ ID NO: 208). In some embodiments, the CM comprises the amino acid sequence LKAAPRWA (SEQ ID NO: 209). In some embodiments, the CM comprises the amino acid sequence GPSHLVLT (SEQ ID NO: 210). In some embodiments, the CM comprises the amino acid sequence LPGGLSPW (SEQ ID NO: 211). In some embodiments, the CM comprises the amino acid sequence MGLFSEAG (SEQ ID NO: 212). In some embodiments, the CM comprises the amino acid sequence SPLPLRVP (SEQ ID NO: 213). In some embodiments, the CM comprises the amino acid sequence RMHLRSLG (SEQ ID NO: 214). In some embodiments, the CM comprises the amino acid sequence LAAPLGLL (SEQ ID NO: 215). In some embodiments, the CM comprises the amino acid sequence AVGLLAPP (SEQ ID NO: 216). In some embodiments, the CM comprises the amino acid sequence LLAPSHRA (SEQ ID NO: 217). In some embodiments, the CM comprises the amino acid sequence PAGLWLDP (SEQ ID NO: 218).

In some embodiments, the CM is a substrate for thrombin. In some embodiments, the CM is a substrate for thrombin and includes the sequence GPRSFGL (SEQ ID NO: 219) or GPRSFG (SEQ ID NO: 220). In some embodiments, the CM comprises the amino acid sequence GPRSFGL (SEQ ID NO: 219). In some embodiments, the CM comprises the amino acid sequence GPRSFG (SEQ ID NO: 220).

In some embodiments, the CM comprises an amino acid sequence selected from the group consisting of NTLSGRSENHSG (SEQ ID NO: 221); NTLSGRSGNHGS (SEQ ID NO: 222); TSTSGRSANPRG (SEQ ID NO: 223); TSGRSANP (SEQ ID NO: 224); VAGRSMRP (SEQ ID NO: 225); VVPEGRRS (SEQ ID NO: 226); ILPRSPAF (SEQ ID NO: 227); MVLGRSLL (SEQ ID NO: 228); QGRAITFI (SEQ ID NO: 229); SPRSIMLA (SEQ ID NO: 230); and SMLRSMPL (SEQ ID NO: 231).

In some embodiments, the CM comprises the amino acid sequence NTLSGRSENHSG (SEQ ID NO: 221). In some embodiments, the CM comprises the amino acid sequence NTLSGRSGNHGS (SEQ ID NO: 222). In some embodiments, the CM comprises the amino acid sequence TSTSGRSANPRG (SEQ ID NO: 223). In some embodiments, the CM comprises the amino acid sequence TSGRSANP (SEQ ID NO: 224). In some embodiments, the CM comprises the amino acid sequence VAGRSMRP (SEQ ID NO: 225). In some embodiments, the CM comprises the amino acid sequence VVPEGRRS (SEQ ID NO: 226). In some embodiments, the CM comprises the amino acid sequence ILPRSPAF (SEQ ID NO: 227).

In some embodiments, the CM comprises the amino acid sequence MVLGRSLL (SEQ ID NO: 228). In some embodiments, the CM comprises the amino acid sequence QGRAITFI (SEQ ID NO: 229). In some embodiments, the CM comprises the amino acid sequence SPRSIMLA (SEQ ID NO: 230). In some embodiments, the CM comprises the amino acid sequence SMLRSMPL (SEQ ID NO: 231).

In some embodiments, the CM is a substrate for a neutrophil elastase. In some embodiments, the CM is a substrate for a serine protease. In some embodiments, the CM is a substrate for uPA. In some embodiments, the CM is a substrate for legumain. In some embodiments, the CM is a substrate for matriptase. In some embodiments, the CM is a substrate for a cysteine protease. In some embodiments, the CM is a substrate for a cysteine protease, such as a cathepsin.

In some embodiments, the CM is a CM1-CM2 substrate and includes the sequence ISSGLLSGRSDNH (SEQ ID NO: 232); ISSGLLSSGGSGGSLSGRSDNH (SEQ ID NO: 233); AVGLLAPPGGTSTSGRSANPRG (SEQ ID NO: 234); TSTSGRSANPRGGGAVGLLAPP (SEQ ID NO: 235); VHMPLGFLGPGGTSTSGRSANPRG (SEQ ID NO: 236); TSTSGRSANPRGGGVHMPLGFLGP (SEQ ID NO: 237); AVGLLAPPGGLSGRSDNH (SEQ ID NO: 238); LSGRSDNHGGAVGLLAPP (SEQ ID NO: 239); VHMPLGFLGPGGLSGRSDNH (SEQ ID NO: 240); LSGRSDNHGGVHMPLGFLGP (SEQ ID NO: 241); LSGRSDNHGGSGGSISSGLLSS (SEQ ID NO: 242); LSGRSGNHGGSGGSISSGLLSS (SEQ ID NO: 243); ISSGLLSSGGSGGSLSGRSGNH (SEQ ID NO: 244); LSGRSDNHGGSGGSQNQALRMA (SEQ ID NO: 245); QNQALRMAGGSGGSLSGRSDNH (SEQ ID NO: 246); LSGRSGNHGGSGGSQNQALRMA (SEQ ID NO: 247); QNQALRMAGGSGGSLSGRSGNH (SEQ ID NO: 248) and/or ISSGLLSGRSGNH (SEQ ID NO: 249); GLSGRSDNHGGAVGLLAPP (SEQ ID NO: 294); GLSGRSDNHGGVHMPLGFLGP (SEQ ID NO: 295); ISSGLLSGRSANPRG (SEQ ID NO: 296), which is also referred to herein as substrate 2003; AVGLLAPPTSGRSANPRG (SEQ ID NO: 297), which is also referred to herein as substrate 2004; AVGLLAPPSGRSANPRG (SEQ ID NO: 298), which is also referred to herein as substrate 2005; ISSGLLSGRSDDH (SEQ ID NO: 299), which is also referred to herein as substrate 2006; ISSGLLSGRSDIH (SEQ ID NO: 300), which is also referred to herein as substrate 2007; ISSGLLSGRSDQH (SEQ ID NO: 301), which is also referred to herein as substrate 2008; ISSGLLSGRSDTH (SEQ ID NO: 302), which is also referred to herein as substrate 2009; ISSGLLSGRSDYH (SEQ ID NO: 303), which is also referred to herein as substrate 2010; ISSGLLSGRSDNP (SEQ ID NO: 304), which is also referred to herein as substrate 2011; ISSGLLSGRSANP (SEQ ID NO: 305), which is also referred to herein as substrate 2012; ISSGLLSGRSANI (SEQ ID NO: 306), which is also referred to herein as substrate 2013; AVGLLAPPGGLSGRSDDH (SEQ ID NO: 307), which is also referred to herein as substrate 3006; AVGLLAPPGGLSGRSDIH (SEQ ID NO: 308), which is also referred to herein as substrate 3007; AVGLLAPPGGLSGRSDQH (SEQ ID NO: 309), which is also referred to herein as substrate 3008; AVGLLAPPGGLSGRSDTH (SEQ ID NO: 310), which is also referred to herein as substrate 3009; AVGLLAPPGGLSGRSDDH (SEQ ID NO: 311), which is also referred to herein as substrate 3010; AVGLLAPPGGLSGRSDNP (SEQ ID NO: 312), which is also referred to herein as substrate 3011; AVGLLAPPGGLSGRSANP (SEQ ID NO: 313), which is also referred to herein as substrate 3012; AVGLLAPPGGLSGRSANI (SEQ ID NO: 314), which is also referred to herein as substrate 3013; ISSGLLSGRSDNI (SEQ ID NO: 315), which is also referred to herein as substrate 2014; and/or AVGLLAPPGGLSGRSDNI (SEQ ID NO: 316), which is also referred to herein as substrate 3014.

In some embodiments, the CM1-CM2 substrate includes the sequence ISSGLLSGRSDNH (SEQ ID NO: 232), which is also referred to herein as substrate 2001. In some embodiments, the CM1-CM2 substrate includes the sequence ISSGLLSSGGSGGSLSGRSDNH (SEQ ID NO: 233). In some embodiments, the CM1-CM2 substrate includes the sequence AVGLLAPPGGTSTSGRSANPRG (SEQ ID NO: 234). In some embodiments, the CM1-CM2 substrate includes the sequence TSTSGRSANPRGGGAVGLLAPP (SEQ ID NO: 235). In some embodiments, the CM1-CM2 substrate includes the sequence VHMPLGFLGPGGTSTSGRSANPRG (SEQ ID NO: 236). In some embodiments, the CM1-CM2 substrate includes the sequence TSTSGRSANPRGGGVHMPLGFLGP (SEQ ID NO: 237). In some embodiments, the CM1-CM2 substrate includes the sequence AVGLLAPPGGLSGRSDNH (SEQ ID NO: 238), which is also referred to herein as substrate 3001. In some embodiments, the CM1-CM2 substrate includes the sequence LSGRSDNHGGAVGLLAPP (SEQ ID NO: 239). In some embodiments, the CM1-CM2 substrate includes the sequence VHMPLGFLGPGGLSGRSDNH (SEQ ID NO: 240). In some embodiments, the CM1-CM2 substrate includes the sequence LSGRSDNHGGVHMPLGFLGP (SEQ ID NO: 241). In some embodiments, the CM1-CM2 substrate includes the sequence LSGRSDNHGGSGGSISSGLLSS (SEQ ID NO: 242). In some embodiments, the CM1-CM2 substrate includes the sequence LSGRSGNHGGSGGSISSGLLSS (SEQ ID NO: 243). In some embodiments, the CM1-CM2 substrate includes the sequence ISSGLLSSGGSGGSLSGRSGNH (SEQ ID NO: 244). In some embodiments, the CM1-CM2 substrate includes the sequence LSGRSDNHGGSGGSQNQALRMA (SEQ ID NO: 245). In some embodiments, the CM1-CM2 substrate includes the sequence QNQALRMAGGSGGSLSGRSDNH (SEQ ID NO: 246). In some embodiments, the CM1-CM2 substrate includes the sequence LSGRSGNHGGSGGSQNQALRMA (SEQ ID NO: 247). In some embodiments, the CM1-CM2 substrate includes the sequence QNQALRMAGGSGGSLSGRSGNH (SEQ ID NO: 248). In some embodiments, the CM1-CM2 substrate includes the sequence ISSGLLSGRSGNH (SEQ ID NO: 249).). In some embodiments, the CM1-CM2 substrate includes the sequence GLSGRSDNHGGAVGLLAPP (SEQ ID NO: 294); GLSGRSDNHGGVHMPLGFLGP (SEQ ID NO: 295); ISSGLLSGRSANPRG (SEQ ID NO: 296). In some embodiments, the CM1-CM2 substrate includes the sequence AVGLLAPPTSGRSANPRG (SEQ ID NO: 297). In some embodiments, the CM1-CM2 substrate includes the sequence AVGLLAPPSGRSANPRG (SEQ ID NO: 298). In some embodiments, the CM1-CM2 substrate includes the sequence ISSGLLSGRSDDH (SEQ ID NO: 299). In some embodiments, the CM1-CM2 substrate includes the sequence ISSGLLSGRSDIH (SEQ ID NO: 300). In some embodiments, the CM1-CM2 substrate includes the sequence ISSGLLSGRSDQH (SEQ ID NO: 301). In some embodiments, the CM1-CM2 substrate includes the sequence ISSGLLSGRSDTH (SEQ ID NO: 302). In some embodiments, the CM1-CM2 substrate includes the sequence ISSGLLSGRSDYH (SEQ ID NO: 303). In some embodiments, the CM1-CM2 substrate includes the sequence ISSGLLSGRSDNP (SEQ ID NO: 304). In some embodiments, the CM1-CM2 substrate includes the sequence ISSGLLSGRSANP (SEQ ID NO: 305). In some embodiments, the CM1-CM2 substrate includes the sequence ISSGLLSGRSANI (SEQ ID NO: 306). In some embodiments, the CM1-CM2 substrate includes the sequence AVGLLAPPGGLSGRSDDH (SEQ ID NO: 307). In some embodiments, the CM1-CM2 substrate includes the sequence AVGLLAPPGGLSGRSDIH (SEQ ID NO: 308). In some embodiments, the CM1-CM2 substrate includes the sequence AVGLLAPPGGLSGRSDQH (SEQ ID NO: 309). In some embodiments, the CM1-CM2 substrate includes the sequence AVGLLAPPGGLSGRSDTH (SEQ ID NO: 310). In some embodiments, the CM1-CM2 substrate includes the sequence AVGLLAPPGGLSGRSDTH (SEQ ID NO: 311). In some embodiments, the CM1-CM2 substrate includes the sequence AVGLLAPPGGLSGRSDNP (SEQ ID NO: 312). In some embodiments, the CM1-CM2 substrate includes the sequence AVGLLAPPGGLSGRSANP (SEQ ID NO: 313). In some embodiments, the CM1-CM2 substrate includes the sequence AVGLLAPPGGLSGRSANI (SEQ ID NO: 314). In some embodiments, the CM1-CM2 substrate includes the sequence ISSGLLSGRSDNI (SEQ ID NO: 315). In some embodiments, the CM1-CM2 substrate includes the sequence AVGLLAPPGGLSGRSDNI (SEQ ID NO: 316).

In some embodiments, the CM is a substrate for at least two proteases. In some embodiments, each protease is selected from the group consisting of those shown in Table 4. In some embodiments, the CM is a substrate for at least two proteases, wherein one of the proteases is selected from the group consisting of a MMP, thrombin, a neutrophil elastase, a cysteine protease, uPA, legumain and matriptase and the other protease is selected from the group consisting of those shown in Table 4. In some embodiments, the CM is a substrate for at least two proteases selected from the group consisting of a MMP, thrombin, a neutrophil elastase, a cysteine protease, uPA, legumain and matriptase.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody in the uncleaved state have the structural arrangement from N-terminus to C-terminus as follows: MM-CM1-CM2-AB or AB-CM2-CM1-MM. In some embodiments, at least one of the first CM and the second CM is a polypeptide that functions as a substrate for a protease selected from the group consisting of a MMP, thrombin, a neutrophil elastase, a cysteine protease, uPA, legumain, and matriptase. In some embodiments, the first CM is cleaved by a first cleaving agent selected from the group consisting of a MMP, thrombin, a neutrophil elastase, a cysteine protease, uPA, legumain, and matriptase in a target tissue and the second CM is cleaved by a second cleaving agent in a target tissue. In some embodiments, the other protease is selected from the group consisting of those shown in Table 4. In some embodiments, the first cleaving agent and the second cleaving agent are the same protease selected from the group consisting of a MMP, thrombin, a neutrophil elastase, a cysteine protease, uPA, legumain, and matriptase, and the first CM and the second CM are different substrates for the enzyme. In some embodiments, the first cleaving agent and the second cleaving agent are the same protease selected from the group consisting of those shown in Table 4. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the activatable antibody is exposed to and cleaved by a protease such that, in the activated or cleaved state, the activated antibody includes a light chain amino acid sequence that includes at least a portion of LP2 and/or CM sequence after the protease has cleaved the CM.

Suitable activatable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a heavy chain variable region amino acid sequence selected from the group consisting of SEQ ID NO: 1 and 3-10, and a light chain variable region amino acid sequence selected from the group consisting of SEQ ID NO: 2, 11, and 12. Suitable activatable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a heavy chain variable region amino acid sequence selected from the group consisting of SEQ ID NO: 7-10, and a light chain variable region amino acid sequence SEQ ID NO: 11. Suitable activatable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a heavy chain variable region amino acid sequence SEQ ID NO: 10, and a light chain variable region amino acid sequence SEQ ID NO: 11.

Suitable activatable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a VH CDR1 comprising the amino acid sequence EYIIH (SEQ ID NO: 13); a VH CDR2 comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable activatable anti-ITGa3 antibodies of the disclosure also include an antibody or antigen binding fragment thereof that binds to the same epitope on human ITGa3 and/or cynomolgus monkey ITGa3 as an anti-ITGa3 antibody comprising a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable activatable anti-ITGa3 antibodies of the disclosure also include an antibody or antigen-binding fragment thereof that binds to the same epitope on human ITGa3 and/or cynomolgus monkey ITGa3 as an anti-ITGa3 antibody comprising a heavy chain variable region amino acid sequence selected from the group consisting of the heavy chain variable region sequences shown in Table 12 and a light chain variable region amino acid sequence selected from the group consisting of the light chain variable region sequences shown in Table 12.

Suitable activatable anti-ITGa3 antibodies of the disclosure also include an antibody or antigen-binding fragment thereof that binds to the same epitope on human ITGa3 and/or cynomolgus monkey ITGa3 as an anti-ITGa3 antibody comprising a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

Suitable activatable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a heavy chain variable region amino acid sequence selected from the group consisting of SEQ ID NO: 1 and 3-10, and a light chain variable region amino acid sequence selected from the group consisting of SEQ ID NO: 2, 11, and 12. Suitable activatable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a heavy chain variable region amino acid sequence selected from the group consisting of SEQ ID NO: 7-10, and a light chain variable region amino acid sequence SEQ ID NO: 11. Suitable activatable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a heavy chain variable region amino acid sequence SEQ ID NO: 10, and a light chain variable region amino acid sequence SEQ ID NO: 11.

Suitable activatable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a VH CDR1 comprising the amino acid sequence EYIIH (SEQ ID NO: 13); a VH CDR2 comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable activatable anti-ITGa3 antibodies of the disclosure also include an antibody or antigen binding fragment thereof that cross-competes for binding to human ITGa3 and/or cynomolgus monkey ITGa3 to an anti-ITGa3 antibody comprising a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21).

Suitable activatable anti-ITGa3 antibodies of the disclosure also include an antibody or antigen-binding fragment thereof that cross-competes for binding to human ITGa3 and/or cynomolgus monkey ITGa3 as an anti-ITGa3 antibody comprising a heavy chain variable region amino acid sequence selected from the group consisting of the heavy chain variable region sequences shown in Table 12 and a light chain variable region amino acid sequence selected from the group consisting of the light chain variable region sequences shown in Table 12.

Suitable activatable anti-ITGa3 antibodies of the disclosure also include an antibody or antigen-binding fragment thereof that cross-competes for binding to human ITGa3 and/or cynomolgus monkey ITGa3 as an anti-ITGa3 antibody comprising a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, the activatable antibody also includes an agent conjugated to the AB. In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is conjugated to the AB via a linker that is cleavable in an intracellular or lysosomal environment. In some embodiments, the agent is a microtubule inhibitor. In some embodiments, the agent is a nucleic acid damaging agent, such as a DNA alkylator a DNA cleaving agent, a DNA cross-linker, a DNA intercalator, or other DNA damaging agent. In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the activatable antibody is conjugated to one or more equivalents of an agent. In some embodiments, the activatable antibody is conjugated to one equivalent of the agent. In some embodiments, the activatable antibody is conjugated to two, three, four, five, six, seven, eight, nine, ten, or greater than ten equivalents of the agent. In some embodiments, the activatable antibody is part of a mixture of activatable antibodies having a homogeneous number of equivalents of conjugated agents. In some embodiments, the activatable antibody is part of a mixture of activatable antibodies having a heterogeneous number of equivalents of conjugated agents. In some embodiments, the mixture of activatable antibodies is such that the average number of agents conjugated to each activatable antibody is between zero to one, between one to two, between two and three, between three and four, between four and five, between five and six, between six and seven, between seven and eight, between eight and nine, between nine and ten, and ten and greater. In some embodiments, the mixture of activatable antibodies is such that the average number of agents conjugated to each activatable antibody is one, two, three, four, five, six, seven, eight, nine, ten, or greater.

In some embodiments, the activatable antibody comprises one or more site-specific amino acid sequence modifications such that the number of lysine and/or cysteine residues is increased or decreased with respect to the original amino acid sequence of the activatable antibody, thus in some embodiments correspondingly increasing or decreasing the number of agents that can be conjugated to the activatable antibody, or in some embodiments limiting the conjugation of the agents to the activatable antibody in a site-specific manner. In some embodiments, the modified activatable antibody is modified with one or more non-natural amino acids in a site-specific manner, thus in some embodiments limiting the conjugation of the agents to only the sites of the non-natural amino acids.

In some embodiments, the agent is an anti-inflammatory agent.

In some embodiments, the activatable antibody also includes a detectable moiety. In some embodiments, the detectable moiety is a diagnostic agent.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 250). Other examples of a spacer joined directly to the N-terminus of MM of the activatable antibody include QGQSGQG (SEQ ID NO: 253), QGQSG (SEQ ID NO: 268), QGQS (SEQ ID NO: 269), QGQ (SEQ ID NO: 270), QG (SEQ ID NO: 271), and Q. Other examples of a spacer joined directly to the N-terminus of MM of the activatable antibody include GQSGQG (SEQ ID NO: 272), QSGQG (SEQ ID NO: 273), SGQG (SEQ ID NO: 274), GQG (SEQ ID NO: 275), and G. In some embodiments, no spacer is joined to the N-terminus of the MM. In some embodiments, the spacer includes at least the amino acid sequence QGQSGQ (SEQ ID NO: 250). In some embodiments, the spacer includes at least the amino acid sequence QGQSGQG (SEQ ID NO: 253). In some embodiments, the spacer includes at least the amino acid sequence QGQSG (SEQ ID NO: 268). In some embodiments, the spacer includes at least the amino acid sequence QGQS (SEQ ID NO: 269). In some embodiments, the spacer includes at least the amino acid sequence QGQ (SEQ ID NO: 270). In some embodiments, the spacer includes at least the amino acid sequence QG (SEQ ID NO: 271). In some embodiments, the spacer includes at least the amino acid residue Q. In some embodiments, the spacer includes at least the amino acid sequence GQSGQG (SEQ ID NO: 272). In some embodiments, the spacer includes at least the amino acid sequence QSGQG (SEQ ID NO: 273). In some embodiments, the spacer includes at least the amino acid sequence SGQG (SEQ ID NO: 274). In some embodiments, the spacer includes at least the amino acid sequence GQG (SEQ ID NO: 275). In some embodiments, the spacer includes at least the amino acid sequence G. In some embodiments, the spacer is absent.

In some embodiments, the AB of the activatable antibody naturally contains one or more disulfide bonds. In some embodiments, the AB can be engineered to include one or more disulfide bonds.

In some embodiments, the activatable antibody is encoded by a nucleic acid sequence that comprises a nucleic acid sequence encoding a heavy chain variable region amino acid sequence selected from the group consisting of SEQ ID NO: 1 and 3-10. In some embodiments, the activatable antibody is encoded by a nucleic acid sequence that comprises a nucleic acid sequence encoding a heavy chain variable region amino acid sequence selected from the group consisting of SEQ ID NO: 3-10. In some embodiments, the activatable antibody is encoded by a nucleic acid sequence that comprises a nucleic acid sequence encoding a heavy chain variable region amino acid sequence SEQ ID NO: 10.

In some embodiments, the activatable antibody is encoded by a nucleic acid sequence that comprises a nucleic acid sequence encoding a light chain variable region amino acid sequence selected from the group consisting of SEQ ID NO: 2, 11, and 12. In some embodiments, the activatable antibody is encoded by a nucleic acid sequence that comprises a nucleic acid sequence encoding a light chain variable region amino acid sequence selected from the group consisting of SEQ ID NO: 11 and 12. In some embodiments, the activatable antibody is encoded by a nucleic acid sequence that comprises a nucleic acid sequence encoding a light chain variable region amino acid sequence SEQ ID NO: 11.

In some embodiments, the activatable antibody is encoded by a nucleic acid sequence that comprises a nucleic acid sequence encoding a heavy chain variable region amino acid sequence selected from the group consisting of SEQ ID NO: 1 and 3-10, and a nucleic acid sequence encoding a light chain variable region amino acid sequence selected from the group consisting of SEQ ID NO: 2, 11, and 12.

In some embodiments, the activatable antibody is encoded by a nucleic acid sequence that comprises a nucleic acid sequence encoding a heavy chain variable region amino acid sequence selected from the group consisting of SEQ ID NO: 3-10, and a nucleic acid sequence encoding a light chain variable region amino acid sequence selected from the group consisting of SEQ ID NO: 11 and 12. In some embodiments, the activatable antibody is encoded by a nucleic acid sequence that comprises a nucleic acid sequence encoding a heavy chain variable region amino acid sequence selected from the group consisting of SEQ ID NO: 7-10, and a nucleic acid sequence encoding a light chain variable region amino acid sequence SEQ ID NO: 11. In some embodiments, the activatable antibody is encoded by a nucleic acid sequence that comprises a nucleic acid sequence encoding a heavy chain variable region amino acid sequence selected from the group consisting of SEQ ID NO: 10, and a nucleic acid sequence encoding a light chain variable region amino acid sequence SEQ ID NO: 11.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence selected from the group consisting of SEQ ID NO: 1 and 3-10. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence comprising selected from the group consisting of SEQ ID NO: 3-10. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence comprising selected from the group consisting of SEQ ID NO: 7-10. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence comprising SEQ ID NO: 10.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 2, 11, and 12. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 11 and 12. In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a light chain variable region amino acid sequence SEQ ID NO: 11.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence selected from the group consisting of SEQ ID NO: 1 and 3-10, and a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 2, 11, and 12.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence selected from the group consisting of SEQ ID NO: 3-10, and a nucleic acid sequence that is at least 90%, 91%, 92%, 93%, 94%, 95%, 96%, 97%, 98% or 99% identical to a nucleic acid sequence encoding a light chain variable region amino acid sequence selected from the group consisting of SEQ ID NO: 11 and 12.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence selected from the group consisting of SEQ ID NO: 7-10, and a nucleic acid sequence that is at least 90%, 91%, 92%, 93%, 94%, 95%, 96%, 97%, 98% or 99% identical to a nucleic acid sequence encoding a light chain variable region amino acid sequence SEQ ID NO: 11.

In some embodiments, the activatable antibody is encoded by a nucleic acid sequence that comprises a nucleic acid sequence that is at least 90%, 91%, 92%, 93%, 94%, 95%, 96%, 97%, 98% or 99% identical to a nucleic acid sequence encoding a heavy chain variable region amino acid sequence SEQ ID NO: 10, and a nucleic acid sequence that is at least 90%, 91%, 92%, 93%, 94%, 95%, 96%, 97%, 98% or 99% identical to a nucleic acid sequence encoding a light chain variable region amino acid sequence SEQ ID NO: 11.

In some embodiments, the activatable antibody is encoded by a nucleic acid sequence that comprises a nucleic acid sequence encoding a heavy chain variable region amino acid sequence selected from the group consisting of the heavy chain variable region sequences shown in Table 12. In some embodiments, the activatable antibody is encoded by a nucleic acid sequence that comprises a nucleic acid sequence encoding a light chain variable region amino acid sequence selected from the group consisting of the light chain variable region sequences shown in Table 12. In some embodiments, the activatable antibody is encoded by a nucleic acid sequence that comprises a nucleic acid sequence encoding a heavy chain variable region amino acid sequence selected from the group consisting of the heavy chain variable region sequences shown in Table 12 and a nucleic acid sequence encoding a light chain variable region amino acid sequence selected from the group consisting of the light chain variable region sequences shown in Table 12.

In some embodiments, the activatable antibody is encoded by a nucleic acid sequence that comprises a nucleic acid sequence encoding a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12. In some embodiments, the activatable antibody is encoded by a nucleic acid sequence that comprises a nucleic acid sequence encoding a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12. In some embodiments, the activatable antibody is encoded by a nucleic acid sequence that comprises a nucleic acid sequence encoding a heavy chain variable region amino acid sequence that is at least 90%, 91%, 92%, 93%, 94%, 95%, 96%, 97%, 98% or 99% identical to an amino acid sequence selected from the group consisting of the heavy chain variable region sequences shown in Table 12 and a nucleic acid sequence that comprises a nucleic acid sequence encoding a light chain variable region amino acid sequence that is at least 90%, 91%, 92%, 93%, 94%, 95%, 96%, 97%, 98% or 99% identical to an amino acid sequence selected from the group consisting of the light chain variable region sequences shown in Table 12.

In some embodiments, the activatable antibody is encoded by a nucleic acid sequence that comprises a nucleic acid sequence encoding a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence shown in Table 13; a VH CDR2 sequence shown in Table 13; a VH CDR3 sequence shown in Table 13; a VL CDR1 sequence shown in Table 13; a VL CDR2 sequence shown in Table 13; and a VL CDR3 sequence shown in Table 13.

In some embodiments, the activatable antibody is encoded by a nucleic acid sequence that comprises a nucleic acid sequence encoding a combination of a VH CDR1 sequence, a VH CDR2 sequence, a VH CDR3 sequence, a VL CDR1 sequence, a VL CDR2 sequence, and a VL CDR3 sequence, wherein at least one CDR sequence is selected from the group consisting of a VH CDR1 sequence that includes a sequence that is at least 90%, 91%, 92%, 93%, 94%, 95%, 96%, 97%, 98%, 99% or more identical to a VH CDR1 sequence shown in Table 13; a VH CD2 sequence that includes a sequence that is at least 90%, 91%, 92%, 93%, 94%, 95%, 96%, 97%, 98%, 99% or more identical to a VH CDR2 sequence shown in Table 13; a VH CDR3 sequence that includes a sequence that is at least 90%, 91%, 92%, 93%, 94%, 95%, 96%, 97%, 98%, 99% or more identical to a VH CDR3 sequence shown in Table 13; a VL CDR1 sequence that includes a sequence that is at least 90%, 91%, 92%, 93%, 94%, 95%, 96%, 97%, 98%, 99% or more identical to a VL CDR1 sequence shown in Table 13; a VL CDR2 sequence that includes a sequence that is at least 90%, 91%, 92%, 93%, 94%, 95%, 96%, 97%, 98%, 99% or more identical to a VL CDR2 sequence shown in Table 13; and a VL CDR3 sequence that includes a sequence that is at least 90%, 91%, 92%, 93%, 94%, 95%, 96%, 97%, 98%, 99% or more identical to a VL CDR3 sequence shown in Table 13.

In some embodiments, the activatable antibody is encoded by a nucleic acid sequence that comprises a nucleic acid sequence encoding a combination of a VH CDR1 sequence, a VH CDR2 sequence, a VH CDR3 sequence, a VL CDR1 sequence, a VL CDR2 sequence, and a VL CDR3 sequence, wherein the combination is a combination of the six CDR sequences (VH CDR1, VH CDR2, VH CDR3, VL CDR1, VL CDR2, and VL CDR3) shown in a single row in Table 13.

In some embodiments, the activatable antibody is encoded by a nucleic acid sequence that comprises a nucleic acid sequence encoding a light chain variable region that comprise a combination of a VL CDR1 sequence, a VL CDR2 sequence, and a VL CDR3 sequence, wherein the combination is a combination of the three light chain CDR sequences (VL CDR1, VL CDR2, VL CDR3) shown in a single row in Table 13.

In some embodiments, the activatable antibody is encoded by a nucleic acid sequence that comprises a nucleic acid sequence encoding a heavy chain variable region that comprise a combination of a VH CDR1 sequence, a VH CDR2 sequence, and a VH CDR3 sequence, wherein the combination is a combination of the three heavy chain CDR sequences (VH CDR1, VH CDR2, VH CDR3) shown in a single row in Table 13.

In some embodiments, the activatable antibody is encoded by a nucleic acid sequence that comprises a nucleic acid sequence encoding a combination of a VH CDR1 sequence, a VH CDR2 sequence, a VH CDR3 sequence, a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of the six CDR sequences (VH CDR1, VH CDR2, VH CDR3, VL CDR1, VL CDR2, and VL CDR3) shown in a single row in Table 13.

In some embodiments, the activatable antibody is encoded by a nucleic acid sequence that comprises a nucleic acid sequence encoding a heavy chain variable region that comprise a combination of a VH CDR1 sequence, a VH CDR2 sequence, and a VH CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three heavy chain CDR sequences (VH CDR1, VH CDR2, VH CDR3) shown in a single row in Table 13.

In some embodiments, the activatable antibody is encoded by a nucleic acid sequence that comprises a nucleic acid sequence encoding a light chain variable region that comprise a combination of a VL CDR1 sequence, a VL CDR2 sequence, and a VL CDR3 sequence, wherein each CDR sequence in the combination comprises a sequence that is at least 90%, 91%, 92%, 93%, 94%, 95%, 96%, 97%, 98%, 99% or more identical to the corresponding CDR sequence in a combination of three light chain CDR sequences (VL CDR1, VL CDR2, VL CDR3) shown in a single row in Table 13.

In some embodiments, the activatable antibody includes one or more polypeptides that include the combination of sequences in a given row of Table D or any combination of a mask sequence (MM), a substrate sequence (CM), a light chain variable domain sequence or light chain variable domain CDR sequences, and a heavy chain variable domain sequence or heavy chain variable domain CDR sequences of Table E.

TABLE D

Anti-ITGa3 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 1 | ECKTRQDFEMHDCVY (SEQ ID NO: 22) | LSGRSDNH (SEQ ID NO: 185) | 19, 20, 21 | 13, 17, 18 |
| 2 | ECKTRQDFEMHDCVY (SEQ ID NO: 22) | ISSGLLSS (SEQ ID NO: 208) | 19, 20, 21 | 13, 17, 18 |
| 3 | ECKTRQDFEMHDCVY (SEQ ID NO: 22) | LSGRSGNH (SEQ ID NO: 276) | 19, 20, 21 | 13, 17, 18 |
| 4 | ECKTRQDFEMHDCVY (SEQ ID NO: 22) | AVGLLAPP (SEQ ID NO: 216) | 19, 20, 21 | 13, 17, 18 |

TABLE D -continued

Anti-ITGa3 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 5 | ECKTRQDFEMHDCVY (SEQ ID NO: 22) | VHMPLGFLGP (SEQ ID NO: 196) | 19, 20, 21 | 13, 17, 18 |
| 6 | ECKTRQDFEMHDCVY (SEQ ID NO: 22) | TSTSGRSANPRG (SEQ ID NO: 223) | 19, 20, 21 | 13, 17, 18 |
| 7 | ECKTRQDFEMHDCVY (SEQ ID NO: 22) | QNQALRMA (SEQ ID NO: 203) | 19, 20, 21 | 13, 17, 18 |
| 8 | ECKTRQDFEMHDCVY (SEQ ID NO: 22) | ISSGLLSGRSDNH (SEQ ID NO: 232) | 19, 20, 21 | 13, 17, 18 |
| 9 | ECKTRQDFEMHDCVY (SEQ ID NO: 22) | ISSGLLSGRSGNH (SEQ ID NO: 249) | 19, 20, 21 | 13, 17, 18 |
| 10 | ECKTRQDFEMHDCVY (SEQ ID NO: 22) | ISSGLLSGRSANPRG (SEQ ID NO: 296) | 19, 20, 21 | 13, 17, 18 |
| 11 | ECKTRQDFEMHDCVY (SEQ ID NO: 22) | AVGLLAPPTSGRSANPRG (SEQ ID NO: 297) | 19, 20, 21 | 13, 17, 18 |
| 12 | ECKTRQDFEMHDCVY (SEQ ID NO: 22) | AVGLLAPPSGRSANPRG (SEQ ID NO: 298) | 19, 20, 21 | 13, 17, 18 |
| 13 | ECKTRQDFEMHDCVY (SEQ ID NO: 22) | ISSGLLSGRSDDH (SEQ ID NO: 299) | 19, 20, 21 | 13, 17, 18 |
| 14 | ECKTRQDFEMHDCVY (SEQ ID NO: 22) | ISSGLLSGRSDIH (SEQ ID NO: 300) | 19, 20, 21 | 13, 17, 18 |
| 15 | ECKTRQDFEMHDCVY (SEQ ID NO: 22) | ISSGLLSGRSDQH (SEQ ID NO: 301) | 19, 20, 21 | 13, 17, 18 |
| 16 | ECKTRQDFEMHDCVY (SEQ ID NO: 22) | ISSGLLSGRSDTH (SEQ ID NO: 302) | 19, 20, 21 | 13, 17, 18 |
| 17 | ECKTRQDFEMHDCVY (SEQ ID NO: 22) | ISSGLLSGRSDYH (SEQ ID NO: 303) | 19, 20, 21 | 13, 17, 18 |
| 18 | ECKTRQDFEMHDCVY (SEQ ID NO: 22) | ISSGLLSGRSDNP (SEQ ID NO: 304) | 19, 20, 21 | 13, 17, 18 |
| 19 | ECKTRQDFEMHDCVY (SEQ ID NO: 22) | ISSGLLSGRSANP (SEQ ID NO: 305) | 19, 20, 21 | 13, 17, 18 |
| 20 | ECKTRQDFEMHDCVY (SEQ ID NO: 22) | ISSGLLSGRSANI (SEQ ID NO: 306) | 19, 20, 21 | 13, 17, 18 |
| 21 | ECKTRQDFEMHDCVY (SEQ ID NO: 22) | ISSGLLSGRSDNI (SEQ ID NO: 307) | 19, 20, 21 | 13, 17, 18 |
| 22 | ECKTRQDFEMHDCVY (SEQ ID NO: 22) | AVGLLAPPGGLSGRSDNH (SEQ ID NO: 238) | 19, 20, 21 | 13, 17, 18 |
| 23 | ECKTRQDFEMHDCVY (SEQ ID NO: 22) | AVGLLAPPGGLSGRSDDH (SEQ ID NO: 307) | 19, 20, 21 | 13, 17, 18 |
| 24 | ECKTRQDFEMHDCVY (SEQ ID NO: 22) | AVGLLAPPGGLSGRSDIH (SEQ ID NO: 308) | 19, 20, 21 | 13, 17, 18 |
| 25 | ECKTRQDFEMHDCVY (SEQ ID NO: 22) | AVGLLAPPGGLSGRSDQH (SEQ ID NO: 309) | 19, 20, 21 | 13, 17, 18 |
| 26 | ECKTRQDFEMHDCVY (SEQ ID NO: 22) | AVGLLAPPGGLSGRSDTH (SEQ ID NO: 310) | 19, 20, 21 | 13, 17, 18 |
| 27 | ECKTRQDFEMHDCVY (SEQ ID NO: 22) | AVGLLAPPGGLSGRSDYH (SEQ ID NO: 311) | 19, 20, 21 | 13, 17, 18 |
| 28 | ECKTRQDFEMHDCVY (SEQ ID NO: 22) | AVGLLAPPGGLSGRSDNP (SEQ ID NO: 312) | 19, 20, 21 | 13, 17, 18 |
| 29 | ECKTRQDFEMHDCVY (SEQ ID NO: 22) | AVGLLAPPGGLSGRSANP (SEQ ID NO: 313) | 19, 20, 21 | 13, 17, 18 |

TABLE D -continued

Anti-ITGa3 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 30 | ECKTRQDFEMHDCVY (SEQ ID NO: 22) | AVGLLAPPGGLSGRSANI (SEQ ID NO: 314) | 19, 20, 21 | 13, 17, 18 |
| 31 | ECKTRQDFEMHDCVY (SEQ ID NO: 22) | AVGLLAPPGGLSGRSDNI (SEQ ID NO: 316) | 19, 20, 21 | 13, 17, 18 |
| 32 | ECKTRQDFEMHDCVY (SEQ ID NO: 22) | ISSGLLSSGGSGGSLSGRSDNH (SEQ ID NO: 233) | 19, 20, 21 | 13, 17, 18 |
| 33 | QCMSRFAFEIGDCVM (SEQ ID NO: 26) | LSGRSDNH (SEQ ID NO: 185) | 19, 20, 21 | 13, 17, 18 |
| 34 | QCMSRFAFEIGDCVM (SEQ ID NO: 26) | ISSGLLSS (SEQ ID NO: 208) | 19, 20, 21 | 13, 17, 18 |
| 35 | QCMSRFAFEIGDCVM (SEQ ID NO: 26) | LSGRSGNH (SEQ ID NO: 276) | 19, 20, 21 | 13, 17, 18 |
| 36 | QCMSRFAFEIGDCVM (SEQ ID NO: 26) | AVGLLAPP (SEQ ID NO: 216) | 19, 20, 21 | 13, 17, 18 |
| 37 | QCMSRFAFEIGDCVM (SEQ ID NO: 26) | VHMPLGFLGP (SEQ ID NO: 196) | 19, 20, 21 | 13, 17, 18 |
| 38 | QCMSRFAFEIGDCVM (SEQ ID NO: 26) | TSTSGRSANPRG (SEQ ID NO: 223) | 19, 20, 21 | 13, 17, 18 |
| 39 | QCMSRFAFEIGDCVM (SEQ ID NO: 26) | QNQALRMA (SEQ ID NO: 203) | 19, 20, 21 | 13, 17, 18 |
| 40 | QCMSRFAFEIGDCVM (SEQ ID NO: 26) | ISSGLLSGRSDNH (SEQ ID NO: 232) | 19, 20, 21 | 13, 17, 18 |
| 41 | QCMSRFAFEIGDCVM (SEQ ID NO: 26) | ISSGLLSGRSGNH (SEQ ID NO: 249) | 19, 20, 21 | 13, 17, 18 |
| 42 | QCMSRFAFEIGDCVM (SEQ ID NO: 26) | ISSGLLSGRSANPRG (SEQ ID NO: 296) | 19, 20, 21 | 13, 17, 18 |
| 43 | QCMSRFAFEIGDCVM (SEQ ID NO: 26) | AVGLLAPPTSGRSANPRG (SEQ ID NO: 297) | 19, 20, 21 | 13, 17, 18 |
| 44 | QCMSRFAFEIGDCVM (SEQ ID NO: 26) | AVGLLAPPSGRSANPRG (SEQ ID NO: 298) | 19, 20, 21 | 13, 17, 18 |
| 45 | QCMSRFAFEIGDCVM (SEQ ID NO: 26) | ISSGLLSGRSDDH (SEQ ID NO: 299) | 19, 20, 21 | 13, 17, 18 |
| 46 | QCMSRFAFEIGDCVM (SEQ ID NO: 26) | ISSGLLSGRSDIH (SEQ ID NO: 300) | 19, 20, 21 | 13, 17, 18 |
| 47 | QCMSRFAFEIGDCVM (SEQ ID NO: 26) | ISSGLLSGRSDQH (SEQ ID NO: 301) | 19, 20, 21 | 13, 17, 18 |
| 48 | QCMSRFAFEIGDCVM (SEQ ID NO: 26) | ISSGLLSGRSDTH (SEQ ID NO: 302) | 19, 20, 21 | 13, 17, 18 |
| 49 | QCMSRFAFEIGDCVM (SEQ ID NO: 26) | ISSGLLSGRSDYH (SEQ ID NO: 303) | 19, 20, 21 | 13, 17, 18 |
| 50 | QCMSRFAFEIGDCVM (SEQ ID NO: 26) | ISSGLLSGRSDNP (SEQ ID NO: 304) | 19, 20, 21 | 13, 17, 18 |
| 51 | QCMSRFAFEIGDCVM (SEQ ID NO: 26) | ISSGLLSGRSANP (SEQ ID NO: 305) | 19, 20, 21 | 13, 17, 18 |
| 52 | QCMSRFAFEIGDCVM (SEQ ID NO: 26) | ISSGLLSGRSANI (SEQ ID NO: 306) | 19, 20, 21 | 13, 17, 18 |
| 53 | QCMSRFAFEIGDCVM (SEQ ID NO: 26) | ISSGLLSGRSDNI (SEQ ID NO: 307) | 19, 20, 21 | 13, 17, 18 |
| 54 | QCMSRFAFEIGDCVM (SEQ ID NO: 26) | AVGLLAPPGGLSGRSDNH (SEQ ID NO: 238) | 19, 20, 21 | 13, 17, 18 |

TABLE D -continued

Anti-ITGa3 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 55 | QCMSRFAFEIGDCVM (SEQ ID NO: 26) | AVGLLAPPGGL TABLE D -continued Anti-ITGa3 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 80 | TCLSRYEFETTDCVM (SEQ ID NO: 44) | ISSGLLSG TABLE D -continued Anti-ITGa3 Activatable Antibody Combinations

| Comb. No. | Mask Sequence (MM) | Substrate Sequence (CM) | VL CDRs SEQ ID NOs | VH CDRs SEQ ID NOs |
|---|---|---|---|---|
| 105 | VCRTRWHFETTDCVM (SEQ ID NO: 45) | ISSGLLSGRSGNH (SEQ ID NO: 249) | 19, 20, 21 | 13, 17, 18 |
| 106 | VCRTRWHFETTDCVM (SEQ ID NO: 45) | ISSGLLSGRSANPRG (SEQ ID NO: 296) | 19, 20, 21 | 13, 17, 18 |
| 107 | VCRTRWHFETTDCVM (SEQ ID NO: 45) | AVGLLAPPTSGRSANPRG (SEQ ID NO: 297) | 19, 20, 21 | 13, 17, 18 |
| 108 | VCRTRWHFETTDCVM (SEQ ID NO: 45) | AVGLLAPPSGRSANPRG (SEQ ID NO: 298) | 19, 20, 21 | 13, 17, 18 |
| 109 | VCRTRWHFETTDCVM (SEQ ID NO: 45) | ISSGLLSGRSDDH (SEQ ID NO: 299) | 19, 20, 21 | 13, 17, 18 |
| 110 | VCRTRWHFETTDCVM (SEQ ID NO: 45) | ISSGLLSGRSDIH (SEQ ID NO: 300) | 19, 20, 21 | 13, 17, 18 |
| 111 | VCRTRWHFETTDCVM (SEQ ID NO: 45) | ISSGLLSGRSDQH (SEQ ID NO: 301) | 19, 20, 21 | 13, 17, 18 |
| 112 | VCRTRWHFETTDCVM (SEQ ID NO: 45) | ISSGLLSGRSDTH (SEQ ID NO: 302) | 19, 20, 21 | 13, 17, 18 |
| 113 | VCRTRWHFETTDCVM (SEQ ID NO: 45) | ISSGLLSGRSDYH (SEQ ID NO: 303) | 19, 20, 21 | 13, 17, 18 |
| 114 | VCRTRWHFETTDCVM (SEQ ID NO: 45) | ISSGLLSGRSDNP (SEQ ID NO: 304) | 19, 20, 21 | 13, 17, 18 |
| 115 | VCRTRWHFETTDCVM (SEQ ID NO: 45) | ISSGLLSGRSANP (SEQ ID NO: 305) | 19, 20, 21 | 13, 17, 18 |
| 116 | VCRTRWHFETTDCVM (SEQ ID NO: 45) | ISSGLLSGRSANI (SEQ ID NO: 306) | 19, 20, 21 | 13, 17, 18 |
| 117 | VCRTRWHFETTDCVM (SEQ ID NO: 45) | ISSGLLSGRSDNI (SEQ ID NO: 307) | 19, 20, 21 | 13, 17, 18 |
| 118 | VCRTRWHFETTDCVM (SEQ ID NO: 45) | AVGLLAPPGGLSGRSDNH (SEQ ID NO: 238) | 19, 20, 21 | 13, 17, 18 |
| 119 | VCRTRWHFETTDCVM (SEQ ID NO: 45) | AVGLLAPPGGLSGRSDDH (SEQ ID NO: 307) | 19, 20, 21 | 13, 17, 18 |
| 120 | VCRTRWHFETTDCVM (SEQ ID NO: 45) | AVGLLAPPGGLSGRSDIH (SEQ ID NO: 308) | 19, 20, 21 | 13, 17, 18 |
| 121 | VCRTRWHFETTDCVM (SEQ ID NO: 45) | AVGLLAPPGGLSGRSDQH (SEQ ID NO: 309) | 19, 20, 21 | 13, 17, 18 |
| 122 | VCRTRWHFETTDCVM (SEQ ID NO: 45) | AVGLLAPPGGLSGRSDTH (SEQ ID NO: 310) | 19, 20, 21 | 13, 17, 18 |
| 123 | VCRTRWHFETTDCVM (SEQ ID NO: 45) | AVGLLAPPGGLSGRSDYH (SEQ ID NO: 311) | 19, 20, 21 | 13, 17, 18 |
| 124 | VCRTRWHFETTDCVM (SEQ ID NO: 45) | AVGLLAPPGGLSGRSDNP (SEQ ID NO: 312) | 19, 20, 21 | 13, 17, 18 |
| 125 | VCRTRWHFETTDCVM (SEQ ID NO: 45) | AVGLLAPPGGLSGRSANP (SEQ ID NO: 313) | 19, 20, 21 | 13, 17, 18 |
| 126 | VCRTRWHFETTDCVM (SEQ ID NO: 45) | AVGLLAPPGGLSGRSANI (SEQ ID NO: 314) | 19, 20, 21 | 13, 17, 18 |
| 127 | VCRTRWHFETTDCVM (SEQ ID NO: 45) | AVGLLAPPGGLSGRSDNI (SEQ ID NO: 316) | 19, 20, 21 | 13, 17, 18 |
| 128 | VCRTRWHFETTDCVM (SEQ ID NO: 45) | ISSGLLSSGGSGGSLSGRSDNH (SEQ ID NO: 233) | 19, 20, 21 | 13, 17, 18 |

TABLE E

Anti-ITGa3 Activatable Antibody Components

| Mask Sequence (MM) | Substrate Sequence (CM) | VL or VL CDRs | VH or VH CDRs |
|---|---|---|---|
| ECKTRQDFEMHDCVY (SEQ ID NO: 22) | LSGRSDNH (SEQ ID NO: 185) | SEQ ID NOS: 19, 20, 21 | SEQ ID NOS: 13, 17, 18 |
| TCHDPYMNIDYTCKL (SEQ ID NO: 23) | TGRGPSWV (SEQ ID NO: 182) | SEQ ID NO: 2 | SEQ ID NOS: 14, 17, 18 |
| VMCYWEGWGFGRCPL (SEQ ID NO: 24) | PLTGRSGG (SEQ ID NO: 188) | SEQ ID NO: 11 | SEQID NOS: 15, 17, 18 |
| VWYCDGGYNECATRS (SEQ ID NO: 25) | TARGPSFK (SEQ ID NO: 184) | SEQ ID NO: 12 | SEQ ID NOS: 16, 17, 18 |
| QCMSRFAFEIGDCVM (SEQ ID NO: 26) | NTLSGRSENHSG (SEQ ID NO: 221) | | SEQ ID NO: 1 |
| AVWCDAYNKNMCWST (SEQ ID NO: 27) | NTLSGRSGNHGS (SEQ ID NO: 222) | | SEQ ID NO: 3 |
| VWYCDGGYNECATRS (SEQ ID NO: 28) | TSTSGRSANPRG (SEQ ID NO: 223) | | SEQ ID NO: 4 |
| ECKTRQDFEMHDCVY (SEQ ID NO: 29) | TSGRSANP (SEQ ID NO: 224) | | SEQ ID NO: 5 |
| KCHDPYINIDYTCNN (SEQ ID NO: 30) | VHMPLGFLGP (SEQ ID NO: 196) | | SEQ ID NO: 6 |
| LITCEMLMLKNCEKN (SEQ ID NO: 31) | AVGLLAPP (SEQ ID NO: 216) | | SEQ ID NO: 7 |
| LGCKKQHHINNTCDR (SEQ ID NO: 32) | AQNLLGMV (SEQ ID NO: 204) | | SEQ ID NO: 8 |
| TCHDPYMNIDYTCKL (SEQ ID NO: 33) | QNQALRMA (SEQ ID NO: 203) | | SEQ ID NO: 9 |
| VMCYWEGWGFGRCPL (SEQ ID NO: 34) | LAAPLGLL (SEQ ID NO: 215) | | SEQ ID NO: 10 |
| TCPTRWHFETTDCVM (SEQ ID NO: 35) | STFPFGMF (SEQ ID NO: 205) | | |
| TCGSRLDFELNDCVM (SEQ ID NO: 36) | ISSGLLSS (SEQ ID NO: 208) | | |
| WCRDRSHFETGDCVM (SEQ ID NO: 37) | PAGLWLDP (SEQ ID NO: 218) | | |
| TCTSRWEFENRDCVM (SEQ ID NO: 38) | VAGRSMRP (SEQ ID NO: 225) | | |
| VCRDRNEFEVGDCVM (SEQ ID NO: 39) | VVPEGRRS (SEQ ID NO: 226) | | |
| TCKNRLEFERGDCVM (SEQ ID NO: 40) | ILPRSPAF (SEQ ID NO: 227) | | |
| VCSSRLEFEQKDCVM (SEQ ID NO: 41) | MVLGRSLL (SEQ ID NO: 228) | | |
| WCRDREHFEKGDCVM (SEQ ID NO: 42) | QGRAITFI (SEQ ID NO: 229) | | |
| YCANRYEFEYGDCVM (SEQ ID NO: 43) | SPRSIMLA (SEQ ID NO: 230) | | |
| TCLSRYEFETTDCVM (SEQ ID NO: 44) | SMLRSMPL (SEQ ID NO: 231) | | |
| VCRTRWHFETTDCVM (SEQ ID NO: 45) | ISSGLLSGRSDNH (SEQ ID NO: 232) | | |

TABLE E -continued

Anti-ITGa3 Activatable Antibody Components

| Mask Sequence (MM) | Substrate Sequence (CM) | VL or VL CDRs | VH or VH CDRs |
|---|---|---|---|
| VCSNRAEFEWGDCVM (SEQ ID NO: 46) | AVGLLAPPGGLSGRSDNH (SEQ ID NO: 238) | | |
| VCASRWHFENTDCVM (SEQ ID NO: 47) | ISSGLLSSGGSGGSLSGRSDNH (SEQ ID NO: 233) | | |
| NCASRWHFENEDCVM (SEQ ID NO: 48) | LSGRSGNH (SEQ ID NO: 276) | | |
| VCSGRLEFELGDCVM (SEQ ID NO: 49) | SGRSANPRG (SEQ ID NO: 277) | | |
| VCSSRWEFETNDCVM (SEQ ID NO: 50) | LSGRSDDH (SEQ ID NO: 278) | | |
| FCRDRLDFDTMDCVM (SEQ ID NO: 51) | LSGRSDIH (SEQ ID NO: 279) | | |
| CCMDRLEFERGDCVM (SEQ ID NO: 52) | LSGRSDQH (SEQ ID NO: 280) | | |
| VCGSRNEFETGDCVM (SEQ ID NO: 53) | LSGRSDTH (SEQ ID NO: 281) | | |
| MCSGRLEFETGDCVM (SEQ ID NO: 54) | LSGRSDYH (SEQ ID NO: 282) | | |
| | LSGRSDNP (SEQ ID NO: 283) | | |
| | LSGRSANP (SEQ ID NO: 284) | | |
| | LSGRSANI (SEQ ID NO: 285) | | |
| | LSGRSDNI (SEQ ID NO: 286) | | |
| | MIAPVAYR (SEQ ID NO: 287) | | |
| | RPSPMWAY (SEQ ID NO: 288) | | |
| | WATPRPMR (SEQ ID NO: 289) | | |
| | FRLLDWQW (SEQ ID NO: 290) | | |
| | ISSGL (SEQ ID NO: 291) | | |
| | ISSGLLS (SEQ ID NO: 292) | | |
| | ISSGLL (SEQ ID NO: 293) | | |
| | ISSGLLSGRSANPRG (SEQ ID NO: 296) | | |
| | AVGLLAPPTSGRSANPRG (SEQ ID NO: 297) | | |
| | AVGLLAPPSGRSANPRG (SEQ ID NO: 298) | | |
| | ISSGLLSGRSDDH (SEQ ID NO: 299) | | |
| | ISSGLLSGRSDIH (SEQ ID NO: 300) | | |

TABLE E -continued

Anti-ITGa3 Activatable Antibody Components

| Mask Sequence (MM) | Substrate Sequence (CM) | VL or VL CDRs | VH or VH CDRs |
|---|---|---|---|
| | ISSGLLSGRSDQH (SEQ ID NO: 301) | | |
| | ISSGLLSGRSDTH (SEQ ID NO: 302) | | |
| | ISSGLLSGRSDYH (SEQ ID NO: 303) | | |
| | ISSGLLSGRSDNP (SEQ ID NO: 304) | | |
| | ISSGLLSGRSANP (SEQ ID NO: 305) | | |
| | ISSGLLSGRSANI (SEQ ID NO: 306) | | |
| | AVGLLAPPGGLSGRSDDH (SEQ ID NO: 307) | | |
| | AVGLLAPPGGLSGRSDIH (SEQ ID NO: 308) | | |
| | AVGLLAPPGGLSGRSDQH (SEQ ID NO: 309) | | |
| | AVGLLAPPGGLSGRSDTH (SEQ ID NO: 310) | | |
| | AVGLLAPPGGLSGRSDYH (SEQ ID NO: 311) | | |
| | AVGLLAPPGGLSGRSDNP (SEQ ID NO: 312) | | |
| | AVGLLAPPGGLSGRSANP (SEQ ID NO: 313) | | |
| | AVGLLAPPGGLSGRSANI (SEQ ID NO: 314) | | |
| | ISSGLLSGRSDNI (SEQ ID NO: 315) | | |
| | AVGLLAPPGGLSGRSDNI (SEQ ID NO: 316) | | |
| | GLSGRSDNHGGAVGLLAPP (SEQ ID NO: 294) | | |
| | GLSGRSDNHGGVHMPLGFLGP (SEQ ID NO: 295) | | |

In some embodiments, an activatable antibody of the present disclosure includes one or more polypeptides that include the combination of sequences selected from Table D or Table E, where the polypeptide includes a combination of a masking sequence selected from the column titled "Mask Sequence (MM)" of Table D or Table E, a substrate sequence from the column titled "Substrate Sequence (CM)" of Table D or Table E, a light chain variable domain or light chain CDRs from the column titled "VL or VL CDRs" or "VL CDRs SEQ ID NOs" of Table D or Table E, and a heavy chain variable domain or heavy chain CDRs from the column titled "VH or VH CDRs" or "VH CDRs SEQ ID Nos" of Table D or Table E. For example, an activatable antibody of the present disclosure includes the amino acid sequences of combination no. 22, which includes the masking sequence of SEQ ID NO: 22, the substrate sequence of SEQ ID NO: 238, a light chain variable domain that includes the VL CDR sequences of SEQ ID NOS: 19, 20, and 21, and a heavy chain variable domain that includes the VH CDR sequences of 13, 17, and 18. Therefore, an activatable antibody that includes at least the combination of sequences in any given row of Table D is described herein. Similarly, any combination of a mask sequence (MM), a substrate sequence (CM), a light chain variable domain sequence or light chain variable domain CDR sequences, and a heavy chain variable domain sequence or heavy chain variable domain CDR sequences of Table E is described herein. An activatable antibody that includes at least any combination of a masking sequence, a substrate sequence, a variable heavy chain or variable heavy chain CDRs, and a variable light chain or variable light chain CDRs selected from the corresponding columns Table D or Table E is also described herein. In some exemplary embodiments, an activatable antibody that includes at least the combination of sequences in any given row of Table D or any combination of a mask sequence (MM), a substrate sequence (CM), a light chain variable domain sequence or light chain variable domain CDR sequences, and a heavy chain variable domain sequence or heavy chain variable domain CDR sequences of Table E can be combined with one or more toxins, including a dolastatin or a derivative thereof, an auristatin or a derivative thereof, a maytansinoid or a derivative thereof, a duocarmycin or a derivative thereof, a calicheamicin or a derivative thereof, or a pyrrolobenzodiazepine or a derivative thereof. In some exemplary embodiments, an activatable antibody that includes at least the combination of sequences in any given row of Table D or any combination of a mask sequence (MM), a substrate sequence (CM), a light chain variable domain sequence or light chain variable domain CDR sequences, and a heavy chain variable domain sequence or heavy chain variable domain CDR sequences of Table E can be combined with one or more toxins, including auristatin E, monomethyl auristatin F (MMAF), monomethyl auristatin E (MMAE), monomethyl auristatin D (MMAD), maytansinoid DM4, maytansinoid DM1, a pyrrolobenzodiazepine, a pyrrolobenzodiazepine dimer, and/or a duocarmycin.

Any of the combinations in Table D or Table E as described above can be combined with human immunoglobulin constant regions to result in fully human IgGs including IgG1, IgG2, IgG4 or mutated constant regions to result in human IgGs with altered functions such as IgG1 N297A, IgG1 N297Q, or IgG4 S228P. The combinations described in Table D or Table E are not limited by the particular combinations shown in any given row, and thus may include any mask sequence from column 2 of Table D (or column 1 of Table E) combined with any substrate sequence from column 3 of Table D (or column 2 of Table E) combined with any VL sequence or set of VL CDR sequences from column 4 of Table D (or column 3 or Table E) combined with any VH sequence or set of VH CDR sequences from column 5 of Table D (or column 4 of Table E). In addition to the mask sequences disclosed in column 2 of Table D or column 1 of Table E, any mask sequence disclosed herein can be used in a combination. In addition to the substrate sequences disclosed in column 3 of Table D or column 2 of Table E, any CM disclosed herein can be used in a combination. In addition to the light chain variable region sequence or light chain CDR sequences disclosed in column 4 of Table D or column 3 of Table E, any light chain variable region sequence or light chain CDR sequences disclosed herein can be used in a combination. In addition to the heavy chain variable region sequence or heavy chain CDR sequences disclosed in column 5 of Table D or column 4 of Table E, any heavy chain variable region sequence or heavy chain CDR sequences disclosed herein can be used in a combination.

In some embodiments, the antibody drug conjugates (ADCs) and activatable antibody drug conjugates (AADCs) can include one or more polypeptides that include the combination of a light chain sequence or a light chain variable domain sequence, and a heavy chain sequence or a heavy chain variable domain sequences, a linker, and a toxin in a given row of Table F or any combination of a light chain sequence or a light chain variable domain sequence, and a heavy chain sequence or a heavy chain variable domain sequence, a linker, and a toxin of Table F.

TABLE F

Anti-ITGa3 ADC and Anti-ITGa3 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 1 | 10 | 11 | vc | MMAD |
| 2 | 10 | 11 | PEG2-vc | MMAD |
| 3 | 10 | 11 | vc | MMAE |
| 4 | 10 | 11 | vc | duocarmycin |
| 5 | 10 | 11 | spdb | DM4 |
| 6 | 320 | 322 | vc | MMAD |
| 7 | 320 | 322 | PEG2-vc | MMAD |
| 8 | 320 | 322 | vc | MMAE |
| 9 | 320 | 322 | vc | duocarmycin |
| 10 | 320 | 322 | spdb | DM4 |
| 11 | 320 | 324 | vc | MMAD |
| 12 | 320 | 324 | PEG2-vc | MMAD |
| 13 | 320 | 324 | vc | MMAE |
| 14 | 320 | 324 | vc | duocarmycin |
| 15 | 320 | 324 | spdb | DM4 |
| 16 | 320 | 396 | vc | MMAD |
| 17 | 320 | 396 | PEG2-vc | MMAD |
| 18 | 320 | 396 | vc | MMAE |
| 19 | 320 | 396 | vc | duocarmycin |
| 20 | 320 | 396 | spdb | DM4 |
| 21 | 10 | 326 | vc | MMAD |
| 22 | 10 | 326 | PEG2-vc | MMAD |
| 23 | 10 | 326 | vc | MMAE |
| 24 | 10 | 326 | vc | duocarmycin |
| 25 | 10 | 326 | spdb | DM4 |
| 26 | 10 | 398 | vc | MMAD |
| 27 | 10 | 398 | PEG2-vc | MMAD |
| 28 | 10 | 398 | vc | MMAE |
| 29 | 10 | 398 | vc | duocarmycin |
| 30 | 10 | 398 | spdb | DM4 |
| 31 | 320 | 328 | vc | MMAD |
| 32 | 320 | 328 | PEG2-vc | MMAD |
| 33 | 320 | 328 | vc | MMAE |
| 34 | 320 | 328 | vc | duocarmycin |
| 35 | 320 | 328 | spdb | DM4 |
| 36 | 320 | 400 | vc | MMAD |
| 37 | 320 | 400 | PEG2-vc | MMAD |
| 38 | 320 | 400 | vc | MMAE |
| 39 | 320 | 400 | vc | duocarmycin |
| 40 | 320 | 400 | spdb | DM4 |
| 41 | 10 | 328 | vc | MMAD |
| 42 | 10 | 328 | PEG2-vc | MMAD |
| 43 | 10 | 328 | vc | MMAE |
| 44 | 10 | 328 | vc | duocarmycin |
| 45 | 10 | 328 | spdb | DM4 |
| 46 | 10 | 402 | vc | MMAD |
| 47 | 10 | 402 | PEG2-vc | MMAD |
| 48 | 10 | 402 | vc | MMAE |
| 49 | 10 | 402 | vc | duocarmycin |
| 50 | 10 | 402 | spdb | DM4 |
| 51 | 320 | 332 | vc | MMAD |
| 52 | 320 | 332 | PEG2-vc | MMAD |
| 53 | 320 | 332 | vc | MMAE |
| 54 | 320 | 332 | vc | duocarmycin |
| 55 | 320 | 332 | spdb | DM4 |
| 56 | 320 | 404 | vc | MMAD |
| 57 | 320 | 404 | PEG2-vc | MMAD |
| 58 | 320 | 404 | vc | MMAE |
| 59 | 320 | 404 | vc | duocarmycin |
| 60 | 320 | 404 | spdb | DM4 |
| 61 | 10 | 334 | vc | MMAD |
| 62 | 10 | 334 | PEG2-vc | MMAD |
| 63 | 10 | 334 | vc | MMAE |
| 64 | 10 | 334 | vc | duocarmycin |
| 65 | 10 | 334 | spdb | DM4 |
| 66 | 10 | 405 | vc | MMAD |
| 67 | 10 | 405 | PEG2-vc | MMAD |
| 68 | 10 | 405 | vc | MMAE |
| 69 | 10 | 405 | vc | duocarmycin |
| 70 | 10 | 405 | spdb | DM4 |
| 71 | 320 | 334 | vc | MMAD |
| 72 | 320 | 334 | PEG2-vc | MMAD |
| 73 | 320 | 334 | vc | MMAE |

TABLE F-continued

Anti-ITGa3 ADC and Anti-ITGa3 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 74 | 320 | 334 | vc | duocarmycin |
| 75 | 320 | 334 | spdb | DM4 |
| 76 | 320 | 406 | vc | MMAD |
| 77 | 320 | 406 | PEG2-vc | MMAD |
| 78 | 320 | 406 | vc | MMAE |
| 79 | 320 | 406 | vc | duocarmycin |
| 80 | 320 | 406 | spdb | DM4 |
| 81 | 10 | 335 | vc | MMAD |
| 82 | 10 | 335 | PEG2-vc | MMAD |
| 83 | 10 | 335 | vc | MMAE |
| 84 | 10 | 335 | vc | duocarmycin |
| 85 | 10 | 335 | spdb | DM4 |
| 86 | 10 | 408 | vc | MMAD |
| 87 | 10 | 335 | PEG2-vc | MMAD |
| 88 | 10 | 335 | vc | MMAE |
| 89 | 10 | 335 | vc | duocarmycin |
| 90 | 10 | 335 | spdb | DM4 |
| 91 | 320 | 336 | vc | MMAD |
| 92 | 320 | 336 | PEG2-vc | MMAD |
| 93 | 320 | 336 | vc | MMAE |
| 94 | 320 | 336 | vc | duocarmycin |
| 95 | 320 | 336 | spdb | DM4 |
| 96 | 320 | 408 | vc | MMAD |
| 97 | 320 | 408 | PEG2-vc | MMAD |
| 98 | 320 | 408 | vc | MMAE |
| 99 | 320 | 408 | vc | duocarmycin |
| 100 | 320 | 408 | spdb | DM4 |
| 101 | 10 | 337 | vc | MMAD |
| 102 | 10 | 337 | PEG2-vc | MMAD |
| 103 | 10 | 337 | vc | MMAE |
| 104 | 10 | 337 | vc | duocarmycin |
| 105 | 10 | 337 | spdb | DM4 |
| 106 | 10 | 409 | vc | MMAD |
| 107 | 10 | 409 | PEG2-vc | MMAD |
| 108 | 10 | 409 | vc | MMAE |
| 109 | 10 | 409 | vc | duocarmycin |
| 110 | 10 | 409 | spdb | DM4 |
| 111 | 320 | 338 | vc | MMAD |
| 112 | 320 | 338 | PEG2-vc | MMAD |
| 113 | 320 | 338 | vc | MMAE |
| 114 | 320 | 338 | vc | duocarmycin |
| 115 | 320 | 338 | spdb | DM4 |
| 116 | 320 | 410 | vc | MMAD |
| 117 | 320 | 410 | PEG2-vc | MMAD |
| 118 | 320 | 410 | vc | MMAE |
| 119 | 320 | 410 | vc | duocarmycin |
| 120 | 320 | 410 | spdb | DM4 |
| 121 | 10 | 339 | vc | MMAD |
| 122 | 10 | 339 | PEG2-vc | MMAD |
| 123 | 10 | 339 | vc | MMAE |
| 124 | 10 | 339 | vc | duocarmycin |
| 125 | 10 | 339 | spdb | DM4 |
| 126 | 10 | 411 | vc | MMAD |
| 127 | 10 | 411 | PEG2-vc | MMAD |
| 128 | 10 | 411 | vc | MMAE |
| 129 | 10 | 411 | vc | duocarmycin |
| 130 | 10 | 411 | spdb | DM4 |
| 131 | 320 | 340 | vc | MMAD |
| 132 | 320 | 340 | PEG2-vc | MMAD |
| 133 | 320 | 340 | vc | MMAE |
| 134 | 320 | 340 | vc | duocarmycin |
| 135 | 320 | 340 | spdb | DM4 |
| 136 | 320 | 412 | vc | MMAD |
| 137 | 320 | 412 | PEG2-vc | MMAD |
| 138 | 320 | 412 | vc | MMAE |
| 139 | 320 | 412 | vc | duocarmycin |
| 140 | 320 | 412 | spdb | DM4 |
| 141 | 10 | 341 | vc | MMAD |
| 142 | 10 | 341 | PEG2-vc | MMAD |
| 143 | 10 | 341 | vc | MMAE |
| 144 | 10 | 341 | vc | duocarmycin |
| 145 | 10 | 341 | spdb | DM4 |
| 146 | 10 | 413 | vc | MMAD |
| 147 | 10 | 413 | PEG2-vc | MMAD |
| 148 | 10 | 413 | vc | MMAE |
| 149 | 10 | 413 | vc | duocarmycin |
| 150 | 10 | 413 | spdb | DM4 |
| 151 | 320 | 342 | vc | MMAD |
| 152 | 320 | 342 | PEG2-vc | MMAD |
| 153 | 320 | 342 | vc | MMAE |
| 154 | 320 | 342 | vc | duocarmycin |
| 155 | 320 | 342 | spdb | DM4 |
| 156 | 320 | 414 | vc | MMAD |
| 157 | 320 | 414 | PEG2-vc | MMAD |
| 158 | 320 | 414 | vc | MMAE |
| 159 | 320 | 414 | vc | duocarmycin |
| 160 | 320 | 414 | spdb | DM4 |
| 161 | 10 | 343 | vc | MMAD |
| 162 | 10 | 343 | PEG2-vc | MMAD |
| 163 | 10 | 343 | vc | MMAE |
| 164 | 10 | 343 | vc | duocarmycin |
| 165 | 10 | 343 | spdb | DM4 |
| 166 | 10 | 415 | vc | MMAD |
| 167 | 10 | 415 | PEG2-vc | MMAD |
| 168 | 10 | 415 | vc | MMAE |
| 169 | 10 | 415 | vc | duocarmycin |
| 170 | 10 | 415 | spdb | DM4 |
| 171 | 320 | 344 | vc | MMAD |
| 172 | 320 | 344 | PEG2-vc | MMAD |
| 173 | 320 | 344 | vc | MMAE |
| 174 | 320 | 344 | vc | duocarmycin |
| 175 | 320 | 344 | spdb | DM4 |
| 176 | 320 | 416 | vc | MMAD |
| 177 | 320 | 416 | PEG2-vc | MMAD |
| 178 | 320 | 416 | vc | MMAE |
| 179 | 320 | 416 | vc | duocarmycin |
| 180 | 320 | 416 | spdb | DM4 |
| 181 | 10 | 345 | vc | MMAD |
| 182 | 10 | 345 | PEG2-vc | MMAD |
| 183 | 10 | 345 | vc | MMAE |
| 184 | 10 | 345 | vc | duocarmycin |
| 185 | 10 | 345 | spdb | DM4 |
| 186 | 10 | 417 | vc | MMAD |
| 187 | 10 | 417 | PEG2-vc | MMAD |
| 188 | 10 | 417 | vc | MMAE |
| 189 | 10 | 417 | vc | duocarmycin |
| 190 | 10 | 417 | spdb | DM4 |
| 191 | 320 | 346 | vc | MMAD |
| 192 | 320 | 346 | PEG2-vc | MMAD |
| 193 | 320 | 346 | vc | MMAE |
| 194 | 320 | 346 | vc | duocarmycin |
| 195 | 320 | 346 | spdb | DM4 |
| 196 | 320 | 418 | vc | MMAD |
| 197 | 320 | 418 | PEG2-vc | MMAD |
| 198 | 320 | 418 | vc | MMAE |
| 199 | 320 | 418 | vc | duocarmycin |
| 200 | 320 | 418 | spdb | DM4 |
| 201 | 10 | 347 | vc | MMAD |
| 202 | 10 | 347 | PEG2-vc | MMAD |
| 203 | 10 | 347 | vc | MMAE |
| 204 | 10 | 347 | vc | duocarmycin |
| 205 | 10 | 347 | spdb | DM4 |
| 206 | 10 | 419 | vc | MMAD |
| 207 | 10 | 419 | PEG2-vc | MMAD |
| 208 | 10 | 419 | vc | MMAE |
| 209 | 10 | 419 | vc | duocarmycin |
| 210 | 10 | 419 | spdb | DM4 |
| 211 | 320 | 348 | vc | MMAD |
| 212 | 320 | 348 | PEG2-vc | MMAD |
| 213 | 320 | 348 | vc | MMAE |
| 214 | 320 | 348 | vc | duocarmycin |
| 215 | 320 | 348 | spdb | DM4 |
| 216 | 320 | 420 | vc | MMAD |
| 217 | 320 | 420 | PEG2-vc | MMAD |
| 218 | 320 | 420 | vc | MMAE |
| 219 | 320 | 420 | vc | duocarmycin |

TABLE F-continued

Anti-ITGa3 ADC and Anti-ITGa3 Activatable ADC Combinations

| Comb. No. | Heavy Chain (HC) or HC Variable Region SEQ ID NO. | Light Chain (LC) or LC Variable Region SEQ ID NO. | Linker | Toxin |
|---|---|---|---|---|
| 220 | 320 | 420 | spdb | DM4 |
| 221 | 10 | 349 | vc | MMAD |
| 222 | 10 | 349 | PEG2-vc | MMAD |
| 223 | 10 | 349 | vc | MMAE |
| 224 | 10 | 349 | vc | duocarmycin |
| 225 | 10 | 349 | spdb | DM4 |
| 226 | 10 | 421 | vc | MMAD |
| 227 | 10 | 421 | PEG2-vc | MMAD |
| 228 | 10 | 421 | vc | MMAE |
| 229 | 10 | 421 | vc | duocarmycin |
| 230 | 10 | 421 | spdb | DM4 |
| 231 | 320 | 350 | vc | MMAD |
| 232 | 320 | 350 | PEG2-vc | MMAD |
| 233 | 320 | 350 | vc | MMAE |
| 234 | 320 | 350 | vc | duocarmycin |
| 235 | 320 | 350 | spdb | DM4 |
| 236 | 320 | 422 | vc | MMAD |
| 237 | 320 | 422 | PEG2-vc | MMAD |
| 238 | 320 | 422 | vc | MMAE |
| 239 | 320 | 422 | vc | duocarmycin |
| 240 | 320 | 422 | spdb | DM4 |
| 241 | 10 | 351 | vc | MMAD |
| 242 | 10 | 351 | PEG2-vc | MMAD |
| 243 | 10 | 351 | vc | MMAE |
| 244 | 10 | 351 | vc | duocarmycin |
| 245 | 10 | 351 | spdb | DM4 |
| 246 | 10 | 423 | vc | MMAD |
| 247 | 10 | 423 | PEG2-vc | MMAD |
| 248 | 10 | 423 | vc | MMAE |
| 249 | 10 | 423 | vc | duocarmycin |
| 250 | 10 | 423 | spdb | DM4 |
| 251 | 320 | 352 | vc | MMAD |
| 252 | 320 | 352 | PEG2-vc | MMAD |
| 253 | 320 | 352 | vc | MMAE |
| 254 | 320 | 352 | vc | duocarmycin |
| 255 | 320 | 352 | spdb | DM4 |
| 256 | 320 | 424 | vc | MMAD |
| 257 | 320 | 424 | PEG2-vc | MMAD |
| 258 | 320 | 424 | vc | MMAE |
| 259 | 320 | 424 | vc | duocarmycin |
| 260 | 320 | 424 | spdb | DM4 |
| 261 | 10 | 353 | vc | MMAD |
| 262 | 10 | 353 | PEG2-vc | MMAD |
| 263 | 10 | 353 | vc | MMAE |
| 264 | 10 | 353 | vc | duocarmycin |
| 265 | 10 | 353 | spdb | DM4 |
| 266 | 10 | 425 | vc | MMAD |
| 267 | 10 | 425 | PEG2-vc | MMAD |
| 268 | 10 | 425 | vc | MMAE |
| 269 | 10 | 425 | vc | duocarmycin |
| 270 | 10 | 425 | spdb | DM4 |
| 271 | 320 | 354 | vc | MMAD |
| 272 | 320 | 354 | PEG2-vc | MMAD |
| 273 | 320 | 354 | vc | MMAE |
| 274 | 320 | 354 | vc | duocarmycin |
| 275 | 320 | 354 | spdb | DM4 |
| 276 | 320 | 426 | vc | MMAD |
| 277 | 320 | 426 | PEG2-vc | MMAD |
| 278 | 320 | 426 | vc | MMAE |
| 279 | 320 | 426 | vc | duocarmycin |
| 280 | 320 | 426 | spdb | DM4 |
| 281 | 10 | 355 | vc | MMAD |
| 282 | 10 | 355 | PEG2-vc | MMAD |
| 283 | 10 | 355 | vc | MMAE |
| 284 | 10 | 355 | vc | duocarmycin |
| 285 | 10 | 355 | spdb | DM4 |
| 286 | 10 | 427 | vc | MMAD |
| 287 | 10 | 427 | PEG2-vc | MMAD |
| 288 | 10 | 427 | vc | MMAE |
| 289 | 10 | 427 | vc | duocarmycin |
| 290 | 10 | 427 | spdb | DM4 |
| 291 | 320 | 356 | vc | MMAD |
| 292 | 320 | 356 | PEG2-vc | MMAD |
| 293 | 320 | 356 | vc | MMAE |
| 294 | 320 | 356 | vc | duocarmycin |
| 295 | 320 | 356 | spdb | DM4 |
| 296 | 320 | 428 | vc | MMAD |
| 297 | 320 | 428 | PEG2-vc | MMAD |
| 298 | 320 | 428 | vc | MMAE |
| 299 | 320 | 428 | vc | duocarmycin |
| 300 | 320 | 428 | spdb | DM4 |
| 301 | 10 | 357 | vc | MMAD |
| 302 | 10 | 357 | PEG2-vc | MMAD |
| 303 | 10 | 357 | vc | MMAE |
| 304 | 10 | 357 | vc | duocarmycin |
| 305 | 10 | 357 | spdb | DM4 |
| 306 | 10 | 429 | vc | MMAD |
| 307 | 10 | 429 | PEG2-vc | MMAD |
| 308 | 10 | 429 | vc | MMAE |
| 309 | 10 | 429 | vc | duocarmycin |
| 310 | 10 | 429 | spdb | DM4 |
| 311 | 320 | 358 | vc | MMAD |
| 312 | 320 | 358 | PEG2-vc | MMAD |
| 313 | 320 | 358 | vc | MMAE |
| 314 | 320 | 358 | vc | duocarmycin |
| 315 | 320 | 358 | spdb | DM4 |
| 316 | 320 | 430 | vc | MMAD |
| 317 | 320 | 430 | PEG2-vc | MMAD |
| 318 | 320 | 430 | vc | MMAE |
| 319 | 320 | 430 | vc | duocarmycin |
| 320 | 320 | 430 | spdb | DM4 |
| 321 | 10 | 359 | vc | MMAD |
| 322 | 10 | 359 | PEG2-vc | MMAD |
| 323 | 10 | 359 | vc | MMAE |
| 324 | 10 | 359 | vc | duocarmycin |
| 325 | 10 | 359 | spdb | DM4 |
| 326 | 10 | 431 | vc | MMAD |
| 327 | 10 | 431 | PEG2-vc | MMAD |
| 328 | 10 | 431 | vc | MMAE |
| 329 | 10 | 431 | vc | duocarmycin |
| 330 | 10 | 431 | spdb | DM4 |

An antibody drug conjugate (ADC) of the present disclosure or activatable antibody drug conjugate (AADC) of the present disclosure may include one or more polypeptides that include the combination of amino acid sequences, a linker, and a toxin listed in a given row of Table F. Therefore, an activatable antibody drug conjugate (ADC) of the present disclosure or activatable antibody drug conjugate (AADC) of the present disclosure that includes the combination of amino acid sequences, a linker, and a toxin listed in a given row or provided as a specific combination is described herein. For example, an activatable antibody drug conjugate of the present disclosure may include the amino acid sequences of combination no. 55, which includes a heavy chain comprising the amino acid sequence of SEQ ID NO: 320, a light chain comprising the amino acid sequence of SEQ ID NO: 332, and a spdb-DM4 linker-toxin. In another example of the AADCs disclosed and described herein, an activatable antibody drug conjugate of the present disclosure may include the amino acid sequences of combination no. 33, which includes a heavy chain comprising the amino acid sequence of SEQ ID NO: 320, a light chain comprising the amino acid sequence of SEQ ID NO: 328, and a vc-MMAE linker-toxin.

Any of the combinations in Table F that list a heavy chain and light chain variable region can be combined with human immunoglobulin constant regions to result in fully human IgGs including IgG1, IgG2, IgG4 or mutated constant regions to result in human IgGs with altered functions such as IgG1 N297A, IgG1 N297Q, or IgG4 S228P. The combinations described in Table F are not limited by the particular combinations shown in any given row, and thus can include any heavy chain sequence or heavy chain variable region sequence from column 2 of Table F combined with any light chain sequence or light chain variable region sequence from column 3 of Table F combined with any linker from column 4 combined with any toxin from column 5. In addition to the heavy chain sequences or heavy chain variable region sequences listed in column 2, any heavy chain sequence or heavy chain variable region sequence disclosed herein can be used in a combination. In addition to the light chain sequences or light chain variable region sequences listed in column 3, any light chain sequence or light chain variable region sequence disclosed herein can be used in a combination. In addition to the linkers listed in column 4, any linker disclosed herein can be used in a combination. In addition to the toxins listed in column 5, any toxin disclosed herein can be used in a combination.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable anti-ITGa3 antibody and/or conjugated activatable anti-ITGa3 antibody is monospecific. In some embodiments, the activatable anti-ITGa3 antibody and/or conjugated activatable anti-ITGa3 antibody is multispecific, e.g., by way of non-limiting example, bispecific or trifunctional. In some embodiments, the activatable anti-ITGa3 antibody and/or conjugated activatable anti-ITGa3 antibody is formulated as part of a pro-Bispecific T Cell Engager (BITE) molecule. In some embodiments, the activatable anti-ITGa3 antibody and/or conjugated activatable anti-ITGa3 antibody is formulated as part of a pro-Chimeric Antigen Receptor (CAR) modified T cell or other engineered receptor.

In some embodiments, the activatable antibody or antigen-binding fragment thereof is incorporated in a multispecific activatable antibody or antigen-binding fragment thereof, where at least one arm of the multispecific activatable antibody specifically binds ITGa3. In some embodiments, the activatable antibody or antigen-binding fragment thereof is incorporated in a bispecific antibody or antigen-binding fragment thereof, where at least one arm of the bispecific activatable antibody specifically binds ITGa3.

In some embodiments, the anti-ITGa3 antibodies, conjugated anti-ITGa3 antibodies, activatable anti-ITGa3 antibodies and/or conjugated activatable anti-ITGa3 antibodies described herein are used in conjunction with one or more additional agents or a combination of additional agents. Suitable additional agents include current pharmaceutical and/or surgical therapies for an intended application, such as, for example, cancer. For example, the anti-ITGa3 antibodies, conjugated anti-ITGa3 antibodies, activatable anti-ITGa3 antibodies and/or conjugated activatable anti-ITGa3 antibodies can be used in conjunction with an additional chemotherapeutic or anti-neoplastic agent.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, ITGa3, TIGIT, TIM-3, B7H4, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In some embodiments, the agonist is selected from the group consisting of Ox40, GITR, CD137, ICOS, CD27, and HVEM.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a ITGa3 inhibitor. In some embodiments, the inhibitor is a TIGIT inhibitor. In some embodiments, the inhibitor is a TIM-3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is Ox40. In some embodiments, the agonist is GITR. In some embodiments, the agonist is CD137. In some embodiments, the agonist is ICOS. In some embodiments, the agonist is CD27. In some embodiments, the agonist is HVEM.

In some embodiments, the anti-ITGa3 antibody, conjugated antibody, activatable antibody and/or conjugated activatable antibody is administered during and/or after treatment in combination with one or more additional agents such as, for example, a chemotherapeutic agent, an anti-inflammatory agent, and/or a an immunosuppressive agent. In some embodiments, the anti-ITGa3 antibody, conjugated anti-ITGa3 antibody, activatable anti-ITGa3 antibody and/or conjugated activatable anti-ITGa3 antibody and the additional agent are formulated into a single therapeutic composition, and the anti-ITGa3 antibody, conjugated anti-ITGa3 antibody, activatable anti-ITGa3 antibody and/or conjugated activatable anti-ITGa3 antibody and additional agent are administered simultaneously. Alternatively, the anti-ITGa3 antibody, conjugated anti-ITGa3 antibody, activatable anti-ITGa3 antibody and/or conjugated activatable anti-ITGa3 antibody and additional agent are separate from each other, e.g., each is formulated into a separate therapeutic composition, and the anti-ITGa3 antibody, conjugated anti-ITGa3 antibody, activatable anti-ITGa3 antibody and/or conjugated activatable anti-ITGa3 antibody and the additional agent are administered simultaneously, or the anti-ITGa3 antibody, conjugated anti-ITGa3 antibody, activatable anti-ITGa3 antibody and/or conjugated activatable anti-ITGa3 antibody and the additional agent are administered at different times during a treatment regimen. For example, the anti-ITGa3 antibody, conjugated anti-ITGa3 antibody, activatable anti-ITGa3 antibody and/or conjugated activatable anti-ITGa3 antibody is administered prior to the administration of the additional agent, the anti-ITGa3 antibody, conjugated anti-ITGa3 antibody, activatable anti-ITGa3 antibody and/or conjugated activatable anti-ITGa3 antibody is administered subsequent to the administration of the additional agent, or the anti-ITGa3 antibody, conjugated anti-ITGa3 antibody, activatable anti-ITGa3 antibody and/or conjugated activatable anti-ITGa3 antibody and the additional agent are administered in an alternating fashion. As described herein, the anti-ITGa3 antibody, conjugated anti-ITGa3 antibody, activatable anti-ITGa3 antibody and/or conjugated activatable anti-ITGa3 antibody and additional agent are administered in single doses or in multiple doses.

In some embodiments, the anti-ITGa3 antibody, conjugated anti-ITGa3 antibody, activatable anti-ITGa3 antibody and/or conjugated activatable anti-ITGa3 antibody and the additional agent(s) are administered simultaneously. For example, the anti-ITGa3 antibody, conjugated anti-ITGa3 antibody, activatable anti-ITGa3 antibody and/or conjugated activatable anti-ITGa3 antibody and the additional agent(s) can be formulated in a single composition or administered as two or more separate compositions. In some embodiments, the anti-ITGa3 antibody, conjugated anti-ITGa3 antibody, activatable anti-ITGa3 antibody and/or conjugated activatable anti-ITGa3 antibody and the additional agent(s) are administered sequentially, or the anti-ITGa3 antibody, conjugated anti-ITGa3 antibody, activatable anti-ITGa3 antibody and/or conjugated activatable anti-ITGa3 antibody and the additional agent are administered at different times during a treatment regimen.

In some embodiments, the anti-ITGa3 antibody, conjugated anti-ITGa3 antibody, activatable anti-ITGa3 antibody and/or conjugated activatable anti-ITGa3 antibody is administered during and/or after treatment in combination with one or more additional agents such as, by way of non-limiting example, a chemotherapeutic agent, an anti-inflammatory agent, and/or an immunosuppressive agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof. In some embodiments the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof against the same target as the first antibody or antigen-binding fragment thereof, the first conjugated antibody or antigen-binding fragment thereof, activatable antibody or antigen-binding fragment thereof and/or a conjugated activatable antibody or antigen-binding fragment thereof, e.g., against ITGa3. In some embodiments the additional agent is another antibody or antigen-binding fragment thereof, another conjugated antibody or antigen-binding fragment thereof, another activatable antibody or antigen-binding fragment thereof and/or another conjugated activatable antibody or antigen-binding fragment thereof against a target different than the target of the first antibody or antigen-binding fragment thereof, the first conjugated antibody or antigen-binding fragment thereof, activatable antibody or antigen-binding fragment thereof and/or a conjugated activatable antibody or antigen-binding fragment thereof.

As a non-limiting example, the antibody or antigen-binding fragment and/or the AB of an activatable antibody is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | ITGa3 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD 125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta1 | Notch 2 | TNFRS12A |
| CD2 | ITGa3 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidylserine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the antibody or antigen-binding fragment and/or the AB of an activatable antibody is or is derived from an antibody listed in Table 2.

TABLE 2

Exemplary sources for Abs

| Antibody Trade Name (antibody name) | Target |
| --- | --- |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Gazyva ™ (Obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

In some embodiments, the additional antibody or antigen binding fragment thereof, conjugated antibody or antigen binding fragment thereof, activatable antibody or antigen binding fragment thereof, and/or conjugated activatable antibody or antigen binding fragment thereof is a monoclonal antibody, domain antibody, single chain, Fab fragment, a F(ab')$_2$ fragment, a scFv, a scAb, a dAb, a single domain heavy chain antibody, or a single domain light chain antibody. In some embodiments, the additional antibody or antigen binding fragment thereof, conjugated antibody or antigen binding fragment thereof, activatable antibody or antigen binding fragment thereof, and/or conjugated activatable antibody or antigen binding fragment thereof is a mouse, other rodent, chimeric, humanized or fully human monoclonal antibody.

The disclosure also provides methods of producing an anti-ITGa3 antibody and/or activatable anti-ITGa3 antibody polypeptide by culturing a cell under conditions that lead to expression of the polypeptide, wherein the cell comprises an isolated nucleic acid molecule encoding an antibody and/or an activatable antibody described herein, and/or vectors that include these isolated nucleic acid sequences. The disclosure provides methods of producing an antibody and/or activatable antibody by culturing a cell under conditions that lead to expression of the antibody and/or activatable antibody, wherein the cell comprises an isolated nucleic acid molecule encoding an antibody and/or an activatable antibody described herein, and/or vectors that include these isolated nucleic acid sequences.

The invention also provides a method of manufacturing activatable antibodies that in an activated state binds ITGa3 by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds ITGa3, (i) wherein the CM is a polypeptide that functions as a substrate for a protease; and (ii) wherein the CM is positioned in the activatable antibody such that, when the activatable antibody is in an uncleaved state, the MM interferes with specific binding of the AB to ITGa3 and in a cleaved state the MM does not interfere or compete with specific binding of the AB to ITGa3; and (b) recovering the activatable antibody. Suitable AB, MM, and/or CM include any of the AB, MM, and/or CM disclosed herein.

In some embodiments, the activatable antibody in the uncleaved state has the structural arrangement from N-terminus to C-terminus as follows: MM-CM-AB or AB-CM-MM. In some embodiments, the activatable antibody comprises a linking peptide between the MM and the CM. In some embodiments, the activatable antibody comprises a linking peptide between the CM and the AB. In some embodiments, the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM. In some embodiments, the two linking peptides need not be identical to each other. In some embodiments, the activatable antibody in the uncleaved state has the structural arrangement from N-terminus to C-terminus as follows: spacer-MM-LP1-CM-LP2-AB or AB-LP2-CM-LP1-MM-spacer.

In some embodiments, at least one of LP1 or LP2 comprises an amino acid sequence selected from the group consisting of (GS)$_n$, (GGS)$_n$, (GSGGS)$_n$ (SEQ ID NO: 165) and (GGGS)$_n$ (SEQ ID NO: 166), where n is an integer of at least one.

In some embodiments, at least one of LP1 or LP2 comprises an amino acid sequence selected from the group consisting of GGSG (SEQ ID NO: 167), GGSGG (SEQ ID NO: 168), GSGSG (SEQ ID NO: 169), GSGGG (SEQ ID NO: 170), GGGSG (SEQ ID NO: 171), and GSSSG (SEQ ID NO: 172).

In some embodiments, LP1 comprises the amino acid sequence GSSGGSGGSGGSG (SEQ ID NO: 173), GSSGGSGGSGG (SEQ ID NO: 174), GSSGGSGGSGGS (SEQ ID NO: 175), GSSGGSGGSGGSGGGS (SEQ ID NO: 176), GSSGGSGGSG (SEQ ID NO: 177), or GSSGGSGGSGS (SEQ ID NO: 178).

In some embodiments, LP2 comprises the amino acid sequence GSS, GGS, GGGS (SEQ ID NO: 179), GSSGT (SEQ ID NO: 180) or GSSG (SEQ ID NO: 181).

The invention provides methods of preventing, delaying the progression of, treating, alleviating a symptom of, or otherwise ameliorating an ITGa3 mediated disease in a subject by administering a therapeutically effective amount of an anti-ITGa3 antibody, conjugated anti-ITGa3 antibody, activatable anti-ITGa3 antibody and/or conjugated activatable anti-ITGa3 antibody described herein to a subject in need thereof.

The invention also provides methods of preventing, delaying the progression of, treating, alleviating a symptom of, or otherwise ameliorating cancer in a subject by administering a therapeutically effective amount of an anti-ITGa3 antibody, conjugated anti-ITGa3 antibody, activatable anti-ITGa3 antibody and/or conjugated activatable anti-ITGa3 antibody described herein to a subject in need thereof. ITGa3 is known to be expressed in a variety of cancers, such as, by way of non-limiting example, any epithelial or squamous cell cancer, any carcinoid, and/or a neuroendocrine cancer. Examples of cancers include, but are not limited to, adenocarcinoma, bile duct (biliary) cancer, bladder cancer, breast cancer, e.g., triple-negative breast cancer, Her2-negative breast cancer, estrogen receptor-positive breast cancer; carcinoid cancer; cervical cancer; cholangiocarcinoma; colorectal; endometrial; glioma; head and neck cancer, e.g., head and neck squamous cell cancer; leukemia; liver cancer; lung cancer, e.g., NSCLC, SCLC; lymphoma; melanoma; osopharyngeal cancer; ovarian cancer; pancreatic cancer; prostate cancer, e.g., metastatic castration-resistant prostate carcinoma; renal cancer; skin cancer; squamous cell cancer; stomach cancer; testis cancer; thyroid cancer; and urothelial cancer.

In some embodiments, the cancer is any epithelial or squamous cancer. In some embodiments, the cancer is prostate cancer, breast cancer, lung cancer, cervical cancer, oropharyngeal cancer, and/or head and neck cancer.

In some embodiments, the cancer is a bladder cancer, a bone cancer, a breast cancer, a carcinoid, a cervical cancer, a colorectal cancer, a colon cancer, an endometrial cancer, an epithelial cancer, a glioma, a head and neck cancer, a liver cancer, a lung cancer, a melanoma, an oropharyngeal cancer, an ovarian cancer, a pancreatic cancer, a prostate cancer, a renal cancer, a sarcoma, a skin cancer, a stomach cancer, a testis cancer, a thyroid cancer, a urogenital cancer, and/or a urothelial cancer.

In some embodiments, the cancer is selected from the group consisting of triple negative breast cancer (TNBC), non-small cell lung cancer (NSCLC), small cell lung cancer (SCLC), Ras mutant colorectal carcinoma, a rare epithelial cancer, oropharyngeal cancer, cervical cancer, head and neck squamous cell carcinoma (HNSCC), and/or prostate cancer. In some embodiments, the cancer is associated with a CD166-expressing tumor.

In some embodiments, the cancer is associated with a ITGa3-expressing tumor. In some embodiments, the cancer is due to a ITGa3-expressing tumor.

An anti-ITGa3 antibody, a conjugated anti-ITGa3 antibody, an activatable anti-ITGa3 antibody and/or a conjugated activatable anti-ITGa3 antibody used in any of the embodiments of these methods and uses can be administered at any stage of the disease. For example, such an anti-ITGa3 antibody, conjugated anti-ITGa3 antibody, activatable anti-ITGa3 antibody and/or conjugated activatable anti-ITGa3 antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian.

The anti-ITGa3 antibody, conjugated anti-ITGa3 antibody, activatable anti-ITGa3 antibody and/or conjugated activatable anti-ITGa3 antibody and therapeutic formulations thereof are administered to a subject suffering from or susceptible to a disease or disorder associated with aberrant ITGa3 expression and/or activity. A subject suffering from or susceptible to a disease or disorder associated with aberrant ITGa3 expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of an anti-ITGa3 antibody, conjugated anti-ITGa3 antibody, activatable anti-ITGa3 antibody and/or conjugated activatable anti-ITGa3 antibody to a patient suffering from a disease or disorder associated with aberrant ITGa3 expression and/or activity is considered successful if any of a variety of laboratory or clinical objectives is achieved. For example, administration of an anti-ITGa3 antibody, conjugated anti-ITGa3 antibody, activatable anti-ITGa3 antibody and/or conjugated activatable anti-ITGa3 antibody to a patient suffering from a disease or disorder associated with aberrant ITGa3 expression and/or activity is considered successful if one or more of the symptoms associated with the disease or disorder is alleviated, reduced, inhibited or does not progress to a further, i.e., worse, state. Administration of an anti-ITGa3 antibody, conjugated anti-ITGa3 antibody, activatable anti-ITGa3 antibody and/or conjugated activatable anti-ITGa3 antibody to a patient suffering from a disease or disorder associated with aberrant ITGa3 expression and/or activity is considered successful if the disease or disorder enters remission or does not progress to a further, i.e., worse, state.

In some embodiments, the anti-ITGa3 antibody, conjugated anti-ITGa3 antibody, activatable anti-ITGa3 antibody and/or conjugated activatable anti-ITGa3 antibody and therapeutic formulations thereof are administered to a subject suffering from or susceptible to a disease or disorder, such as subjects suffering from cancer or other neoplastic condition, wherein the subject's diseased cells are expressing ITGa3. In some embodiments, the diseased cells are associated with aberrant ITGa3 expression and/or activity. In some embodiments, the diseased cells are associated with normal ITGa3 expression and/or activity. A subject suffering from or susceptible to a disease or disorder wherein the subject's diseased cells express ITGa3 is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

In some embodiments, the anti-ITGa3 antibody, conjugated anti-ITGa3 antibody, activatable anti-ITGa3 antibody and/or conjugated activatable anti-ITGa3 antibody and therapeutic formulations thereof are administered to a subject suffering from or susceptible to a disease or disorder associated with cells expressing ITGa3 or the presence, growth, proliferation, metastasis, and/or activity of such cells, such as subjects suffering from cancer or other neoplastic conditions. In some embodiments, the cells are associated with aberrant ITGa3 expression and/or activity. In some embodiments, the cells are associated with normal ITGa3 expression and/or activity. A subject suffering from or susceptible to a disease or disorder associated with cells that express ITGa3 is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of an anti-ITGa3 antibody, conjugated anti-ITGa3 antibody, activatable anti-ITGa3 antibody and/or conjugated activatable anti-ITGa3 antibody to a patient suffering from a disease or disorder associated with cells expressing ITGa3 is considered successful if any of a variety of laboratory or clinical objectives is achieved. For example, administration of an anti-ITGa3 antibody, conjugated anti-ITGa3 antibody, activatable anti-ITGa3 antibody and/or conjugated activatable anti-ITGa3 antibody to a patient suffering from a disease or disorder associated with cells expressing ITGa3 is considered successful if one or more of the symptoms associated with the disease or disorder is alleviated, reduced, inhibited or does not progress to a further, i.e., worse, state. Administration of an anti-ITGa3 antibody, conjugated anti-ITGa3 antibody, activatable anti-ITGa3 antibody and/or conjugated activatable anti-ITGa3 antibody to a patient suffering from a disease or disorder associated with cells expressing ITGa3 is considered successful if the disease or disorder enters remission or does not progress to a further, i.e., worse, state.

In some embodiments, the anti-ITGa3 antibody, conjugated anti-ITGa3 antibody, activatable anti-ITGa3 antibody and/or conjugated activatable anti-ITGa3 antibody is administered during and/or after treatment in combination with one or more additional agents such as, for example, a chemotherapeutic agent, an anti-inflammatory agent, and/or an immunosuppressive agent. In some embodiments, the anti-ITGa3 antibody, conjugated anti-ITGa3 antibody, activatable anti-ITGa3 antibody and/or conjugated activatable anti-ITGa3 antibody and the additional agent(s) are administered simultaneously. For example, the anti-ITGa3 antibody, conjugated anti-ITGa3 antibody, activatable anti-ITGa3 antibody and/or conjugated activatable anti-ITGa3 antibody and the additional agent(s) can be formulated in a single composition or administered as two or more separate compositions. In some embodiments, the anti-ITGa3 antibody, conjugated anti-ITGa3 antibody, activatable anti-ITGa3 antibody and/or conjugated activatable anti-ITGa3 antibody and the additional agent(s) are administered sequentially.

The invention also provides methods and kits for using the activatable anti-ITGa3 antibodies and/or conjugated activatable anti-ITGa3 antibodies in a variety of diagnostic and/or prophylactic indications. For example, the invention provides methods and kits for detecting the presence or absence of a cleaving agent and a target of interest in a subject or a sample by (i) contacting a subject or sample with an anti-ITGa3 activatable antibody, wherein the anti-ITGa3 activatable antibody comprises a masking moiety (MM), a cleavable moiety (CM) that is cleaved by the cleaving agent, and an antigen binding domain or fragment thereof (AB) that specifically binds the target of interest, wherein the anti-ITGa3 activatable antibody in an uncleaved, non-activated state comprises a structural arrangement from N-terminus to C-terminus as follows: MM-CM-AB or AB-CM-MM; (a) wherein the MM is a peptide that inhibits binding of the AB to ITGa3, and wherein the MM does not have an amino acid sequence of a naturally occurring binding partner of the AB and is not a modified form of a natural binding partner of the AB; and (b) wherein, when the AB is in an uncleaved, non-activated state, the MM interferes with specific binding of the AB to ITGa3, and when the AB is in a cleaved, activated state the MM does not interfere or compete with specific binding of the AB to ITGa3; and (ii) measuring a level of activated anti-ITGa3 activatable antibody in the subject or sample, wherein a detectable level of activated anti-ITGa3 activatable antibody in the subject or sample indicates that the cleaving agent and ITGa3 are present in the subject or sample and wherein no detectable level of activated anti-ITGa3 activatable antibody in the subject or sample indicates that the cleaving agent, ITGa3 or both the cleaving agent and ITGa3 are absent in the subject or sample.

In some embodiments, the activatable anti-ITGa3 antibody is an activatable anti-ITGa3 antibody to which a therapeutic agent is conjugated. In some embodiments, the activatable anti-ITGa3 antibody is not conjugated to an agent. In some embodiments, the activatable anti-ITGa3 antibody comprises a detectable label. In some embodiments, the detectable label is positioned on the AB. In some embodiments, measuring the level of activatable anti-ITGa3 antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods and kits, the activatable anti-ITGa3 antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods and kits, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method is used to identify or otherwise refine a patient population suitable for treatment with an anti-ITGa3 activatable antibody of the disclosure, followed by treatment by administering that activatable anti-ITGa3 antibody and/or conjugated activatable anti-ITGa3 antibody to a subject in need thereof. For example, patients that test positive for both the target (e.g., ITGa3) and a protease that cleaves the substrate in the cleavable moiety (CM) of the anti-ITGa3 activatable antibody being tested in these methods are identified as suitable candidates for treatment with such an anti-ITGa3 activatable antibody comprising such a CM, and the patient is then administered a therapeutically effective amount of the activatable anti-ITGa3 antibody and/or conjugated activatable anti-ITGa3 antibody that was tested. Likewise, patients that test negative for either or both of the target (e.g., ITGa3) and the protease that cleaves the substrate in the CM in the activatable antibody being tested using these methods might be identified as suitable candidates for another form of therapy. In some embodiments, such patients can be tested with other anti-ITGa3 activatable antibodies until a suitable anti-ITGa3 activatable antibody for treatment is identified (e.g., an anti-ITGa3 activatable antibody comprising a CM that is cleaved by the patient at the site of disease). In some embodiments, the patient is then administered a therapeutically effective amount of the activatable anti-ITGa3 antibody and/or conjugated for which the patient tested positive. Suitable AB, MM, and/or CM include any of the AB, MM, and/or CM disclosed herein.

Pharmaceutical compositions according to the invention can include an antibody of the invention and a carrier. These pharmaceutical compositions can be included in kits, such as, for example, diagnostic kits.

BRIEF DESCRIPTION OF THE DRAWINGS

FIGS. 15A to 15D depict exemplary studies of the ability of various anti-ITGa3 activatable antibodies of the present disclosure to bind human ITGa3 on various human-derived cell lines.

FIGS. 16A to 16D depict exemplary studies of the cytotoxicity of anti-CD71 antibody drug conjugates of the present disclosure on various cell lines.

FIGS. 17A and 17B depict exemplary studies of the ability of various anti-ITGa3 activatable antibodies of the present disclosure to bind human ITGa3 on various human-derived cell lines.

DETAILED DESCRIPTION OF THE INVENTION

Figure 1:
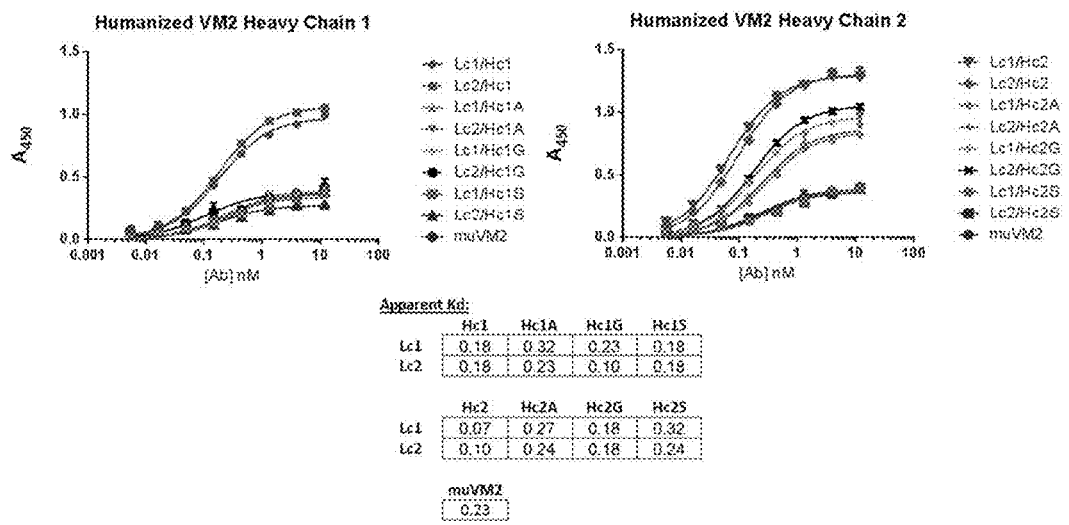
FIG. 1 is a graph depicting the ability of various anti-ITGa3 antibodies of the disclosure to bind human ITGa3.

The present invention provides monoclonal antibodies (mAbs) and activatable monoclonal antibodies that specifically bind Integrin Alpha 3 (ITGa3), also known as traCD49C; GAP-B3; GAPB3; ILNEB; MSK18; VCA-2; VL3A; VLA3a. The use of the term "ITGa3" is intended to cover any variation thereof, such as, by way of non-limiting example, ITGa-3, ITGa3, ITGA-3, ITG a3, ITG-a3, ITG A3, ITGA3, ITG-A3, ITGα3, ITG-α3, ITG α3, and all variations are used herein interchangeably. In some embodiments, the monoclonal antibodies and activatable monoclonal antibodies are internalized by ITGa3-containing cells.

ITGa3 is a member of the integrin family. Integrins are a family of cell surface adhesion molecules. Each integrin consists of a pair of non-covalently associated alpha and beta chains. The α3 subunit is associated with β1. α3/β1 is a laminin receptor involved in basement membrane integrity. Patients with an α3 gene mutation show compromised barrier functions in kidney, lung, and skin. In cancer, α3/β1 plays a role in invasion and metastasis ITGa3 is highly expressed and highly prevalent in specific cancer types, such as, for example, pancreatic cancer, ovarian cancer, and bladder cancer. ITGa3 is also expressed in normal tissues. ITGa3 is believed to have potential oncogenic function, as ITGa3 knockout mice show reduced tumorigenesis. ITGa3 expression is retained metastatic disease.

Aberrant expression and/or activity of ITGa3 and ITGa3-related signaling has been implicated in the pathogenesis of many diseases and disorders, such as cancer. ITGa3 is overexpressed in many cancers.

The disclosure provides anti-ITGa3 antibodies, conjugated anti-ITGa3 antibodies, activatable anti-ITGa3 antibodies, and/or conjugated activatable anti-ITGa3 antibodies that are useful in methods of treating, preventing, delaying the progression of, ameliorating and/or alleviating a symptom of a disease or disorder associated with aberrant ITGa3 expression and/or activity. For example, the activatable anti-ITGa3 antibodies are used in methods of treating, preventing, delaying the progression of, ameliorating and/or alleviating a symptom of a cancer or other neoplastic condition.

The disclosure provides anti-ITGa3 antibodies, conjugated anti-ITGa3 antibodies, activatable anti-ITGa3 antibodies, and/or conjugated activatable anti-ITGa3 antibodies that are useful in methods of treating, preventing, delaying the progression of, ameliorating and/or alleviating a symptom of a disease or disorder associated with cells expressing ITGa3. In some embodiments, the cells are associated with aberrant ITGa3 expression and/or activity. In some embodiments, the cells are associated with normal ITGa3 expression and/or activity. For example, the activatable anti-ITGa3 antibodies are used in methods of treating, preventing, delaying the progression of, ameliorating and/or alleviating a symptom of a cancer or other neoplastic condition.

The disclosure provides anti-ITGa3 antibodies, conjugated anti-ITGa3 antibodies, activatable anti-ITGa3 antibodies, and/or conjugated activatable anti-ITGa3 antibodies that are useful in methods of treating, preventing, delaying the progression of, ameliorating and/or alleviating a symptom of a disease or disorder in which diseased cells express ITGa3. In some embodiments, the diseased cells are associated with aberrant ITGa3 expression and/or activity. In some embodiments, the diseased cells are associated with normal ITGa3 expression and/or activity. For example, the activatable anti-ITGa3 antibodies are used in methods of treating, preventing, delaying the progression of, ameliorating and/or alleviating a symptom of a cancer or other neoplastic condition.

The activatable anti-ITGa3 antibodies and/or conjugated activatable anti-ITGa3 antibodies include an antibody or antigen-binding fragment thereof that specifically binds ITGa3 coupled to a masking moiety (MM), such that coupling of the MM reduces the ability of the antibody or antigen-binding fragment thereof to bind ITGa3. In some embodiments, the MM is coupled via a sequence that includes a substrate for a protease, for example, a protease that is co-localized with ITGa3 at a treatment site in a subject.

Exemplary activatable anti-ITGa3 antibodies of the invention include, for example, activatable antibodies that include a heavy chain and a light chain that are, or are derived from, the heavy chain variable and light chain variable sequences shown below (CDR sequences, defined using Kabat et al. 1991. Sequences of Proteins of Immunological Interests, Fifth edition, NIH Publication No. 91-3242, U.S. Department of Health and Human Services, are shown in bold and underline):

```
mITGa3 Hc variable heavy chain:
                                                      (SEQ ID NO: 1)
EVQLQESGAELVKPGTSVRLSCKASGYTFTEYIIHWVKQRSGQGLEWIGWFYPESGSVEYNETFKGRATL

TADKSSSIVYMELSRLISEDSAVYFCARHEERDYYGYYAMDYWGQGTSVIVSS mITGa3 Lc variable light chain:
                                                      (SEQ ID NO: 2)
DIVMTQTPTTLAASPGEKIIITCSASSSISSNYLHWYQQKPGESPKLLIYRTSNLASGVPARFSGSGSGT

SYSLTIGTMEAEDVATYYCQQGSSIPRFTSGSGTKLEIK hvH1 variable heavy chain:
                                                      (SEQ ID NO: 3)
QVQLVQSGAEVKKPGSSVKVSCKASGYTFTEYIIHWVRQAPGQGLEWIGWFYPESGSVEYNETFKGRATL

TADKSTSTAYMELSSLRSEDTAVYYCARHEERDYYGYYAMDYWGQGTIVIVSS hvH1(N60S) variable heavy chain:
                                                      (SEQ ID NO: 4)
QVQLVQSGAEVKKPGSSVKVSCKASGYTFTEYIIHWVRQAPGQGLEWIGWFYPESGSVEYSETFKGRATL

TADKSTSTAYMELSSLRSEDTAVYYCARHEERDYYGYYAMDYWGQGTIVIVSS hvH1(I62A) variable heavy chain:
                                                      (SEQ ID NO: 5)
QVQLVQSGAEVKKPGSSVKVSCKASGYTFTEYIIHWVRQAPGQGLEWIGWFYPESGSVEYNEAFKGRATL

TADKSTSTAYMELSSLRSEDTAVYYCARHEERDYYGYYAMDYWGQGTIVIVSS hvH1(I62G) variable heavy chain:
                                                      (SEQ ID NO: 6)
QVQLVQSGAEVKKPGSSVKVSCKASGYTFTEYIIHWVRQAPGQGLEWIGWFYPESGSVEYNEGFKGRATL

TADKSTSTAYMELSSLRSEDTAVYYCARHEERDYYGYYAMDYWGQGTIVIVSS
```

-continued hvH2 variable heavy chain:
(SEQ ID NO: 7)
QVQLVQSGAEVKKPGSSVKVSCKASGYTFTEYIIHWVRQAPGQGLEWIGWFYPESGSVEYNETFKGRATI

TADKSTSTAYMELSSLRSEDTAVYYCARHEERDYYGYYAMDYWGQGTIVIVSS hvH2(N60S) variable heavy chain:
(SEQ ID NO: 8)
QVQLVQSGAEVKKPGSSVKVSCKASGYTFTEYIIHWVRQAPGQGLEWIGWFYPESGSVEYSETFKGRATI

TADKSTSTAYMELSSLRSEDTAVYYCARHEERDYYGYYAMDYWGQGTIVIVSS hvH2(I62A) variable heavy chain:
(SEQ ID NO: 9)
QVQLVQSGAEVKKPGSSVKVSCKASGYTFTEYIIHWVRQAPGQGLEWIGWFYPESGSVEYNEAFKGRATI

TADKSTSTAYMELSSLRSEDTAVYYCARHEERDYYGYYAMDYWGQGTIVIVSS hvH2(I62G) variable heavy chain:
(SEQ ID NO: 10)
QVQLVQSGAEVKKPGSSVKVSCKASGYTFTEYIIHWVRQAPGQGLEWIGWFYPESGSVEYNEGFKGRATI

TADKSTSTAYMELSSLRSEDTAVYYCARHEERDYYGYYAMDYWGQGTIVIVSS hvL1 variable light chain:
(SEQ ID NO: 11)
DIQMIQSPSSLSASVGDRVTITCSASSSISSNYLHWYQQKPGKVPKLLIYRTSNLASGVPSRFSGSGSGT

DYTLTISSLQPEDVATYYCQQGSSIPRFTSGGGTKVEIK hvL2 variable light chain:
(SEQ ID NO: 12)
DIQMIQSPSSLSASVGDRVIITCSASSSISSNYLHWYQQKPGKVPKLLIYRTSNLASGVPSRFSGSGSGT

DYTLTISSLQPEDVATYYCQQGSSIPRFTSGGGTKVEIK

Exemplary activatable anti-ITGa3 antibodies of the invention include, for example, activatable antibodies that include a combination of a variable heavy chain complementarity determining region 1 (VH CDR1, also referred to herein as CDRH1) sequence, a variable heavy chain complementarity determining region 2 (VH CDR2, also referred to herein as CDRH2) sequence, a variable heavy chain complementarity determining region 3 (VH CDR3, also referred to herein as CDRH3) sequence, a variable light chain complementarity determining region 1 (VL CDR1, also referred to herein as CDRL1) sequence, a variable light chain complementarity determining region 2 (VL CDR2, also referred to herein as CDRL2) sequence, and a variable light chain complementarity determining region 3 (VL CDR3, also referred to herein as CDRL3) sequence, wherein at least one CDR sequence is selected from the group consisting of a VH CDR1 sequence comprising the amino acid sequence EYIIH (SEQ ID NO: 13); a VH CDR2 sequence comprising the amino acid sequence WFYPESGSVKYNETFKG (SEQ ID NO: 14) or WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 sequence comprising the amino acid sequence HEERDYYGYYAMDY (SEQ ID NO: 18); a VL CDR1 sequence comprising the amino acid sequence SASSSISSNYLH (SEQ ID NO: 19; a VL CDR2 sequence comprising the amino acid sequence RTSNLA (SEQ ID NO: 20); and a VL CDR3 sequence comprising the amino acid sequence QQGSSIPRFT (SEQ ID NO: 21).

In some embodiments, the activatable anti-ITGa3 antibody includes a heavy chain that comprises or is derived from a heavy chain amino acid sequence shown in PCT Publication No. WO 1998/09651, and/or in US Patent Application Publication Nos. US2014235833, US20090203538, the contents of each of which are hereby incorporated by reference in their entirety.

In some embodiments, the activatable anti-ITGa3 antibody includes a heavy chain that comprises or is derived from a heavy chain amino acid sequence shown in Table 12. In some embodiments, the activatable anti-ITGa3 antibody includes a light chain that comprises or is derived from a heavy chain amino acid sequence shown in Table 12. In some embodiments, the activatable anti-ITGa3 antibody includes a heavy chain that comprises or is derived from a heavy chain amino acid sequence shown in Table 12, and a light chain that comprises or is derived from a light chain amino acid sequence shown in Table 12.

In some embodiments, the activatable anti-ITGa3 antibody includes a heavy chain that comprises or is derived from a heavy chain amino acid sequence shown in Table 12. In some embodiments, the activatable anti-ITGa3 antibody includes a light chain that comprises or is derived from a heavy chain amino acid sequence shown in Table 12. In some embodiments, the activatable anti-ITGa3 antibody includes a heavy chain that comprises or is derived from a heavy chain amino acid sequence shown in Table 12, and a light chain that comprises or is derived from a light chain amino acid sequence shown in Table 12. In some embodiments, the activatable anti-ITGa3 antibody includes a combination of heavy chain variable region and light chain variable region sequences from the combinations shown in Group A in Table 12. In some embodiments, the activatable anti-ITGa3 antibody includes the combination of heavy chain variable region and light chain variable region sequences shown in Group B in Table 12. In some embodiments, the activatable anti-ITGa3 antibody includes the combination of heavy chain variable region and light chain variable region sequences shown in Group C in Table 12.

In some embodiments, the activatable anti-ITGa3 antibody includes a combination of the complementarity determining region (CDR) sequences of a heavy chain sequence from the heavy chain sequences shown in Group A Table 12.

In some embodiments, the activatable anti-ITGa3 antibody includes a combination of the CDRs of a light chain sequence from the light chain sequences shown in Group A Table 12. In some embodiments, the activatable anti-ITGa3 antibody includes a combination of the CDRs of a heavy chain sequence from the heavy chain sequences shown in Group A Table 12 and the CDRs of a light chain sequence from the heavy chain sequences shown in Group A Table 12.

In some embodiments, the activatable anti-ITGa3 antibody includes a combination of CDRs of a heavy chain sequence from the heavy chain sequences shown in Group B Table 12. In some embodiments, the activatable anti-ITGa3 antibody includes a combination of the CDRs of a light chain sequence from the light chain sequences shown in Group B Table 12. In some embodiments, the activatable anti-ITGa3 antibody includes a combination of the CDRs of a heavy chain sequence from the heavy chain sequences shown in Group B Table 12 and the CDRs of a light chain sequence from the heavy chain sequences shown in Group B Table 12.

In some embodiments, the activatable anti-ITGa3 antibody includes a combination of the CDRs of a heavy chain sequence from the heavy chain sequences shown in Group C Table 12. In some embodiments, the activatable anti-ITGa3 antibody includes a combination of the CDRs of a light chain sequence from the light chain sequences shown in Group C Table 12. In some embodiments, the activatable anti-ITGa3 antibody includes a combination of the CDRs of a heavy chain sequence from the heavy chain sequences shown in Group C Table 12 and the CDRs of a light chain sequence from the heavy chain sequences shown in Group C Table 12.

TABLE 12

Variable Heavy Chain Region (VH) and Variable Light Chain Region (VL) Sequences for Activatable Antibodies that Bind ITGa3

VH QVQLVQSGAEVKKPGASVKVSCKASGYTFTSYGTSWVRQAPGQGLEWMGWISAYNGNTNYAQKLQ
GRVTMTTDTSTSTAYMELRSLRSDDTAVYYCATAASLKYYYDSSGYYYWGQGTLVTVSR (SEQ ID NO: 56)

VL SSELTQDPAVSVALGQTVRITCQGDSLRSYYASWYQQKPGQAPVLVISGKNNRPSGTPDRFSGSS
SGDTASLTITGAQAEDEANYYCNSRDSSGYPSWVFGGGTKLTVLG (SEQ ID NO: 57)

VH QVQLQESGPGLVKPSETLSLTCTVSGGSISSYYWSWIRQPAGKGLEWIGRIYTSGSTNYNPSLKS
RVTMSVDTSKNQFSLKLSSVTAADTAVYYCARERAYCSSTSCYRNAFDIWGQGTTVTVSR (SEQ ID NO: 58)

VL QSVLTQPPSVSGAPGQRVNISCAGSSSNIGAGYDVHWYQQIPGTAPKLLMYGNSNRPSGVPDRFS
GSKSGASASLAITRLQAEDEADYYCQSYDSSLSGSRVFGTGTKVTVLG (SEQ ID NO: 59)

VH EVQLVESGGGVVQPGRSLRLSCAASGFTFSSYGMHWVRQAPGKGLEWVTVISFDGSNKYYADSVK
GRFTISRDNSKNTLYLQMNSLRAEDTAVYYCAKAYTNTWWPDAFDIWGQGTTVTVSR (SEQ ID NO: 60)

VL DIQMTQSPSSLSASVGDRVTITCQASQDISNYLNWYQQKPGKAPKLLIYDASNLETGVPSRFSGS
GSGTDFTFTISSLQPEDIATYYCQQYDNLPPTFGPGTKVDIK (SEQ ID NO: 61)

VH QVQLQESGPGLVKPSETLSLTCTVSGSSISSYYWSWIRQPPGKGLEWIGYIYYSGSTNYNPSLKS
RVTISVDTSKNQFSLKLSSVTAADTAVYYCARDLYWNDAFDIWGQGTTVTVSR (SEQ ID NO: 62)

VL QSALTQPLSASGTPGQRVTISCSGSSSNIGSNTVNWYQQLPGTAPKLLIYSNNQRPSGVPDRFSG
SKSGTSASLAISGLQSEDEADYYCAAWDDSLNGPVFGGGTKLTVLG (SEQ ID NO: 63)

VH QVQLQESGPGLVKPSETLSLTCTVSGSSISSYYWSWIRQPPGKGLEWIGYIYYSGSTNYNPSLKS
RVTISVDTSKNQFSLKLSSVTAADTAVYYCARDLYWNDAFDIWGQGTTVTVSR (SEQ ID NO: 64)

VL QSVLTQPPSASGTPGQSVTISCSGSSSNIGSNTVNWYQQLPGTAPKLLIYSNNQRPSGVPDRFSG
SKSGTSASLAISGLQSEDEADYYCAAWDDSLNGPVFGGGTKLTVLG (SEQ ID NO: 65)

VH QVQLQQSGPGLVKPSQTLSLTCAISGDSVSSNSAAWNWIRQSPSRGLEWLGRTYYRSKWYNDYAV
SVKSRITINPDTSKNQFSLQLNSVTPEDTAVYYCARESWLWGTGGDAFDIWGQGTTVTVSR (SEQ ID NO: 66)

VL QSVLTQPPSVSGAPRQTVTISCSGSSSNIGQNSVTWYQRLPGEAPKLLIYYDDLLHSGVSDRFSG
SKSGTSASLAISGLQSEDEAEYYCASWDDSLKGPVFGGGTKLTVLG (SEQ ID NO: 67)

VH EVQLVESGGGLVQPGGSLRLSCAASGFTVSSNYMSWVRQAPGKGLEWVSVIYSGGSTYYADSVKG
RFTISRDNSKNTLYLQMNSLRAEDTAVYYCAREFDYWGQGTLVTVSR (SEQ ID NO: 68)

VL DIQMIQSPSSLSASVGDRVTITCQASQDISNYLNWYQQKPGKAPKLLIYDASNLETGVPSRFSGS
GSGTDFTFTISSLQPEDIATYYCQQYDNPAFGGGTKVEIK (SEQ ID NO: 69)

VH QVQLVQSGAEVKKPGASVKVSCKASGYTFTNYGLTWVRQAPGQGLEWMGWISTYNSNTNYAEKLQ
GRVTMTTDTSTSTAYMELRSLTSDDTAVYYCARGPTYSFDSSGYFFDYWGQGTLVTVSR (SEQ ID NO: 70)

VL SSELTQDPAMSVALGQTVKITCQGDSLTNYYPSWYQQKPGQAPVLVMYGKDSRPSGTSDRFSGSS
SGTSASLTITGAQAEDEADYYCNSRDGSAHRLVFGGGTKLTVLG (SEQ ID NO: 71)

TABLE 12 -continued

Variable Heavy Chain Region (VH) and Variable Light Chain Region (VL)
Sequences for Activatable Antibodies that Bind ITGa3

VH QVQLVQSGAEVKKPGASVKVSCKASGYTFTSYGTSWVRQAPGQGLEWMGWISAYNGNTNYAQKLQ
GRVTMTTDTSTSTAYMELRSLRSDDTAVYYCARDRYYGSGFGMDVWGQGTMVTVSR (SEQ ID
NO: 72)

VL SSELTQDPAVSVALGQTVRITCQGDSLRSYYASWYQQKPGQAPVLVIYGKNNRPSGTPDRFSGSS
SGNTASLTITGAQAEDEADYYCNSRDSSGNHWVFGGGTKLTVLG (SEQ ID NO: 73)

VH QVQLVQSGAEVKKPGASVKVSCKASGYTFTSYGTSWVRQAPGQGLEWMGWISAYNGNTNYAQKLQ
GRVTMTTDTSTSTAYMELRSLRSDDTAVYYCARDTYSSGWYFDYWGQGTLVTVSR (SEQ ID
NO: 74)

VL SSELTQDPAVSVALGQTVRITCQGDSLRNYYASWYQQKPGQAPVLVIYGKNNRPSGTPDRFSGSS
SGNTASLTITGAQAEDEADYYCNSRDSSGNHLYVFGTGTKVTVLG (SEQ ID NO: 75)

VH QVQLVQSGAEVKKPGASVKVSCKASGYTFTSYGTSWVRQAPGQGLEWMGWISAYNGNTNYAQKLQ
GRVTMTTDTSTSTAYMELSSLRSEDTAVYYCATLNISGSYYFDYWGQGTLVTVSR (SEQ ID
NO: 76)

VL SSELTQDPAVSVALGQTVRITCQGDSLRSYYATWYQQKPGQAPVLVISGKNNRPSGTPDRFSGSS
SGNTASLTITGAQAEDEADYYCNSRDSSGYPSWVFGGGTKLTVLG (SEQ ID NO: 77)

VH QVQLQESGPGLVKPSETLSLTCTVSGGSISSSSYYWGWIRQPPGKGLEWIGSIYYSGSTYYNPSL
KSRVTISVDTSKNQFSLKLSSVTAADTAVYYCARHWGNYAFDIWGQGTTVTVSR (SEQ ID
NO: 78)

VL QSVLTQPPSASGTPGQRVTISCSGSSSNIGSNYVYWYQQLPGTAPKLLIYSNNQRPSGVPDRFSG
SKSGTSASLAISGLRSEDEADYYCAAWDDSLSGQVFGGGTQLTVLG (SEQ ID NO: 79)

VH EVQLVESGAEVKKPGASVKVSCKASGYTFTSYGTSWVRQAPGQGLEWMGWISAYNGNTNYAQKLQ
GRVTMTTDTSTSTAYMELRSLRSDDTAVYYCAREKYSSGWYFDYWGQGTLVTVSR (SEQ ID
NO: 80)

VL SSELTQDPAVSVALGQTVRITCQGDSLRSYYASWYQQKPGQAPVLVIYGKNNRPSGTPDRFSGSS
SGNTASLTITGAQAEDEADYYCNSRDSSGNHHYVFGTGTKVTVLG (SEQ ID NO: 81)

In some embodiments, the activatable anti-ITGa3 antibody includes a CDR sequence shown in Table 13, a combination of VL CDR sequences (VL CDR1, VL CDR2, VL CDR3) selected from the group consisting of those combinations shown in a single row Table 13, a combination of VH CDR sequences (VH CDR1, VH CDR2, VH CDR3) selected from the group consisting of those combinations shown in Table 13, or a combination of VL CDR and VH CDR sequences (VL CDR1, VL CDR2, VL CDR3, VH CDR1, VH CDR2, VH CDR3) selected the group consisting of those combinations shown in Table 13.

TABLE 13

CDR Sequences for Antibodies and Activatable
Antibodies that Bind ITGa3

| VH | | | VL | | |
|---|---|---|---|---|---|
| CDR1 (SEQ ID NO) | CDR2 (SEQ ID NO) | CDR3 (SEQ ID NO) | CDR1 (SEQ ID NO) | CDR2 (SEQ ID NO) | CDR3 (SEQ ID NO) |
| SYGTS (82) | WISAYNGNTNYA QKLQG (83) | AASLKYYY DSSGYYY (84) | QGDSLRSYYAS (85) | GKNNRPS (86) | NSRDSSGYPS (87) |
| SYYWS (88) | RIYTSGSTNYNP SLKS (89) | ERAYCSST SCYRNAFD I (90) | AGSSSNIGAGY DVH (91) | GNSNRPS (92) | QSYDSSLSGS (93) |
| SYGMH (94) | VISFDGSNKYYA DSVKG (95) | AYTNTWWP DAFDI (96) | QASQDISNYLN (97) | DASNLET (98) | QQYDNLP (99) |
| SYYWS (88) | YIYYSGSTNYNP SLKS (100) | DLYWNDAF DI (101) | SGSSSNIGSNT VN (102) | SNNQRPS (103) | AAWDDSLNG (104) |
| SNSAAWN (105) | RTYYRSKWYNDY AVSVKS (106) | ESWLWGTG GDAFDI (107) | SGSSSNIGQNS VT (108) | YDDLLHS (109) | ASWDDSLKG (110) |

TABLE 13 -continued

CDR Sequences for Antibodies and Activatable Antibodies that Bind ITGa3

| VH | | | VL | | |
|---|---|---|---|---|---|
| CDR1 (SEQ ID NO) | CDR2 (SEQ ID NO) | CDR3 (SEQ ID NO) | CDR1 (SEQ ID NO) | CDR2 (SEQ ID NO) | CDR3 (SEQ ID NO) |
| SNYMS (111) | VIYSGGSTYYAD SVKG (112) | EFDY (113) | QASQDISNYLN (114) | DASNLET (115) | QQYDN (116) |
| SYGTS (82) | WISAYNGNTNYA QKLQG (83) | DRYYGSGF GMDV (117) | QGDSLTNYYPS (118) | GKDSRPS (119) | NSRDGSAHR (120) |
| NYGLT (121) | WISTYNSNTNYA EKLQG (122) | GPTYSFDS SGYFFDY (123) | QGDSLRSYYAS (85) | GKNNRPS (86) | NSRDSSGNH (124) |
| SYGTS (82) | WISAYNGNTNYA QKLQG (83) | DTYSSGWY FDY (125) | QGDSLRNYYAS (126) | GKNNRPS (86) | NSRDSSGNHL (127) |
| SYGTS (82) | WISAYNGNTNYA QKLQG (83) | LNISGSYY FDY (128) | QGDSLRSYYAT (129) | GKNNRPS (86) | NSRDSSGYPS (87) |
| SSSYYWG (130) | SIYYSGSTYYNP SLKS (131) | HWGNYAFD I (132) | SGSSSNIGSNY VY (133) | SNNQRPS (103) | AAWDDSLSG (134) |
| SYGTS (82) | WISAYNGNTNYA QKLQG (83) | EKYSSGWY FDY (135) | QGDSLRSYYAS (85) | GKNNRPS (86) | NSRDSSGNHH (136) |

The anti-ITGa3 antibodies and the ABs in the activatable antibodies of the disclosure specifically bind a ITGa3 target, such as, for example, mammalian ITGa3, and/or human ITGa3. Also included in the disclosure are anti-ITGa3 antibodies and ABs that bind to the same ITGa3 epitope as an antibody of the disclosure and/or an activated activatable antibody described herein. Also included in the disclosure are anti-ITGa3 antibodies and ABs that compete with an anti-ITGa3 antibody and/or an activated anti-ITGa3 activatable antibody described herein for binding to a ITGa3 target, e.g., human ITGa3. Also included in the disclosure are anti-ITGa3 antibodies and ABs that cross-compete with an anti-ITGa3 antibody and/or an activated anti-ITGa3 activatable antibody described herein for binding to a ITGa3 target, e.g., human ITGa3.

The activatable anti-ITGa3 antibodies provided herein include a masking moiety. In some embodiments, the masking moiety is an amino acid sequence that is coupled or otherwise attached to the anti-ITGa3 antibody and is positioned within the activatable anti-ITGa3 antibody construct such that the masking moiety reduces the ability of the anti-ITGa3 antibody to specifically bind ITGa3. Suitable masking moieties are identified using any of a variety of known techniques. For example, peptide masking moieties are identified using the methods described in PCT Publication No. WO 2009/025846 by Daugherty et al., the contents of which are hereby incorporated by reference in their entirety.

The activatable anti-ITGa3 antibodies provided herein include a cleavable moiety. In some embodiments, the cleavable moiety includes an amino acid sequence that is a substrate for a protease, usually an extracellular protease. Suitable substrates are identified using any of a variety of known techniques. For example, peptide substrates are identified using the methods described in U.S. Pat. No. 7,666,817 by Daugherty et al.; in U.S. Pat. No. 8,563,269 by Stagliano et al.; and in PCT Publication No. WO 2014/026136 by La Porte et al., the contents of each of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

Exemplary substrates include but are not limited to substrates cleavable by one or more of the following enzymes or proteases listed in Table 4.

TABLE 4

| Exemplary Proteases and/or Enzyme | | |
|---|---|---|
| ADAMS, ADAMTS, e.g. ADAM8 ADAM9 ADAM10 ADAM12 ADAM15 ADAM17/TACE ADAMDEC1 ADAMTS1 ADAMTS4 | Cysteine proteinases, e.g., Cruzipain Legumain Otubain-2  KLKs, e.g., KLK4 KLK5 KLK6 KLK7 | Serine proteases, e.g., activated protein C Cathepsin A Cathepsin G Chymase coagulation factor proteases (e.g., FVIIa, FIXa, FXa, FXIa, FXIIa) Elastase Granzyme B |

TABLE 4-continued

| Exemplary Proteases and/or Enzyme | | |
|---|---|---|
| ADAMTS5 | KLK8 | Guanidinobenzoatase |
|  | KLK10 | HtrA1 |
| Aspartate proteases, e.g., | KLK11 | Human Neutrophil Elastase |
| BACE | KLK13 | Lactoferrin |
| Renin | KLK14 | Marapsin |
|  |  | NS3/4A |
| Aspartic cathepsins, e.g., | Metallo proteinases, e.g., | PACE4 |
| Cathepsin D | Meprin | Plasmin |
| Cathepsin E | Neprilysin | PSA |
|  | PSMA | tPA |
| Caspases, e.g., | BMP-1 | Thrombin |
| Caspase 1 |  | Tryptase |
| Caspase 2 | MMPs, e.g., | uPA |
| Caspase 3 | MMP1 |  |
| Caspase 4 | MMP2 | Type II Transmembrane |
| Caspase 5 | MMP3 | Serine Proteases (TTSPs), e.g., |
| Caspase 6 | MMP7 | DESC1 |
| Caspase 7 | MMP8 | DPP-4 |
| Caspase 8 | MMP9 | FAP |
| Caspase 9 | MMP10 | Hepsin |
| Caspase 10 | MMP11 | Matriptase-2 |
| Caspase 14 | MMP12 | MT-SP1/Matriptase |
|  | MMP13 | TMPRSS2 |
| Cysteine cathepsins, e.g., | MMP14 | TMPRSS3 |
| Cathepsin B | MMP15 | TMPRSS4 |
| Cathepsin C | MMP16 |  |
| Cathepsin K | MMP17 |  |
| Cathepsin L | MMP19 |  |
| Cathepsin S | MMP20 |  |
| Cathepsin V/L2 | MMP23 |  |
| Cathepsin X/Z/P | MMP24 |  |
|  | MMP26 |  |
|  | MMP27 |  |

The activatable anti-ITGa3 antibodies described herein overcome a limitation of antibody therapeutics, particularly antibody therapeutics that are known to be toxic to at least some degree in vivo. Target-mediated toxicity constitutes a major limitation for the development of therapeutic antibodies. The activatable anti-ITGa3 antibodies provided herein are designed to address the toxicity associated with the inhibition of the target in normal tissues by traditional therapeutic antibodies. These activatable anti-ITGa3 antibodies remain masked until proteolytically activated at the site of disease. Starting with an anti-ITGa3 antibody as a parental therapeutic antibody, the activatable anti-ITGa3 antibodies of the invention were engineered by coupling the antibody to an inhibitory mask through a linker that incorporates a protease substrate.

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

In some embodiments, the dissociation constant (Kd) of the MM towards the AB is approximately equal to the Kd of the AB towards the target. In some embodiments, the dissociation constant (Kd) of the MM towards the AB is no more than the dissociation constant of the AB towards the target.

In some embodiments, the dissociation constant (Kd) of the MM towards the AB is less than the dissociation constant of the AB towards the target.

In some embodiments, the dissociation constant (Kd) of the MM towards the AB is greater than the dissociation constant of the AB towards the target.

In some embodiments, the MM has a Kd for binding to the AB that is no more than the Kd for binding of the AB to the target.

In some embodiments, the MM has a Kd for binding to the AB that is no less than the Kd for binding of the AB to the target.

In some embodiments, the MM has a Kd for binding to the AB that is approximately equal to the Kd for binding of the AB to the target.

In some embodiments, the MM has a Kd for binding to the AB that is less than the Kd for binding of the AB to the target.

In some embodiments, the MM has a Kd for binding to the AB that is greater than the Kd for binding of the AB to the target.

In some embodiments, the MM has a Kd for binding to the AB that is no more than 2, 3, 4, 5, 10, 25, 50, 100, 250, 500, or 1,000 fold greater than the Kd for binding of the AB to the target. In some embodiments, the MM has a Kd for binding to the AB that is between 1-5, 2-5, 2-10, 5-10, 5-20, 5-50, 5-100, 10-100, 10-1,000, 20-100, 20-1000, or 100-1,000 fold greater than the Kd for binding of the AB to the target.

In some embodiments, the MM has an affinity for binding to the AB that is less than the affinity of binding of the AB to the target.

In some embodiments, the MM has an affinity for binding to the AB that is no more than the affinity of binding of the AB to the target.

In some embodiments, the MM has an affinity for binding to the AB that is approximately equal of the affinity of binding of the AB to the target.

In some embodiments, the MM has an affinity for binding to the AB that is no less than the affinity of binding of the AB to the target.

In some embodiments, the MM has an affinity for binding to the AB that is greater than the affinity of binding of the AB to the target.

In some embodiments, the MM has an affinity for binding to the AB that is 2, 3, 4, 5, 10, 25, 50, 100, 250, 500, or 1,000 less than the affinity of binding of the AB to the target. I In some embodiments, the MM has an affinity for binding to the AB that is between 1-5, 2-5, 2-10, 5-10, 5-20, 5-50, 5-100, 10-100, 10-1,000, 20-100, 20-1000, or 100-1,000 fold less than the affinity of binding of the AB to the target. In some embodiments, the MM has an affinity for binding to the AB that is 2 to 20 fold less than the affinity of binding of the AB to the target. In some embodiments, a MM not covalently linked to the AB and at equimolar concentration to the AB does not inhibit the binding of the AB to the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for at least one protease.

The elements of the activatable antibodies are arranged so that the MM and CM are positioned such that in a cleaved (or relatively active) state and in the presence of a target, the AB binds a target while the activatable antibody is in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or of the parental AB towards the target. Conversely, the binding affinity of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

When the AB is modified with a MM and a CM and is in the presence of the target but not in the presence of a modifying agent (for example at least one protease), specific binding of the AB to its target is reduced or inhibited, as compared to the specific binding of the AB not modified with an MM and a CM or of the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by at least one protease. The term uncleaved state, as used herein, refers to the condition of the activatable antibodies in the absence of cleavage of the CM by a protease. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target when the activatable antibody is in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM, i.e., a protease, than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for a given target, and the CM represents a substrate for a protease. In some embodiments, the protease is co-localized with the target at a treatment site or diagnostic site in a subject. As used herein, co-localized refers to being at the same site or relatively close nearby. In some embodiments, a protease cleaves a CM yielding an activated antibody that binds to a target located nearby the cleavage site. The activatable antibodies disclosed herein find particular use where, for example, a protease capable of cleaving a site in the CM, i.e., a protease, is present at relatively higher levels in target-containing tissue of a treatment site or diagnostic site than in tissue of non-treatment sites (for example in healthy tissue). In some embodiments, a CM of the disclosure is also cleaved by one or more other proteases. In some embodiments, it is the one or more other proteases that is co-localized with the target and that is responsible for cleavage of the CM in vivo.

In some embodiments activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of at least one protease capable of cleaving the CM of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM is specifically cleaved by at least one protease at a rate of about $0.001\text{-}1500\times10^4 M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^{-1}$. In some embodiments, the CM is specifically cleaved at a rate of about $100,000\ M^{-1}S^{-1}$. In some embodiments, the CM is specifically cleaved at a rate from about $1\times10E2$ to about $1\times10E6\ M^{-1}S^{-1}$ (i.e., from about $1\times10^2$ to about $1\times10^6 M^{-1}S^{-1}$).

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 165) and (GGGS)n (SEQ ID NO: 166), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 167), Gly-Gly-Ser-Gly-Gly (SEQ ID NO: 168), Gly-Ser-Gly-Ser-Gly (SEQ ID NO: 169), Gly-Ser-Gly-Gly-Gly (SEQ ID NO: 170), Gly-Gly-Gly-Ser-Gly (SEQ ID NO: 171), Gly-Ser-Ser-Ser-Gly (SEQ ID NO: 172), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

The disclosure also provides compositions and methods that include an activatable anti-ITGa3 antibody that includes an antibody or antibody fragment (AB) that specifically binds ITGa3, where the AB is coupled to a masking moiety (MM) that decreases the ability of the AB to bind its target. In some embodiments, the activatable anti-ITGa3 antibody further includes a cleavable moiety (CM) that is a substrate for a protease. The compositions and methods provided herein enable the attachment of one or more agents to one or more cysteine residues in the AB without compromising the activity (e.g., the masking, activating or binding activity) of the activatable anti-ITGa3 antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable anti-ITGa3 antibody that is conjugated to one or more agents, e.g., any of a variety of therapeutic, diagnostic and/or prophylactic agents, for example, in some embodiments, without any of the agent(s) being conjugated to the MM of the activatable anti-ITGa3 antibody. The compositions and methods provided herein produce conjugated activatable anti-ITGa3 antibodies in which the MM retains the ability to effectively and efficiently mask the AB of the activatable antibody in an uncleaved state. The compositions and methods provided herein produce conjugated activatable anti-ITGa3 antibodies in which the activatable antibody is still activated, i.e., cleaved, in the presence of a protease that can cleave the CM.

The activatable anti-ITGa3 antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable anti-ITGa3 antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable anti-ITGa3 antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to an activatable anti-ITGa3 antibody resulting in selectivity in the placement of the agent is provided. The method generally includes partially reducing the activatable anti-ITGa3 antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable anti-ITGa3 antibody will vary depending on the activatable antibody. In some embodiments, the ratio of reducing agent to activatable anti-ITGa3 antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable anti-ITGa3 antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

The invention also provides partially reduced activatable anti-ITGa3 antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to ITGa3, a masking moiety (MM) that inhibits the binding of the AB of the activatable antibody in an uncleaved state to the ITGa3 target, and a cleavable moiety (CM) coupled to the AB, wherein the CM is a polypeptide that functions as a substrate for a protease. In some embodiments the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, e.g., ITGa3, a masking moiety (MM) that inhibits the binding of the AB of the activatable antibody in an uncleaved state to the target, and a cleavable moiety (CM) coupled to the AB, wherein the CM is a polypeptide that functions as a substrate for at least one protease. In some embodiments, the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In yet other embodiments, a method of reducing and conjugating an agent, e.g., a drug, to an activatable anti-ITGa3 antibody resulting in selectivity in the placement of the agent by providing an activatable anti-ITGa3 antibody with a defined number and positions of lysine and/or cysteine residues. In some embodiments, the defined number of lysine and/or cysteine residues is higher or lower than the number of corresponding residues in the amino acid sequence of the parent antibody or activatable antibody. In some embodiments, the defined number of lysine and/or cysteine residues may result in a defined number of agent equivalents that can be conjugated to the anti-ITGa3 antibody or activatable anti-ITGa3 antibody. In some embodiments, the defined number of lysine and/or cysteine residues may result in a defined number of agent equivalents that can be conjugated to the anti-ITGa3 antibody or activatable anti-ITGa3 antibody in a site-specific manner. In some embodiments, the modified activatable antibody is modified with one or more non-natural amino acids in a site-specific manner, thus in some embodiments limiting the conjugation of the agents to only the sites of the non-natural amino acids. In some embodiments, the anti-ITGa3 antibody or activatable anti-ITGa3 antibody with a defined number and positions of lysine and/or cysteine residues may be partially reduced with a reducing agent as discussed herein such that any conjugation sites in the masking moiety or other non-AB portion of the activatable antibody are not reduced, and conjugating the agent to interchain thiols in the AB.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker. In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." In some embodiments, the agent is linked to the AB using a maleimide PEG-valine-citrulline linker. In some embodiments, the agent is monomethyl auristatin D (MMAD) linked to the AB using a maleimide bis-PEG-valine-citrulline-para-aminobenzyloxycarbonyl linker, and this linker payload construct is referred to herein as "PEG2-vc-MMAD." The structures of vc-MMAD, vc-MMAE, and PEG2-vc-MMAD. The structures of vc-MMAD and vc-MMAE are shown below:

sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some

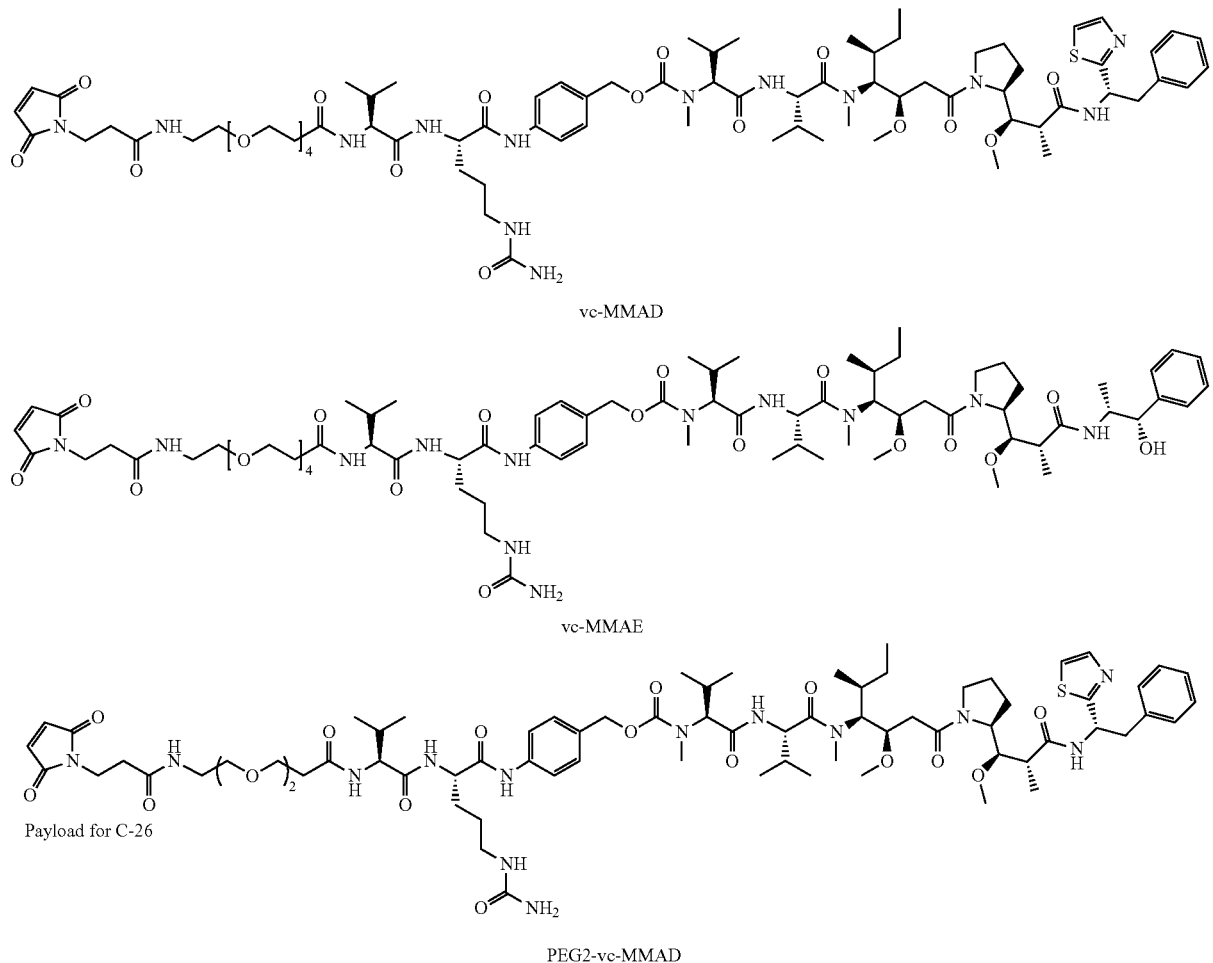

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and cleavable moiety (CM) coupled to the AB, and the CM is a polypeptide that functions as a substrate for at least one MMP protease.

In some embodiments, the MMAD-conjugated activatable antibody can be conjugated using any of several methods for attaching agents to ABs: (a) attachment to the carbohydrate moieties of the AB, or (b) attachment to embodiments, the linker is a cleavable linker. In some embodiments, the linker is a non-cleavable linker. In some embodiments, the linker is selected from the group consisting of the linkers shown in Tables 6 and 7. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

In some embodiments, the polyethylene glycol (PEG) component of a linker of the present disclosure is formed from 2 ethylene glycol monomers, 3 ethylene glycol monomers, 4 ethylene glycol monomers, 5 ethylene glycol monomers, 6 ethylene glycol monomers, 7 ethylene glycol monomers 8 ethylene glycol monomers, 9 ethylene glycol monomers, or at least 10 ethylene glycol monomers. In some embodiments of the present disclosure, the PEG component is a branched polymer. In some embodiments of the present disclosure, the PEG component is an unbranched polymer. In some embodiments, the PEG polymer component is functionalized with an amino group or derivative thereof, a carboxyl group or derivative thereof, or both an amino group or derivative thereof and a carboxyl group or derivative thereof.

In some embodiments, the PEG component of a linker of the present disclosure is an amino-tetra-ethylene glycol-carboxyl group or derivative thereof. In some embodiments, the PEG component of a linker of the present disclosure is an amino-tri-ethylene glycol-carboxyl group or derivative thereof. In some embodiments, the PEG component of a linker of the present disclosure is an amino-di-ethylene glycol-carboxyl group or derivative thereof. In some embodiments, an amino derivative is the formation of an amide bond between the amino group and a carboxyl group to which it is conjugated. In some embodiments, a carboxyl derivative is the formation of an amide bond between the carboxyl group and an amino group to which it is conjugated. In some embodiments, a carboxyl derivative is the formation of an ester bond between the carboxyl group and an hydroxyl group to which it is conjugated.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 5 lists some of the exemplary pharmaceutical agents that may be employed in the herein described disclosure but in no way is meant to be an exhaustive list.

TABLE 5

Exemplary Pharmaceutical Agents for Conjugation

CYTOTOXIC AGENTS

| | |
|---|---|
| Auristatins | Turbostatin |
| Auristatin E | Phenstatins |
| Monomethyl auristatin D (MMAD) | Hydroxyphenstatin |
| Monomethyl auristatin E (MMAE) | Spongistatin 5 |
| Desmethyl auristatin E (DMAE) | Spongistatin 7 |
| Auristatin F | Halistatin 1 |
| Monomethyl auristatin F (MMAF) | Halistatin 2 |
| Desmethyl auristatin F (DMAF) | Halistatin 3 |
| Auristatin derivatives, e.g., amides thereof | Modified Bryostatins |
| Auristatin tyramine | Halocomstatins |
| Auristatin quinoline | Pyrrolobenzimidazoles (PBI) |
| Dolastatins | Cibrostatin6 |
| Dolastatin derivatives | Doxaliform |
| Dolastatin 16 DmJ | Anthracyclins analogues |
| Dolastatin 16 Dpv | Cemadotin analogue (CemCH2-SH) |
| Maytansinoids, e.g. DM-1; DM-4 | *Pseudomonas* toxin A (PE38) variant |
| Maytansinoid derivatives | *Pseudomonas* toxin A (ZZ-PE38) variant |
| Duocarmycin | ZJ-101 |
| Duocarmycin derivatives | OSW-1 |
| Alpha-amanitin | 4-Nitrobenzyloxycarbonyl Derivatives of |
| Anthracyclines | O6-Benzylguanine |
| Doxorubicin | Topoisomerase inhibitors |
| Daunorubicin | Hemiasterlin |
| Bryostatins | Cephalotaxine |
| Camptothecin | Homoharringtonine |
| Camptothecin derivatives | Pyrrolobenzodiazepine dimers (PBDs) |
| 7-substituted Camptothecin | Pyrrolobenzodiazepenes |
| 10,11-Difluoromethylenedioxycamptothecin | Functionalized pyrrolobenzodiazepenes |
| | Functionalized pyrrolobenzodiazepene |
| Combretastatins | dimers |
| Debromoaplysiatoxin | Calicheamicins |
| Kahalalide-F | Podophyllotoxins |
| Discodermolide | Taxanes |
| Ecteinascidins | Vinca alkaloids |

TABLE 5-continued

Exemplary Pharmaceutical Agents for Conjugation

| | |
|---|---|
| ANTIVIRALS | CONJUGATABLE DETECTION REAGENTS |
| Acyclovir | |
| Vira A | Fluorescein and derivatives thereof |
| Symmetrel | Fluorescein isothiocyanate (FITC) |
| ANTIFUNGALS | RADIOPHARMACEUTICALS |
| Nystatin | $^{125}$I |
| ADDITIONAL ANTI-NEOPLASTICS | $^{131}$I |
| Adriamycin | $^{89}$Zr |
| Cerubidine | $^{111}$In |
| Bleomycin | $^{123}$I |
| Alkeran | $^{131}$I |
| Velban | $^{99m}$Tc |
| Oncovin | $^{201}$Tl |
| Fluorouracil | $^{133}$Xe |
| Methotrexate | $^{11}$C |
| Thiotepa | $^{62}$Cu |
| Bisantrene | $^{18}$F |
| Novantrone | $^{68}$Ga |
| Thioguanine | $^{13}$N |
| Procarabizine | $^{15}$O |
| Cytarabine | $^{38}$K |
| ANTI-BACTERIALS | $^{82}$Rb |
| Aminoglycosides | $^{99m}$Tc (Technetium) |
| Streptomycin | HEAVY METALS |
| Neomycin | Barium |
| Kanamycin | Gold |
| Amikacin | Platinum |
| Gentamicin | ANTI-MYCOPLASMALS |
| Tobramycin | Tylosine |
| Streptomycin B | Spectinomycin |
| Spectinomycin | |
| Ampicillin | |
| Sulfanilamide | |
| Polymyxin | |
| Chloramphenicol | |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC ((succinimidyl 4-(N-maleimidomethyl)cyclohexane-1-carboxylate), sulfo-SMCC (sulfosuccinimidyl 4-(N-maleimidomethyl)cyclohexane-1-carboxylate), SPDB (N-succinimidyl-4-(2-pyridyldithio) butanoate), or sulfo-SPDB (N-succinimidyl-4-(2-pyridyldithio)-2-sulfo butanoate).

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM and associated linkers and then attached to the linker for conjugation purposes.

Branched Linkers:

In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers:

Peptide linkers that are susceptible to cleavage by enzymes of the complement system, such as but not limited to u-plasminogen activator, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a u-plasminogen activator, a tissue plasminogen activator, plasmin, or trypsin. These cleavable linkers are useful in conjugated activatable antibodies that include an extracellular toxin, e.g., by way of non-limiting example, any of the extracellular toxins shown in Table 5.

Non-limiting examples of cleavable linker sequences are provided in Table 6.

TABLE 6

Exemplary Linker Sequences for Conjugation

| Types of Cleavable Sequences | Amino Acid equence |
|---|---|
| Plasmin cleavable sequences | |
| Pro-urokinase | PRFKIIGG (SEQ ID NO: 137) |
| | PRFRIIGG (SEQ ID NO: 138) |
| TGFβ | SSRHRRALD (SEQ ID NO: 139) |
| Plasminogen | RKSSIIIRMRDVVL (SEQ ID NO: 140) |
| Staphylokinase | SSSFDKGKYKKGDDA (SEQ ID NO: 141) |
| | SSSFDKGKYKRGDDA (SEQ ID NO: 142) |
| Factor Xa cleavable sequences | IEGR (SEQ ID NO: 143) |
| | IDGR (SEQ ID NO: 144) |
| | GGSIDGR (SEQ ID NO: 145) |
| MMP cleavable sequences | |
| Gelatinase A | PLGLWA (SEQ ID NO: 146 |
| Collagenase cleavable sequences | |
| Calf skin collagen (α1(I) chain) | GPQGTAGQ (SEQ ID NO: 147) |
| Calf skin collagen (α2(I) chain) | GPQGLLGA (SEQ ID NO: 148) |
| Bovine cartilage collagen (α1(II) chain) | GTAGQ (SEQ ID NO: 149) |
| Human liver collagen (α1(III) chain) | GPLGTAGT (SEQ ID NO: 150) |
| Human α$_2$M | GPEGLRVG (SEQ ID NO: 151) |
| Human PZP | YGAGLGVV (SEQ ID NO: 152) |
| | AGLGVVER (SEQ ID NO: 153) |
| | AGLGTSST (SEQ ID NO: 154) |
| Rat α$_1$M | EPQALAMS (SEQ ID NO: 155) |
| | QALAMSAI (SEQ ID NO: 156) |
| Rat α$_2$M | AAYHLVSQ (SEQ ID NO: 157) |
| | MDAFLESS (SEQ ID NO: 158) |
| Rat α$_1$I$_3$(2J) | ESLPVVAV (SEQ ID NO: 159) |
| Rat α$_1$I$_3$(27J) | SAPAVESE (SEQ ID NO: 160) |
| Human fibroblast collagenase (autolytic cleavages) | DVAQFVLT (SEQ ID NO: 161) |
| | VAQFVLTE (SEQ ID NO: 162) |
| | AQFVLTEG (SEQ ID NO: 163) |
| | PVQPIGPQ (SEQ ID NO: 164) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In some embodiments, the reducing agent that would modify a CM would also modify the linker of the conjugated activatable antibody.

Spacers and Cleavable Elements:

In some embodiments, it may be necessary to construct the linker in such a way as to optimize the spacing between the agent and the AB of the activatable antibody. This may be accomplished by use of a linker of the general structure:

W-(CH$_2$)$n$-Q wherein
W is either —NH—CH$_2$— or —CH$_2$—;
Q is an amino acid, peptide; and
n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 5.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 7.

TABLE 7

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
| --- | --- | --- | --- |
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines Sulfhydryls | Stable maleimide reactive group Enzyme-antibody conjugation Hapten-carrier protein conjugation | 11.6 Å |

TABLE 7-continued

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
| --- | --- | --- | --- |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be W-(CH$_2$)$_n$-Q wherein
W is either —NH—CH$_2$— or —CH$_2$—;
Q is an amino acid, peptide; and
n is an integer from 0 to 20.

Non-Cleavable Conjugates:

In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments, ≤100 nM and in some embodiments, ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 µM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Green, Eds., Sinauer Associates, Sunderland, Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Antibodies and/or activatable antibodies of the disclosure specifically bind a given target, e.g., a human target protein such as human ITGa3. Also included in the disclosure are antibodies and/or activatable antibodies that bind to the same epitope as the antibodies and/or activatable antibodies described herein. Also included in the disclosure are antibodies and/or antibodies activatable antibodies that compete with an anti-ITGa3 antibody and/or an anti-ITGa3 activatable antibody described herein for binding to ITGa3, e.g., human ITGa3. Also included in the disclosure are antibodies and/or antibodies activatable antibodies that cross-compete with an anti-ITGa3 antibody and/or an anti-ITGa3 activatable antibody described herein for binding to ITGa3, e.g., human ITGa3.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. An alternative method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific anti-ITGa3 activatable antibodies. The multispecific activatable antibodies provided herein are multispecific antibodies that recognize ITGa3 and at least one or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for at least one protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof that binds ITGa3 and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds ITGa3, where the AB2 is attached to a masking moiety (MM2) such that coupling of the MM2 reduces the ability of the AB2 to bind ITGa3. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds ITGa3, where the AB2 is attached to a masking moiety (MM2) such that coupling of the MM2 reduces the ability of the AB2 to bind ITGa3. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the ITGa3-targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a ITGa3-targeting antibody or antigen-binding fragment thereof and a T-cell engaging antibody or antigen-binding portion thereof, where at least one of the ITGa3-targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds ITGa3, where the AB2 is attached to a masking moiety (MM2) such that coupling of the MM2 reduces the ability of the AB2 to bind ITGa3. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds ITGa3, where the AB2 is attached to a masking moiety (MM2) such that coupling of the MM2 reduces the ability of the AB2 to bind ITGa3.

In some embodiments of an immune effector cell engaging multispecific activatable antibody, one antigen is ITGa3, and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PDL1, PDL2, or TNFSF9.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds ITGa3, where the AB2 is attached to a masking moiety (MM2) such that coupling of the MM2 reduces the ability of the AB2 to bind ITGa3. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds ITGa3, where the AB2 is attached to a masking moiety (MM2) such that coupling of the MM2 reduces the ability of the AB2 to bind ITGa3.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a cleavable moiety (CM) is attached to and masks an antigen binding domain of the IgG. In some embodiments, a masking moiety (MM) linked to a cleavable moiety (CM) is attached to and masks an antigen binding domain of at least one scFv. In some embodiments, a masking moiety (MM) linked to a cleavable moiety (CM) is attached to and masks an antigen binding domain of an IgG and a masking moiety (MM) linked to a cleavable moiety (CM) is attached to and masks an antigen binding domain of at least one scFv.

The disclosure provides examples of multispecific activatable antibody structures which include, but are not limited to, the following: (VL-CL)₂:(VH-CH1-CH2-CH3-L4-VH*-L3-VL*-L2-CM-L1-MM)₂; (VL-CL)₂: (VH-CH1-CH2-CH3-L4-VL*-L3-VH*-L2-CM-L1-MM)₂; (MM-L1-CM-L2-VL-CL)₂:(VH-CH1-CH2-CH3-L4-VH*-L3-VL*)₂; (MM-L1-CM-L2-VL-CL)₂:(VH-CH1-CH2-CH3-L4-VL*-L3-VH*)₂; (VL-CL)₂:(MM-L1-CM-L2-VL*-L3-VH*-L4-VH-CH1-CH2-CH3)₂; (VL-CL)₂: (MM-L1-CM-L2-VH*-L3-VL*-L4-VH-CH1-CH2-CH3)₂; (MM-L1-CM-L2-VL-CL)₂:(VL*-L3-VH*-L4-VH-CH1-CH2-CH3)₂; (MM-L1-CM-L2-VL-CL)₂: (VH*-L3-VL*-L4-VH-CH1-CH2-CH3)₂; (VL-CL-L4-VH*-L3-VL*-L2-CM-L1-MM)₂: (VH-CH1-CH2-CH3)₂; (VL-CL-L4-VL*-L3-VH*-L2-CM-L1-MM)₂:(VH-CH1-CH2-CH3)₂; (MM-L1-CM-L2-VL*-L3-VH*-L4-VL-CL)₂:(VH-CH1-CH2-CH3)₂; (MM-L1-CM-L2-VH*-L3-VL*-L4-VL-CL)₂:(VH-CH1-CH2-CH3)₂; (VL-CL-L4-VH*-L3-VL*-L2-CM-L1-MM)₂: (MM-L1-CM-L2-VL*-L3-VH*-L4-VH-CH1-CH2-CH3)₂; (VL-CL-L4-VH*-L3-VL*-L2-CM-L1-MM)₂: (MM-L1-CM-L2-VH*-L3-VL*-L4-VH-CH1-CH2-CH3)₂; (VL-CL-L4-VL*-L3-VH*-L2-CM-L1-M M)₂: (MM-L1-CM-L2-VL*-L3-VH*-L4-VH-CH1-CH2-CH3)₂; (VL-CL-L4-VL*-L3-VH*-L2-CM-L1-MM)₂: (MM-L1-CM-L2-VH*-L3-VL*-L4-VH-CH1-CH2-CH3)₂; (VL-CL-L4-VH*-L3-VL*)₂: (MM-L1-CM-L2-VL*-L3-VH*-L4-VH-CH1-CH2-CH3)₂; (VL-CL-L4-VH*-L3-VL*)₂: (MM-L1-CM-L2-VH*-L3-VL*-L4-VH-CH1-CH2-CH3)₂; (VL-CL-L4-VL*-L3-VH*)₂: (MM-L1-CM-L2-VL*-L3-VH*-L4-VH-CH1-CH2-CH3)₂; (VL-CL-L4-VL*-L3-VH*)₂: (MM-L1-CM-L2-VH*-L3-VL*-L4-VH-CH1-CH2-CH3)₂; (VL-CL-L4-VH*-L3-VL*-L2-CM-L1-MM)₂: (VH*-L3-VH*-L4-VH-CH1-CH2-CH3)₂; (VL-CL-L4-VH*-L3-VL*-L2-CM-L1-MM)₂: (VH*-L3-VL*-L4-VH-CH1-CH2-CH3)₂; (VL-CL-L4-VL*-L3-VH*-L2-CM-L1-MM)₂: (VL*-L3-VH*-

L4-VH-CH1-CH2-CH3)₂; or (VL-CL-L4-VL*-L3-VH*-L2-CM-L1-MM)₂: (VH*-L3-VL*-L4-VH-CH1-CH2-CH3)₂, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is ITGa3, and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor.

In some embodiments, the targeting antibody is an anti-ITGa3 antibody disclosed herein. In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and comprises or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

(SEQ ID NO: 251)
GGGSGGGGSGSGGGSGGGGSGGGEIVLTQSPGTLSLSPGERATLSCRASQ

SVSSSYLAWYQQKPGQAPRLLIYGASSRATGTPDRFSGSGSGTDFTLTIS

RLEPEDFAVYYCQQYGSSPLTFGGGTKVEIKRSGGSTITSYNVYYTKLSS

SGTQVQLVQTGGGVVQPGRSLRLSCAASGSTFSSYAMSWVRQAPGKGLEW

VSAISGSGGSTYYADSVKGRFTISRDNSKNTLYLQMNSLRAEDTAVYYCA

TNSLYWYFDLWGRGTLVTVSSAS

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 251.

In some embodiments, the anti-CDR scFv includes the amino acid sequence:

(SEQ ID NO: 252)
GGGSGGGGSGSGGGSGGGGSGGGQVQLQQSGAELARPGASVKMSCKASGY

TFTRYTMHWVKQRPGQGLEWIGYINPSRGYTNYNQKFKDKATLTTDKSSS

-continued

TAYMQLSSLTSEDSAVYYCARYYDDHYCLDYWGQGTTLTVSSGGGGSGGG

GSGGGGSQIVLTQSPAIMSASPGEKVTMTCSASSSVSYMNWYQQKSGTSP

KRWIYDTSKLASGVPAHFRGSGSGTSYSLTISGMEAEDAATYYCQQWSSN

PFTFGSGTKLEINR

In some embodiments, the anti-CDR scFv includes the amino acid sequence that is at least 90%, 91%, 92%, 93%, 94%, 95%, 96%, 97%, 98%, 99% or more identical to the amino acid sequence of SEQ ID NO: 252.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 5. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody. Suitable AB, MM, and/or CM include any of the AB, MM, and/or CM disclosed herein.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a first cleavable moiety (CM1) sequence that includes a substrate for a protease, for example, a protease that is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody. Suitable AB, MM, and/or CM include any of the AB, MM, and/or CM disclosed herein.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody. Suitable AB, MM, and/or CM include any of the AB, MM, and/or CM disclosed herein.

In some embodiments, the multispecific activatable antibody further includes at least one cleavable moiety (CM) that is a substrate for a protease, where the CM links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first cleavable moiety (CM1) to a masking moiety (MM1) that decreases the ability of AB1 to bind its target. In some bispecific activatable antibody embodiments, AB1 is coupled via CM1 to MM1, and AB2 is coupled via a second cleavable moiety (CM2) to a second masking moiety (MM2) that decreases the ability of AB2 to bind its target. In some embodiments, the multispecific activatable antibody comprises more than two AB regions; in some of these embodiments, AB1 is coupled via CM1 to MM1, AB2 is coupled via CM2 to MM2, and AB3 is coupled via a third cleavable moiety (CM3) to a third masking moiety (MM3) that decreases the ability of AB3 to bind its target, and so on for each AB in the multispecific activatable antibody. Suitable AB, MM, and/or CM include any of the AB, MM, and/or CM disclosed herein.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a cleavable linker (CL) and antibody or antibody fragment (AB) that binds a target; an activatable antibody that includes a binding partner for a non-binding steric moiety (BP), a CL and an AB; and an activatable antibody that includes a BP to which an NB has been recruited, a CL and an AB that binds the target. Activatable antibodies in which the NB is covalently linked to the CL and AB of the activatable antibody or is associated by interaction with a BP that is covalently linked to the CL and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

Anti-ITGa3 activatable antibodies that include a non-binding steric moiety (NB) can be made using the methods set forth in PCT Publication No. WO 2013/192546, the contents of which are hereby incorporated by reference in their entirety.

Use of Antibodies, Conjugated Antibodies, Activatable Antibodies, and Conjugated Activatable Antibodies It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include an anti-ITGa3 antibody and/or activatable anti-ITGa3 antibody, such as by way of non-limiting example, an antibody, a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include an antibody, a conjugated antibody, an activatable antibody and/or a conjugated activatable antibody, are used to treat or otherwise ameliorate a cancer or other neoplastic condition, inflammation, an inflammatory disorder, and/or an autoimmune disease. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the antibody and/or the activatable antibody is conjugated is a microtubule inhibitor. In some embodiments, the agent to which the antibody and/or the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the antibody, conjugated antibody, activatable antibody and/or conjugated activatable antibody confers a clinical benefit.

An antibody, a conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the antibody, the conjugated antibody, activatable antibody and/or conjugated activatable antibody contains a detectable label. An intact antibody, or a fragment thereof (e.g., Fab, scFv, or F(ab)$_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The antibodies, conjugated antibodies, activatable antibodies and/or conjugated activatable antibodies of the disclosure are also useful in a variety of diagnostic and prophylactic formulations. In one embodiment, an antibody, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments of the disclosure, an antibody, a conjugated antibody, an activatable antibody and/or a conjugated activatable antibody is administered to human individuals diagnosed with a clinical indication associated with one or more of the aforementioned disorders. Upon diagnosis, an antibody, a conjugated antibody, an activatable antibody and/or a conjugated activatable antibody is administered to mitigate or reverse the effects of the clinical indication.

An antibody, a conjugated antibody, an activatable antibody, and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, an antibody, a conjugated antibody, an activatable antibody and/or a conjugated activatable antibody of the disclosure is immobilized on a solid support (e.g., the well(s) of a microtiter plate). The immobilized antibody, conjugated antibody, activatable antibody and/or conjugated activatable antibody serves as a capture antibody for any target that may be present in a test sample. Prior to contacting the immobilized antibody and/or activatable antibody, and/or conjugated versions thereof, with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies and activatable antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

An antibody, a conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be substrate for at least one protease found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with at least one protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease that is specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the activatable antibody.

These techniques are also useful in kits and/or as reagents for the detection, identification or characterization of protease activity in a variety of cells, tissues, and organisms based on the protease-specific CM in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a cleavable moiety (CM) that is cleaved by the cleaving agent, e.g., a protease, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a cleavable moiety (CM) that is cleaved by the cleaving agent, e.g., a protease, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a cleavable moiety (CM) that is cleaved by the cleaving agent, e.g., a protease, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a cleavable moiety (CM) that is cleaved by the cleaving agent, e.g., a protease, an antigen binding domain (AB) that specifically binds the target, and a detectable label, wherein the activatable antibody in an uncleaved, non-activated state comprises a structural arrangement from N-terminus to C-terminus as follows: MM-CM-AB or AB-CM-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, e.g., a protease, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, e.g., a protease, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target (e.g., the target) and the protease that cleaves the substrate in the CM in the activatable antibody being tested using these methods might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the activatable antibody for which the patient tested positive.

In some embodiments in vivo imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested in these methods are identified as suitable candidates for treatment with such an activatable antibody comprising such a CM. Likewise, patients that test negative for both of the targets (e.g., the target) and the protease that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease). In some embodiments, patients that test negative for either of the target (e.g., the target) are identified as suitable candidates for treatment with such an activatable antibody comprising such a CM. In some embodiments, patients that test negative for either of the target (e.g., the target) are identified as not being suitable candidates for treatment with such an activatable antibody comprising such a CM. In some embodiments, such patients can be tested with other activatable antibodies until a suitable activatable antibody for treatment is identified (e.g., an activatable antibody comprising a CM that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the substrate in the cleavable moiety (CM) of the activatable antibody and/or conjugated activatable antibody being tested in these methods are identified as suitable candidates for treatment with such antibody and/or such a conjugated activatable antibody comprising such a CM, and the patient is then administered a therapeutically effective amount of the activatable antibody and/or conjugated activatable antibody that was tested. Likewise, patients that test negative for either or both of the target (e.g., the target) and the protease that cleaves the substrate in the CM in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM that is cleaved by the patient at the site of disease). In some embodiments, the patient is then administered a therapeutically effective amount of the activatable antibody and/or conjugated activatable antibody for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM. In some embodiments of these methods and kits, the activatable antibody comprises a linker peptide, where the linker peptide is positioned between the AB and the CM. In some embodiments of these methods and kits, the activatable antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 165) and (GGGS)n (SEQ ID NO: 166), where n is an integer of at least one. In some embodiments of these methods and kits, at least one of L1 and L2 comprises an amino acid sequence having the formula $(GGS)_n$, where n is an integer of at least one. In some embodiments of these methods and kits, at least one of L1 and L2 comprises an amino acid sequence selected from the group consisting of Gly-Gly-Ser-Gly (SEQ ID NO: 167, Gly-Gly-Ser-Gly-Gly (SEQ ID NO: 168), Gly-Ser-Gly-Ser-Gly (SEQ ID NO: 169, Gly-Ser-Gly-Gly-Gly (SEQ ID NO: 170), Gly-Gly-Gly-Ser-Gly (SEQ ID NO: 171), and Gly-Ser-Ser-Ser-Gly (SEQ ID NO: 172).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM is a polypeptide that functions as a substrate for the protease, wherein the protease cleaves the CM in the activatable antibody when the activatable antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

The antibodies, conjugated antibodies, activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments of the disclosure, an antibody, a conjugated antibody, an activatable antibody and/or a conjugated activatable antibody is administered to human individuals diagnosed with a clinical indication associated with one or more of the aforementioned disorders. Upon diagnosis, an antibody, a conjugated antibody, an activatable antibody and/or a conjugated activatable antibody is administered to mitigate or reverse the effects of the clinical indication.

Antibodies, conjugated antibodies, activatable antibodies and/or conjugated activatable antibodies of the disclosure are also useful in the detection of the target in patient samples and accordingly are useful as diagnostics. For example, the antibodies, conjugated antibodies, the activatable antibodies and/or conjugated activatable antibodies of the disclosure are used in in vitro assays, e.g., ELISA, to detect target levels in a patient sample.

In one embodiment, an antibody and/or activatable antibody of the disclosure is immobilized on a solid support (e.g., the well(s) of a microtiter plate). The immobilized antibody and/or activatable antibody serves as a capture antibody for any target that may be present in a test sample. Prior to contacting the immobilized antibody and/or activatable antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies and/or activatable antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Antibodies, conjugated antibodies, activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the activatable antibody.

These techniques are also useful in kits and/or as reagents for the detection, identification or characterization of protease activity in a variety of cells, tissues, and organisms based on the protease-specific CM in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target and the protease that cleaves the substrate in the CM in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

In some embodiments in vivo imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

Pharmaceutical Compositions

The antibodies, conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the antibody, the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Characterization of Anti-ITGa3 Antibodies

The studies provided herein were designed to evaluate binding of anti-ITGa3 antibodies of the disclosure.

Binding of various anti-ITGa3 antibodies of the disclosure was confirmed by ELISA (FIG. 1). The following anti-ITGa3 antibodies of the present disclosure were tested: Lc1/Hc1 (VH of SEQ ID NO: 3 and VL of SEQ ID NO: 11); Lc2/Hc1 (VH of SEQ ID NO: 3 and VL of SEQ ID NO: 12); Lc1/Hc1A (VH of SEQ ID NO: 5 and VL of SEQ ID NO: 11), Lc2/Hc1A (VH of SEQ ID NO: 5 and VL of SEQ ID NO: 12), Lc1/Hc1G (VH of SEQ ID NO: 6 and VL of SEQ ID NO: 11), Lc2/Hc1G (VH of SEQ ID NO: 7 and VL of SEQ ID NO: 11), Lc1/Hc1S (VH of SEQ ID NO: 4 and VL of SEQ ID NO: 11), and Lc1/Hc1S (VH of SEQ ID NO: 4 and VL of SEQ ID NO: 12).

The antibody ITGa3-VM2 (VH of SEQ ID NO: 1, VL of SEQ ID NO: 2) was used as a positive control. The VM2 antibody is a mouse IgG1 monoclonal antibody produced by the ATCC HB-8530 hybridoma, and described in U.S. Pat. No. 4,886,745. The anti-ITGa3 antibodies of the present disclosure are humanized versions of the VM2 antibody.

This Example and FIG. 1 show that various humanized anti-ITGa3 antibodies of the present disclosure can bind ITGa3 polypeptide. In this study, an ITGa3 binding ELISA was used to evaluate the binding of the humanized VM2 sequences of the present disclosure. Using a standard ELISA protocol, human ITGa3 protein was absorbed to ELISA plates and subsequently incubated with the indicated concentration of anti-ITGa3 antibody. Bound humanized antibody was detected with an anti-human FAB-peroxidase secondary, and bound mVM2 was detected with an anti-mouse FAB-peroxidase secondary.

Example 2. Mask Discovery

The studies provided herein were designed to identify and characterize masking moieties for use in activatable anti-ITGa3 antibodies of the disclosure.

Figure 2:
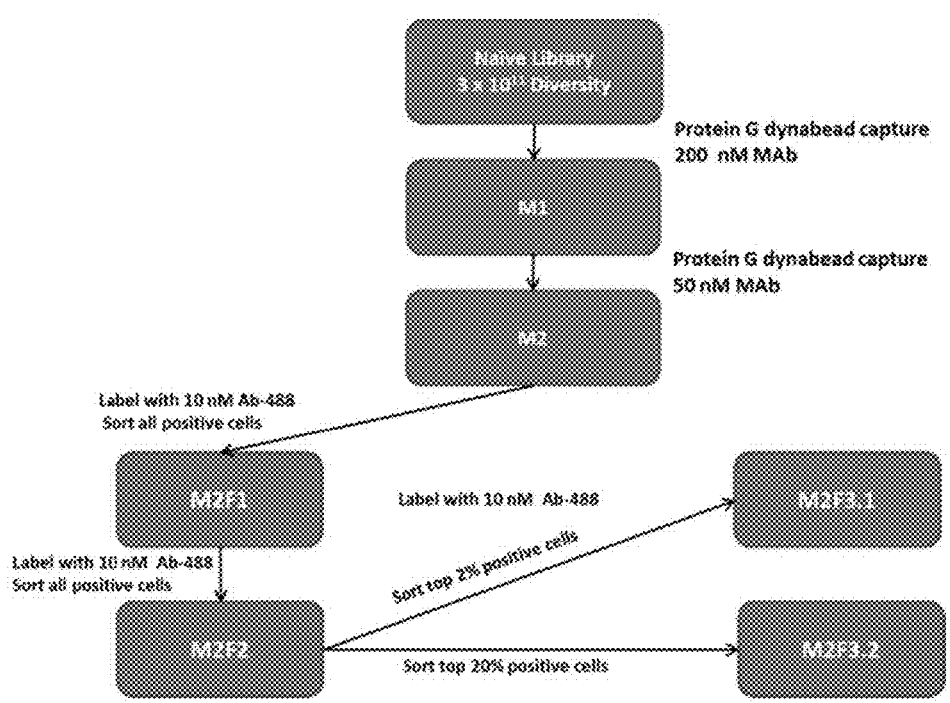
FIG. 2 is a schematic representation of the initial screening and sorting of masking peptides of the disclosure.

In this study, mouse anti-ITGa3 Mab VM2 (VH of SEQ ID NO: 1 and VL of SEQ ID NO: 2) was used to screen a cysteine-constrained random $X_{15}$ peptide library with a total diversity of $3\times10^{11}$, where X is any amino acid, using a method similar to that described in PCT International Publication Number WO 2010/081173, published 15 Jul. 2010. The screening consisted of two rounds of MACS and three rounds of FACS sorting. The sort process is outlined in FIG. 2.

Individual clones from the F3.1 and F3.2 populations were sequenced and certain of the masking moieties are shown in Table A.

TABLE A

Anti-ITGa3 masking moieties (MM)

| Clone # | sequence |
|---|---|
| VM2 F3 | |
| 570 | ECKTRQDFEMHDCVY (SEQ ID NO: 22) |
| 674 | TCHDPYMNIDYTCKL (SEQ ID NO: 23) |
| 686 | VMCYWEGWGFGRCPL (SEQ ID NO: 24) |
| 691 | VWYCDGGYNECATRS (SEQ ID NO: 25) |
| VM2 F3.1 | |
| 574 | QCMSRFAFEIGDCVM (SEQ ID NO: 26) |
| 693 | AVWCDAYNKNMCWST (SEQ ID NO: 27) |
| 695 | VWYCDGGYNECATRS (SEQ ID NO: 28) |
| 696 | ECKTRQDFEMHDCVY (SEQ ID NO: 29) |
| 697 | KCHDPYINIDYTCNN (SEQ ID NO: 30) |
| 700 | LITCEMLMLKNCEKN (SEQ ID NO: 31) |
| 701 | LGCKKQHHTNNTCDR (SEQ ID NO: 32) |
| 702 | TCHDPYMNIDYTCKL (SEQ ID NO: 33) |
| 710 | VMCYWEGWGFGRCPL (SEQ ID NO: 34) |

Figure 3:
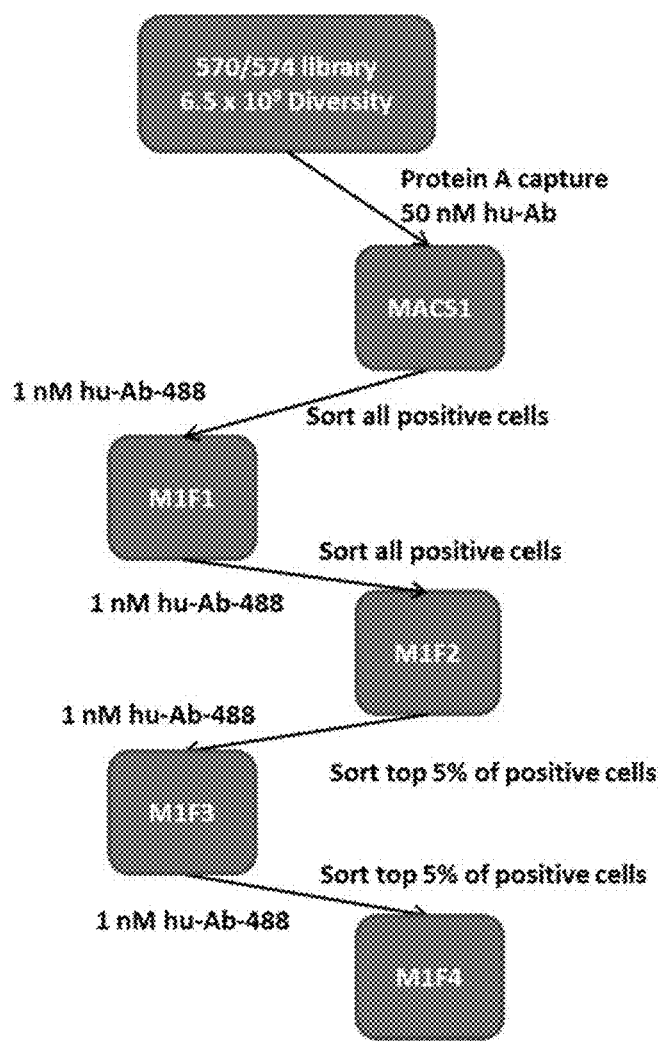
FIG. 3 is a schematic representation of the affinity maturation of the masking peptides of the disclosure.

To affinity mature masking peptides, a library designed using peptides 570 (SEQ ID NO: 22) and 574 (SEQ ID NO: 26) was constructed. The humanized VM2 antibody consisting of the vHc2 (SEQ ID NO: 7) and vLc1 (SEQ ID NO: 11) was used to screen a library as outlined in FIG. 3. Certain of the affinity-matured masking moieties are shown in Table B.

570/574 combination library design where x equals any amino acid xCxxRxxFExxDCVx (SEQ ID NO: 55)

TABLE B

| 570/574 Maturation Library Masking Peptides | |
|---|---|
| 2321 | TCPTRWHFETTDCVM (SEQ ID NO: 35) |
| 2322 | TCGSRLDFELNDCVM (SEQ ID NO: 36) |
| 2323 | WCRDRSHFETGDCVM (SEQ ID NO: 37) |
| 2324 | TCTSRWEFENRDCVM (SEQ ID NO: 38) |
| 2325 | VCRDRNEFEVGDCVM (SEQ ID NO: 39) |
| 2326 | TCKNRLEFERGDCVM (SEQ ID NO: 40) |
| 2327 | VCSSRLEFEQKDCVM (SEQ ID NO: 41) |
| 2329 | WCRDREHFEKGDCVM (SEQ ID NO: 42) |
| 2330 | YCANRYEFEYGDCVM (SEQ ID NO: 43) |
| 2331 | TCLSRYEFETTDCVM (SEQ ID NO: 44) |
| 2332 | VCRTRWHFETTDCVM (SEQ ID NO: 45) |
| 2333 | VCSNRAEFEWGDCVM (SEQ ID NO: 46) |
| 2334 | VCASRWHFENTDCVM (SEQ ID NO: 47) |
| 2335 | NCASRWHFENEDCVM (SEQ ID NO: 48) |
| 2337 | VCSGRLEFELGDCVM (SEQ ID NO: 49) |

TABLE B -continued

570/574 Maturation Library Masking Peptides

| | | |
|---|---|---|
| 2338 | VCSSRWEFETNDCVM | (SEQ ID NO: 50) |
| 2339 | FCRDLDFDTMDCVM | (SEQ ID NO: 51) |
| 2341 | CCMDRLEFERGDCVM | (SEQ ID NO: 52) |
| 2342 | VCGSRNEFETGDCVM | (SEQ ID NO: 53) |
| 2343 | MCSGRLEFETGDCVM | (SEQ ID NO: 54) |

These masking peptides of the present disclosure were used to generate anti-ITGa3 activatable antibodies of the disclosure. The sequences for certain of these anti-ITGa3 activatable antibodies are shown below in Table C. It is envisioned that anti-ITGa3 activatable antibodies of the present disclosure can include cleavable moiety 2001 (ISSGLLSGRSDNH; SEQ ID NO: 232) or cleavability moiety 3001 (AVGLLAPPGGLSGRSDNH; SEQ ID NO: 238), as indicated.

While certain sequences shown below include the spacer sequence of SEQ ID NO: 253, those of ordinary skill in the art appreciate that the activatable anti-ITGa3 antibodies of the disclosure can include any suitable spacer sequence, such as, for example, a spacer sequence selected from the group consisting of QGQSGQG (SEQ ID NO: 253), QGQSGQ (SEQ ID NO: 250), QGQSGQ (SEQ ID NO: 267), QGQSG (SEQ ID NO: 268), QGQS (SEQ ID NO: 269), QGQ (SEQ ID NO: 270), QG (SEQ ID NO: 271), GQSGQG (SEQ ID NO: 272), QSGQG (SEQ ID NO: 273), SGQG (SEQ ID NO: 274), GQG (SEQ ID NO: 275), G, or Q. In some embodiments, the anti-ITGa3 activatable antibodies of the present disclosure can have no spacer sequence joined to its N-terminus.

TABLE C

Anti-ITGa3 Activatable Antibody Sequences huVM2 Hc2T62G Heavy Chain:
Amino Acid sequence
QVQLVQSGAEVKKPGSSVKVSCKASGYTFTEYIIHWVRQAPGQGLEWIGWFYPESGSVKYNEGFKGRATI
TADKSTSTAYMELSSLRSEDTAVYYCARHEERDYYGYYAMDYWGQGTTVTVSSASTKGPSVFPLAPSSKS
TSGGTAALGCLVKDYFPEPVTVSWNSGALTSGVHTFPAVLQSSGLYSLSSVVTVPSSSLGTQTYTCNVNH
KPSNTKVDKKVEPKSCDKTHTCPPCPAPELLGGPSVFLFPPKPKDTLMISRTPEVTCVVVDVSHEDPEVK
FNWYVDGVEVHNAKTKPREEQYNSTYRVVSVLIVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 320)

Nucleotide sequence
CAGGTGCAGCTGGTGCAGTCTGGCGCCGAAGTGAAGAAACCCGGCTCCTCCGTGAAGGTGTCCTGCAAGG
CCTCCGGCTACACCTTCACCGAGTACATCATCCACTGGGTGCGACAGGCCCCAGGCCAGGGCCTGGAATG
GATCGGCTGGTTCTACCCCGAGTCCGGCTCCGTGAAGTACAACGAGGGCTTCAAGGGCAGAGCCACCATC
ACCGCCGACAAGTCCACCTCCACCGCCTACATGGAACTGTCCTCCCTGCGGAGCGAGGACACCGCCGTGT
ACTACTGCGCCAGACACGAGGAACGGGACTACTACGGCTACTACGCCATGGACTACTGGGGCCAGGGCAC
CACCGTGACCGTGTCCTCTGCCTCCACCAAGGGCCCCTCCGTGTTCCCTCTGGCCCCCTCCAGCAAGTCC
ACATCTGGCGGCACCGCCGCTCTGGGCTGCCTGGTGAAAGACTACTTCCCCGAGCCTGTGACAGTGTCCT
GGAACTCTGGCGCCCTGACCTCTGGCGTGCACACCTTCCCTGCCGTGCTGCAGTCCTCCGGCCTGTACTC
CCTGTCCTCCGTGGTGACAGTGCCCTCCTCCAGCCTGGGCACCCAGACCTACATCTGCAACGTGAACCAC
AAGCCCTCCAACACCAAGGTGGACAAGAAGGTGGAACCCAAGTCCTGCGACAAGACCCACACCTGTCCCC
CCTGCCCTGCCCCTGAACTGCTGGGCGGACCTTCCGTGTTTCTGTTCCCCCCAAAGCCCAAGGACACCCT
GATGATCTCCCGGACCCCCGAAGTGACCTGCGTGGTGGTGGACGTGTCCCACGAGGACCCTGAAGTGAAG
TTCAATTGGTACGTGGACGGCGTGGAAGTGCACAACGCCAAGACCAAGCCCAGAGAGGAACAGTACAACT
CCACCTACCGGGTGGTGTCCGTGCTGACCGTGCTGCACCAGGACTGGCTGAACGGCAAAGAGTACAAGTG
CAAGGTGTCCAACAAGGCCCTGCCTGCCCCCATCGAAAAGACCATCTCCAAGGCCAAGGGCCAGCCCCGC
GAGCCCCAGGTGTACACACTGCCCCCTAGCCGGGAAGAGATGACCAAGAACCAGGTGTCCCTGACCTGTC
TGGTGAAAGGCTTCTACCCCTCCGATATCGCCGTGGAATGGGAGTCCAACGGCCAGCCCGAGAACAACTA
CAAGACCACCCCCCCTGTGCTGGACTCCGACGGCTCATTCTTCCTGTACTCCAAGCTGACCGTGGACAAG
TCCCGGTGGCAGCAGGGCAACGTGTTCTCCTGCAGCGTGATGCACGAGGCCCTGCACAACCACTACACCC
AGAAGTCCCTGTCCCTGAGCCCCGGCAAG (SEQ ID NO: 321)

huVM2 Hc2 Heavy Chain:
Amino Acid sequence
QVQLVQSGAEVKKPGSSVKVSCKASGYTFTEYIIHWVRQAPGQGLEWIGWFYPESGSVKYNETFTGRATI
TADKSTSTAYMELSSLRSEDTAVYYCARHEERDYYGYYAMDYWGQGTTVTVSSASTKGPSVFPLAPSSKS
TSGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEVK
FNWYVDGVEVHNAKTKPREEQYNSTYRVVSVLIVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGK (SEQ ID NO: 254)

huVM2 Lc1 Light Chain
Amino Acid Sequence
DIQMTQSPSSLSASVGDRVTITCSASSSISSNYLHWYQQKPGKVPKLLIYRTSNLASGVPSRFSGSGSGT
DYTLTISSLQPEDVATYYCQQGSSIPRFTSGGGTKVEIKRTVAAPSVFIFPPSDEQLKSGTASVVCLLNN
FYPREAKVQWKVDNALQSGNSQESVTEQDSKDSTYSLSSTLTLSKADYEKHKVYACEVTHQGLSSPVTKS
FNRGEC (SEQ ID NO: 322)

huVM2 Lc1 Light Chain
Nucleotide Sequence
GACATCCAGATGACCCAGTCCCCATCCAGCCTGTCCGCCTCCGTGGGCGACAGAGTGACAATCACCTGTT
CCGCCAGCTCCTCCATCTCCAGCAACTACCTGCACTGGTATCAGCAGAAACCCGGCAAGGTGCCCAAGCT
GCTGATCTACCGGACCTCCAACCTGGCCTCCGGCGTGCCCTCCAGATTCTCCGGCTCTGGCTCCGGCACC
GACTACACCCTGACCATCAGCTCCCTGCAGCCCGAGGACGTGGCCACCTACTACTGCCAGCAGGGCTCCA

TABLE C -continued

Anti-ITGa3 Activatable Antibody Sequences

```
GCATCCCCCGGTTCACCTCTGGCGGAGGCACCAAGGTGGAAATCAAGCGGACCGTGGCCGCTCCCTCCGT
GTTCATCTTCCCACCCTCCGACGAGCAGCTGAAGTCCGGCACCGCCAGCGTCGTGTGCCTGCTGAACAAC
TTCTACCCCCGCGAGGCCAAGGTGCAGTGGAAGGTGGACAACGCCCTGCAGTCCGGCAACTCCCAGGAAT
CCGTCACCGAGCAGGACTCCAAGGACAGCACCTACTCCCTGTCCTCCACCCTGACCCTGTCCAAGGCCGA
CTACGAGAAGCACAAGGTGTACGCCTGCGAAGTGACCCACCAGGGCCTGTCCAGCCCCGTGACCAAGTCC
TTCAACCGCGGCGAGTGC (SEQ ID NO: 323)
```

[spacer (SEQ ID NO: 253)][huVM2 Lc1 570-2001 Light Chain (SEQ ID NO: 255)]
Amino Acid sequence
[QGQSGQG][ECKTRQDFEMHDCVYGGGSSGGSISSGLLSGRSDNHGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIKRTVAAPSVFIFPPSDEQLKSGTASVVCLLNNFYPREAKVQWKVDNALQSGN
SQESVIEQDSKDSTYSLSSILTLSKADYEKHKVYACEVTHQGLSSPVIKSENRGEC] (SEQ ID NO: 324)

[spacer (SEQ ID NO: 265)][huVM2 Lc1 570-2001 Light Chain (SEQ ID NO: 256)]
Nucleotide sequence
```
[CAGGGCCAGTCTGGACAGGGCHGAGTGCAAGACCCGGCAGGACTTCGAGATGCACGACTGCGTGTACG
GCGGAGGCTCCTCCGGCGGCTCCATCTCCTCTGGCCTGCTGTCCGGCAGATCCGACAACCATGGCGGCGG
ATCCGACATCCAGATGACCCAGTCCCCATCCAGCCTGTCCGCCTCCGTGGGCGACAGAGTGACAATCACC
TGTTCCGCCAGCTCCTCCATCTCCAGCAACTACCTGCACTGGTATCAGCAGAAACCCGGCAAGGTGCCCA
AGCTGCTGATCTACCGGACCTCCAACCTGGCCTCCGGCGTGCCCTCCAGATTCTCCGGCTCTGGCTCCGG
CACCGACTACACCCTGACCATCAGCTCCCTGCAGCCCGAGGACGTGGCCACCTACTACTGCCAGCAGGGC
TCCAGCATCCCCCGGTTCACCTCTGGCGGAGGCACCAAGGTGGAAATCAAGCGGACCGTGGCCGCTCCCT
CCGTGTTCATCTTCCCACCCTCCGACGAGCAGCTGAAGTCCGGCACCGCCAGCGTCGTGTGCCTGCTGAA
CAACTTCTACCCCCGCGAGGCCAAGGTGCAGTGGAAGGTGGACAACGCCCTGCAGTCCGGCAACTCCCAG
GAATCCGTCACCGAGCAGGACTCCAAGGACAGCACCTACTCCCTGTCCTCCACCCTGACCCTGTCCAAGG
CCGACTACGAGAAGCACAAGGTGTACGCCTGCGAAGTGACCCACCAGGGCCTGTCCAGCCCCGTGACCAA
GTCCTTCAACCGCGGCGAGTGC] (SEQ ID NO: 325)
```

[spacer (SEQ ID NO: 253)][huVM2 Lc1 574-2001 Light Chain (SEQ ID NO: 257)]
Amino Acid sequence
[QGQSGQG][QCMSRFAFEIGDCVMGGGSSGGSISSGLLSGRSDNHGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC] (SEQ ID NO: 326)

[spacer (SEQ ID NO: 266)][huVM Lc1 574-2001 Light Chain (SEQ ID NO: 258)]
Nucleotide sequence
```
[CAAGGCCAGTCTGGCCAGGGT][CAGTGCATGTCACGTTTTGCTTTTGAGATTGGTGATTGCGTTATGG
GAGGTGGCTCGAGCGGCGGCTCTATCTCTTCCGGACTGCTGTCCGGCAGATCCGACAATCACGGCGGAGG
CTCTGACATCCAGATGACCCAGTCCCCATCCAGCCTGTCCGCCTCCGTGGGCGACAGAGTGACAATCACC
TGTTCCGCCAGCTCCTCCATCTCCAGCAACTACCTGCACTGGTATCAGCAGAAACCCGGCAAGGTGCCCA
AGCTGCTGATCTACCGGACCTCCAACCTGGCCTCCGGCGTGCCCTCCAGATTCTCCGGCTCTGGCTCCGG
CACCGACTACACCCTGACCATCAGCTCCCTGCAGCCCGAGGACGTGGCCACCTACTACTGCCAGCAGGGC
TCCAGCATCCCCCGGTTCACCTCTGGCGGAGGCACCAAGGTGGAAATCAAGCGGACCGTGGCCGCTCCCT
CCGTGTTCATCTTCCCACCCTCCGACGAGCAGCTGAAGTCCGGCACCGCCAGCGTCGTGTGCCTGCTGAA
CAACTTCTACCCCCGCGAGGCCAAGGTGCAGTGGAAGGTGGACAACGCCCTGCAGTCCGGCAACTCCCAG
GAATCCGTCACCGAGCAGGACTCCAAGGACAGCACCTACTCCCTGTCCTCCACCCTGACCCTGTCCAAGG
CCGACTACGAGAAGCACAAGGTGTACGCCTGCGAAGTGACCCACCAGGGCCTGTCCAGCCCCGTGACCAA
GTCCTTCAACCGCGGCGAGTGC] (SEQ ID NO: 327)
```

[spacer (SEQ ID NO: 253)][huVM Lc1 2331-2001 Light Chain (SEQ ID NO: 259)]
Amino Acid sequence
[QGQSGQG][TCLSRY E FETTDCVMGGGSSGGSISSGLLSGRSDNHGGGSDIVMTQTPTTLAASPGEKII
ITCSASSSISSNYLHTNYQQKPGES PKLL TY RTSNLASGVPARFSGSGSGTSYSLT IGTMEAEDVATYYCQ
QGSSI PRETSGSGT KLEIKRTVAAPSVFIFPPSDEQLKSGTASVVCLLNNFY PREAKVQWKVDNALQSGN
SQESVT EQDSKDSTYSLSSTLTLSKADY EKHKVYACEVTHQGLSSPVT KS FNRGEC] (SEQ ID NO: 328)

[spacer (SEQ ID NO: 266)][huVM Lc1 2331-2001 Light Chain (SEQ ID NO: 260)]
Nucleotide sequence
```
[CAAGGCCAGTCTGGCCAGGGT][ACGTGCCTGAGTAGGTATGAGTTTGAGACGACTGATTGCGTTATGG
GAGGTGGCTCGAGCGGCGGCTCTATCTCTTCCGGACTGCTGTCCGGCAGATCCGACAATCACGGCGGAGG
CTCTGACATCCAGATGACCCAGTCCCCATCCAGCCTGTCCGCCTCCGTGGGCGACAGAGTGACAATCACC
TGTTCCGCCAGCTCCTCCATCTCCAGCAACTACCTGCACTGGTATCAGCAGAAACCCGGCAAGGTGCCCA
AGCTGCTGATCTACCGGACCTCCAACCTGGCCTCCGGCGTGCCCTCCAGATTCTCCGGCTCTGGCTCCGG
CACCGACTACACCCTGACCATCAGCTCCCTGCAGCCCGAGGACGTGGCCACCTACTACTGCCAGCAGGGC
TCCAGCATCCCCCGGTTCACCTCTGGCGGAGGCACCAAGGTGGAAATCAAGCGGACCGTGGCCGCTCCCT
CCGTGTTCATCTTCCCACCCTCCGACGAGCAGCTGAAGTCCGGCACCGCCAGCGTCGTGTGCCTGCTGAA
CAACTTCTACCCCCGCGAGGCCAAGGTGCAGTGGAAGGTGGACAACGCCCTGCAGTCCGGCAACTCCCAG
GAATCCGTCACCGAGCAGGACTCCAAGGACAGCACCTACTCCCTGTCCTCCACCCTGACCCTGTCCAAGG
CCGACTACGAGAAGCACAAGGTGTACGCCTGCGAAGTGACCCACCAGGGCCTGTCCAGCCCCGTGACCAA
GTCCTTCAACCGCGGCGAGTGC] (SEQ ID NO: 329)
```

TABLE C -continued

Anti-ITGa3 Activatable Antibody Sequences

[spacer (SEQ ID NO: 253)][huVM Lc1 2332-2001 Light Chain (SEQ ID NO: 261)]
Amino Acid sequence
[QGQSGQG][VCRTRWHFETTDCVMGGGSSGGSISSGLLSGRSDNHGGGSDIVMTQTPTTLAASPGEKII
ITCSASSSISSNYLHWYQQKPGESPKLLTYRTSNLASGVPARFSGSGSGTSYSLTIGTMEAEDVATYYCQ
QGSSIPRETSGSGTKLEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC] (SEQ ID NO: 330)

[spacer (SEQ ID NO: 266)][huVM Lc1 2332-2001 Light Chain (SEQ ID NO: 262)]
Nucleotide sequence
[CAAGGCCAGTCTGGCCAGGGT][GTGTGCCGGACTAGGTGGCATTTTGAGACTACGGATGCGTTATGG
GAGGTGGCTCGAGCGGCGGCTCTATCTCTTCCGGACTGCTGTCCGGCAGATCCGACAATCACGGCGGAGG
CTCTGACATCCAGATGACCCAGTCCCCATCCAGCCTGTCCGCCTCCGTGGGCGACAGAGTGACAATCACC
TGTTCCGCCAGCTCCTCCATCTCCAGCAACTACCTGCACTGGTATCAGCAGAAACCCGGCAAGGTGCCCA
AGCTGCTGATCTACCGGACCTCCAACCTGGCCTCCGGCGTGCCCTCCAGATTCTCCGGCTCTGGCTCCGG
CACCGACTACACCCTGACCATCAGCTCCCTGCAGCCCGAGGACTTCGCCACCTACTACTGCCAGCAGGGC
TCCAGCATCCCCCGGTTCACCTCTGGCGGAGGCACCAAGGTGGAAATCAAGCGGACCGTGGCCGCTCCCT
CCGTGTTCATCTTCCCACCCTCCGACGAGCAGCTGAAGTCCGGCACCGCCAGCGTCGTGTGCCTGCTGAA
CAACTTCTACCCCCGCGAGGCCAAGGTGCAGTGGAAGGTGGACAACGCCCTGCAGTCCGGCAACTCCCAG
GAATCCGTCACCGAGCAGGACTCCAAGGACAGCACCTACTCCCTGTCCTCCACCCTGACCCTGTCCAAGG
CCGACTACGAGAAGCACAAGGTGTACGCCTGCGAAGTGACCCACCAGGGCCTGTCCAGCCCCGTGACCAA
GTCCTTCAACCGCGGCGAGTGC] (SEQ ID NO: 331)

[spacer (SEQ ID NO: 253)][huVM Lc1 570-2001 VL (SEQ ID NO: 436)]
Amino Acid sequence
[QGQSGQG][ECKTRQDFEMHDCVYGGGSSGGSISSGLLSGRSDNHGGGSDIQMTQSPSSLSASVGDRVT
ITCSASSSISSNYLHWYQQKPGKVPKLLTYRTSNLASGVPSRFSGSGSGTDYTLTISSLQPEDVATYYCQ
QGSSIPRFTSGGGTKVEIK] (SEQ ID NO: 396)

[spacer (SEQ ID NO: 253)][huVM Lc1 574-2001 VL (SEQ ID NO: 438)]
Amino Acid sequence
[QGQSGQG][QCMSRFAFEIGDCVMGGGSSGGSISSGLLSGRSDNHGGGSDIQMTQSPSSLSASVGDRVT
ITCSASSSISSNYLHWYQQKPGKVPKLLTYRTSNLASGVPSRFSGSGSGTDYTLTISSLQPEDVATYYCQ
QGSSIPRFTSGGGTKVEIK] (SEQ ID NO: 398)

[spacer (SEQ ID NO: 253)][huVM Lc1 2331-2001 VL (SEQ ID NO: 4440)]
Amino Acid sequence
[QGQSGQG][TCLSRYEFETTDCVMGGGSSGGSISSGLLSGRSDNHGGGSDIVMTQTPTTLAASPGEKII
ITCSASSSISSNYLHWYQQKPGESPKLLTYRTSNLASGVPARFSGSGSGTSYSLTIGTMEAEDVATYYCQ
QGSSIPRFTSGSGTKLEIK] (SEQ ID NO: 400)

[spacer (SEQ ID NO: 253)][huVM Lc1 2332-2001 VL (SEQ ID NO: 402)]
Amino Acid sequence
[QGQSGQG][VCRTRWHFETTDCVMGGGSSGGSISSGLLSGRSDNHGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIK] (SEQ ID NO: 402)

[spacer (SEQ ID NO: 253)][huVM Lc1 570-3001 Light Chain (SEQ ID NO: 364)]
Amino Acid sequence
[QGQSGQG][ECKTRQDFEMHDCVYGGGSSGGSAVGLLAPPGGLSGRSDNHGGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID
NO: 332)

[spacer (SEQ ID NO: 253)][huVM Lc1 574-3001 LIGHT CHAIN (SEQ ID NO: 365)]
Amino Acid sequence
[QGQSGQG][QCMSRFAFEIGDCVMGGGSSGGSAVGLLAPPGGLSGRSDNHGGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID
NO: 333)

[spacer (SEQ ID NO: 253)][huVM Lc1 2331-3001 LIGHT CHAIN (SEQ ID NO: 366)]
Amino Acid sequence
[QGQSGQG][TCLSRYEFETTDCVMGGGSSGGSAVGLLAPPGGLSGRSDNHGGGSDIVMTQTPTTLAASPG
EKIIITCSASSSISSNYLHTNYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID
NO: 334)

[spacer (SEQ ID NO: 253)][huVM Lc1 2332-3001 LIGHT CHAIN (SEQ ID NO: 367)]
Amino Acid sequence
[QGQSGQG][VCRTRWHFETTDCVMGGGSSGGSAVGLLAPPGGLSGRSDNHGGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID
NO: 335)

TABLE C -continued

Anti-ITGa3 Activatable Antibody Sequences

[spacer (SEQ ID NO: 253)][huVM Lc1 570-3001 VL (SEQ ID NO: 444)]
Amino Acid sequence
[QGQSGQG][ECKTRQDFEMHDCVYGGGSSGGSAVGLLAPPGGLSGRSDNHGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 404)

[spacer (SEQ ID NO: 253)][huVM Lc1 574-3001 VL (SEQ ID NO: 445)]
Amino Acid sequence
[QGQSGQG][QCMSRFAFEIGDCVMGGGSSGGSAVGLLAPPGGLSGRSDNHGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 405)

[spacer (SEQ ID NO: 253)][huVM Lc1 2331-3001 VL (SEQ ID NO: 446)]
Amino Acid sequence
[QGQSGQG][TCLSRYEFETTDCVMGGGSSGGSAVGLLAPPGGLSGRSDNHGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIK] (SEQ ID NO: 406)

[spacer (SEQ ID NO: 253)][huVM Lc1 2332-3001 VL (SEQ ID NO: 447)]
Amino Acid sequence
[QGQSGQG][VCRTRWHFETTDCVMGGGSSGGSAVGLLAPPGGLSGRSDNHGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIK] (SEQ ID NO: 407)

[spacer (SEQ ID NO: 253)][huVM Lc1 570-2008 Light Chain (SEQ ID NO: 368)]
Amino Acid sequence
[QGQSGQG][ECKTRQDFEMHDCVYGGGSSGGSISSGLLSGRSDQHGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 336)

[spacer (SEQ ID NO: 253)][huVM Lc1 574-2008 LIGHT CHAIN (SEQ ID NO: 369)]
Amino Acid sequence
[QGQSGQG][QCMSRFAFEIGDCVMGGGSSGGSISSGLLSGRSDQHGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 337)

[spacer (SEQ ID NO: 253)][huVM Lc1 2331-2008 LIGHT CHAIN (SEQ ID NO: 370)]
Amino Acid sequence
[QGQSGQG][TCLSRYEFETTDCVMGGGSSGGSISSGLLSGRSDQHGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 338)

[spacer (SEQ ID NO: 253)][huVM Lc1 2332-2008 LIGHT CHAIN (SEQ ID NO: 371)]
Amino Acid sequence
[QGQSGQG][VCRTRWHFETTDCVMGGGSSGGSISSGLLSGRSDQHGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 339)

[spacer (SEQ ID NO: 253)][huVM Lc1 570-2008 VL (SEQ ID NO: 448)]
Amino Acid sequence
[QGQSGQG][ECKTRQDFEMHDCVYGGGSSGGSISSGLLSGRSDQHGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIK] (SEQ ID NO: 408)

[spacer (SEQ ID NO: 253)][huVM Lc1 574-2008 VL (SEQ ID NO: 449)]
Amino Acid sequence
[QGQSGQG][QCMSRFAFEIGDCVMGGGSSGGSISSGLLSGRSDQHGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIK] (SEQ ID NO: 409)

[spacer (SEQ ID NO: 253)][huVM Lc1 2331-2008 VL (SEQ ID NO: 450)]
Amino Acid sequence
[QGQSGQG][TCLSRYEFETTDCVMGGGSSGGSISSGLLSGRSDQHGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIK] (SEQ ID NO: 410)

[spacer (SEQ ID NO: 253)][huVM Lc1 2332-2008 VL (SEQ ID NO: 451)]
Amino Acid sequence
[QGQSGQG][VCRTRWHFETTDCVMGGGSSGGSISSGLLSGRSDQHGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIK] (SEQ ID NO: 411)

TABLE C -continued

Anti-ITGa3 Activatable Antibody Sequences

[spacer (SEQ ID NO: 253)][huVM Lc1 570-3008 Light Chain (SEQ ID NO: 372)]
Amino Acid sequence
[QGQSGQG][ECKTRQDFEMHDCVYGGGSSGGSAVGLLAPPGGLSGRSDQHGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 340)

[spacer (SEQ ID NO: 253)][huVM Lc1 574-3008 LIGHT CHAIN (SEQ ID NO: 373)]
Amino Acid sequence
[QGQSGQG][QCMSRFAFEIGDCVMGGGSSGGSAVGLLAPPGGLSGRSDQHGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 341)

[spacer (SEQ ID NO: 253)][huVM Lc1 2331-3008 LIGHT CHAIN (SEQ ID NO: 374)]
Amino Acid sequence
[QGQSGQG][TCLSRYEFETTDCVMGGGSSGGSAVGLLAPPGGLSGRSDQHGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 342)

[spacer (SEQ ID NO: 253)][huVM Lc1 2332-3008 LIGHT CHAIN (SEQ ID NO: 375)]
Amino Acid sequence
[QGQSGQG][VCRTRWHFETTDCVMGGGSSGGSAVGLLAPPGGLSGRSDQHGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 343)

[spacer (SEQ ID NO: 253)][huVM Lc1 570-3008 VL (SEQ ID NO: 452)]
Amino Acid sequence
[QGQSGQG][ECKTRQDFEMHDCVYGGGSSGGSAVGLLAPPGGLSGRSDQHGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 412)

[spacer (SEQ ID NO: 253)][huVM Lc1 574-3008 VL (SEQ ID NO: 453)]
Amino Acid sequence
[QGQSGQG][QCMSRFAFEIGDCVMGGGSSGGSAVGLLAPPGGLSGRSDQHGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 413)

[spacer (SEQ ID NO: 253)][huVM Lc1 2331-3008 VL (SEQ ID NO: 454)]
Amino Acid sequence
[QGQSGQG][TCLSRYEFETTDCVMGGGSSGGSAVGLLAPPGGLSGRSDQHGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIK] (SEQ ID NO: 414)

[spacer (SEQ ID NO: 253)][huVM Lc1 2332-3008 VL (SEQ ID NO: 455)]
Amino Acid sequence
[QGQSGQG][VCRTRTA7HFETTDCVMGGGSSGGSAVGLLAPPGGLSGRSDQHGGSDIVMTQTPTTLAASPG
EKIIITCSASSSISSNYLHTNYQQKPGESPKLL IYRTSNLASGVPARFSGSGSGTSYSLTIGTMEAEDVAT
YYCQQGSSIPRFTSGSGTKLEIK] (SEQ ID NO: 415)

[spacer (SEQ ID NO: 253)][huVM Lc1 570-2011 Light Chain (SEQ ID NO: 376)]
Amino Acid sequence
[QGQSGQG][ECKTRQDFEMHDCVYGGGSSGGSISSGLLSGRSDNPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRETSGGGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC] (SEQ ID NO: 344)

[spacer (SEQ ID NO: 253)][huVM Lc1 574-2011 LIGHT CHAIN (SEQ ID NO: 377)]
Amino Acid sequence
[QGQSGQG][QCMSRFAFEIGDCVMGGGSSGGSISSGLLSGRSDNPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRETSGGGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC] (SEQ ID NO: 345)

[spacer (SEQ ID NO: 253)][huVM Lc1 2331-2011 LIGHT CHAIN (SEQ ID NO: 378)]
Amino Acid sequence
[QGQSGQG][TCLSRYEFETTDCVMGGGSSGGSISSGLLSGRSDNPGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 346)

TABLE C -continued

Anti-ITGa3 Activatable Antibody Sequences

[spacer (SEQ ID NO: 253)][huVM Lc1 2332-2011 LIGHT CHAIN (SEQ ID NO: 379)]
Amino Acid sequence
[QGQSGQG][VCRTRWHFETTDCVMGGGSSGGSISSGLLSGRSDNPGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSENRGEC] (SEQ ID NO: 347)

[spacer (SEQ ID NO: 253)][huVM Lc1 570-2011 VL (SEQ ID NO: 456)]
Amino Acid sequence
[QGQSGQG][ECKTRQDFEMHDCVYGGGSSGGSISSGLLSGRSDNPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIK] (SEQ ID NO: 416)

[spacer (SEQ ID NO: 253)][huVM Lc1 574-2011 VL (SEQ ID NO: 457)]
Amino Acid sequence
[QGQSGQG][QCMSRFAFEIGDCVMGGGSSGGSISSGLLSGRSDNPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIK] (SEQ ID NO: 417)

[spacer (SEQ ID NO: 253)][huVM Lc1 2331-2011 VL (SEQ ID NO: 458)]
Amino Acid sequence
[QGQSGQG][TCLSRYEFETTDCVMGGGSSGGSISSGLLSGRSDNPGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIK] (SEQ ID NO: 418)

[spacer (SEQ ID NO: 253)][huVM Lc1 2332-2011 VL (SEQ ID NO: 459)]
Amino Acid sequence
[QGQSGQG][VCRTRWHFETTDCVMGGGSSGGSISSGLLSGRSDNPGGGSDIVMTQTPTTLAASPGEKII
ITCSASSSISSNYLHWYQQKPGESPKLLIYRTSNLASGVPARFSGSGSGTSYSLTIGTMEAEDVATYYCQ
QGSSIPRFTSGSGTKLEIK] (SEQ ID NO: 419)

[spacer (SEQ ID NO: 253)][huVM Lc1 570-3011 Light Chain (SEQ ID NO: 380)]
Amino Acid sequence
[QGQSGQG][ECKTRQDFEMHDCVYGGGSSGGSAVGLLAPPGGLSGRSDNPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSENRGEC] (SEQ ID NO: 348)

[spacer (SEQ ID NO: 253)][huVM Lc1 574-3011 LIGHT CHAIN (SEQ ID NO: 381)]
Amino Acid sequence
[QGQSGQG][QCMSRFAFEIGDCVMGGGSSGGSAVGLLAPPGGLSGRSDNPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSENRGEC] (SEQ ID NO: 349)

[spacer (SEQ ID NO: 253)][huVM Lc1 2331-3011 LIGHT CHAIN (SEQ ID NO: 382)]
Amino Acid sequence
[QGQSGQG][TCLSRYEFETTDCVMGGGSSGGSAVGLLAPPGGLSGRSDNPGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSENRGEC] (SEQ ID NO: 350)

[spacer (SEQ ID NO: 253)][huVM Lc1 2332-3011 LIGHT CHAIN (SEQ ID NO: 283)]
Amino Acid sequence
[QGQSGQG][VCRTRWHFETTDCVMGGGSSGGSAVGLLAPPGGLSGRSDNPGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSENRGEC] (SEQ ID NO: 351)

[spacer (SEQ ID NO: 253)][huVM Lc1 570-3011 VL (SEQ ID NO: 460)]
Amino Acid sequence
[QGQSGQG][ECKTRQDFEMHDCVYGGGSSGGSAVGLLAPPGGLSGRSDNPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 420)

[spacer (SEQ ID NO: 253)][huVM Lc1 574-3011 VL (SEQ ID NO: 461)]
Amino Acid sequence
[QGQSGQG][QCMSRFAFEIGDCVMGGGSSGGSAVGLLAPPGGLSGRSDNPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 421)

[spacer (SEQ ID NO: 253)][huVM Lc1 2331-3011 VL (SEQ ID NO: 462)]
Amino Acid sequence
[QGQSGQG][TCLSRYEFETTDCVMGGGSSGGSAVGLLAPPGGLSGRSDNPGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIK] (SEQ ID NO: 422)

TABLE C -continued

Anti-ITGa3 Activatable Antibody Sequences

[spacer (SEQ ID NO: 253)][huVM Lc1 2332-3011 VL (SEQ ID NO: 463)]
Amino Acid sequence
[QGQSGQG][VCRTRTA7HFETTDCVMGGGSSGGSAVGLLAPPGGLSGRSDNPGGSDIVMTQTPTTLAASPG
EKIIITCSASSSISSNYLHTNYQQKPGESPKLLIYRTSNLASGVPARFSGSGSTSYSLTIGTMEAEDVAT
YYCQQGSSIPRFTSGSGTKLEIK] (SEQ ID NO: 423)

[spacer (SEQ ID NO: 253)][huVM Lc1 570-2012 Light Chain (SEQ ID NO: 384)]
Amino Acid sequence
[QGQSGQG][ECKTRQDFEMHDCVYGGGSSGGSISSGLLSGRSANPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 352)

[spacer (SEQ ID NO: 253)][huVM Lc1 574-2012 LIGHT CHAIN (SEQ ID NO: 385)]
Amino Acid sequence
[QGQSGQG][QCMSRFAFEIGDCVMGGGSSGGSISSGLLSGRSANPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 353)

[spacer (SEQ ID NO: 253)][huVM Lc1 2331-2012 LIGHT CHAIN (SEQ ID NO: 386)]
Amino Acid sequence
[QGQSGQG][TCLSRYEFETTDCVMGGGSSGGSISSGLLSGRSANPGGGSDIVMTQTPTTLAASPGEKII
ITCSASSSISSNYLHWYQQKPGESPKLLIYRTSNLASGVPARFSGSGSTSYSLTIGTMEAEDVATYYCQ
QGSSIPRFTSGSGTKLEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSENRGEC] (SEQ ID NO: 354)

[spacer (SEQ ID NO: 253)][huVM Lc1 2332-2012 LIGHT CHAIN (SEQ ID NO: 387)]
Amino Acid sequence
[QGQSGQG][VCRTRWHFETTDCVMGGGSSGGSISSGLLSGRSANPGGGSDIVMTQTPTTLAASPGEKII
ITCSASSSISSNYLHWYQQKPGESPKLLIYRTSNLASGVPARFSGSGSTSYSLTIGTMEAEDVATYYCQ
QGSSIPRFTSGSGTKLEIKRTVAAPSVFIFPPSDEQLKSGTASVVCLLNNEYPREAKVQWKVDNALQSGN
SQESVTEQDSKDSTYSLSSTLTLSKADYEKHKVYACEVTHQGLSSPVTKSFNRGEC] (SEQ ID NO: 355)

[spacer (SEQ ID NO: 253)][huVM Lc1 570-2012 VL (SEQ ID NO: 464)]
Amino Acid sequence
[QGQSGQG][ECKTRQDFEMHDCVYGGGSSGGSISSGLLSGRSANPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIK] (SEQ ID NO: 424)

[spacer (SEQ ID NO: 253)][huVM Lc1 574-2012 VL (SEQ ID NO: 465)]
Amino Acid sequence
[QGQSGQG][QCMSRFAFEIGDCVMGGGSSGGSISSGLLSGRSANPGGGSDIQMTQSPSSLSASVGDRVT
ITCSASSSISSNYLHWYQQKPGKVPKLLIYRTSNLASGVPSRFSGSGSGTDYTLTISSLQPEDVATYYCQ
QGSSIPRFTSGGGTKVEIK] (SEQ ID NO: 425)

[spacer (SEQ ID NO: 253)][huVM Lc1 2331-2012 VL (SEQ ID NO: 466)]
Amino Acid sequence
[QGQSGQG][TCLSRYEFETTDCVMGGGSSGGSISSGLLSGRSANPGGGSDIVMTQTPTTLAASPGEKII
ITCSASSSISSNYLHWYQQKPGFSPKLLIYRTSNLASGVPARFSGSGSTSYSLTIGTMEAEDVATYYCQ
QGSSIPRFTSGSGTKLEIK] (SEQ ID NO: 426)

[spacer (SEQ ID NO: 253)][huVM Lc1 2332-2012 VL (SEQ ID NO: 467)]
Amino Acid sequence
[QGQSGQG][VCRTRWHFETTDCVMGGGSSGGSISSGLLSGRSANPGGGSDIVMTQTPTTLAASPGEKII
ITCSASSSISSNYLHWYQQKPGFSPKLLIYRTSNLASGVPARFSGSGSTSYSLTIGTMEAEDVATYYCQ
QGSSIPRFTSGSGTKLEIK] (SEQ ID NO: 427)

[spacer (SEQ ID NO: 253)][huVM Lc1 570-3012 Light Chain (SEQ ID NO: 388)]
Amino Acid sequence
[QGQSGQG][ECKTRQDFEMHDCVYGGGSSGGSAVGLLAPPGGLSGRSANPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSENRGEC] (SEQ ID NO: 356)

[spacer (SEQ ID NO: 253)][huVM Lc1 574-3012 LIGHT CHAIN (SEQ ID NO: 389)]
Amino Acid sequence
[QGQSGQG][QCMSRFAFEIGDCVMGGGSSGGSAVGLLAPPGGLSGRSANPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 357)

[spacer (SEQ ID NO: 253)][huVM Lc1 2331-3012 LIGHT CHAIN (SEQ ID NO: 390)]
Amino Acid sequence
[QGQSGQG][TCLSRYEFETTDCVMGGGSSGGSAVGLLAPPGGLSGRSANPGGSDIVMTQTPTTLAASPG
EKIIITCSASSSISSNYLHWYQQKPGESPKLLIYRTSNLASGVPARFSGSGSTSYSLTIGTMEAEDVAT
YYCQQGSSIPRFTSGSGTKLEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 358)

TABLE C -continued

Anti-ITGa3 Activatable Antibody Sequences

```
[spacer (SEQ ID NO: 253)][huVM Lc1 2332-3012 LIGHT CHAIN (SEQ ID NO: 391)]
Amino Acid sequence
[QGQSGQG][VCRTRWHFETTDCVMGGGSSGGSAVGLLAPPGGLSGRSANPGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIKRTVAAPSVFIFPPSDEQLKSGTASVVCLLNNEYPREAKVQWKVDNAL
QSGNSQESVTEQDSKDSTYSLSSTLTLSKADYEKHKVYACEVTHQGLSSPVTKSENRGEC] (SEQ ID NO: 359)

[spacer (SEQ ID NO: 253)][huVM Lc1 570-3012 VL (SEQ ID NO: 468)]
Amino Acid sequence
[QGQSGQG][ECKTRQDFEMHDCVYGGGSSGGSAVGLLAPPGGLSGRSANPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 428)

[spacer (SEQ ID NO: 253)][huVM Lc1 574-3012 VL (SEQ ID NO: 469)]
Amino Acid sequence
[QGQSGQG][QCMSRFAFEIGDCVMGGGSSGGSAVGLLAPPGGLSGRSANPGGSDIQMTQSPSSLSASVG
DRVTITCSASSSISSNYLHWYQQKPGKVPKLLIYRTSNLASGVPSRFSGSGSGTDYTLTISSLQPEDVAT
YYCQQGSSIPRFTSGGGTKVEIK] (SEQ ID NO: 429)

[spacer (SEQ ID NO: 253)][huVM Lc1 2331-3012 VL (SEQ ID NO: 470)]
Amino Acid sequence
[QGQSGQG][TCLSRYEFETTDCVMGGGSSGGSAVGLLAPPGGLSGRSANPGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIK] (SEQ ID NO: 430)

[spacer (SEQ ID NO: 253)][huVM Lc1 2332-3012 VL (SEQ ID NO: 471)]
Amino Acid sequence
[QGQSGQG][VCRTRWHFETTDCVMGGGSSGGSAVGLLAPPGGLSGRSANPGGSDIVMTQTPTTLAASPG
EKIIITCSASSSISSNYLHWYQQKPGESPKLLIYRTSNLASGVPARFSGSGSGTSYSLTIGTMEAEDVAT
YYCQQGSSIPRFTSGSGTKLEIK] (SEQ ID NO: 431)
```

Example 3. Generation and Characterization of Activatable Anti-ITGa3 Antibodies

The studies provided herein were designed to generate activatable anti-ITGa3 antibodies of the present disclosure.

Figure 4:
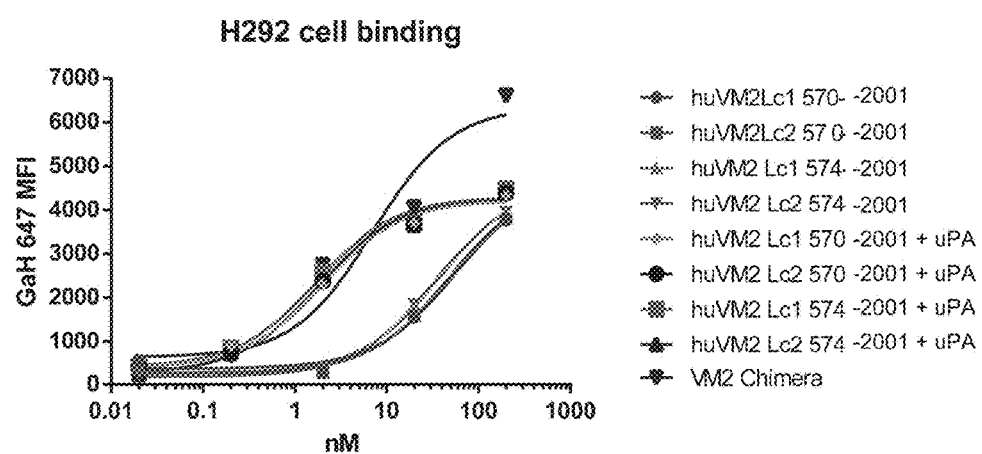
FIG. 4 is a graph depicting the ability of various anti-ITGa3 activatable antibodies of the disclosure to bind human ITGa3 when proteolytically activated.

FIG. 4 shows that certain of the anti-ITGa3 activatable antibodies of the present disclosure showed a range of masking efficiencies when binding ITGa3 on H292 cells compared to the VM2 chimera anti-ITGa3 antibody. FIG. 4 also shows that proteolytic activation the anti-ITGa3 activatable antibodies of the present disclosure with uPA protease resulted in recovery of binding ability to the H292 cells to one of that similar to the binding ability of the VM2 anti-ITGa3 antibody. In this study, In this study, the binding of activatable anti-ITGa3 antibodies of the present disclosure comprising the VH of SEQ ID NO: 7, a VL selected from the VL of SEQ ID NO: 11 and the VL of SEQ ID NO: 12, with a masking moiety selected from the 570 masking moiety (SEQ ID NO: 22) and the 574 masking moiety (SEQ ID NO: 26), and the CM1 substrate comprising the sequence ISSGLLSGRSDNH (SEQ ID NO: 232) to the H292 cell line was evaluated using a cell-binding FACS assay. The VM2 chimera (VH of SEQ ID NO: 1 and VL of SEQ ID NO: 2) was used for comparison. Using a standard labeling protocol for FACS, cells were labeled with anti-ITGa3 antibody or anti-ITGa3 activatable antibody of the present disclosure at the indicated concentrations, and the bound antibody was detected with a goat anti-human IgG Alexa Fluor 647 secondary antibody.

Figure 5A:
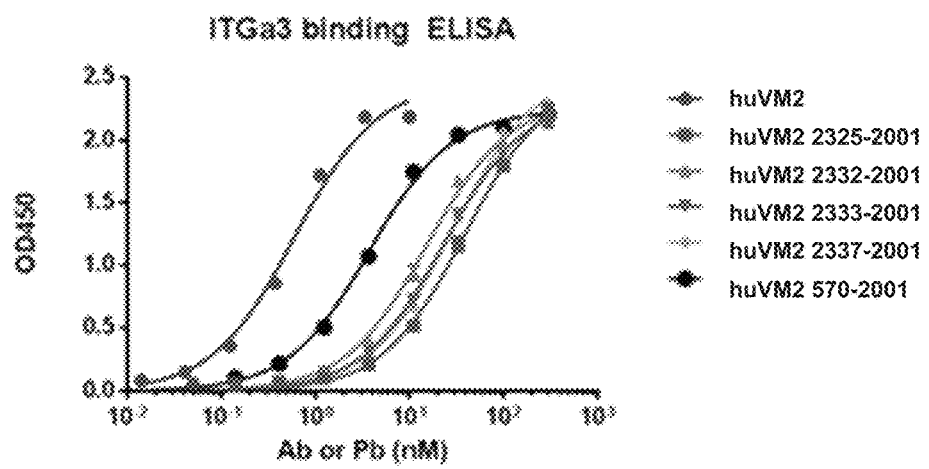
FIGS. 5A, 5B, and 5C provide graphs depicting activatable anti-ITGa3 antibodies of the disclosure that include an affinity-matured masking moiety (MM) have better masking efficiency than the activatable anti-ITGa3 antibodies that include a non-affinity matured MM.
Figure 5B:
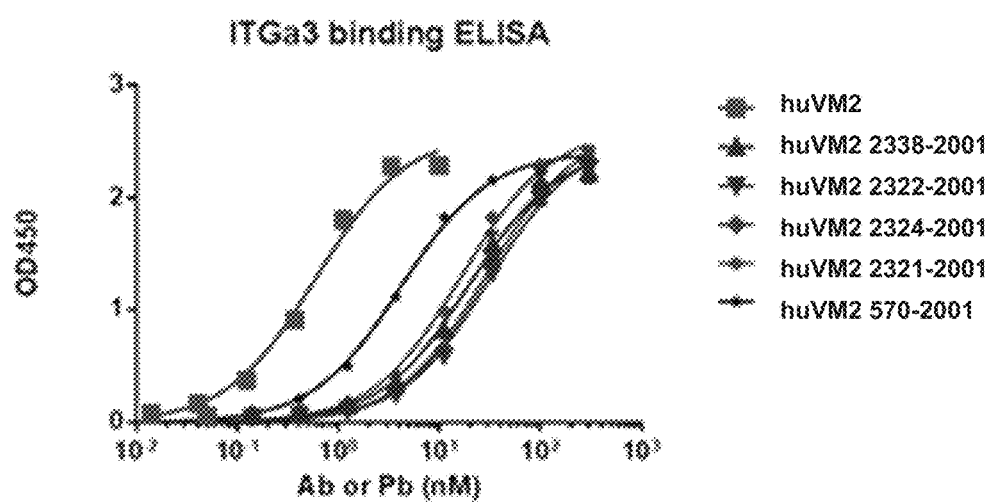
Figure 5C:
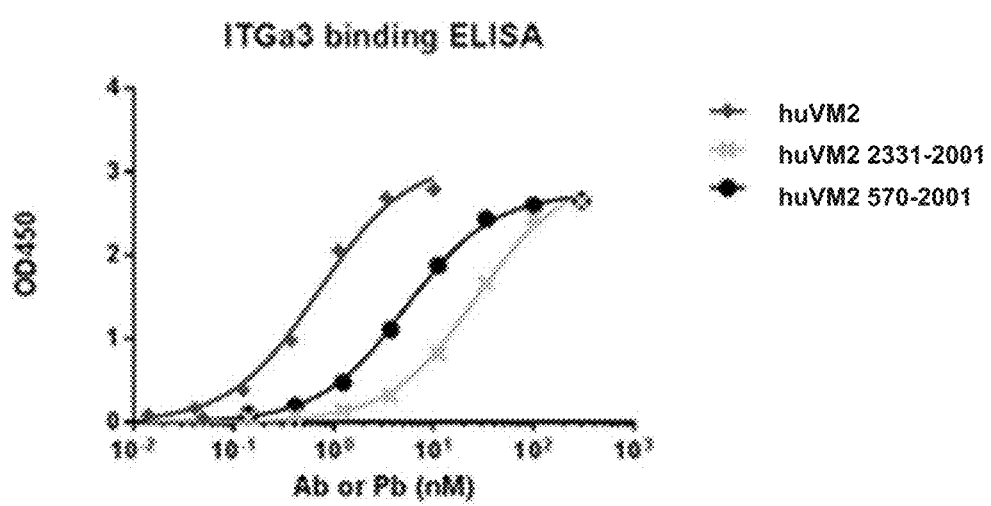

FIG. 5 shows that activatable anti-ITGa3 antibodies of the present disclosure that include the VH of SEQ ID NO: 10 and the VL of SEQ ID NO: 11 with masks from the 570/574 affinity maturation library show better masking efficiencies than an activatable anti-ITGa3 antibody of the present disclosure that includes the 570 mask. This study used the antibody huVM2 of the present disclosure (VH of SEQ ID NO: 7 and VL of SEQ ID NO: 11) and the activatable anti-ITGa3 antibodies of the present disclosure having the VH of SEQ ID NO: 10, the VL of SEQ ID NO: 11, the MM of SEQ ID NOS: 35, 36, 38, 39, 44, 45, 46, 49, or 50 (corresponding respectively to masking moieties nos. 2321, 2322, 2324, 2325, 2331, 2332, 2333, 2337 or 2338 as shown in Table C), and the CM1 sequence of SEQ ID NO: 232, and the activatable anti-ITGa3 antibody of the present disclosure having the VH of SEQ ID NO: 10, the VL of SEQ ID NO: 11, the MM of SEQ ID NO: 22, and the CM1 sequence of SEQ ID NO: 232 ("huVM2 570-2001"). In this study, the ability of anti-ITGa3 antibody and activatable anti-ITGa3 antibodies of the present disclosure to bind ITGa3 polypeptide were evaluated using a ITGa3 binding ELISA. Using a standard ELISA protocol, human ITGa3 protein was absorbed to ELISA plates and subsequently incubated with the indicated concentration of anti-ITGa3 antibody or activatable anti-ITGa3 antibody of the present disclosure. Bound anti-ITGa3 antibody or activatable anti-ITGa3 antibody of the present disclosure were detected with an anti-human FAB-peroxidase secondary.

Figure 6:
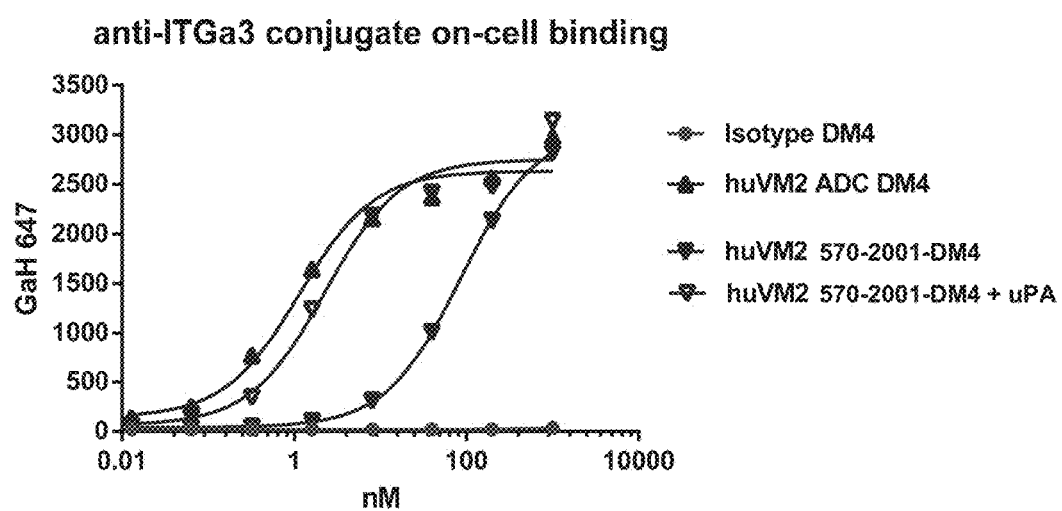
FIG. 6 is a graph comparing the ability of a conjugated activatable anti-ITGa3 antibody of the disclosure to bind human ITGa3 when the AADC was intact or proteolytically-activated.

FIG. 6 shows that anti-ITGa3 activatable antibody drug conjugate (AADC) of the present disclosure demonstrates a masking efficiency when binding to HCC1806 cells compared to an anti-ITGa3 antibody drug conjugate (ADC) of the present disclosure, and the anti-ITGa3 AADC shows equivalent binding to the anti-ITGa3 ADC after proteolytic activation of the former with uPA protease. In this study, the binding of the huVM2 ADC of the present disclosure (VH of SEQ ID NO: 7, VL of SEQ ID NO: 11, conjugated to DM4), a conjugated activatable anti-ITGa3 antibody of the present disclosure having the VH of SEQ ID NO: 7, VL of SEQ ID NO: 11, the 570 masking moiety of SEQ ID NO: 22, the CM1 sequence of SEQ ID NO: 232, conjugated to DM4; and activated (i.e., cleaved) conjugated activatable anti-ITGa3 antibody having the VH of SEQ ID NO: 7, VL of SEQ ID NO: 11, the 570 masking moiety of SEQ ID NO: 22, the CM1 sequence of SEQ ID NO: 232, conjugated to DM4 were evaluated on HCC1806 cells. In this study, using a standard labeling protocol for FACS, the bound anti-ITGa3 antibody, the anti-ITGa3 activatable antibody of the present disclosure, or the uPA-activated anti-ITGa3 activatable antibody of the present disclosure was detected with a goat anti-human IgG-Alexa Fluor 647 secondary antibody.

Figure 7:
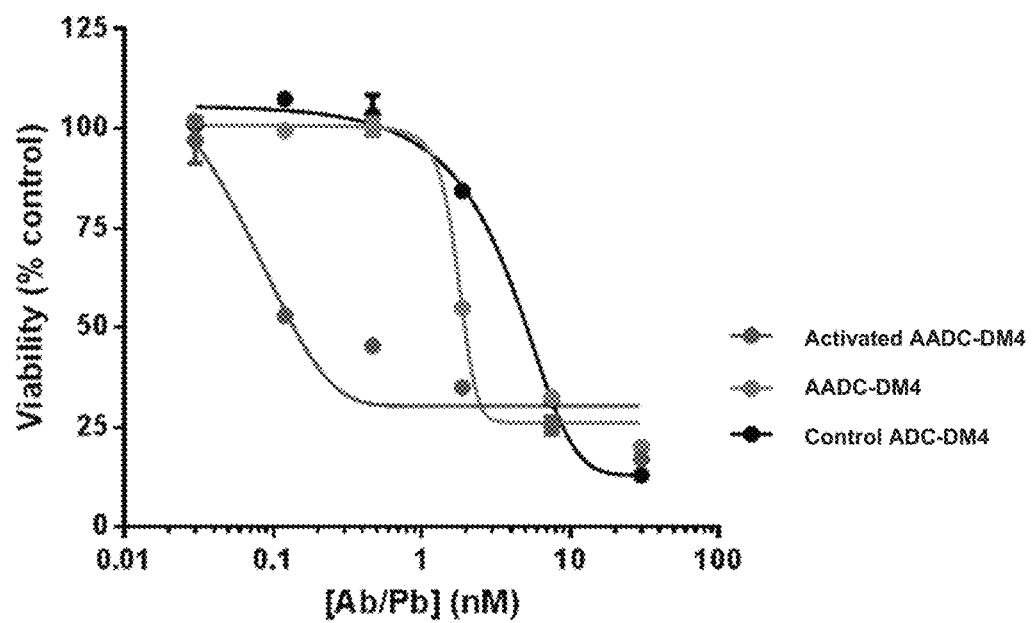
FIG. 7 is a graph depicting the in vitro cytotoxicity of intact and activated conjugated anti-ITGa3 activatable antibodies of the disclosure.

FIG. 7 shows that conjugated activatable antibody of the present disclosure ("AADC-DM4") demonstrated a lower cytotoxicity to HCC1806 cells compared to an unmasked conjugated anti-ITGa3 antibody, but activation of such AADC led to recovery of toxicity. In this study, the cytotoxicity of the huVM2 ADC of the present disclosure (VH of SEQ ID NO: 7, VL of SEQ ID NO: 11, conjugated to DM4; "Control ADC-DM4"), a conjugated activatable anti-ITGa3 antibody of the present disclosure having the VH of SEQ ID NO: 10, VL of SEQ ID NO: 11, the 570 masking moiety of SEQ ID NO: 22, the CM1 sequence of SEQ ID NO: 232, conjugated to DM4 ("AADC-DM4"); and activated (i.e., cleaved) conjugated activatable anti-ITGa3 antibody of the present disclosure having the VH of SEQ ID NO: 10, VL of SEQ ID NO: 11, the 570 masking moiety of SEQ ID NO: 22, the CM1 sequence of SEQ ID NO: 232, conjugated to DM4 ("Activated AADC-DM4") were evaluated for cytotoxicity to HCC1806 cells. All DM4-conjugated activatable antibodies disclosed herein were produced by TCRS (The Chemistry Research Solution).

Figure 8A:
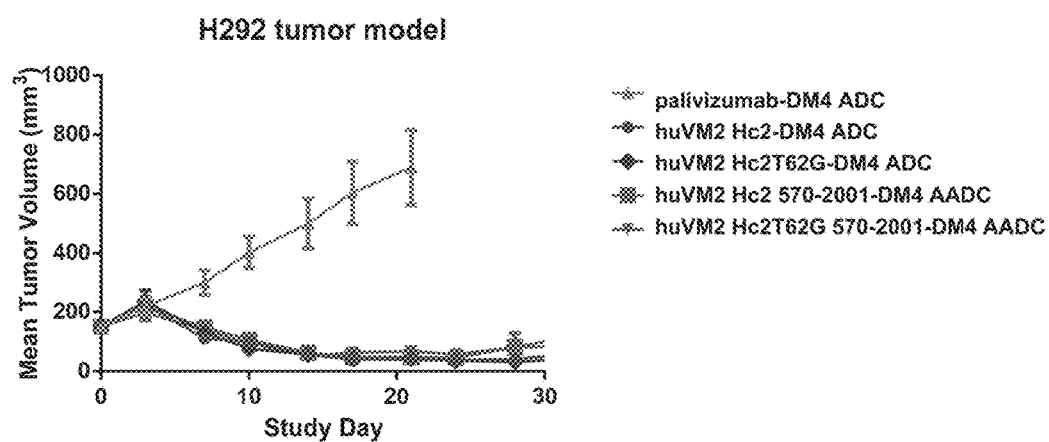
FIGS. 8A and 8B are graphs that depict the efficacy of a conjugated activatable anti-ITGa3 antibody of the disclosure in a NCI H292 (also referred to herein as H292) model and in a non-small cell lung cancer (NSCLC) xenograft tumor model.
Figure 8B:
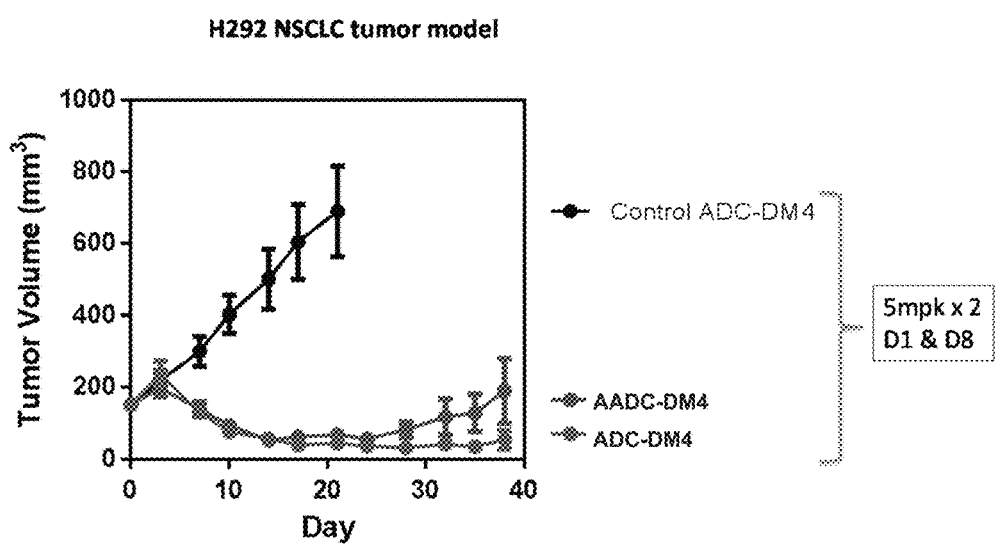

FIGS. 8A and 8B show that anti-ITGa3 antibody drug conjugates (ADCs) and anti-ITGa3 activatable antibody drug conjugates (AADCs) of the present disclosure show a higher efficacy against an isotype control in an in vivo tumor xenograft model. The huVM2 Hc2-DM4 ADC treated animals show equivalent efficacy to that of the huVM2 Hc2T62G-DM4 ADC treated animals. Further, both activatable anti-ITGa3 antibodies AADCs show equivalent efficacy to the respective ADCs. In this study, H292 xenograft tumors were treated with isotype-DM4 ADC control (palivizumab-DM4), and certain anti-ITGa3 antibody drug conjugates (ADC) and anti-ITGa3 activatable antibody drug conjugates (AADC) of the present disclosure, including huVM2 Hc2-DM4 ADC (VH of SEQ ID NO: 7, VL of SEQ ID NO: 11, conjugated to DM4), huVM2 Hc2 570-2001-DM4 AADC (VH of SEQ ID NO: 7, VL of SEQ ID NO: 11, the 570 masking moiety of SEQ ID NO: 22, the CM1 sequence 2001 of SEQ ID NO: 232, conjugated to DM4), huVM2 Hc2T62G-DM4 ADC (VH of SEQ ID NO: 10, VL of SEQ ID NO: 11, the CM1 sequence 2001 of SEQ ID NO: 232, conjugated to DM4), and huVM2 Hc2T62G 570-2001-DM4 AADC (VH of SEQ ID NO: 10, VL of SEQ ID NO: 11, the 570 masking moiety of SEQ ID NO: 22, the CM1 sequence of SEQ ID NO: 232, conjugated to DM4). Tumors were grown to an average of 150 mm$^3$; then the mice were randomized into groups of eight and dosed on day 0 and 7 with 5 mg/kg of the indicated test articles. The mean tumor volume±SEM is plotted for each time point.

Figure 9:
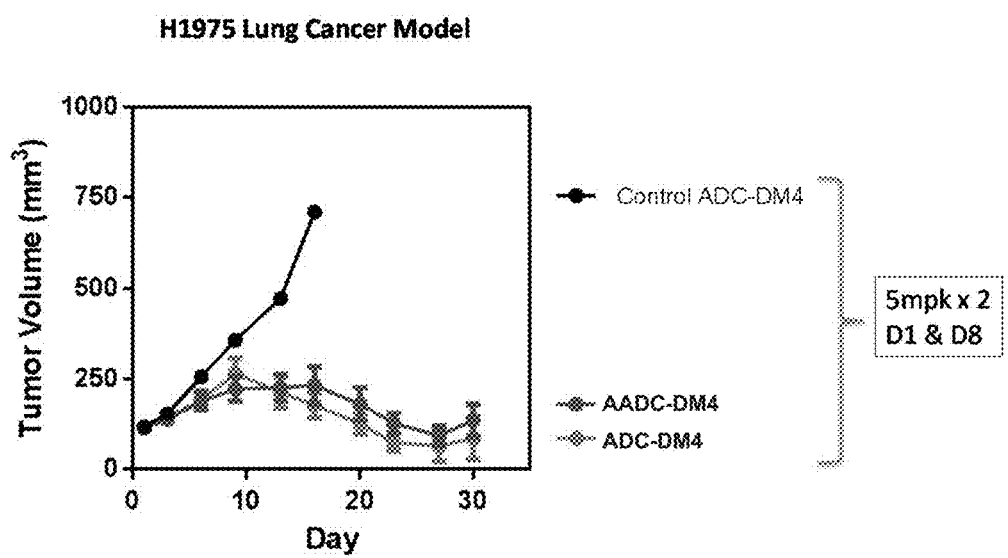
FIG. 9 is a graph depicting the efficacy of a conjugated activatable anti-ITGa3 antibody of the disclosure in a H1975 non-small cell lung cancer (NSCLC) xenograft tumor model.

FIG. 9 is a graph depicting the efficacy of the conjugated activatable anti-ITGa3 antibody of the present disclosure ("AADC-DM4") is equivalent to the conjugated anti-ITGa3 antibody of the present disclosure ("ADC-DM4"). In this study, the efficacy against H1975 lung cancer xenograft tumors were studied by comparing the efficacy of an AADC ("AADC-DM4") having the VH of SEQ ID NO: 10, VL of SEQ ID NO: 11, the 570 masking moiety of SEQ ID NO: 22, the CM1 sequence of SEQ ID NO: 232, conjugated to DM4, as compared to the corresponding ADC ("ADC-DM4") having the VH of SEQ ID NO: 10 and the VL of SEQ ID NO: 11, conjugated to DM4 and a conjugated antibody isotype control ADC (palivizumab conjugated to DM4). In this study, xenograft tumors were grown to an average of 150 mm$^3$; then the mice were randomized into groups of eight and dosed on day 0 and 7 with 5 mg/kg of the indicated test articles. The mean tumor volume±SEM is plotted for each time point.

Figure 10:
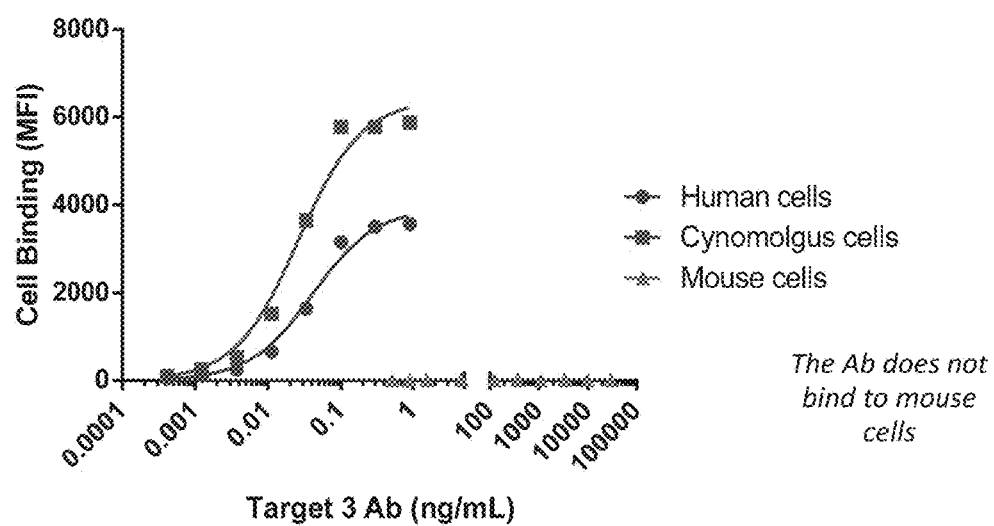
FIG. 10 is a graph depicting that the anti-ITGa3 antibodies of the disclosure bind to human and cynomolgus monkey ITGa3.

FIG. 10 is a graph that demonstrates that a humanized anti-ITGa3 antibody of the present disclosure having the VH of SEQ ID NO: 10 and the VL of SEQ ID NO: 11 binds to human ITGa3 on human-derived H292 NSCLC cells and cynomolgus monkey ITGa3 on cynomolgus-derived primary kidney epithelial cells, but does not bind to mouse ITGa3 on mouse-derived Renca renal carcinoma cells. In this study, the binding was measured using a standard labeling protocol for FACS, where cells were labeled with anti-ITGa3 antibody at the indicated concentrations, and the bound antibody was detected with a goat anti-human IgG Alexa Fluor 647 secondary antibody.

Figure 11:
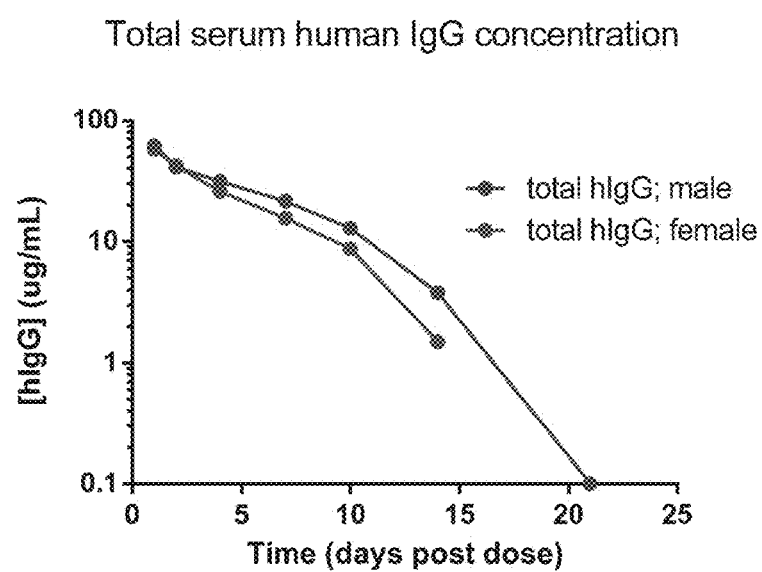
FIG. 11 is a graph depicting the pharmacokinetics of a conjugated activatable anti-ITGa3 antibody of the disclosure when administered to cynomolgus monkeys.
Figure 12:
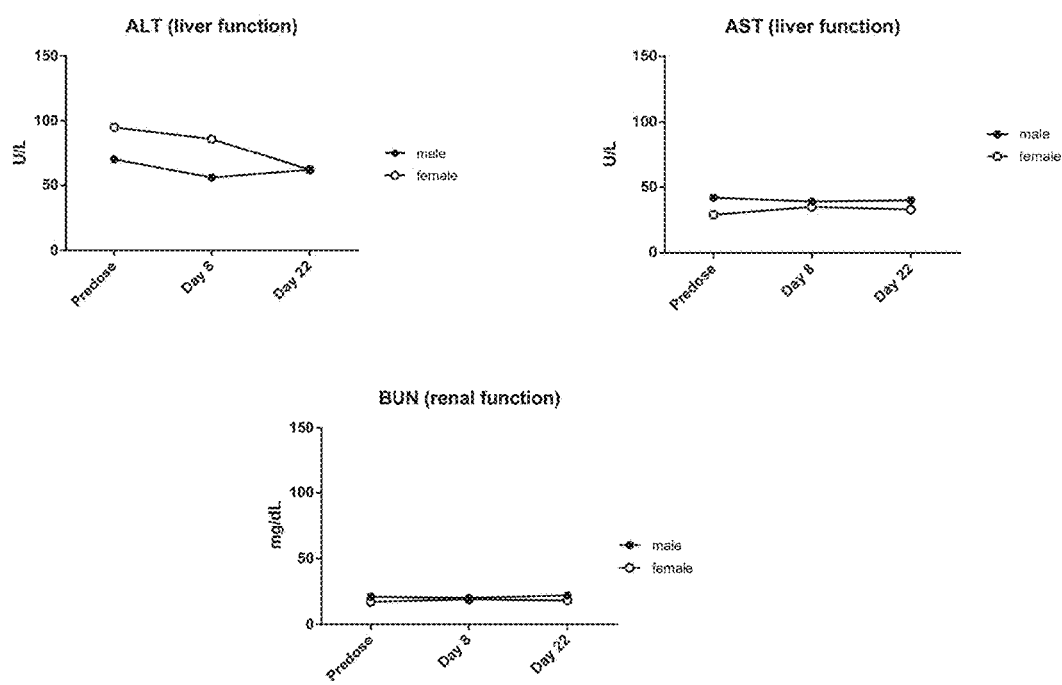
FIG. 12 provides graphs depicting the tolerability of a conjugated activatable anti-ITGa3 antibody of the disclosure when administered to cynomolgus monkeys.

FIG. 11 show the pharmacokinetics of the huVM2 T62G 570-2001-DM4 activatable antibody drug conjugate (AADC) of the present disclosure in cynomolgus monkeys, demonstrating that the AADC is relatively well-tolerated in both the male and female animals that were studied. In this study, a single 5 mg/kg dose of conjugate was given to one male and female monkey. The total serum level of human IgG was measured using an anti-human IgG sandwich ELISA using standard protocols. FIG. 12 shows that the conjugated activatable anti-ITGa3 antibodies of the present disclosure tested did not trigger an increase in markers of liver (based on levels of alanine transaminase (ALT) or aspartate transaminase (AST)) or kidney toxicity (based on blood urea nitrogen (BUN) levels).

Example 4: Characterization of the Efficacy of an Anti-Human ITGa3 AADC in a H292 Xenograft Model This Example shows the ability of an activatable anti-ITGa3 AADC of the present disclosure to demonstrate efficacy in a H292 xenograft tumor model as compared to various controls.

Figure 13:
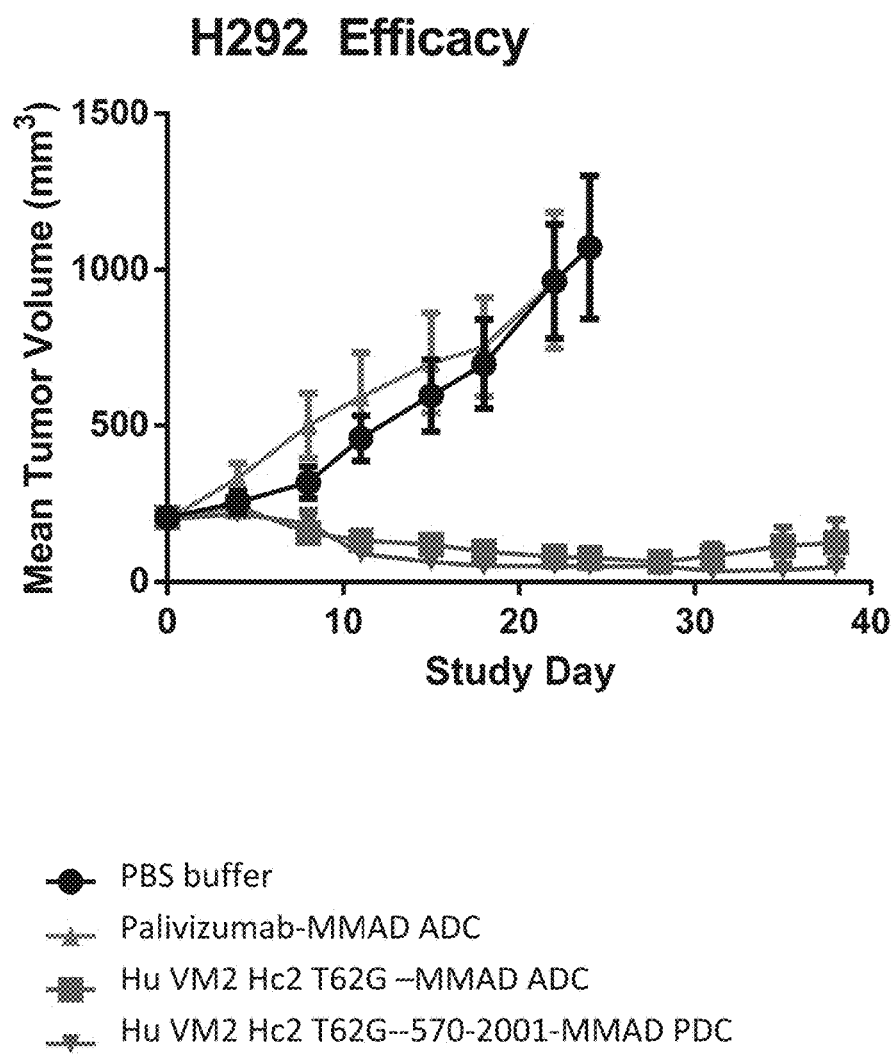
FIG. 13 is a graph depicting the efficacy of a conjugated activatable anti-ITGa3 antibody of the disclosure in H292 non-small cell lung cancer (NSCLC) xenograft tumors.

FIG. 13 shows that both an anti-ITGa3 ADC and an anti-ITGa3 AADC of the present disclosure were nearly equivalently efficacious against an H292 xenograft tumor, and both were more efficacious as compared to a PBS buffer control and an isotype-MMAD ADC control (palivizumab-MMAD). In this study, an anti-ITGa3 ADC of the present disclosure (huVM2 Hc2T62G-MMAD ADC, including VH of SEQ ID NO: 10, VL of SEQ ID NO: 11, conjugated to MMAD), and an anti-ITGa3 AADC of the present disclosure (huVM2 Hc2T62G 570-2001-MMAD AADC, including VH of SEQ ID NO: 10, VL of SEQ ID NO: 11, the 570 masking moiety of SEQ ID NO: 22, the CM1 sequence of SEQ ID NO: 232, conjugated to MMAD) were used. Tumors were grown to an average of 150 mm$^3$; then the mice were randomized into groups of eight and dosed on days 0 and 7 with 3 mg/kg of the indicated test articles. The mean tumor volume±SEM is plotted for each time point. The animals treated with the anti-ITGa3 AADC of the present disclosure showed essentially equivalent efficacy to that of the animals treated with the anti-ITGa3 ADC of the present disclosure. In contrast, none (0/8) of the animals treated with either PBS buffer control or the palivizumab-MMAD ADC isotype control showed complete response or were tumor free at day 43. From the animals treated with anti-ITGa3 ADC, 6 of the 8 treated animals showed complete response and 5 of the 8 treated animals were tumor-free at day 43. From the animals treated with activatable anti-Hu VM2 anti-ITGa3 AADC, 7 of the 8 treated animals showed a complete response and 7 of the 8 treated animals were tumor-free at day 43.

Example 5: Characterization of the Inhibitory Activity of the Anti-ITGA3 Antibody This Example showed that the anti-ITGa3 VM2 antibody does not inhibit the binding of the integrin α3β1 complex to laminin.

Figure 14:
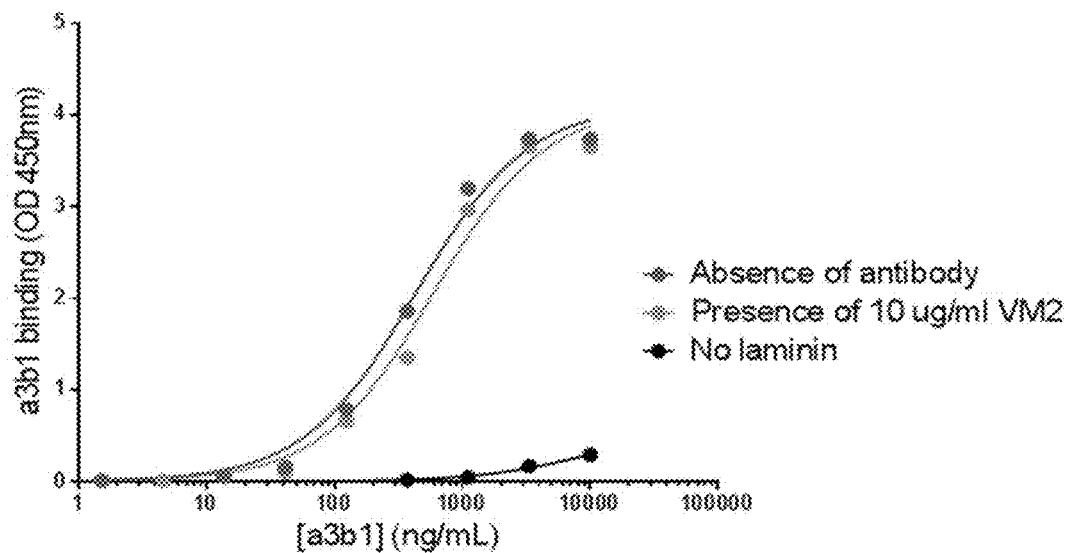
FIG. 14 is a graph showing that anti-ITGa3 antibodies of the present disclosure do not inhibit the binding of integrin α3β1 to laminin.

FIG. 14 shows that the ability of recombinant human integrin α3β1 to bind recombinant human laminin is essentially equivalent in the presence or absence of anti-ITGa3 VM2 antibody. In this study, a solid phase binding assay was used to evaluate the binding of the recombinant human laminin alpha 4 (rh laminin α4) to recombinant human integrin alpha3beta1 (α3β1). Rh laminin α4 protein (1 μg/ml) was absorbed to ELISA plates and subsequently incubated with the indicated concentration of recombinant human integrin alpha3beta1 in the presence or absence of VM2 anti-human ITGa3 antibody (10 μg/ml). The bound alpha3beta1 was detected with a biotinylated-anti-beta1 antibody and streptavidin-conjugated peroxidase.

Example 6: ITGa3 Expression on HT29, BxPc3, FaDu and MDA MB 231 Cell Lines

This Example shows that activatable anti-human ITGa3 antibodies of the present disclosure bind ITGα3 on multiple cell lines with a higher dissociation constant than that of the unmasked anti-human ITGa3 antibody of the present disclosure, thus showing the effect of the mask in reducing binding of the antibody prior to activation.

FIGS. 15A to 15D shows the amount of binding of anti-ITGa3 activatable and parental antibodies of the present disclosure to the cell lines HT29 (FIG. 15A), BxPc3 (FIG. 15B), FaDu (FIG. 15C), and MDA MB 231 (FIG. 15D). In this study, the binding of the antibodies of the present disclosure to the indicated cell lines were performed using a standard FACS labelling method. Briefly, cells were labeled with the indicated antibodies of the present disclosure: anti-human ITGa3 antibody (anti-ITGA3 huVM2 Hc2T62G antibody, "ITGa3 Ab") or an anti-human ITGa3 activatable antibody (anti-ITGA3 Hc2T62G-570-2001 "ITGa3-ActAb" at the indicated concentrations and subsequently detected with an Alexa Fluor 647 labeled goat anti-human IgG secondary antibody. Table 7 below shows the apparent dissociation constants based on the binding curves depicted in FIGS. 15A to 15D. These results show that anti-human ITGA3 antibody (ITGA3-Ab) binds all cell lines with similar Kd (0.24 to 0.91 nM), while the binding of anti-human ITGA3 activatable antibody (ITGA3-ActAb) to the cell lines were significantly shifted to the right (8 to 25 fold), which is indicative of the masking efficiency of the masking moiety.

TABLE 7

Exemplary Observed ITGa3 Binding Activity of Activatable Anti-ITGa3

| Cell Line | ITGa3 Ab Kd (nM) | ITGa3 ActAb Kd (nM) | Bmax | Apparent Masking Efficiency |
|---|---|---|---|---|
| MDA MB231 | 0.91 | 7.42 | 9000 | 8 |
| BxPC3 | 0.77 | 7.39 | 5000 | 10 |
| FaDu | 0.32 | 4.58 | 1500 | 14 |
| HT29 | 0.24 | 6.03 | 1000 | 25 |

Example 7. In Vitro Cytotoxicity of Conjugated Anti-ITGa3 Antibody Drug Conjugates Against Various Cancer-Derived Cell Lines The exemplary studies provided herein were designed to evaluate the in vitro efficacy of anti-ITGa3 antibody drug conjugates of the present disclosure against endometrial cancer-derived cell lines.

In these exemplary studies, the in vitro cytotoxicity of anti-ITGa3 antibody drug conjugates (anti-ITGa3 (Hc2T62G/Lc1)-spdb-DM4, "ITGa3-ADC") were tested against multiple human cancer-derived cell lines. In a typical assay, the cells were incubated with concentrations of ITGa3-ADC for 3 days at various concentrations (from 0.1 nM to 50 nM). Cell viability was measured using the CellTiter Glo assay. The cytotoxicity of the ITGa3-ADC was compared to a negative isotype control (chKTI-spdb-DM4. The results of these cytotoxicity assays is summarized below in Table 8.

TABLE 8

In vitro Cytotoxicity of Anti-ITGa3 Antibody Drug Conjugate to Human Cancer Cells

| Cell Type | Cancer Type | Cytotoxicity of ITGa3-ADC? |
|---|---|---|
| ZR75-1 | Human breast ductal carcinoma (estrogen receptor positive) | Yes |
| ZR75-30 | Human breast ductal carcinoma (estrogen receptor positive) | Yes |
| MDA-MB-361 | Human breast adenocarcinoma (estrogen receptor positive) | Yes |
| HCC1954 | Human breast ductal carcinoma (triple-negative) | Yes |
| HCC1143 | Human breast cancer (triple-negative) | Yes |

Example 8: Anti-ITGa3-ADC Cytotoxicity on HT29, BxPc3, FaDu and MDA MB 231 Cell Lines This Example shows that anti-human ITGa3 antibody drug conjugates of the present disclosure demonstrate a higher cytotoxicity against multiple cell lines compared to an isotype control ADC.

FIGS. 16A to 16D show that anti-human ITGa3 antibody (ADC) and activatable antibody (AADC) of the present disclosure conjugated to various toxins demonstrate higher in vitro cytotoxicity against various ITGa3-expressing cell lines as compared to an isotype control ADC. In this study, anti-human ITGa3 (huVM2 Hc2T62G/Lc1) and anti-human ITGa3 activatable antibody (anti-ITGa3-570-2001 or anti-ITGa3-2331-3001) of the present disclosure conjugated to either spdb-DM4 ("ITGa3-570-2001-DM4" or "ITGa3-2331-3001-DM4") or vc-MMAD ("ITGa3-570-2001-

MMAD") or an isotype control (palivizumab), conjugated to either spdb-DM4 ("Isotype-DM4") or vc-MMAD ("Isotype-DM4") as applied at the indicated concentrations to BxPc3, a human pancreatic adenocarcinoma-derived cell line (FIGS. 16A and 16B), NCI-H292, a human non-small cell lung cancer cell line (FIG. 16C), and HCC1806, a human triple-negative breast cancer cell line (FIG. 16D). The cytotoxicity was determined as a percentage of a population of untreated cells that were used as a control. The results demonstrate a cytotoxicity of both the ITGa3-ADC and ITGa3-AADC against multiple cell lines Example 9: Cell-Binding Assay with Anti-ITGa3 Antibody Constructs This Example shows that activatable anti-human ITGa3 antibodies, activatable antibodies, and activatable antibody drug conjugates of the present disclosure bind ITGa3 on multiple cell lines.

FIG. 17A shows the amount of binding of anti-ITGa3 activatable antibody drug conjugates of the present disclosure to the H292 (human non-small lung cancer cell line). FIG. 17B shows the amount of binding of anti-ITGa3 activatable antibodies and activatable antibody drug conjugates of the present disclosure to the MDA MB 231 (human triple-negative breast cancer cell line). In this study, the binding of the antibodies of the present disclosure to the indicated cell lines were performed using a standard FACS labelling method. Briefly, in FIG. 17A cells were labeled with the indicated antibodies of the present disclosure: anti-human ITGa3 antibody drug conjugate (anti-ITGa3 huVM2 Hc2/Lc1-spdb-DM4, "ITGa-DM4") or an anti-human ITGa3 activatable antibody drug conjugate (anti-ITGA3 Hc2-570-2001-spdb-DM4, "ITGA3-570-2001-DM4"), where the anti-ITGa3 AADC was used with and without activation by a protease that recognized the substrate sequence. In FIG. 17B cells were labeled with the indicated antibodies of the present disclosure: anti-human ITGa3 antibody (anti-ITGa3 huVM2 Hc2T62G/Lc1 antibody, "ITGa3 Ab") or an anti-human ITGa3 activatable antibody (anti-ITGA3 Hc2T62G-570-2001, "ITGA3-570-2001; anti-ITGA3 Hc2T62G-2331-3001, "ITGA3-2331-3001") and their corresponding AADCs conjugated to vc-MMAD at the indicated concentrations and subsequently detected with an Alexa Fluor 647 labeled goat anti-human IgG secondary antibody. Table 9 below shows the apparent dissociation constants based on the binding curves depicted in FIG. 17B. These results show that anti-human ITGA3 antibody (ITGA3-Ab) binds all cell lines with similar Kd (0.24 to 0.91 nM), while the binding of anti-human ITGA3 activatable antibody (ITGA3-ActAb) to the cell lines were significantly shifted to the right (8 to 25 fold), which is indicative of the masking efficiency of the masking moiety.

TABLE 9

Exemplary Observed ITGa3 Binding Activity of Activatable Anti-ITGa3

| Anti | ITGa3 Ab Kd (nM) |
| --- | --- |
| ITGa3 Ab | 0.9058 |
| ITGa3 570-2001 | 17.99 |
| ITGa3 2331-3001 | 51.94 |
| ITGa3 Ab-MMAD | 1.079 |
| ITGa3 570-2001-MMAD | 17.49 |
| ITGa3 2331-3001-MMAD | 148.7 |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed:

1. An isolated antibody or an antigen binding fragment thereof (AB) that specifically binds to mammalian ITGa3, wherein the AB specifically binds human ITGa3 and cynomolgus monkey ITGa3, wherein the AB comprises a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYY-GYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), and wherein the AB is humanized.

2. The AB of claim 1, wherein the AB comprises:
 (i) a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), or
 (ii) a heavy chain variable region comprising the amino acid sequence of SEQ ID NO: 10, and a light chain variable region comprising the amino acid sequence of SEQ ID NO: 11.

3. The AB of claim 1, wherein the AB comprises a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11 and 12.

4. An activatable antibody that, in an activated state, binds ITGa3 comprising:
 an antibody or an antigen binding fragment thereof (AB) that specifically binds to mammalian ITGa3, wherein the AB specifically binds human ITGa3 and cynomolgus monkey ITGa3, wherein the AB comprises a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), and wherein the AB is humanized;
 a masking moiety (MM) coupled to the AB that inhibits the binding of the AB to ITGa3 when the activatable antibody is in an uncleaved state; and
 a cleavable moiety (CM) coupled to the AB, wherein the CM is a polypeptide that functions as a substrate for a protease.

5. The activatable antibody of claim 4, wherein the MM has one or more of the characteristics selected from the group consisting of:
 (i) the MM has a dissociation constant for binding to the AB that is greater than the dissociation constant of the AB to ITGa3;
 (ii) the MM does not interfere or compete with the AB for binding to ITGa3 when the activatable antibody is in a cleaved state;
 (iii) the MM is a polypeptide of no more than 40 amino acids in length;
 (iv) the MM polypeptide sequence is different from that of human ITGa3;
 (v) the MM polypeptide sequence is no more than 50% identical to any natural binding partner of the AB; and
 (vi) the MM comprises an amino acid sequence selected from the group consisting of SEQ ID NOs: 22-54.

6. The activatable antibody of claim 4, wherein the CM comprises an amino acid sequence selected from the group consisting of SEQ ID NOs: 182-249 and 276-316.

7. The activatable antibody of claim 4, wherein the antigen binding fragment thereof is selected from the group consisting of a Fab fragment, a F(ab')₂ fragment, a scFv, a scAb, a dAb, a single domain heavy chain antibody, and a single domain light chain antibody.

8. The activatable antibody of claim 4, wherein the AB has one or more of the characteristics selected from the group consisting of:
  (i) the AB comprises a VH CDR1 comprising the amino acid sequence EYIIH (SEQ ID NO: 13); a VH CDR2 comprising the amino acid sequence WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21); and
  the AB comprises a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11 and 12.

9. The activatable antibody of claim 4, wherein the AB is linked to the CM.

10. The activatable antibody of claim 4, wherein the AB is linked directly to the CM.

11. The activatable antibody of claim 4, wherein the AB is linked to the CM via a linking peptide.

12. The activatable antibody of claim 4, wherein the MM is linked to the CM such that the activatable antibody in an uncleaved state comprises the structural arrangement from N-terminus to C-terminus as follows: MM-CM-AB or AB-CM-MM.

13. The activatable antibody of claim 4, wherein the activatable antibody comprises a linking peptide between the MM and the CM, a linking peptide between the CM and the AB, or both a linking peptide between the MM and the CM and a linking peptide between the CM and the AB.

14. The activatable antibody of claim 4, wherein the activatable antibody comprises a first linking peptide (LP1) and a second linking peptide (LP2), and wherein the activatable antibody in the uncleaved state has the structural arrangement from N-terminus to C-terminus as follows: MM-LP1-CM-LP2-AB or AB-LP2-CM-LP1-MM.

15. The activatable antibody of claim 14, wherein the two linking peptides are not identical to each other.

16. The activatable antibody of claim 14, wherein each of LP1 and LP2 is a peptide of about 1 to 20 amino acids in length.

17. The activatable antibody of claim 4, wherein the activatable antibody has one or more of the characteristics selected from the group consisting of:
  (a) the activatable antibody comprises the heavy chain sequence of SEQ ID NO: 320 and a light chain comprising an amino acid sequence selected from the group consisting of SEQ ID NOs: 255, 257, 259, 261, 322, 324, 326, 328, 330, 332-359, and 364-391;
  (b) the activatable antibody comprises a combination of amino acid sequences, wherein for a given combination of amino acid sequences,
    (i) the heavy chain of the AB comprises a VH sequence selected from the group consisting of SEQ ID NOs: 4-6 and 8-10 or a set of VH CDR sequences selected from the group consisting of SEQ ID NOs: 13, 15, and 18; SEQ ID NOs: 13, 16, and 18; and SEQ ID NOs: 13, 17, and 18,
    (ii) the light chain of the AB comprises the VL sequence selected from the group consisting of SEQ ID NOs: 11 and 12 or the VL CDR sequences of SEQ ID NOs: 19, 20, and 21,
    (iii) the MM comprises the amino acid sequence selected from the group consisting of SEQ ID NOs: 22-54, and
    (iv) the CM comprises the amino acid sequence selected from the group consisting of SEQ ID NOs: 182-249 and 276-316; and
  (c) the activatable antibody comprises a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11, 12, 396, 398, 400, 402, 404-431, 436, 438, 440, 442, and 444-471.

18. An activatable antibody comprising an antibody or an antigen binding fragment thereof (AB) that specifically binds to mammalian ITGa3, a masking moiety (MM), and a cleavable moiety (CM), wherein the activatable antibody has one or more of the following characteristics selected from the group consisting of:
  (i) the activatable antibody comprises a heavy chain comprising an amino acid sequence of SEQ ID NO: 320; and a light chain sequence comprising an amino acid sequence selected from the group consisting of SEQ ID NOs: 255, 257, 259, 261, 322, 324, 326, 328, 330, 332-359, and 364-391;
  (ii) the AB comprises a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21);
  (iii) the AB comprises a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11 and 12; and
  (iv) the AB comprises a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), the MM comprises an amino acid sequence selected from the group consisting of SEQ ID NOs: 22-54, and the CM comprises an amino acid sequence selected from the group consisting of SEQ ID NOs: 182-249 and 276-316.

19. A conjugated activatable antibody comprising the activatable antibody of claim 4 conjugated to an agent.

20. The conjugated activatable antibody of claim 19, wherein the agent has one or more of the characteristics selected from the group consisting of:
   (a) the agent is a toxin or fragment thereof;
   (b) the agent is a microtubule inhibitor;
   (c) the agent is a nucleic acid damaging agent;
   (d) the agent is a dolastatin or a derivative thereof;
   (e) the agent is an auristatin or a derivative thereof;
   (f) the agent is a maytansinoid or a derivative thereof;
   (g) the agent is a duocarmycin or a derivative thereof;
   (h) the agent is a calicheamicin or a derivative thereof;
   (i) the agent is a pyrrolobenzodiazepine or a derivative thereof;
   (j) the agent is auristatin E or a derivative thereof;
   (k) the agent is monomethyl auristatin E (MMAE);
   (l) the agent is monomethyl auristatin D (MMAD);
   (m) the agent is the maytansinoid DM1;
   (n) the agent is the maytansinoid DM4;
   (o) the agent is a detectable moiety; and
   (p) the agent is a diagnostic agent.

21. The conjugated activatable antibody of claim 19, wherein the agent is conjugated to the AB via a linker.

22. The conjugated activatable antibody of claim 21, wherein the linker with which the agent is conjugated to the AB comprises an SPDB moiety, a vc moiety, or a PEG2-vc moiety.

23. The conjugated activatable antibody of claim 19, wherein the agent is a toxin conjugated to the AB via a linker, and wherein the linker and the toxin conjugated to the AB comprise a moiety selected from the group consisting of: an SPDB-DM4 moiety, a vc-MMAD moiety, a vc-MMAE moiety, a vc-duocarmycin moiety, or a PEG2-vc-MMAD moiety.

24. The conjugated activatable antibody of claim 21, wherein the linker is a cleavable linker.

25. The conjugated activatable antibody of claim 21, wherein the linker is a non-cleavable linker.

26. A conjugated activatable antibody that, in an activated state, binds ITGa3 comprising:
   (a) an activatable antibody comprising:
      (i) an antibody or an antigen binding fragment thereof (AB) that specifically binds to mammalian ITGa3, wherein the AB specifically binds human ITGa3 and cynomolgus monkey ITGa3, wherein the AB comprises a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), and wherein the AB is humanized;
      (ii) a masking moiety (MM) coupled to the AB that inhibits the binding of the AB to ITGa3 when the activatable antibody is in an uncleaved state; and
      (iii) a cleavable moiety (CM) coupled to the AB, wherein the CM is a polypeptide that functions as a substrate for a protease; and
   (b) an agent conjugated to the AB.

27. The conjugated activatable antibody of claim 26, wherein the agent is selected from the group consisting of a dolastatin or a derivative thereof, an auristatin or a derivative thereof, a maytansinoid or a derivative thereof, a duocarmycin or a derivative thereof, a calicheamicin or a derivative thereof, a pyrrolobenzodiazepine or a derivative thereof, auristatin E, monomethyl auristatin F (MMAF), monomethyl auristatin E (MMAE), monomethyl auristatin D (MMAD), maytansinoid DM4, maytansinoid DM1, a duocarmycin, a calicheamicin, a pyrrolobenzodiazepine, and a pyrrolobenzodiazepine dimer.

28. The conjugated activatable antibody of claim 26, wherein the agent is conjugated to the AB via a linker.

29. The conjugated activatable antibody of claim 28, wherein the linker with which the agent is conjugated to the AB comprises an SPDB moiety, a vc moiety, or a PEG2-vc moiety.

30. The conjugated activatable antibody of claim 26, wherein the agent is a toxin conjugated to the AB via a linker, and wherein the linker and the toxin conjugated to the AB comprise a moiety selected from the group consisting of: an SPDB-DM4 moiety, a vc-MMAD moiety, a vc-MMAE moiety, a vc-duocarmycin moiety, or a PEG2-vc-MMAD moiety.

31. The conjugated activatable antibody of claim 26, wherein the activatable antibody has one or more of the characteristics selected from the group consisting of:
   (i) the activatable antibody comprises a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21);
   (ii) the activatable antibody comprises a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11, 12, 396, 398, 400, 402, 404-431, 436, 438, 440, 442, and 444-471; and
   (iii) the activatable antibody comprises a heavy chain comprising an amino acid sequence of SEQ ID NO: 320; and a light chain sequence comprising an amino acid sequence selected from the group consisting of SEQ ID NOs: 255, 257, 259, 261, 322, 324, 326, 328, 330, 332-359, and 364-391.

32. The conjugated activatable antibody of claim 26, wherein the MM comprises an amino acid sequence selected from the group consisting of SEQ ID NOs: 22-54.

33. The conjugated activatable antibody of claim 26, wherein the CM comprises an amino acid sequence selected from the group consisting of SEQ ID NOs: 182-249 and 276-316.

34. The conjugated activatable antibody of claim 26, wherein
   the activatable antibody comprises a combination of amino acid sequences, wherein for a given combination of amino acid sequences,
   (i) the heavy chain of the AB comprises a VH sequence selected from the group consisting of SEQ ID NOs: 4-6 and 8-10 or a set of VH CDR sequences selected from the group consisting of SEQ ID NOs: 13, 15, and 18; SEQ ID NOs: 13, 16, and 18; and SEQ ID NOs: 13, 17, and 18, (ii) the light chain of the AB comprises the VL sequence selected from the group consisting of SEQ ID NOs: 11 and 12 or the VL CDR sequences of SEQ ID NOs: 19, 20, and 21, (iii) the MM comprises the amino acid sequence selected from the group consisting of SEQ ID NOs: 22-54, and (iv) the CM comprises the amino acid sequence selected from the group consisting of SEQ ID NOs: 182-249 and 276-316.

35. A conjugated antibody comprising:
(a) an antibody or an antigen binding fragment thereof (AB) that specifically binds to mammalian ITGa3, wherein the AB comprises:
   (i) a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), or
   (ii) a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11 and 12; or
   (iii) a heavy chain comprising an amino acid sequence selected from the group consisting of SEQ ID NO: 320, and a light chain comprising an amino acid sequence selected from the group consisting of SEQ ID NO: 322; and
(b) an agent conjugated to the AB, wherein the agent is selected from the group consisting of auristatin E, monomethyl auristatin F (MMAF), monomethyl auristatin E (MMAE), monomethyl auristatin D (MMAD), maytansinoid DM4, maytansinoid DM1, a calicheamicin, a pyrrolobenzodiazepine, a pyrrolobenzodiazepine dimer, and a duocarmycin.

36. A conjugated activatable antibody that, in an activated state, binds to ITGa3, comprising:
(a) an activatable antibody comprising:
   (i) an antibody or an antigen binding fragment thereof (AB) that specifically binds to mammalian ITGa3, wherein the AB specifically binds human ITGa3 and cynomolgus monkey ITGa3;
   (ii) a masking moiety (MM) coupled to the AB that inhibits the binding of the AB to ITGa3 when the activatable antibody is in an uncleaved state;
   (iii) a cleavable moiety (CM) coupled to the AB, wherein the CM is a polypeptide that functions as a substrate for a protease; and
(b) an agent conjugated to the AB,
wherein the activatable antibody comprises:
   (i) a VH CDR1 comprising the amino acid sequence EYIIH (SEQ ID NO: 13); a VH CDR2 comprising the amino acid sequence WFYPESGSVKYSETFKG (SEQ ID NO: 15) or WFYPESGSVKYNEAFKG (SEQ ID NO: 16) or WFYPESGSVKYNEGFKG (SEQ ID NO: 17); a VH CDR3 comprising the amino acid sequence HEERDYYGYYAMDY (SEQ ID NO: 18); a VL CDR1 comprising the amino acid sequence SASSSISSNYLH (SEQ ID NO: 19); a VL CDR2 comprising the amino acid sequence RTSNLA (SEQ ID NO: 20); and a VL CDR3 comprising the amino acid sequence QQGSSIPRFT (SEQ ID NO: 21), or
   (ii) a heavy chain variable region comprising an amino acid sequence selected from the group consisting of SEQ ID NOs: 4-6 and 8-10, and a light chain variable region comprising an amino acid sequence selected from the group consisting of SEQ ID NOs: 11, 12, 396, 398, 400, 402, 404-431, 436, 438, 440, 442, and 444-471; or
   (iii) a heavy chain comprising an amino acid sequence selected from the group consisting of SEQ ID NO: 320, and a light chain comprising an amino acid sequence selected from the group consisting of SEQ ID NOS: 255, 257, 259, 261, 322, 324, 326, 328, 330, 332-359, and 364-391; and
wherein the agent is selected from the group consisting of auristatin E, monomethyl auristatin F (MMAF), monomethyl auristatin E (MMAE), monomethyl auristatin D (MMAD), maytansinoid DM4, maytansinoid DM1, a calicheamicin, a pyrrolobenzodiazepine, a pyrrolobenzodiazepine dimer, and a duocarmycin.

37. The conjugated activatable antibody of claim 36, wherein the MM comprises an amino acid sequence selected from the group consisting of SEQ ID NOs: 22-54.

38. The conjugated activatable antibody of claim 36, wherein the CM comprises an amino acid sequence selected from the group consisting of SEQ ID NOs: 182-249 and 276-316.

39. The conjugated activatable antibody of claim 36, wherein the agent is conjugated to the AB via a linker, and wherein the linker to which the agent is conjugated to the AB comprises an SPDB moiety, a vc moiety, or a PEG2-vc moiety.

40. The conjugated antibody or conjugated activatable antibody of claim 36, wherein the linker and toxin conjugated to the AB comprises an SPDB-DM4 moiety, a vc-MMAD moiety, a vc-MMAE moiety, a vc-duocarmycin moiety, or a PEG2-vc-MMAD moiety.

41. A pharmaceutical composition comprising the activatable antibody of claim 4 and a carrier.

42. The pharmaceutical composition of claim 41 comprising an additional agent.

43. The pharmaceutical composition of claim 42, wherein the additional agent is a therapeutic agent.

44. A pharmaceutical composition comprising the conjugated activatable antibody of claim 19; and a carrier.

45. The pharmaceutical composition of claim 44 comprising an additional agent.

46. The activatable antibody of claim 4, wherein the MM is linked to the CM.

47. The activatable antibody of claim 4, wherein the MM is linked directly to the CM.

48. The activatable antibody of claim 4, wherein the MM is linked to the CM via a linking peptide.

* * * * *